(12) United States Patent
Plettner et al.

(10) Patent No.: US 9,497,963 B2
(45) Date of Patent: Nov. 22, 2016

(54) **METHODS AND COMPOSITIONS FOR CONTROL OF GYPSY MOTH, *LYMANTRIA DISPAR***

(75) Inventors: Erika Plettner, Burnaby (CA); Yongmei Gong, Beijing (CN); Regine Gries, Coquitlam (CA)

(73) Assignee: Simon Fraser University, Burnaby, British Columbia (CA)

( * ) Notice: Subject to any disclaimer, the term of this patent is extended or adjusted under 35 U.S.C. 154(b) by 631 days.

(21) Appl. No.: 13/592,036

(22) Filed: Aug. 22, 2012

(65) Prior Publication Data
US 2013/0045178 A1 Feb. 21, 2013

Related U.S. Application Data

(63) Continuation-in-part of application No. 12/755,867, filed on Apr. 7, 2010, now abandoned, which is a continuation-in-part of application No. 12/622,423, filed on Nov. 19, 2009, now abandoned.

(60) Provisional application No. 61/116,245, filed on Nov. 19, 2008.

(51) Int. Cl.
*A01N 31/16* (2006.01)
*A01N 43/12* (2006.01)

(52) U.S. Cl.
CPC ............... *A01N 31/16* (2013.01); *A01N 43/12* (2013.01)

(58) Field of Classification Search
CPC ... A01N 31/16; A01N 2300/00; A01N 25/06
See application file for complete search history.

(56) References Cited

U.S. PATENT DOCUMENTS

| | | | | |
|---|---|---|---|---|
| 4,283,878 A * | 8/1981 | Hill | ...................... | A01M 1/023 43/114 |
| 5,342,618 A * | 8/1994 | Leonhardt | .............. | A01N 25/18 424/405 |
| 6,264,939 B1 * | 7/2001 | Light | ...................... | A01M 1/02 424/405 |
| 2010/0160451 A1 | 6/2010 | Plettner et al. | | |
| 2010/0297059 A1 | 11/2010 | Plettner et al. | | |
| 2013/0131185 A1 | 5/2013 | Plettner et al. | | |

FOREIGN PATENT DOCUMENTS

JP 2001187702 A * 7/2001

OTHER PUBLICATIONS

Paduraru et al., J. Comb. Chem. 2008, 10, 123-134.*
Liu, W, et al. "Compact Biocompatible Quantum Dots via RAFT-Mediated Synthesis of Imidazole-Based Random Copolymer Ligand." J Am Chem Soc 2010;132(2):472-83.
Magde, D., et al. "Solvent Dependence of the Fluorescence Lifetimes of Xanthene Dyes." Photochem Photobiol 1999;70(5):737-44.
Mahler, B., et al., "Towards non-blinking colloidal quantum dots." Nat Mater 2008;7(8):659-64.
Mathew, N.T., et al., "Rearrangement of allyl phenyl eher over Al-MCM-41." J of Catalysis 2004;229(1):105-113.
McCabe, E.T., et al., "Insect Repellents. III. N,N-Diethylamides." J Org Chem 1954;19(4)493-498.
Meijerink, J., et al., "Identification of olfactory stimulants for Anopheles gambiae from human sweat samples." J Chem Ecol 2000;26(6):1367-1382.
Micha, S.G. and Wyss, U., "Aphid Alarm pheromone €-beta-farnesene: a host finding kairomone for the aphid primary parasitoid Aphidius uzbekistanicus (Hymnoptera: Aphidiinae)." Chemoecology1996;7(3):132-139.
Miller, J.R., et al., "Gypsy Moth Field Trapping and Electroantennogram Studies with Pheromone Enantiomers." J Insect Physiol 1977;23(11-12):1447-1453.

(Continued)

*Primary Examiner* — Kyle Purdy
(74) *Attorney, Agent, or Firm* — Steptoe & Johnson LLP

(57) ABSTRACT

The invention provides in part dialkoxybenzene and eugenol compounds for controlling infestation by a *Lymantria dispar*, and methods thereof. The compounds include a compound of Formula I:

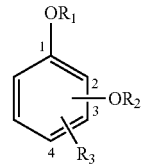

Formula I where R1 may be methyl, ethyl, propyl, n-butyl, isopentyl (3-methylbutyl) or allyl; R2 may be at positions 2, 3 or 4 and may be H, methyl, ethyl, propyl, n-butyl, isopentyl (3-methylbutyl) or allyl; and R3 may be optionally present at positions 2, 3 and 4, and is allyl; with the provisos that when R2 is at position 2, R3 if present is at position 3, or when R2 is at position 3, R3 if present is at positions 2 or 4, or when R2 is at position 4, R3 if present is at position 2;
or of Formula II:

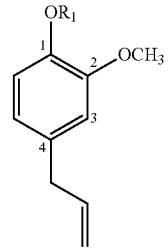

Formula II where R1 may be methyl, ethyl, propyl, n-butyl, isopentyl (3-methylbutyl) or allyl; or mixtures thereof.

10 Claims, 20 Drawing Sheets

(56) References Cited

OTHER PUBLICATIONS

Montgomery, M. E. and Wallner, W. E., "The Gypsy Moth, A Westward Migrant." Dynamics of Forest Insect Populations: Patterns, Causes, Implications. Ed. Berryman, A. A., Plenum, Springer, N. Y. 1988:353-375.

Murray, C.B., et al., "Synthesis and characterization of nearly monodisperse CdE (E = sulfur, selenium, tellurium) semiconductor nanocrystallites." J Am Chem Soc 1993;115(19):8706-8715.

Murugan, K., et al., "Larvicidal and repellent potential of Alizzia amara Boivin and Ocimum basilicum Linn against dengue vector, Aedes aegypti (Insecta:Diptera:Culicidae)." Bioresour Technol 2007;98(1):198-201.

Obeng-Ofori, D. and Reichmuth, C., "Bioactivity of eugenol, a moajor component of essential oil of Ocimum suave (Wild.) against four species of stored-product Coleoptera." Int J Pest Manag 1997;43(1):89-94.

Ollevier, T., and Mwene-Mbeja, T.M. "Bismuth Triflate Catalyzed [1,3] Rearrangement of Aryl 3-Methylbut-2-enyl Ethers." Synthesis 2006;23:3963-3966.

Paduraru, P.M., et al., "Synthesis of substituted alkoxy benzene minilibraries, for the discovery of new insect olfaction or gustation inhibitors." J Comb Chem 2008;10(1)123-134.

Park, I.K., et al., "Larvicidal activity of lignans identified in Phryma leptostachya Var. asiatica roots against three mosquito species." J Agric Good Chem 2005;53(4):969-972.

Parrish, J.P., et al., "Improved Cs2Co3 Promoted O-Alkylation of Phenols." Synth Commun 1999;29(24):4423-4431.

Peng, X., et al., "Epitaxial Growth of Highly Luminescent CdSe/CdS Core/Shell Nanocrystals with Photostability and Electronic Accessibility." J Am Chem Soc 1997;119(30):7019-29.

Plettner, E., et al. "Discrimination of Pheromone Enantiomers by Two Pheromone Binding Proteins from the Gypsy Moth *Lymnatria dispar*." Biochemistry 2000;39(30):8953-8962.

Plettner, E. and Gries, R., "Agonsists and Antagonists of Antennal Responses of Gypsy Moth (*Lymantria dispar*) to the Pheromone (+)-Disparlure and Other Odorants." J Agri Food Chem 2010;58(6):3708-3719.

Plimmer, J.R., et al., "Contrasting Effectiveness of (+) and (−) Enantiomers of Disparlure for Trapping Native Populations of Gypsy Moth in Massachusetts". Environ Entomol 1977;6(4):518-522.

Plimmer, J.R., et al., "Management of the Gypsy Moth with Its Sex Attractant Pheromone." Insect Pheromone technology: Chemistry and Applications. ACS 1982;190(13):231-242.

Reich, N.W., et al., "Gold(I)-Catalyzed Synthesis of Dihydrobenzofurans from Aryl Allyl Ethers." Synlett 2006;8:1278-1280.

Renou, M., et al., "Disruption of responses to pheromone by (Z)-11-hexadecenyl trifluoromethyl ketone, an analogue of the pheromone, in the cabbage armyworm *Mamestra brassicae*." Pest Manag Sci 2002;58(8):839-844.

Salunke, B.K., et al., "Efficacy of flavonoids in controlling Callosobruchus chinensis (L.)(Coleoptera: Bruchidae), a post-harvest pest of grain legumes." Crop Protection 2005;24(10):888-893.

Schneider, C., et al., "Insecticidal rocaglamide derivatives from Aglaia spectabilis (Meliaceae)." Phytochemistry 2000;54(8):731-736.

Schneider, D., "Insect Olfaction: Deciphering System for Chemical Messages." Science 1969;163 (3871):1031-1070.

Snee, P.T., et al., "Whispering-Gallery-Mode Lasing from a Semiconductor Nanocrystal/Microshpere Resonator Composite." Adv Mater 2005;17(9):1131-1136.

Staddon, B.W. and Everton, I.J., "Haemolymph of the milkweed bug *Oncopeltus fasciatus* (Heptoptera; lygaeidae): Inorganic constituents and amino acids." Comp Biochem Physiol A 1980;65(3):371-374.

Topazzini, A. et al., "Electroantennogram responses of five Lepidoptera species to 26 general odorants." J Insect Physiol 1990;36(9):619-624.

Upasani, S.M., et al., "Partial characterization and insecticidal properties of Ricinus communis L foliage flavinoids." Pest Manag Sci 2003;59(12)1349-54.

Van Embden J., Jasieniak J., Mulvaney P., Mapping the Optical Properties of CdSe/CdS Heterostructure Nanocrystals: The Effects of Core Size and Shell Thickness. J Am Chem Soc 2009;131(40):14299-14309.

Vergassola, M., et al., "Infotaxis' as a strategy for searching without gradients." Nature 2007;445:406-409.

White, W.N. et al., "The ortho-Claisen Rearrangement.I. The Effect of Substituents on the Rearrangement of Allyl p-X-Phenyl Ethers." J Am Chem Soc 1958;80(13):3271-3277.

White, W.N. and Slater, C.D., "The ortho-Claisen Rearrangement. V. The Products of Rearrangement of Allyl m-X-Phenyl Ethers." J Org Chem 1961;26(10):3631-3638.

Xie, R., et al. "Synthesis and Characterization of Highly Luminescent CdSe-Core CdS/Zn0.5Cd0.5S/ZnS Multishell Nanocrystals." J Am Chem Soc 2005;127(20):7480-7488.

Yadav, G.D. et al., "A Novel and Efficient Solid Superacid Catalyst for Claisen Rearrangement of Substituted Allyl Phenyl Ethers." Synth Commun 2007;37(6):941-946.

Dewick, P. M., "The Shikimate Pathway: Aromatic Amino Acids and Phenylpropanoids." Medicinal Natural Products: A Biosynthetic Approach, 3rd ed. Chichester, West Sussex, England: Wiley, 2002:121-166.

"Gypsy Moth in North America." Gypsy Moth in North America. USDA Forest Service—Northeastern Research Station, Jul. 9, 2011. Web. http://www.fs.fed.us/ne/morgantown/4557/gmoth/.

"Gypsy Moth" Wikipedia. Wikimedia Foundation, Jul. 9, 2011. Web. http://en.wikipedia.org/wiki/Gypsy_moth.

Martin, D. and Bohlmann, J., "Chapter Two: Molecular biochemistry and genomics of terpenoid defenses in conifers." Recent advances in phytochemistry, Ed. J. T. Romeo, Elsevier, 2005;39:29-56.

Mustaparta, H. and Stranden, M., "Chapter Ten: Olfaction and learning in months and weevils living on angiosperm and gymnosperm hosts." Recent advances in phytochemistry, Ed. J. T. Romeo, Elsevier, 2005;39:269-285.

Parrish, J.P., et al., "Improved Cs2CO3 Promoted 0-Alkylation of Phenols." Synthetic Communications 1999;29(24):4423-4431.

Plettner, E., "The peripheral pheromone olfactory system in insects: targets for species-selective insect control agents." Insect Pheromone Biochemistry and Molecular Biology 2003:477-507.

Raffa, K.F., et al., "Chapter Four Interactions among conifer terpenoids and bark beetles across multiple levels of scale: An attempt to understand links between population patterns and physiological processes." Recent Advances in Phytochemistry 2005;39: 79-118.

Akhtar, Y., et al., "Screening of diallkoxybenzenes and disubstituted cyclopentene derivatives against the cabbage looper, Trichoplusia ni, for the discovery of new feeding and oviposition deterrents." J Agric Food Chem 2007;55(25):10323-10330.

Barthel, W.F., et al., "Insect Repellents. I. Esters of Mandelic and Substituted Mandelic Acids." J Org Chem 1954;19(4):485-489.

Bau, J., et al. "Pheromone-triggered Orientation Flight of Male Moths can be Disrupted by Trifluoromethyl Ketones." Chem Senses 1999;24(5):473-480.

Bengtsson, M., et al. "Plant volatiles mediate attraction to host and non-host plant in apple fruit moth, *Argyresthia conjugella*." Entomol Exp Appl 2006;118(1):77-85.

Bierl, B., et al, "Isolation, Identification, and Synthesis of the Gypsy Moth Sex Attractant." J Econ Entomol 1972;65(3):659-664.

Bierl B., et al., "Potent Sex Attractant of the Gypsy Moth: Its Isolation, Identification and Synthesis." Science 1970;170(3953):87-89.

Bortolomeazzi R., et al. "Comparative evaluation of the antioxidant capacity of smoke flavouring phenols by crocin belaching inhibition, DPPH radical scavenging and oxidation potential." Food Chem 2007;100(4):1481-1489.

Campion, D. G., "Survey of pheromone uses in pest control." Techniques in pheromone research. Springer New York, 1984. 405-449.

(56) References Cited

OTHER PUBLICATIONS

Carde, R.T., et al. "Attractancy of optically active pheromone for male gypsy moths." Environmental Entomology 1977; 6(6):768-772.

Carde, R.T., et al. "Attractancy of racemic disparlure and certain analogues to male gypsy moths and the effect of trap placement." Environmental Entomology 1977; 6(6): 765-767.

Cerboneschi, A., et al. "Influence of microclimatic variations on EAG responses of Lymantria dispar (Lepidoptera, Lymantridae) males to sex pheromone." Italian Journal of Zoology 1998;65(3): 267-272.

Chen, Y., et al. ""Giant" multishell CdSe nanocrystal quantum dots with suppressed blinking." Journal of the American Chemical Society 2008;130(15): 5026-5027.

Da Porto, C., et al., "A study on the composition of distillates obtained from smoked marc." Analytica chimica acta 2006;563(1):396-400.

De Moraes, C.M., et al., "Herbivore-infested plants selectively attract parasitoids." Nature 1998;393(6685): 570-573.

Dickens, J.C. "Green leaf volatiles enhance aggregation pheromone of boll weevil, *Anthonomus grandis*." Entomologia Experimentalis et Applicata 1989;52(3):191-203.

Dickens, J.C., et al. "Enhancement of insect pheromone responses by green leaf volatiles." Naturwissenschaften 1990;77(1): 29-31.

Dickens, J.C., et al., "Green leaf volatiles enhance sex attractant pheromone of the tobacco budworm, *Heliothis virescens* (Lep.: Noctuidae)." Chemoecology 1993;4(3-4): 175-177.

Erbilgin, N., et al., "Modulation of predator attraction to pheromones of two prey species by stereochemistry of plant volatiles." Oecologia 2001;127(3): 444-453.

Goering, H.L. and Jacobsen, R.R., "A Kinetic Study of the ortho-Claisen Rearrangement1." Journal of the American Chemical Society 1958;80(13): 3277-3285.

Gozzo, F.C., et al. "Regioselectivity in aromatic Claisen rearrangements." The Journal of organic chemistry 2003;68 (14): 5493-5499.

Grant, G.G., et al. "Olefin inhibitor of gypsy moth, *Lymantria dispar*, is a synergistic pheromone component of nun moth, *L. monacha*". Naturwissenschaffen, 1996;83(7), 328-330.

Grant, V.H., Liu B. "Iridium (III)-catalyzed tandem Claisen rearrangement—intramolecular hydroaryloxylation of aryl allyl ethers to form dihydrobenzofurans." Tetrahedron letters 2005;46(8):1237-1239.

Gries, G., et al. "Reproductive character displacement in Lymantria monacha from northern Japan?." Journal of chemical ecology 2001;27(6):1163-1176.

Gries, G., et al. "Specificity of nun and gypsy moth sexual communication through multiple-component pheromone blends." Naturwissenschaften 1996;83(8):382-385.

Gries, R., et al., "(7R, 8S)-cis-7, 8-epoxy-2-methyloctadec-17-ene: A novel trace component from the sex pheromone gland of gypsy moth, *Lymantria dispar*." Journal of chemical ecology 2005;31(1): 49-62.

Guillen, M.D.., et al., "Characteristics of smoke flavourings obtained from mixtures of oak (*Quercus* sp.) wood and aromatic plants (*Thymus vulgaris* L. and *Salvia lavandulifolia* Vahl.)." Flavour and fragrance journal 2005;20(6): 676-685.

Guchu, E., et al. "Influence of the species and geographical location on volatile composition of Spanish oak wood (*Quercus petraea* Liebl. and *Quercus robur* L.)." Journal of agricultural and food chemistry 2006;54(8): 3062-3066.

Hallem, E.A., et al. "Olfaction: mosquito receptor for human-sweat odorant." Nature 2004;427(6971): 212-213.

Hansen, K., "Discrimination and production of disparlure enantiomers by the gypsy moth and the nun moth." Physiological entomology 1984;9(1): 9-18.

Harborne J.B. "Recent advances in chemical ecology." Nat. Prod. Rep. 1989;6(1): 85-109.

Hildebrand, J.G.,"Olfactory control of behavior in moths: central processing of odor information and the functional significance of olfactory glomeruli." J Comp Physiol A 1996;178(1): 5-19.

Hines, M.A. and Guyoy-Sionnest, P., "Synthesis and characterization of strongly luminescing ZnS-capped CdSe nanocrystals." J Phys Chem 1996;100(2):468-471.

Honson, N.S., et al. Structure-activity studies with pheromone-bidning proteins of the gysy moth, *Lymantria dispar*. Chem Senses 2003;28(6):479-89.

Honson, N.S., et al., "Chapter Nine: Structure and function of insect odorant and pheromone-binding proteins (OBPs and PBPs) and chemosensory-specific proteins (CSPs)." Recent Advances in Phytochemistry 2005;39, 227-268.

Isman, M.B., "Problems and opportunities for the commercialization of insecticides." Regnault-Roger, B.J.R. Philog'ene and C.Vincent (eds.), Biopesticides of Plant Origin,Lavoisier, Paris, 2005:283-291.

Ito, F., et al., "Boron Trichloride Mediated Regioselective Claisen Rearrangement of Resorcinol Derivatives: Application to Resorcinol Carvonyl Ethers." Synthesis 2007;12:1785-1796.

Ito Y., et al., "Intramolecular cyclization of phenol derivatives with C=C double bond in a side chain." J Organometallic Chem 2007;692:691-697.

Ivanov, S.A., et al. "Type-II core/shell CdS/ZnSe nanocrystals: synthesis, electronic structures, and spectroscopic properties." J Am Chem Soc 2007 129(38):11708-11719.

Jacquin-Joly, E. and Merlin C., "Insect olfactory receptors: contributions of molecular biology to chemical ecology." J Chem Ecol 2004;30(12)2359-2397.

Jha, P.P., and Guyot-Sionnest, P., "Trion decay in colloidal quantum dots." Acs Nano, 2009;3(4):1011-1015.

Khambay, B.P., et al. A new insecticidal pyranocyclohexenedione from Kunzea ericifolia. J Natl Prod 1999;62(10):1423-1424.

Khambay, B.P., et al. "The pyrethins and related compounds. Part XLII:Structure-activity relationship in fluoro-olefin non-ester pyrethoids." Pest Sci 1999;55(7)703-10.

Kim, D.H. and Ahn Y.J., "Contact and fumigant activities of constituents of Foeniculum vulgare fruit against three coleopteran stored-product insects." Pest Manag Sci 2001;57(3):301-306.

Kotkar, H.M., et al., "Antimicrobial and pesticide activity of partially purified flavonoids of Annona squamosa." Pest Manag Sci 2002;58(1):33-37.

Kuno, M., et al., "The band edge luminescence of surface modified CdSe nanocrystallites: Probing the luminescing state." J Chem Phys 1997;106(23):9869-9882.

Kuntz E., et al., "Palladium TPPTS catalyst in water: C-allylation of phenol and guaiacol with allyl alcohol and novel isomerisation of allyl ethers of phenol and guiaiacol." J Mol Catal A: Chem 2006;244(1-2):124-138.

Landolt, P.J. and Phillips, T.W., "Host Plant Influences on Sex Pheromone Behavior of Phytophagous Insects." Annu Rev Entomol 1997;42:371-391.

Leatherdale C.A., et al. On the Absorption Cross Section of CdSe Nanocrystal Quantum Dots. J Phys Chem B 2002;106(31):7619-7622.

Lee, J.C., et al., Facile synthesis of Alkyl Phenyl Ethers using Cesium carbonate. Synth Commun 1995;25 (9):1367-1370.

Li J.J. et al., "Large-scale synthesis of nearly monodisperse CdSe/CdS core/shell nanocrystals using air-stable reagents via successive ion layer adsorption and reaction." J Am Chem Soc 2003;125(41)12567-12575.

* cited by examiner

EAG traces of (+)-disparlure (1000ng)
and mixtures of (+)-disparlure (1000 ng) with 3C{1, 3} in different ratio Peaks:  A, (+)-disparlure (1µg);
B, (+)-disparlure (1µg) / 3C{1, 3} (100 µg);
C, (+)-disparlure (1µg) / 3C{1, 3} (300 µg);
D, (+)-disparlure (1µg) / 3C{1, 3} (500 µg);
E, (+)-disparlure (1µg) / 3C{1, 3} (700 µg);
F, (+)-disparlure (1µg) / 3C{1, 3} (1000 µg);
G, (+)-disparlure (1µg) / 3C{1, 3} (1500 µg);
H, (+)-disparlure (1µg) / 3C{1, 3} (2000 µg).

METHODS AND COMPOSITIONS FOR CONTROL OF GYPSY MOTH, *LYMANTRIA DISPAR*

This application is a Continuation-in-Part of U.S. application Ser. No. 12/755,867, filed Apr. 7, 2010, which is a Continuation-in-Part of U.S. application Ser. No. 12/622,423, filed Nov. 19, 2009, which claims priority benefit of U.S. Provisional Application No. 61/116,245, filed Nov. 19, 2008, each of which is incorporated by reference in its entirety.

FIELD OF INVENTION

The present invention relates to insect control agents. More specifically, the present invention relates to methods and compositions for control of the gypsy moth, *Lymantria dispar*.

BACKGROUND OF THE INVENTION

The behavioral manipulation of insect pests for their management, as an alternative to broad-spectrum insecticides, has been investigated for many years.

In addition to the development of resistance against insecticides by the target organism, broad-spectrum insecticides have also negative impacts on natural enemies of the pest insect, on pollinators and on other non-target organisms. Therefore, there is an increased interest in the behavioral manipulation of insect pests for their management as an alternative to broad-spectrum insecticides. Of particular interest are compounds that do not exhibit substantial toxicity or demonstrate some degree of selectivity towards a pest insect and not towards natural enemies, pollinators or the environment. In practice, manipulation may be achieved through the use of stimuli that either enhance or inhibit a particular behavior and ultimately change its expression. Many natural plant defensive chemicals discourage insect herbivory, for example, by deterring feeding and oviposition or by impairing larval growth, rather than by killing insects.

Eugenol is a volatile member of the phenylpropanoid class of compounds from essential oils of many spices, particularly clove (Dewick 2002). Cloves are useful in the home as moth deterrents and the main odorant from cloves, eugenol, has been reported to be perceived as a long-range stimulus by several lepidopterans (Topazzini et al. 1990). One problem with phenylpropanoids such as eugenol and compounds with a cinnamyl framework is that they can produce toxic metabolites after benzylic/allylic oxidation by certain cytochrome P450 enzymes (Dewick 2002).

Several polyphenolic compounds are also known for their toxic/insecticidal effects (Kim and Ahn 2001; Schneider et al. 2000; Khambay et al. 1999; Harborne 1989). Flavonoids isolated from *Annona squamosa* (Kotkar et al. 2002), *Ricinus communis* (Upasani 2003) and *Calotropis procera* (Salunke et al. 2005), are toxic to the pulse beetle. *Callosobruchus chinensis* and *R. communis* also caused oviposition deterrent and ovicidal affects in addition to toxicity. Larvicidal activity of lignans, leptostachyol acetate and analogues from the roots of *Phryma leptostachya* have been reported against three mosquito species (*Culex pipiens pallens*, *Aedes aegypti*, and *Ocheratatos togoi*) (Park et al. 2005).

Compounds derived from aromatic amino acids, such as phenolics, have been reported to be involved in defense of the plant against herbivores and pathogens, as well as in attracting pollinators. For example, phenol derivatives such as guaiacol (1-hydroxy-2-methoxybenzene), 1,2-dimethoxybenzene, 1-ethoxy-2-methoxybenzene, 1-propoxy-2-methoxybenzene, eugenol and isoeugenol, occur in smoke (Guillen and Manzanos 2005; Murugan et al. 2006) and are reported to have insect-repellent and insecticidal activities (Murugan et al. 2006). Furthermore, smoke phenolics taste and smell pleasantly (to humans) (Guillen and Manzanos 2005) and may have antioxidant activity (Bortolomeazzi, et al. 2006). Eugenol (2-methoxy-4-(2-propenyl) phenol), is found in herbs (such as basil, *Ocimum suave* (Wild.)) and has been reported to have activity against grain beetles as a toxicant and deterrent (Obeng-Ofor and Reichmuth 1997). Other benzene derivatives, such as benzyl alcohol, benzonitrile, phenylethanol, 4-methyl phenol, 4-ethylphenol, 2-methylphenol and benzaldehyde are reported components of human odor that malaria mosquitoes respond to (Hallem et al. 2004; Meijerink et al. 2000).

The gypsy moth, *Lymantria dispar*, is native to Europe and Asia, where it is a forest pest. It was introduced to Eastern North America in 1868, and it has spread significantly from the original point of introduction (Massachusetts) (Montgomery and Wallner 1988). The moth larvae defoliate mainly deciduous trees, including oak, aspen, ash, willow, apple, alder, birch and poplar. If population density is high, the moth larvae may also attack cottonwood, hemlock, cypress, pine and spruce. This defoliation will weaken healthy trees, but can kill an already weakened tree. During outbreaks, large areas of forest can be defoliated (Montgomery and Wallner 1988). For example, 6 million ha of mixed oak forest were defoliated in 1981 in Pennsylvania during an outbreak. The damage was estimated at $72 million in lost timber and the cost of the spraying program was estimated at $9 million (Montgomery and Wallner 1988).

The gypsy moth begins its life cycle as egg masses, deposited by the flightless female moths on the branches and trunks of host trees. The eggs can be moved around accidentally through the wind and contact with infested trees. This has caused shipment of the moth to other parts of the world (for example, in the early 1990's gypsy moths were accidentally transferred from Asia to British Columbia on ships). The eggs overwinter and hatch in the spring, concurrent with the first buds on the host trees. Larvae then feed on the leaves, causing defoliation. The larvae are very mobile: they spin silken threads that enable them to be carried by the wind or to glide from one branch to another. During mid summer, the larvae reach the pupal stage and 1-2 weeks later the adult moths emerge (Montgomery and Wallner 1988). When females are ready to mate, they emit a sex attractant pheromone. The males follow the plumes of this pheromone upwind, until they reach the female and mate. The females then lay their egg masses in the late summer and the cycle begins anew (Montgomery and Wallner 1988).

The structure of this sex attractant pheromone was determined to be cis (7,8)-epoxy-2-methyloctadecane (disparlure), by isolation of the compound from ~$10^5$ female gypsy moths (Bierl et al. 1970; Bierl et al. 1972). Further research, in which the enantiomers of disparlure were tested against the antennae of male gypsy moths (Grant et al. 1996; Gries et al. 1996; Hansen 1984; Miller et al. 1977) and in field trapping experiments (Miller 1977; Cardé et al. 1977; Plimmer et al. 1977), revealed that (+)-disparlure, cis-(7R,8S)-7,8-epoxy-2-methyloctadecane (+)-1, is the main active component of the sex attractant pheromone of *L. dispar*. The enantiomer, (−)-1 has been identified as a major component of the pheromone of the nunmoth, a closely related species (Grant et al. 1996; Gries et al. 1996). This enantiomer is not attractive by itself to either species, but prevents upwind flight behavior in the gypsy moth, when presented with (+)-1. The nunmoth also uses (+)-1 as a component in its attractant pheromone, and enantiomer (−)-1 neither attracts nor inhibits the nunmoth (Grant et al. 1996; Gries et al. 1996) This discrimination between blends of enantiomeric and other components has been proposed as one mechanism for species differentiation (Grant et al. 1996; Gries et al. 1996; Gries et al. 2001; Gries et al. 2005).

The structures of gypsy moth sex attractant pheromone, (+)-1, and two behavioral antagonists are as follows.

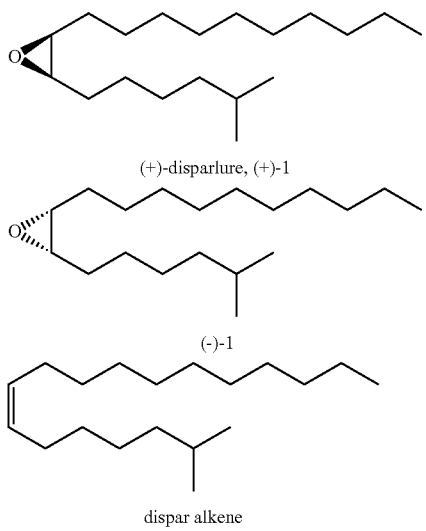

The moths perceive the pheromone through sensory hairs, *sensilla trichodea*, on their feather-like antennae (Schneider 1969). Electrophysiological studies with male gypsy moth antennae have revealed that the gypsy moth has innervated sensory hairs that respond only to (+)-1 or only to (−)-1 (Hansen 1984). This means that the moth detects both enantiomers of 1, distinguishes them and integrates the information in the brain. A practical consequence of this enantiomer discrimination is that the number of moths caught in pheromone-baited traps is highest with (+)-1 of high enantiomeric purity (≥98% ee) (Miller 1977). Thus, the pheromone plays a central role in the reproduction of this moth species, and eavesdropping into this pheromone communication has been used in attempts to control the moth.

Gypsy moths are controlled by natural enemies (birds, small mammals, spiders and wasps) as well as some diseases such as nuclear polyhedrosis virus (NPV). For unknown reasons, outbreaks occur on approximately a 10 year cycle, and this is when the moth does the most damage (Montgomery and Wallner 1988). Gypsy moth is monitored successfully with pheromone-baited traps and with selective pesticide applications. Outbreaks in or near urban areas, however, can be a problem because it is difficult to deploy pesticides in these areas. It is also difficult and harmful to other species to deploy insecticides in dense forests. Urban areas and very dense, inaccessible forests are places where non-toxic alternatives to insecticides might be most useful to maintain infestations at or below acceptable levels.

Pheromone-based control methods that have been tested for the gypsy moth fall into three classes: 1) saturation of the air with pheromone to mask the females and cause mating disruption, 2) trapping large numbers of males into strategically placed traps, 3) trapping samples of males in monitoring traps and spraying the appropriate area with an insecticide. (Plimmer et al. 1982; Campion 1984). Of these three methods, the third is widely used to pre-empt outbreaks (Campion (1984). The second approach (mass trapping) has had only limited success because the areas in which mass trapping is necessary, to have a significant impact, are very large. The first approach (mating disruption) carries the risk that large numbers of moths will be attracted to the treated area by the applied pheromone from nearby non-treated zones (Campion (1984). For gypsy moth, mating disruption is complicated by the hydrophobicity of the pheromone, which makes formulation and biodegradation difficult (Campion (1984) and by the high cost of (+)-1.

In nature, host plant odors have been known to synergize with pheromone responses (Bengtsson et al. 2006; Dickens 1989; Dickens et al. 1990; Dickens et al. 1993; Erbilgin and Raffa 2001) and non-host plant odors sometimes antagonize pheromone responses (Landolt and Phillips 1997). Natural (Grant et al. 1996) or synthetic pheromone mimics can also antagonize the response of an insect to its pheromone (Bau et al. (1999); Renou et al. 2002).

SUMMARY OF THE INVENTION

The present invention provides in part methods and compositions for controlling infestation by *Lymantria dispar*.

In one aspect, the invention provides a method for controlling infestation by a *Lymantria dispar* by applying an effective amount of a compound of Formula I:

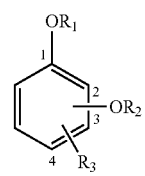

Formula I where R1 may be methyl, ethyl, propyl, n-butyl, isopentyl (3-methylbutyl) or allyl; R2 may be at positions 2, 3 or 4 and may be H, methyl, ethyl, propyl, n-butyl, isopentyl (3-methylbutyl) or allyl; and R3 may be optionally present at positions 2, 3 and 4, and is allyl; with the provisos that when R2 is at position 2, R3 if present is at position 3, or when R2 is at position 3, R3 if present is at positions 2 or 4, or when R2 is at position 4, R3 if present is at position 2; or of Formula II:

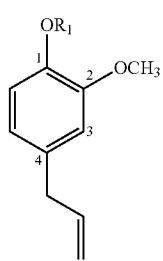

Formula II where R1 may be methyl, ethyl, propyl, n-butyl, isopentyl (3-methylbutyl) or allyl; or mixtures thereof; to a site of interest whereby the infestation is controlled.

In an alternative aspect, the invention provides a method of protecting a plant from infestation by a *Lymantria dispar* comprising applying an effective amount of a compound of Formula I or II, to a site of interest whereby the plant is protected.

In alternative embodiments, the controlling may be feeding deterrence, feeding stimulation, attraction, or olfactory inhibition.

The compound of Formula I may be a feeding deterrent, such as one or more of methyl eugenol, 3a{6,6}, 3c{2,2} 3c{2,3}, 3c{3,6} and 3b{3,6}.

The compound of Formula I may be a feeding stimulant, such as one or more of 3c{1,1} and 5b{1,1}.

The compound of Formula I may be an attractant, such as one or more of methyl eugenol, 3c{2,3}, or 3c{1,3}.

The compound of Formula I may be an olfactory inhibitor, such as one or more of 3c{3,1-5}, 3c{2,3}, 3c{4,1-5}, 3c{5,1-5}, 3a{4,4}, 3b{3,6}, 3b{3,3}, 3b{2,2}, 3c{1,3}, 3c{3,6}, 3a{3,3}, 3b{6,6}, 5b{1,1}, 5b{2,1}, 3c{3,3}, 3c{6,1-5}, 5b{1,2-3}3b{1,1-5}, 3b{4,6}, 2c{4}, 3a{1,1-5}, 4a{1-5}, 5a{2,1-5}, 3b{2,6}, 2c{6}, 3c{3,4}, 5b{3,1}, 5a{3,1-5}, or ethyl eugenol.

In alternative embodiments, the compound of Formula I or II may be non-toxic.

In alternative embodiments, two or more compounds of Formula I or II may be combined and/or may be applied simultaneously or sequentially. In alternative embodiments, the compound of Formula I or II may be applied in combination with another compound or treatment, such as an oviposition deterrent, an oviposition stimulant, a feeding deterrant, a feeding stimulant, an attractant, or a toxicant.

In alternative embodiments, the *L. dispar* may be a larva or an adult, such as a male adult.

In alternative embodiments, the site of interest may be a plant or part thereof such as a tree within the host range of *L. dispar*.

In alternative embodiments, the compound of Formula I or II may be provided in a formulation selected from one or more of the group consisting of a spray, aerosol, solid, or liquid. The liquid may be an aqueous solution, oil-in-water emulsion or dispersion.

In alternative embodiments, the compound of Formula I or II may be provided in a controlled release form.

In an alternative aspect, the invention provides a composition comprising one or more compounds of Formula I or II selected from one or more of a feeding deterrent, a feeding stimulant, an olfactory inhibitor or an attractant.

The feeding deterrent composition may include one or more of a compound selected from methyl eugenol, 3a{6,6}, 3c{2,3}, 3c{3,6}, 3c{2,2}, or 3b{3,6} and a carrier.

The feeding stimulant composition may include one or more of a compound selected from 3c{1,1} or 5b{1,1} and a carrier.

The olfactory inhibitor composition may include one or more of a compound selected from 3c{3,1-5}, 3c{2,3}, 3c{4,1-5}, 3c{5,1-5}, 3a{4,4}, 3b{3,6}, 3b{3,3}, 3b{2,2}, 3c{1,3}, 3c{3,6}, 3a{3,3}, 3b{6,6}, 5b{1,1}, 5b{2,1}, 3c{3,3}, 3c{6,1-5}, 5b{1,2-3}3b{1,1-5}, 3b{4,6}, 2c{4}, 3a{1,1-5}, 4a{1-5}, 5a{2,1-5}, 3b{2,6}, 2c{6}, 3c{3,4}, 5b{3,1}, 5a{3,1-5}, or ethyl eugenol and a carrier.

The attractant composition may include one or more of a compound selected from methyl eugenol, 3c{2,3}, or 3c{1,3} and a carrier.

In alternative embodiments, these compounds may be combined with the sex pheromone of the gypsy moth, (+)-disparlure.

This summary of the invention does not necessarily describe all features of the invention.

BRIEF DESCRIPTION OF THE DRAWINGS

These and other features of the invention will become more apparent from the following description in which reference is made to the appended drawings wherein:

FIG. 5 shows graphs for the EAG assay for the compounds tested in Example 5. The puffs are numbered i-vi and were: i=air, ii=pure pheromone (+)-disparlure, (+)-1, (100 ng), iii-v=disparlure mixed with the test compound, the latter at three different doses, vi=pure (+)-1. Depolarizations from the resting potential are labeled d; hyperpolarizations seen during the recovery phase after a puff are labeled r. Subscripts refer to the puff number.

FIG. 6 shows graphs of SAR for long-term inhibition, LTI, of EAG responses towards (+)-1. In FIG. 5, the depolarization for puff vi (second pure (+)-1 puff) is much smaller than for puff ii (first pure (+)-1 puff). The percentage difference between these two puffs is the LTI. Positive values denote inhibition, negative ones enhancement. FIG. 6D. Individual ortho dialkoxybenzenes (3c{3,n},1-propoxy-4- alkoxybenzenes). The dashed line indicates the LTI value obtained for DEET (±S. E., shown with the solid lines).

FIG. 8 shows the Structure-Activity Relationship (SAR) for short-term inhibition (STI) activity, for puff v (mixture of (+)-1 100 ng with the compound or set 100 μg). These values reflect the decrease (inhibition, positive values) or increase (enhancement, negative values) relative to the first pure disparlure puff in Example 5.

FIG. 9 shows graphs with the responses of the antennae to alternating stimuli of pure (+)-1 or inhibitors. No mixtures of (+)-1 and inhibitor were used.

FIG. 13 shows an examples of a compound (FIG. 13A) or set (FIG. 13B) that cause broadening (delayed activation) of the mixed pheromone+modulator stimulus with 100 μg of the compound and 100 ng of pheromone.

DETAILED DESCRIPTION

Figure 1:
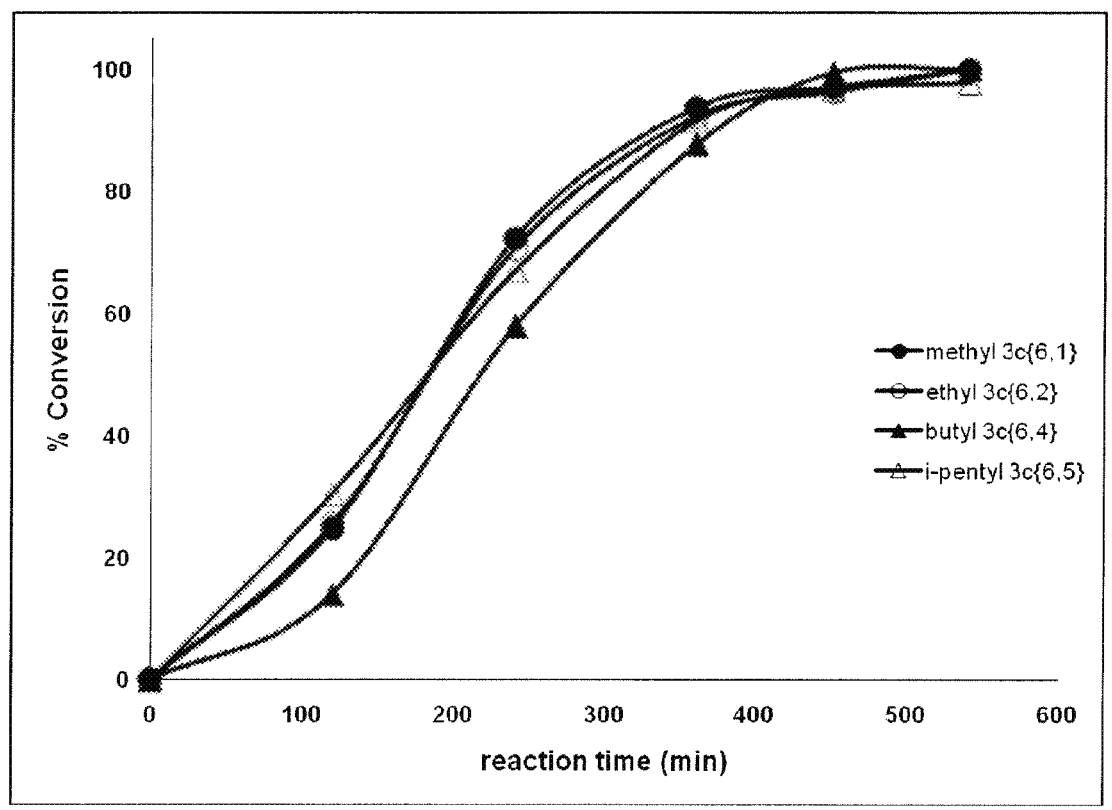
FIG. 1 shows graphs with the progress of the Claisen rearrangement reaction of the 3c{6,1-5} library.

The present invention provides in part methods and compositions for controlling infestation by the gypsy moth, *Lymantria dispar*.

*L. dispar*, is native to Europe and Asia, where it is a forest pest. It was introduced to Eastern North America in 1868, and it has spread significantly from the original point of introduction (Massachusetts) (Montgomery and Wallner 1988). The moth begins its life cycle as egg masses, deposited by the flightless female moths on the branches and trunks of host trees. The eggs overwinter and hatch in the spring, concurrent with the first buds on the host trees. Larvae then feed on the leaves, causing defoliation. The larvae are very mobile: they spin silken threads that enable them to be carried by the wind or to glide from one branch to another. A "larva" or "larvae" as used herein refers to any caterpillar stage of *L. dispar*. During mid summer, the larvae reach the pupal stage and 1-2 weeks later the adult moths emerge ((Montgomery and Wallner 1988). When females are ready to mate, they emit a sex attractant pheromone, disparlure. The males follow the plumes of this pheromone upwind, until they reach the female and mate.

The gypsy moth larvae can feed on many species of shrubs and trees, including hardwoods and conifers. Plants at risk for infestation by gypsy moths, i.e., a "host plant" or a "plant within the host range of *L. dispar*" include without limitation deciduous trees, including oak, aspen, ash, willow, hawthorn, apple, alder, birch or poplar. The moth larvae can also attack cottonwood, hemlock, cypress, pine or spruce. The moth larvae can also attack ash, sycamore, butternut, black walnut, balsam fir, cedar, rhododendron, etc. In some embodiments, the plants are plants of economic interest.

The invention provides, in part, compounds for use in controlling infestation by L. dispar.

By "infestation" is meant the undesirable colonization of a site or the consumption of a plant (e.g., a tree or shrub) by L. dispar. In some embodiments, infestation refers to an undesirable number of L. dispar, sufficient to cause damage, for example, economic damage to a plant. By "control of infestation" or "controlling infestation" is meant reduction or inhibition of infestation of a plant by L. dispar by at least about 25% to at least about 100%, or any value therebetween for example about 25%, 30%, 35%, 40%, 45%, 50%, 55%, 60%, 65%, 70%, 75%, 80%, 85%, 90%, 95%, 99%, or 100% when compared to a control plant. In alternative embodiments, by "control of infestation" or "controlling infestation" is meant reduction or inhibition of infestation of a plant by L. dispar by at least about 1-fold or more, for example, about 1.5-fold to about 100-fold, or any value therebetween for example about 2.0, 2.5, 3.0, 3.5, 4.0, 4.5, 5.0, 5.5, 6.0, 6.5, 7.0, 7.5, 8.0, 8.5, 9.0, 9.5, 10, 15, 20, 25, 30, 35, 40, 45, 50, 55, 60, 65, 70, 75, 80, 85, 90, 95-fold when compared to a control plant. Infestation may be determined using standard techniques as known in the art or described herein. For example, infestation may be measured by comparing physical features and characteristics such as leaf damage, plant or tree growth, or number of gypsy moths present. In an alternative embodiment, controlling infestation includes protecting a plant from infestation. By "protecting a plant from infestation" is meant reducing the probability that a L. dispar infestation will be established in a plant or tree. In alternative embodiments, "control of infestation" includes feeding deterrence, feeding stimulation, attraction, olfactory inhibition, or toxicity.

By "feeding deterrence" is meant a decrease in feeding by L. dispar larvae by at least about 35% to at least about 100%, or any value therebetween for example about 40%, 45%, 50%, 55%, 60%, 65%, 70%, 75%, 80%, 85%, 90%, 95%, 99%, or 100% when compared to a control. Feeding may be determined using standard techniques as known in the art or described herein.

By "feeding stimulation" is meant an increase in feeding by L. dispar larvae by at least about 10% to at least about 100%, or any value therebetween for example about 10% to at least about 100%, or any value therebetween for example about 10%, 15%, 20%, 25%, 30%, 35%, 40%, 45%, 50%, 55%, 60%, 65%, 70%, 75%, 80%, 85%, 90%, 95%, 99%, or 100% when compared to a control. Feeding may be determined using standard techniques as known in the art or described herein.

By "attraction" is meant an increase in the number of L. dispar in a site of interest by at least about 10% to at least about 100%, or any value therebetween for example about 10% to at least about 100%, or any value therebetween for example about 10%, 15%, 20%, 25%, 30%, 35%, 40%, 45%, 50%, 55%, 60%, 65%, 70%, 75%, 80%, 85%, 90%, 95%, 99%, or 100% when compared to a control. Attraction may be measured by for example antennal responses to a reference odorant or attraction to a lure as described herein or known in the art, or by standard techniques as known in the art.

By "olfactory inhibition" is meant a decrease in L. dispar antennal responses, for example temporal or by intensity, to a reference odorant as described herein or known in the art by at least about 20% to at least about 100%, or any value therebetween for example about 25%, 30%, 35%, 40%, 45%, 50%, 55%, 60%, 65%, 70%, 75%, 80%, 85%, 90%, 95%, 99%, or 100% when compared to a control. Olfactory inhibition may be determined using standard techniques as known in the art or described herein.

In alternative embodiments, the invention provides compounds for use in feeding deterrence, feeding stimulation, attraction or olfactory inhibition as described herein.

We have prepared small libraries of alkoxy benzenes (with 4-5 compounds) according to Formula I, whose members separate easily by GC and can therefore be monitored during assays. Sets of known composition and total purity with respect to the compounds of interest have been prepared by three reactions: 1) alkylation of 1-hydroxy-2,3, or 4-alkoxybenzenes, 2) thermal ortho-Claisen rearrangement of 1-allyloxy, 2, 3 or 4-alkoxybenzenes and 3) a second alkylation of the rearrangement products. Reactions of all three types worked well for ortho, meta and para compounds, while minimal (in the case of ortho) or no para-allyl migration occurred. The Claisen rearrangement of the para compounds was followed by a cyclization to dihydrobenzofurans upon prolonged heating.

Accordingly, compounds for use in control of L. dispar infestation include compounds according to Formula I, and mixtures thereof:

Formula I

Accordingly to Formula I, R1 may be methyl, ethyl, propyl, n-butyl, isopentyl (3-methylbutyl) or allyl; R2 may be at positions 2, 3 or 4 and may be H, methyl, ethyl, propyl, n-butyl, isopentyl (3-methylbutyl) or allyl; and R3 may be optionally present at positions 2, 3 and 4, and is allyl; with the provisos that when R2 is at position 2, R3 if present is at position 3, or when R2 is at position 3, R3 if present is at positions 2 or 4, or when R2 is at position 4, R3 if present is at position 2.

In alternative embodiments, compounds for use in control of L. dispar infestation also include compounds according to Formula II, and mixtures thereof:

Formula II

Accordingly to Formula II, R1 may be methyl, ethyl, propyl, n-butyl, isopentyl (3-methylbutyl) or allyl.

The compounds were screened in L. dispar, using three methods: 1) electroantennogram detection of GC traces (GC-EAD), 2) in vitro screen for pheromone-binding protein (PBP) binding activity and 3) competitive electroantennograms (EAG), in which libraries and individual compounds were assayed for inhibition of the antennal responses to the sex pheromone cis-(7R,8S)-7,8-epoxy-2-methyloctadecane of L. dispar (also known as (+)-disparlure).

The para-substituted compounds assayed here did not elicit substantial antennal responses when tested alone. However, when puffed simultaneously with the sex attractant pheromone of the gypsy moth, compounds with two medium-sized alkoxy groups (one ethyl-, propyl- or butyl- and one isopentyl group) elicited significant inhibition of the antennal response to the pheromone. The para compounds tested here did not bind strongly to either of the two pheromone-binding proteins (PBPs) of the gypsy moth. Para-dialkoxybenzenes with small substituents (methyl, ethyl) bound slightly more strongly to PBPs than compounds with larger substituents.

The activities detected in the EAG assays were short-term and long-term inhibition or enhancement of the antennal response to pheromone (+)-1. Short-term inhibition or enhancement was seen with mixed (+)-1/compound stimuli and long-term inhibition of pure (+)-1 stimuli was seen after administration of mixed (+)-1/compound stimuli.

In some embodiments, the compounds according to Formula I or II are not substantially perceived by themselves. In alternative embodiments, the compounds either enhance or interfere with the perception of naturally emitted pheromone plumes.

In some embodiments, compounds according to Formula I or II, such as methyl eugenol, 3a{6,6}, 3c{2,3}, 3c{3,6}, 3c{2,2}, or 3b{3,6} may be feeding deterrents.

In some embodiments, compounds according to Formula I, such as 3c{1,1} or 5b{1,1} may be feeding stimulants.

In some embodiments, compounds according to Formula I or II, such as 3c{3,1-5}, 3c{2,3}, 3c{4,1-5}, 3c{5,1-5}, 3a{4,4}, 3b{3,6}, 3b{3,3}, 3b{2,2}, 3c{1,3}, 3c{3,6}, 3a{3,3}, 3b{6,6}, 5b{1,1}, 5b{2,1}, 3c{3,3}, 3c{6,1-5}, 5b{1,2-3} 3b{1,1-5}, 3b{4,6}, 2c{4}, 3a{1,1-5}, 4a{1-5}, 5a{2,1-5}, 3b{2,6}, 2c{6}, 3c{3,4}, 5b{3,1}, 5a{3,1-5}, ethyl eugenol are olfactory inhibitors. In alternative embodiments, compounds according to Formula I, such as 3c{2,3}, 3c{1,3}, 3b{3,6}, 3a{2,1-5}, or 5b{1,1} may be olfactory inhibitors.

In some embodiments, the compounds according to Formula I or II, such as methyl eugenol, 3c{2,3}, 3c{1,3}, may be attractants. In alternative embodiments, these compounds may be combined with the sex pheromone of the gypsy moth, (+)-disparlure. In alternative embodiments, these compounds may be combined with the sex pheromone of the gypsy moth, (+)-disparlure at ratios from about 1:300 (0.3%) to 1:2000 (0.5Π=500 ppm) or or from about 1:300 (0.3%) to 1:10,000 (0.5Π=500 ppm) or greater, e.g., at ratios of about 1:300, 1:350, 1:400, 1:450, 1:500, 1:550, 1:600, 1:650, 1:700, 1:750, 1:800, 1:850, 1:900, 1:950, 1:1000, 1:1050, 1:1100, 1:1150, 1:1200, 1:1250, 1:1300, 1:1350, 1:1400, 1:1450, 1:1500, 1:1550, 1:1600, 1:1650, 1:1700, 1:1750, 1:1800, 1:1850, 1:1900, 1:1950, 1:2000, 1:2500, 1:3000, 1:3500, 1:4000, 1:4500, 1:5000.

In alternative embodiments, a compound according to Formula I or II is non-toxic. By "non-toxic" is meant a mortality rate of adult or larval L. dispar of less than about 25%, 30%, 35%, 40%, 45%, 50%, 55%, 60%, 65%, 70%, 75%, 80%, 85%, 90%, 95%, 99%, or 100% when compared to a control. Toxicity may be determined using standard techniques as known in the art or described herein.

In alternative embodiments, a compound according to Formula I or II is selective. By "selective" is meant that a compound exhibits an activity such as one or more of feeding deterrence, feeding stimulation, attraction, olfactory inhibition, or toxicity towards L. dispar but not other pests, such as other noctuid moths or insects. In some embodiments, by "selective" is meant that a compound exhibits an activity such as one or more of feeding deterrence, feeding stimulation, attraction, olfactory inhibition, or toxicity towards larval L. dispar but not adults, and vice versa.

In alternative embodiments, a compound according to the invention, as used herein, may include one or more than one compound as described in in Formula I or II, or in the Tables and Figures herein. Accordingly, in some embodiments, sets or mixtures of the compounds as described in in Formula I or II, or in the Tables and Figures herein are included in the meaning of the term "compound". In alternative embodiments, one or more than one compound as described in in Formula I, or in the Tables and Figures herein, may be specifically excluded from the methods or compositions according to the invention.

A compound according to the invention may be applied to a site of interest to control infestation by L. dispar. By "site of interest" is meant any area or region that is infested with, or at risk of infestation by, L. dispar or is in the vicinity of such an area or region. Sites of interest include without limitation a plant, an area that contains a plant, an area that is intended to contain a plant, an area that is in the vicinity of a plant, etc. Accordingly, a site of interest may be a host plant (e.g., a tree or shrub), forest, logging site, arboretum, garden, park, bait, lure, trap, film, etc. In alternative embodiments, a site of interest may be an area or region containing alternative host plants, so that the L. dispar may be lured to the alternative host plants. In alternative embodiments, a site of interest may specifically exclude a greenhouse. In alternative embodiments, a site of interest may specifically exclude a site that contains substantial quantities of grass, such as greater than 10%, 20%, 30%, 40%, 50%, 60%, 70%, 80%, or 90% grass. In alternative embodiments, a site of interest may specifically exclude a site that contains grass. In alternative embodiments, a site of interest that is a forest site may be a site that does not contain substantial quantities of grass, such as greater than 10%, 20%, 30%, 40%, 50%, 60%, 70%, 80%, or 90% grass.

By "applied" or "applying" is meant contacting a L. dispar with an effective amount of a compound. In alternative embodiments, by "applied" or "applying" is meant placing an effective amount of a compound on, in, or in the vicinity of a site of interest, as appropriate. The application method may take any form such as spraying, fogging, dusting, sprinkling, aerosolizing, e.g., of a forest or logging site, or targetted applications such as direct application to a host plant or part thereof, placement in a bait or trap, etc.

By "effective amount" is meant an amount or concentration of a compound that is sufficient to modulate the number of L. dispar in a site of interest by at least about 25% to at least about 100%, or any value therebetween for example about 25%, 30%, 35%, 40%, 45%, 50%, 55%, 60%, 65%, 70%, 75%, 80%, 85%, 90%, 95%, 99%, or 100% when compared to a similar site in the absence of the compound. In alternative embodiments, by "effective amount" is meant an amount or concentration of a compound that is sufficient to modulate the number of L. dispar in a site of interest by at least about 1-fold or more, for example, about 1.5-fold to about 100-fold, or any value therebetween for example about 2.0, 2.5, 3.0, 3.5, 4.0, 4.5, 5.0, 5.5, 6.0, 6.5, 7.0, 7.5, 8.0, 8.5, 9.0, 9.5, 10, 15, 20, 25, 30, 35, 40, 45, 50, 55, 60, 65, 70, 75, 80, 85, 90, 95-fold when compared to a similar site in the absence of the compound. By "modulate," "modulation" or "modulating" is meant changing, by either increase or decrease. Accordingly, for a compound having for example olfactory inhibition, feeding deterrent, or toxicant activity, the appropriate modulation would be to decrease the number of L. dispar in a site of interest (such as a forest or logging site or also, for a toxicant, bait or trap). Conversely, for a compound having for example attraction or feeding stimulation activity, the appropriate modulation would be to increase the number of *L. dispar* in a site of interest (such as a bait or trap). It is to be understood that the effective amount of a compound will vary, depending on such factors as contemplated use, life stage of *L. dispar*, population density, site of interest, release rate, time of year, host crop, ambient moisture, temperature, etc.

In alternative embodiments, two or more compounds according to the invention may be applied to control infestation by *L. dispar*.

In alternative embodiments, a compound according to the invention may be applied in combination with one or more other compounds, treatments, or systems to control infestation by *L. dispar*. For example, feeding stimulants such as fructose, fucose, glucose, or sucrose; feed such as molasses; toxicants such as insecticides, fungicides, nematocides, bactericides, acaricides; attractants such as pheromones; growth regulators such as rooting stimulants; repellents, etc. may be combined with a compound according to the invention.

The application may be simultaneous or sequential. For example, an attractant or feeding stimulant as described herein may be combined with a toxicant, such as an insecticide, in a "lure and kill" or "attract and kill" treatment. In other embodiments, a toxicant as described herein may be combined with a with a feeding stimulant, feed, or attractant such as (+)-disparlure. Alternatively, a feeding deterrent may be applied to target larvae and an olfactory inhibitor may be applied to target male adults at different times. The application may be varied to, for example, minimize the build up of resistance to a particular treatment or compound.

The compounds or compositions according to the invention may be substantially pure compounds or mixtures thereof or may be formulated with a suitable additive as appropriate depending on the contemplated end use. For example, a compound or composition may be formulated with suitable additives such as carriers, diluents, emulsifiers, antioxidants, thickeners, fillers, preservatives, surfactants, etc., including without limitation crop spray oils, or any other suitable additive. It is to be understood that any suitable formulation may be used, depending on the contemplated end use. For example, the formulations may be generally non-toxic, except for those containing a toxicant or insecticide where high mortality is a desired outcome.

In some embodiments, the compounds or compositions may be formulated in controlled release forms. The formulations may be solid, such as granules, dusts, or pellets, such as granules for direct use (i.e., without admixture with a liquid), water-dispersible granules; etc.; powders e.g., wettable powders, dry (soluble) powders; etc. or may be liquid, such as an aqueous solution, flowable formulation, an emulsion e.g., oil-in-water emulsion, a suspension, a dispersion, etc. In some embodiments, the compounds may be formulated with a co-solvent, such as isopropanol. The compounds may be formulated for direct use (e.g., a "ready-to-use" formulation) or as a concentrate.

In some embodiments, the compounds or compositions may be provided in any appropriate trap, dispensor or device known in the art.

The compounds or compositions may be used to control infestion by *L. dispar*. In alternative embodiments, selected compounds or compositions may be used to deter or stimulate larval feeding or to deter or stimulate adult male olfactory or odorant response. Accordingly, in alternative embodiments, the compounds or compositions may be used to influence host plant selection by *L. dispar*.

Kits

The invention provides kits for use in control of *L. dispar* infestation. In one embodiment, the kit includes a composition containing an effective amount of a compound according to the invention for application to a site of interest. In alternative embodiments, the kit may include a container containing another compound or treatment such as a toxicant such as an insecticide, attractant, etc; the container may be any suitable container depending on the contemplated end use. The compound according to the invention may be provided together with instructions for administration to a site of interest. The instructions may include directions for use and may be provided as part of the kit or separately.

EXAMPLES

The following examples are intended to illustrate embodiments of the invention and should not be construed as limiting.

Example 1

Synthesis of Dialkoxybenzene Test Compounds

Synthesis Scheme.

Dialkoxybenzene minilibraries (consisting of four to five compounds) and pure compounds were synthesized. Briefly, dialkoxybenzenes were synthesized from the corresponding dihydroxybenzenes (1 (a-c)) by monoalkylation (Scheme 1). The pure monoalkylated compounds were mixed in equimolar amounts, for the synthesis of minilibraries, and subjected to a second round of alkylation. Thus, the minilibraries include compounds with one alkyl group constant and the other one variable.

Scheme 1. General approach for the synthesis of mini-libraries

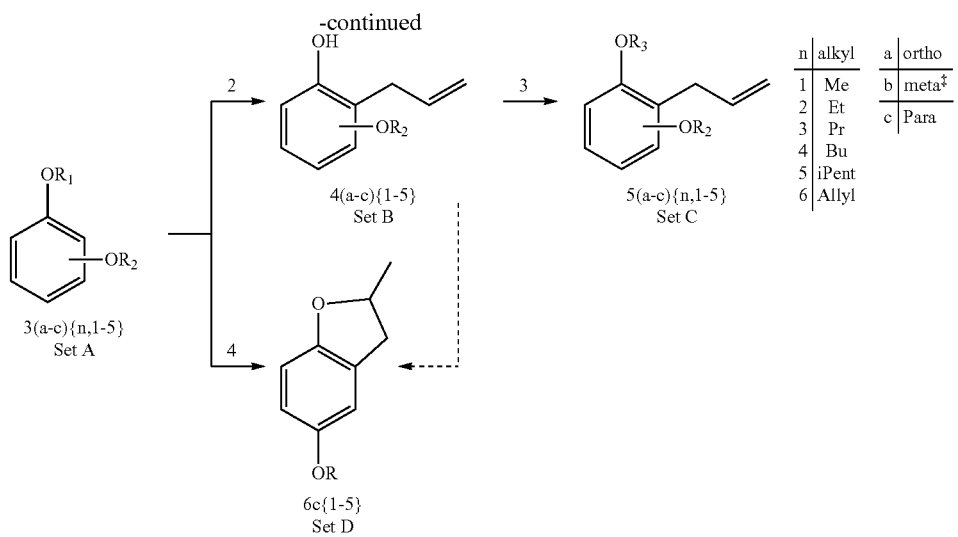

Reaction conditions: 1) base (NaH, K$_2$CO$_3$ or Cs$_2$CO$_3$), solvent (DMF or acetone), alkyl halide (MeI, EtI, PrI, BuBr, iPentBr or AllylBr), room temperature or reflux; 2) for 3(a-c){6,1-5} neat, 180° C., 10 h (Scheme 2); (3) K$_2$CO$_3$, alkyl halide, acetone, reflux; 4) for 3c{6,1-5} neat, 180° C., 30 h (Scheme 2). ‡The meta product from the Claisen Rearrangement (Set B) results in two products and will be identified as: 4b$^x${n} for 5-alkoxy-2-allyl phenol and 4b$^y${n} for 3-alkoxy-2-allyl phenol (see Scheme 2) (similarly for their alkylated derivatives).

An alternate depiction of Scheme 1 is described in more detail below (Scheme 1-1):

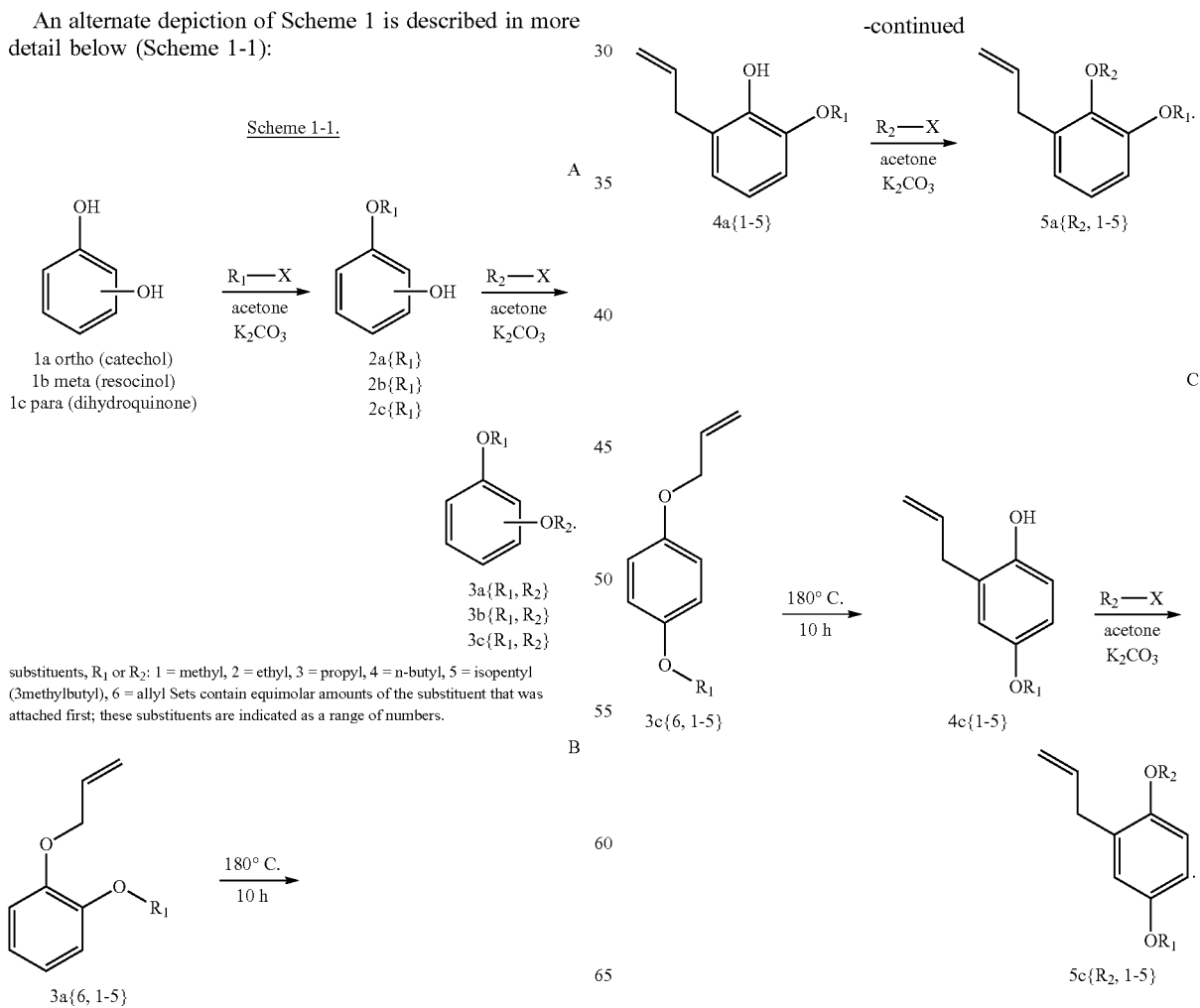

substituents, R$_1$ or R$_2$: 1 = methyl, 2 = ethyl, 3 = propyl, 4 = n-butyl, 5 = isopentyl (3methylbutyl), 6 = allyl Sets contain equimolar amounts of the substituent that was attached first; these substituents are indicated as a range of numbers.

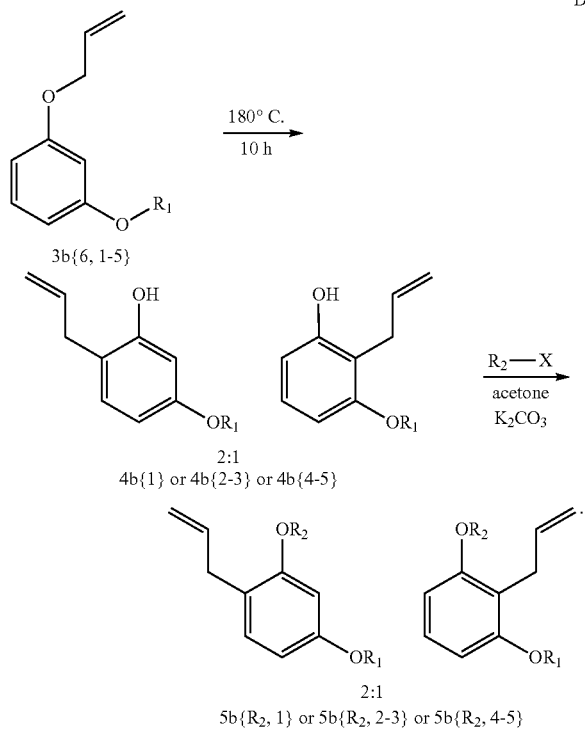

A. Synthesis of dialkoxybenzenes from catechol (1a), resorcinol (1b) or dihydroquinone (1c). Details of the synthesis and analyses are described below. B. Synthesis of Claisen rearranged products from 1-allyl-2-alkoxybenzenes. C. Snythesis of Claisen rearranged products from 1-allyl-4-alkoxybenzene. D. Synthesis of Claisen rearranged products from 1-allyl-3-alkoxybenzene.

All solvents used were of analytical grade. Resorcinol monoacetate was from Aldrich. Compounds 2c{1}, 2c{2} and 2c{3} were synthesized and also purchased from Aldrich. Commercial grade solvents were distilled under nitrogen prior to use with the exceptions as follow: dried THF was obtained from a MBRAUN LTS 350 solvent purification system and HPLC grade acetone was used without further treatment. Reagents were used without further purification. The $^1$H and $^{13}$C NMR spectra were recorded in CDCl$_3$ on Bruker 400 or 600 MHz spectrometers or a Varian 500 MHz spectrometer.

Gas chromatography (GC) was done on Hewlett Packard 5890 using a SPB-5 column Supelco, 30 m, 0.25 mm i d, (0.25 nm film), programmed at 100° C. (5 min), 10° C./min, and 200° C. (0 min), 50° C./min, 250° C. (4-14 min). The gas chromatographic data are reported as retention indices (RI). MS: GCmass spectra were recorded on a Varian Saturn 2000 MS coupled to a CP 300 GC, equipped with a SPB-5 GC column (same type as above), programmed as above. Mass spectra were acquired in EI mode [2 μscans (0.55 s/scan), emission current (30 μamp), scanning single ion storage SIS (49-375 m/z)]. HRMS was recorded on a 6210 Series Time-of-Flight LC/MS System.

The identity of the members in each library was confirmed by $^1$H NMR and GC-MS techniques.

Optimization of the mono alkylation of dihydroxybenzenes 1(a-c) revealed that direct alkylation resulted in high yields. Ortho (a), meta (b) or para (c) substituted dihydroxy benzene 1(a-c) was deprotonated and reacted with an alkyl halide to afford mono 2(a-c){n} and dialkoxy 3(a-c) {n, n} products (Scheme 1 or 1-1). Tuning of the experimental conditions (base, solvent and reaction time, see Methods A-E) allowed the preferential synthesis of either monoalkylated or dialkylated products. Mono- and dialkylated products were separated using their acid/base properties. The monoalkoxy compounds 2(a-c){n} were used for the synthesis of libraries, and the dialkoxy compounds 3(a-c) {n, n} with identical alkyl groups were used for characterization and biological testing (Table 1).

TABLE 1

Purity of Dialkoxy Compounds 3(a-c){n, n} Synthesized for Characterization and Biological Evaluation

| no. | Compound | Purity [a] |
|---|---|---|
| 1 | 3a{1, 1} | 94 |
| 2 | 3a{2, 2} | 100 |
| 3 | 3a{3, 3} | 100 |
| 4 | 3a{4, 4} | 100 |
| 5 | 3a{5, 5} | 100 |
| 6 | 3a{6, 6} | 99 |
| 7 | 3b{1, 1} | 94 |
| 8 | 3b{2, 2} | 98 |
| 9 | 3b{3, 3} | 98 |
| 10 | 3b{4, 4} | 100 |
| 11 | 3b{5, 5} | 100 |
| 12 | 3b{6, 6] | 95 |
| 13 | 3c{1, 1} | 95 |
| 14 | 3c{2, 2} | 95 |
| 15 | 3c{3, 3} | 96 |
| 16 | 3c{4, 4} | 99 |
| 17 | 3c{5, 5} | 98 |
| 18 | 3c{6, 6} | 99 |

[a] Purity was determined by GC.

Synthesis of Alkoxy Phenols and Dialkoxy Benzenes

Method A:

Anhydrous K$_2$CO$_3$ (5 eq) was added to a solution of acetoxy-alkoxy benzene (1 eq) in CH$_3$OH (25 mL) and the mixture was stirred at room temperature and monitored by TLC (hexanes-EtOAc, 8:2). When reaction was complete, it was concentrated under reduced pressure. The residue was then diluted with CHCl$_3$ (25 mL) and water (25 mL), the organic layer was dried over anhydrous Na$_2$SO$_4$ and concentrated under reduced pressure. In certain cases the crude product was purified by flash column chromatography (hexanes: EtOAc, 7:3) to afford pure alkoxy phenol.

Method B:

The dihydroxybenzene (hydroquinone, resorcinol or catechol, 1 eq) was added to a suspension of anhydrous K$_2$CO$_3$ (10 eq) in CH$_3$OH (30 mL). The mixture was stirred at room temperature for 1 h then the alkylating reagent (10 eq) was added and reaction was monitored by TLC (hexanes-EtOAc, 7:3). When reaction was complete, the mixture was concentrated under reduced pressure and diluted with CHCl$_3$ (30 mL) and water (30 mL). The organic layer was separated, dried over anhydrous Na$_2$SO$_4$ and concentrated under reduced pressure to afford a crude solid which was purified by flash column chromatography (hexane-EtOAc, 7:3) to yield pure products.

Method C:

The dihydroxybenzene (hydroquinone, resorcinol or catechol, 1 eq) was added to a suspension of Cs$_2$CO$_3$ (0.5 eq) in DMF (5 mL) and the mixture was stirred at room temperature for 2 h. The alkylating reagent (1 eq) was then added and the reaction mixture was heated at reflux and monitored by TLC (hexanes-EtOAc, 25:1). When reaction was complete (usually after 20 h), HCl (1%, 20 mL) was added and the mixture was extracted with CHCl$_3$ (3×30 mL). The combined organic layers were washed with water (3×30 mL) and brine (30 mL), dried over anhydrous Na$_2$SO$_4$ and concentrated under reduced pressure. The crude obtained was purified by flash chromatography (hexanes-EtOAc, 25:1) to yield pure products.

Method D:

The dihydroxybenzene (hydroquinone, resorcinol or catechol, 1 eq) was added to a suspension of K$_2$CO$_3$ (1 eq) in acetone (20 mL) and the mixture was stirred at room temperature for 2 h. The alkylating reagent (1.2 eq) was then added and the reaction mixture was heated at reflux and monitored by TLC(CHCl$_3$). When reaction was complete, the mixture was filtered and the filtrate was concentrated under reduced pressure. The residue was diluted with C$_6$H$_6$ (30 mL) and washed with aqueous NaOH (10%, 40 mL). The organic layer was dried over anhydrous Na$_2$SO$_4$ and concentrated under reduced pressure to afford the corresponding pure dialkoxy benzene product. The basic aqueous layer was cooled in an ice bath and acidified with concentrated HCl. The solid alkoxy phenol was collected from this mixture by vacuum filtration.

Method E:

The dihydroxybenzene (hydroquinone, resorcinol or catechol, 1 eq) was added to a suspension of NaH (5 eq) in DMF (3 mL). The alkylating reagent (5 eq) was then added and the reaction mixture was stirred at room temperature and monitored by TLC. When reaction was complete, a solution of saturated NH$_4$Cl (10 mL) was slowly added and the aqueous phase was extracted with CHCl$_3$ (2×15 mL). The combined organic layers were washed with water (10×15 mL), dried over anhydrous Na$_2$SO$_4$ and concentrated under reduced pressure. The crude oil was purified by flash column chromatography using hexanes:EtOAc as solvents to afford the corresponding pure compounds.

2-Ethoxy phenol 2(a){2} (Method C, 28%, Method D, 70%): GC (RI 1157, 96.7%); $^1$H NMR δ: 1.46 (t, J=7.0 Hz, 3H, CH$_3$), 4.12 (q, J=7.0 Hz, 2H, OCH$_2$), 5.76 (broad s, 1H, OH), 6.83-6.90 (m, 3H, ArH), 6.94-6.97 (m, 1H, ArH); $^{13}$C NMR δ: 14.8, 64.3, 111.6, 114.4, 120.0, 121.3, 145.7, 145.8; MS m/z (relative intensity): 139 (M$^+$+H, 41%), 138 (M$^+$, 100%); IR (cm$^{-1}$): 3535 (broad), 3054, 2984, 1611, 1596, 1502, 1040, 925, 743.

2-Propoxy phenol 2a{3} (Method C, 26%, Method D, 80%): GC (RI 1251, 100%); $^1$H NMR δ: 0.94 (t, J=7.4 Hz, 3H, CH$_3$), 1.70-1.77 (m, 2H, CH$_2$), 3.89 (q, J=6.5 Hz, 2H, OCH$_2$), 5.64 (broad s, 1H, OH), 6.70-6.86 (m, 4H, ArH); $^{13}$C NMR δ: 10.4, 22.5, 70.3, 111.6, 114.4, 120.1, 121.2, 145.8, 145.9; MS m/z (relative intensity): 153 (M$^+$+H, 19%), 152 (M$^+$, 100%); IR (cm$^1$): 3540 (broad), 3054, 2968, 2878, 1612, 1596, 1503, 1260, 978, 743.

2-Butoxy phenol 2a{4} (Method C, 51%): GC (RI 1353, 98.7%); $^1$H NMR δ: 1.00 (t, J=7.4 Hz, 3H CH$_3$), 1.47-1.55 (m, 2H, CH$_2$), 1.78-1.84 (m, 2H, CH$_2$), 4.05 (t, J=6.5 Hz, 2H, OCH$_2$), 5.69 (broad s, 1H, OH), 6.82-6.88 (m, 3H, ArH), 6.92-6.95 (m, 1H, ArH); $^{13}$C NMR δ: 13.8, 19.2, 31.2, 68.5, 111.5, 114.4, 120.0, 121.2, 145.8; MS m/z (relative intensity): 165 (M$^+$+H, 20%), 166 (M$^+$, 100%); IR (cm$^{-1}$): 3542 (broad), 3054, 2962, 2872, 1612, 1597, 1503, 1261, 1106, 783, 741.

2-(3-Methyl-butyloxy) phenol 2a{5} (Method C, 52%): GC (RI 1412, 99.9%); $^1$H NMR δ: 0.99 (d, J=6.6 Hz, 6H, CH$_3$), 1.73 (apparent q, J=6.8 Hz, 2H, CH$_2$), 1.81-1.89 (m, 1H, CH), 4.08 (t, J=6.6 Hz, 2H, OCH$_2$), 5.70 (broad s, 1H, OH), 6.82-6.90 (m, 3H, ArH), 6.95-6.96 (m, 1H, ArH); $^{13}$C NMR δ: 22.5, 25.1, 37.9, 67.2, 111.5, 114.4, 120.0, 121.2, 145.7, 145.9; MS m/z (relative intensity): 181 (M$^+$+H, 19%), 180 (M$^+$, 100%); IR (cm$^{-1}$): 3544 (broad), 3054, 2872, 1611, 1597, 1503, 1260, 742.

2-Allyloxy phenol 2a{6} (Method D, 54%): GC (RI 1240, 100%); $^1$H NMR δ: 4.61 (dt, J=5.5, 1.4 Hz, 2H, OCH$_2$), 5.32 (dq, 10.5, 1.3 Hz, 1H, CH$_2$), 5.41 (dq, J=17.3, 1.5 Hz, 1H, CH$_2$), 5.66 (s, 1H, OH), 6.03-6.11 (m, 1H, CH), 6.81-6.95 (m, 4H, ArH); $^{13}$C NMR δ: 69.8, 112.2, 114.7, 118.3, 120.0, 121.7, 132.8, 145.5, 145.9; MS m/z (relative intensity): 151 (M$^+$+H, 25%), 150 (M$^+$, 100%); IR (cm$^{-1}$): 3526 (broad), 2870, 1597, 1503, 1465, 1107, 791, 746.

3-Methoxy phenol 2b{1} (Method A, 50%): GC (RI 1219, 100%); $^1$H NMR δ: 3.7 (s, 3H, CH$_3$), 5.38 (s, 1H, OH), 6.46-6.49 (m, 2H, ArH), 6.52-6.54 (m, 1H, ArH), 7.14 (t, J=8.1 Hz, 1H, ArH); $^{13}$C NMR δ: 55.2, 101.5, 106.4, 108.0, 130.2, 156.6, 160.6; IR (cm$^{-1}$): 3397 (broad), 1598, 1286, 1148, 1041, 765.

3-Ethoxy phenol 2b{2} (Method A, 50%): GC (RI 1311, 96.7%); $^1$H NMR δ: 1.39 (t, J=7.0 Hz, 3H, CH$_3$), 3.99 (q, J=7.0 Hz, 2H, OCH$_2$), 6.26 (broad s, 1H, OH), 6.45-6.48 (m, 2H, ArH), 6.50-6.53 (m, 1H, ArH), 7.13 (t, J=8.0 Hz, ArH); $^{13}$C NMR δ: 14.6, 63.6, 102.1, 107.1, 107.9, 130.1, 156.6, 160.0; IR (cm$^{-1}$): 3449 (broad), 2981, 1596, 976, 765.

3-Propoxy phenol 2b{3} (Method A, 47%): GC (RI 1404, 100%); $^1$H NMR δ: 1.03 (t, J=7.4 Hz, 3H, CH$_3$), 1.76-1.83 (m, 2H, CH$_2$), 3.89 (q, J=6.7 Hz, 2H, OCH$_2$), 5.67 (broad s, 1H, OH), 6.43-6.45 (m, 2H, ArH), 6.50-6.53 (m, 1H, ArH), 7.11-7.14 (m, 1H, ArH); $^{13}$C NMR δ: 10.4, 22.4, 69.6, 102.1, 107.1, 107.7, 130.1, 156.5, 160.3; IR (cm$^{-1}$): 3415 (broad), 2966, 2878, 1596, 1493, 1146, 1004, 766.

3-(3-Methyl-butyloxy) phenol 2b{4} (Method B, 9%): GC (RI 1556, 99.9%); $^1$H NMR δ: 0.96 (d, J=6.7 Hz, 6H, CH$_3$), 1.67 (apparent q, J=6.7 Hz, 2H, CH$_2$), 1.78-1.86 (m, 1H, CH), 3.96 (t, J=6.7 Hz, 2H, OCH$_2$), 5.46 (broad s, 1H, OH), 6.42-6.44 (m, 2H, ArH), 6.50-6.52 (m, 1H, ArH), 7.10-7.15 (m, 1H, ArH); $^{13}$C NMR δ: 22.53, 25.00, 37.9, 66.5, 102.1, 107.1, 107.6, 130.1, 156.6, 160.4; IR (cm$^{-1}$): 3419 (broad), 2955, 2870, 1599, 1467, 1142, 839, 764.

4-Methoxy phenol (Method A, 77%) 2c{1}: GC (RI 1170, 98.0%); $^1$H NMR δ: 3.76 (s, 3H, CH$_3$), 5.53 (s, 2H, OH), 6.76-6.80 (m, 4H, ArH); $^{13}$C NMR δ: 55.8, 114.9, 116.1, 149.5, 153.5; MS m/z (relative intensity): 125 (M$^+$+H, 31%), 124 (M$^+$, 100%), 109 (80), 81 (54).

4-Ethoxy phenol 2c{2}: GC (RI 1248, 98.5%); $^1$H NMR δ: 1.39 (t, J=7.0 Hz, 3H, CH$_3$), 3.99 (q, J=7.0 Hz, 2H, OCH$_2$), 5.91 (s, 1H, OH), 6.75-6.80 (m, 4H, ArH); $^{13}$C NMR δ: 14.8, 64.3, 115.8, 116.1, 149.5, 152.7.

4-Propoxy phenol 2c{3}: GC (RI 1325, 95.0%); $^1$H NMR δ: 1.01 (t, J=7.4 Hz, 3H, CH$_3$), 1.74-1.81 (m, 2H, CH$_2$), 3.86 (q, J=6.5 Hz, 2H, OCH$_2$), 1.68 (broad s, 1H, OH), 6.74-6.80 (m, 4H, ArH); $^{13}$C NMR δ: 10.1, 22.3, 70.2, 115.5, 115.9, 149.6, 152.5; IR (cm$^{-1}$): 3397 (broad), 2873, 1511, 1455, 1237, 982, 823, 793.

4-Butoxy phenol 2c{4} (Method C, 42%, Method D, 40%): GC (RI 1483, 99.9%); $^1$H NMR δ: 0.96 (t, J=7.3 Hz, 3H, CH$_3$), 1.44-1.52 (m, 2H, CH$_2$), 1.71-1.77 (m, 2H, CH$_2$), 3.91 (t, J=6.5 Hz, 2H, OCH$_2$), 4.79 (broad s, 1H, OH), 6.74-6.80 (m, 4H, ArH); $^{13}$C NMR δ: 13.8, 19.2, 68.5, 115.7, 116.0, 149.3, 153.1; MS m/z (relative intensity): 167 (M$^+$+H, 43%), 166 (M$^+$, 100%); IR (cm$^{-1}$): 3403 (broad), 2957, 2871, 1514, 1374, 1242, 971, 822, 768.

4-(3-Methyl-butyloxy) phenol 2c{5} (Method B, 24%, Method C, 29%; Method D, 32%): GC (RI 1552, 100%); $^1$H NMR δ: 0.96 (d, J=6.7 Hz, 5H, CH$_3$), 1.65 (apparent q, J=6.8 Hz, 2H, CH$_2$), 1.78-1.86 (m, 1H, CH), 3.92 (t, J=6.6 Hz, 2H, OCH$_2$), 4.67 (broad s, 1H, OH), 6.74-6.80 (m, 4H, ArH); $^{13}$C NMR δ: 22.6, 25.0, 38.1, 67.1, 115.6, 116.0, 149.3, 153.3; MS m/z (relative intensity): 181 (M$^+$+H, 18%), 180 (M$^+$, 100%), 110 (95%); IR (cm$^{-1}$): 3404 (broad), 2959, 2866, 1622, 1426, 1386, 1236, 820, 749.

4-Allyloxy phenol 2c{6} (Method D, 18%): GC (RI 1372, 100%); $^1$H NMR δ: 4.48 (d, J=5.4 Hz, 2H), 5.28 (dd, J=10.5, 1.1 Hz, 1H), 5.40 (dd, J=17.3, 1.6 Hz, 1H), 5.45 (broad s, 1H, OH), 6.01-6.09 (m, 1H), 6.75-6.77 (m, 2H, ArH), 6.80-6.82 (m, 2H, ArH); $^{13}$C NMR 8:69.7, 115.9, 116.0, 117.7, 133.4, 149.5, 152.5; MS m/z (relative intensity): 151 (M$^+$+H, 55%), 150 (M$^+$, 100%).

1,2-Dimethoxy benzene 3a{1,1} (Method E from 2c-1 as starting material, 72%): GC (RI 1152, 99%); $^1$H NMR δ: 3.88 (s, 6H, CH$_3$), 6.87-6.94 (m, 4H, ArH); $^{13}$C NMR δ: 55.6, 111.2, 120.7, 148.9; MS m/z (relative intensity): 139 (M$^+$+H, 11%), 138 (M$^+$, 100%), 123 (50%), 95 (56%), 77 (69%); IR (cm$^{-1}$): 3065, 2936, 2835, 1593, 1254, 1123, 1028, 746.

1,2-Diethoxy benzene 3a{2,2} (Method D, 24%): GC (RI 1240, 100%); $^1$H NMR δ: 1.46 (t, J=7.0 Hz, 6H, CH$_3$), 4.10 (q, J=7.0 Hz, 4H, CH$_2$), 6.90 (s, 4H, ArH); $^{13}$C NMR δ: 14.8, 64.4, 113.5, 120.9, 128.2, 148.7; MS m/z (relative intensity): 167 (M$^+$+H, 100%), 166 (M$^+$, 96%); IR (cm$^{-1}$): 3063, 2987, 2871, 1592, 1506, 1392, 1034, 930, 738.

1,2-Dipropoxy benzene 3a{3,3} (Method D, 18%): GC (RI 1420, 100%); $^1$H NMR δ: 0.94 (t, J=7.4 Hz, 6H, CH$_3$), 1.70-1.78 (m, 4H, CH$_2$), 3.86 (q, J=6.6 Hz, 4H, CH$_2$), 6.74-6.82 (m, 4H, ArH); $^{13}$C NMR δ: 10.5, 22.6, 70.7, 114.1, 121.0, 149.2; MS m/z (relative intensity): 195 (M$^+$+H, 100%), 194 (M$^+$, 84%); IR (cm$^{-1}$): 3064, 2963, 2876, 1593, 1503, 1255, 1125, 981, 739.

1,2-Dibutoxy benzene 3a{4,4} (Method E from 2a{4} as starting material, 30%): GC (RI 1603, 100%); $^1$H NMR δ: 0.98 (t, J=7.4 Hz, 6H, CH$_3$), 1.47-1.56 (m, 4H, CH$_2$), 1.77-1.83 (m, 4H, CH$_2$), 4.00 (t, J=6.6 Hz, 4H, OCH$_2$), 6.87-6.91 (m, 4H, ArH); $^{13}$C NMR δ: 13.9, 19.2, 31.4, 68.9, 114.0, 120.9, 149.2; MS m/z (relative intensity): 223 (M$^+$+H, 6%), 222 (M$^+$, 41%); 110 (100%); IR (cm$^{-1}$): 2958, 2872, 1593, 1502, 1253, 1221, 737.

1,2-Di-(3-methyl-butyloxy) benzene 3a{5,5} (Method E from 2c-i5 as starting material, 53%): GC (RI 1708, 100%); $^1$H NMR δ: 0.96 (d, J=6.7 Hz, 12H, CH$_3$), 1.71 (apparent q, J=6.8 Hz, 4H, CH$_2$), 1.82-1.90 (m, 2H, CH), 4.02 (t, J=6.7 Hz, 4H, OCH$_2$), 6.87-6.91 (m, 4H, ArH); $^{13}$C NMR δ: 22.6, 25.1, 38.0, 67.6, 114.0, 120.9, 149.2; MS m/z (relative intensity): 251 (M$^+$+H, 10%), 250 (M$^+$, 53%); 180 (21%); 110 (100%); IR (cm$^{-1}$): 3064, 2953, 2870, 1593, 1506, 1385, 1055, 982, 739.

1,2-Diallyloxy benzene 3a{6,6} (Method D, 24%): GC (RI 1411, 100%); $^1$H NMR δ: 4.62 (dt, J=5.3, 1.5 Hz, 4H, OCH$_2$), 5.27-5.30 (m, 2H, CH$_2$), 5.41-5.45 (m, 2H, CH$_2$), 6.06-6.14 (m, 2H, CH), 6.89-6.94 (m, 4H, ArH); $^{13}$C NMR δ: 69.8, 114.2, 117.4, 121.2, 133.5, 148.5; MS m/z (relative intensity): 191 (M$^+$+H, 62%), 190 (M$^+$, 100%); IR (cm$^{-1}$): 3081, 2858, 1648, 1591, 1507, 1124, 921, 740.

1,3-Dimethoxy benzene 3b{1,1} (Method E, 76%): GC (RI 1181, 94.0%); $^1$H NMR δ: 3.81 (s, 6H, CH$_3$), 6.51-6.56 (m, 3H, ArH), 7.16 (t, J=8.2 Hz, 1H, ArH); $^{13}$C NMR δ 55.1, 100.4, 106.1, 129.8, 160.8; IR (cm$^{-1}$): 3001, 2957, 2835, 1593, 1337, 1152, 1050, 763.

1,3-Diethoxy benzene 3b{2,2} (Method E): GC (RI 1321, 98.3%); $^1$H NMR δ: 1.42 (t, J=7.0 Hz, 6H, CH$_3$), 4.02 (q, J=7.0 Hz, 4H, CH$_2$), 6.47-6.51 (m, 3H, ArH), 7.16 (t, J=8.2 Hz, 1H, ArH); $^{13}$C NMR δ: 14.8, 63.3, 101.3, 106.6, 129.7, 160.1; IR (cm$^{-1}$): 2980, 1603, 1493, 1475, 1150, 1048.

1,3-Dipropoxy benzene 3b{3,3} (Method E, 65%): GC (RI 1504, 98%); $^1$H NMR δ: 1.04 (t, J=7.4 Hz, 6H, CH$_3$), 1.77-1.85 (m, 4H, CH$_2$), 3.91 (q, J=6.5 Hz, 4H, CH$_2$), 6.48-6.51 (m, 3H, ArH), 7.16 (t, J=8.2 Hz, 1H, ArH); $^{13}$C NMR δ: 10.5, 22.6, 69.4, 101.4, 106.6, 129.7, 160.3; IR (cm$^{-1}$): 2964, 2877, 1601, 1492, 1470, 1287, 1263, 759.

1,3-Dibutoxy benzene 3b{4,4} (Method B, 16%): GC (RI 1701, 100%); $^1$H NMR δ: 0.97 (t, J=7.4 Hz, 6H, CH$_3$), 1.44-1.52 (m, 4H, CH$_2$), 1.73-1.78 (m, 4H, CH$_2$) 3.94 (t, J=6.5 Hz, 4H, CH$_2$), 6.46-6.49 (m, 3H, ArH), 7.15 (t, J=8.1 Hz, 1H, ArH); $^{13}$C NMR δ: 13.9, 19.2, 31.3, 67.6, 101.4, 106.6, 129.7, 160.3; MS m/z (relative intensity): 223 (M$^+$+H, 36%), 222 (M$^+$, 100%).

1,3-Di-(3-methyl-butyloxy) benzene 3b{5,5} (Method E, 63%): GC (RI 1826, 100%); $^1$H NMR δ: 0.97 (d, J=6.5 Hz, 12H, CH$_3$), 1.68 (apparent q, J=6.8 Hz, 4H, CH$_2$), 1.80-1.88 (m, 2H, CH), 3.98 (t, J=6.7 Hz, 4H, OCH$_2$), 6.47-6.61 (m, 3H, ArH), 7.16 (t, J=8.2 Hz, 1H, ArH); $^{13}$C NMR δ: 22.6, 25.0, 38.0, 66.3, 101.4, 106.6, 129.7, 160.4; MS m/z (relative intensity): 251 (M$^+$+H, 48%), 250 (M$^+$, 100%); IR (cm$^{-1}$): 2948, 2866, 1580, 1471, 1288, 1158, 850, 762, 689.

1,3-Diallyloxy benzene 3b{6,6} (Method B, 41%): GC (RI 1486, 95%); $^1$H NMR δ: 4.52 (dt, J=1.5 and 5.3 Hz, 4H, OCH$_2$), 5.29 (dq, J=1.3 and 10.5 Hz, 2H, CH=CH$_2$), 5.42 (dq, J=1.6 and 17.3 Hz, 2H, CH=CH$_2$), 6.06 (ddt, J=5.3, 10.6 and 17.2 Hz, 2H, CH), 6.51-6.54 (m, 3H, ArH), 7.17 (t, J=8.0 Hz, 1H, ArH); $^{13}$C NMR δ: 68.8, 101.9, 107.1, 117.7, 129.8, 133.2, 159.7; MS m/z (relative intensity): 191 (M$^+$+H, 70%), 190 (M$^+$, 100%).

1,4-Dimethoxy benzene 3c{1,1} (Method B, 65%): GC (RI 1115, 95.0%); $^1$H NMR δ: 3.77 (s, 6H, CH$_3$), 6.84 (s, 4H, ArH); $^{13}$C NMR δ 55.7, 114.6, 153.7.

1,4-Diethoxy benzene 3c{2,2} (Method B): GC (RI 1250, 95.0%); $^1$H NMR δ: 1.40 (t, J=6.8 Hz, 6H, CH$_3$), 3.98 (q, J=7.1 Hz, 4H, CH$_2$), 6.84 (s, 4H, ArH); $^{13}$C NMR δ: 14.9, 63.9, 115.3, 153.0; IR (cm$^{-1}$): 2985, 1508, 1394, 1116, 1048, 926, 749, 533.

1,4-Dipropoxy benzene 3c{3,3} (Method B): GC (RI 1434, 96.0%); $^1$H NMR δ: 1.03 (t, J=7.4 Hz, 6H, CH$_3$), 1.75-1.86 (m, 4H, CH$_2$), 3.87 (q, J=6.5 Hz, 4H, CH$_2$), 6.83 (s, 4H, ArH); $^{13}$C NMR δ: 10.5, 22.7, 70.1, 115.4, 153.2; IR (cm$^{-1}$): 2964, 2876, 1509, 1228, 981, 825, 531.

1,4-Dibutoxy benzene 3c{4,4} (Method B, 6%; Method C, 28%; Method D, 15%, Method E, 80%): GC (RI and ratio) 1849, 99.0%; $^1$H NMR δ: 0.96 (d, J=6.7 Hz, 12H, CH$_3$), 1.65 (apparent q, J=6.8 Hz, 4H, CH$_2$), 1.78-1.86 (m, 2H, CH), 3.93 (t, J=6.6 Hz, 4H, OCH$_2$), 6.83 (s, 4H, ArH); $^{13}$C NMR δ: 22.6, 25.0, 38.1, 67.0, 115.4, 153.2; MS m/z (relative intensity): 223 (M$^+$+H, 20%), 222 (M$^+$, 100%); IR (cm$^{-1}$): 2954, 2871, 1511, 1399, 1237, 1043, 830, 767, 535.

1,4-Di-(3-methyl-butyloxy) benzene 3c{5,5} (Method C, 28%, Method D, 20%): GC (RI and ratio) 1623, 98.0%; $^1$H NMR δ: 0.98 (d, J=7.4 Hz, 6H, CH$_3$), 1.45-1.53 (m, 4H, CH$_2$), 1.72-1.78 (m, 4H, CH$_2$), 3.91 (t, J=6.5 Hz, 4H, OCH$_2$), 6.83 (s, 4H, ArH); $^{13}$C NMR δ: 13.9, 19.2, 31.4, 68.3, 115.3, 153.2; MS I/l/z (relative intensity): 251 (M$^+$+H, 24%), 250 (M$^+$, 100%); IR (cm$^{-1}$): 2954, 2868, 1509, 1474, 1237, 1061, 821, 740, 523.

1,4-Diallyloxy benzene 3c{6,6} (Method D, 48%): GC (RI and ratio) 1481, 100%; $^1$H NMR δ: 4.49 (dt, J=5.4, 1.5 Hz, 4H), 5.27-5.30 (m, 2H), 5.39-5.44 (m, 2H), 6.03-6.10 (m, 2H), 6.86 (s, 4H, ArH); $^{13}$C NMR δ: 69.36, 115.5, 117.4, 133.5, 152.8; MS m/z (relative intensity): 191 (M$^+$+H, 21%), 190 (M$^+$, 100%).

Synthesis of Compounds 4c{3} and 6c{3}

Compound 4c{3} was obtained according to method D in 88% yield. GC (RI and ratio) 1495, 100%; $^1$H NMR δ: 1.04 (t, J=7.4 Hz, 3H, CH$_3$), 1.76-1.83 (m, 2H), 3.88 (t, J=6.6 Hz, 2H, OCH$_2$), 4.49 (dt, J=5.3, 1.5 Hz, 2H), 5.27-5.30 (m, 1H), 5.39-5.43 (m, 1H), 6.02-6.10 (m, 1H), 6.83-6.87 (m, 4H, ArH); $^{13}$C NMR δ: 10.5, 22.6, 69.4, 70.0, 115.3, 115.6, 117.4, 133.6, 152.6, 153.4; MS m/z (relative intensity): 193 (M$^+$+H, 48%), 192 (M$^+$, 100%).

The 4c{3} compound (0.3277 g) was heated at 180° C. in a sealed tube, under a nitrogen atmosphere for 5 days. The viscous dark black oil was purified by column chromatography with chloroform to afford 0.1253 g of pure 6c{3} library in 38% yield. GC (RI and ratio) 1529, 98%; $^1$H NMR δ: 1.02 (t, J=7.4 Hz, 3H, CH$_3$), 1.45 (d, J=6.3 Hz, 3H, CH$_3$), 1.73-1.80 (m, 2H), 2.77-2.81 (m, 1H), 3.24-3.29 (m, 1H), 3.85 (t, J=6.6 Hz, 2H, OCH$_2$), 4.85-4.92 (m, 1H), 6.64 (d, J=1.5 Hz, 2H, ArH), 6.77 (s, 1H, ArH); $^{13}$C NMR δ: 10.5, 21.7, 22.7, 37.6, 70.5, 79.6, 109.0, 112.2, 113.6, 127.9, 153.4, 153.5; MS m/z (relative intensity): 193 (M$^+$+H, 27%), 192 (M$^+$, 100%).

The following procedures were used to generate mini-libraries in Set A and Set C as set out in Table 2

Method F:

A mixture of mono-alkoxy phenols (1 eq) in DMF (2 mL) was added to a suspension of NaH (5 eq) in DMF (3 mL). The alkylating reagent (MeI, EtI, PrI, BuBr, bromo-3-methyl butane or allyl bromide, 3 eq) was then added and the reaction mixture was stirred at room temperature and monitored by GC. When reaction was complete (between 1 to 4 h), a solution of saturated NH$_4$Cl (25 mL) was slowly added and the aqueous phase was extracted with CHCl$_3$ (3×20 mL). The combined organic layers were washed with water (4×25 mL) and brine (2×25 mL), dried over anhydrous Na$_2$SO$_4$ and concentrated under reduced pressure. The crude oil was purified by flash column chromatography using hexane:EtOAc (4:1) to afford the corresponding library as pure oil. (Note: the 1,3 dialkoxy benzene libraries required a second purification by flash column chromatography, with hexanes:EtOAc, 4:1).

Method G:

A mixture of mono-alkoxy phenols (1 eq) in acetone (5 mL) was added to a suspension of K$_2$CO$_3$ (10 eq) in acetone (20 mL) and the mixture was stirred at room temperature for 2 h. The alkylating reagent (MeI, EtI, PrI, BuBr, 1-bromo-3-methylbutane or allyl bromide, 3 eq) was then added and the reaction mixture was heated at reflux and monitored by GC. When the reaction was complete, the mixture was filtered and the filtrate was concentrated under reduced pressure. The residue obtained was diluted with CHCl$_3$ (30 mL) and water (20 mL). The layers were separated; the organic layer was dried over anhydrous Na$_2$SO$_4$ and concentrated under reduced pressure to afford the corresponding library as pure oil. For compound sets 5b{n,n}, the oils were decolorized with flash chromatography (5% EtOAc in Hexane), even though GC analysis indicated that the compounds were pure.

Method H:

A mixture of mono-alkoxy phenols (1 eq) in acetone (5 mL) was added to a suspension of Cs$_2$CO$_3$ (2 eq) in acetone (15 mL) and the mixture was stirred at room temperature for 2 h. The alkylating reagent (3 eq) was then added and the reaction mixture was heated at reflux and monitored by GC. When the reaction was complete, the mixture was filtered and the filtrate was concentrated under reduced pressure. The residue obtained was diluted with CHCl$_3$ (30 mL) and water (20 mL). The layers were separated; the organic layer was dried over anhydrous Na$_2$SO$_4$ and concentrated under reduced pressure to afford the corresponding library as pure oil.

The following data were generated for mini-libraries in Set A and Set C.

3a{1,1-5} Methyl library (Method A, 27% yield; Method C, 72% yield): $^1$H NMR δ: 0.95-0.99 (m, 8.9H), 1.04 (t, J=7.5 Hz, 3H, CH$_3$ (Pr)), 1.45-1.52 (m, 5H), 1.75 (q, J=7.0 Hz, 2H, CH$_2$ (i-Pent)), 1.80-1.91 (m, 5.4H), 3.86, 3.865, 3.87 (s, 8.5H), 3.88 (s, 3H, OCH$_3$ (Me)), 3.89 (s, 6H, OCH$_3$ (Me)), 3.98 (t, J=6.9 Hz, 2H), 4.01-4.06 (m, 4.3H), 4.11 (q, J=7.0 Hz, 2H, OCH$_2$ (Et)), 6.88-6.94 (m, 19H, ArH); GC RI: MS m/z (relative intensity, %): 1,2-dimethoxy benzene 3a{1,1} 1145: 139 (M$^+$+H, 29), 138 (M$^+$, 100), 123 (44); 1-ethoxy-2-methoxy benzene 3a{1,2} 1190: 153 (M$^+$+H, 23), 152 (M$^+$, 100), 124 (58), 109 (91); 1-methoxy-2-propoxy benzene 3a{1,3} 1280: 167 (M$^+$+H, 18), 166 (M$^+$, 100), 124 (66), 109 (76); 1-butoxy-2-methoxy benzene 3a{1,4} 1377: 181 (M$^+$+H, 15), 180 (M$^+$, 100), 124 (57), 109 (52); 1-methoxy-2-(3-methyl-butoxy) benzene 3a{1,5} 1434: 195 (M$^+$+H, 15), 194 (M$^+$, 100), 124 (68), 109 (46).

3a{2,1-5} Ethyl library (Method A, 57% yield), 3a{3,1-5} propyl library (Method A, 67% yield), 3a{4,1-5} butyl library (Method A, 62% yield), 3a{5,1-5} isopentyl library (Method A, 43% yield), 3a{6,1-5} allyl library (Method B, 94% yield): $^1$H NMR and GC-MS data:

3a{2,1-5} Ethyl library (Method A, 57% yield): $^1$H NMR δ: 0.96-0.99 (m, 9.4H), 1.04 (t, J=7.5 Hz, 3H, CH$_3$ (Pr)), 1.41-1.53 (m, 5H), 1.73 (q, J=6.9 Hz, 2H, CH$_2$ (i-Pent)), 1.79-1.89 (m, 5.4H), 3.88 (s, 3H, OCH$_3$ (Me)), 3.97 (t, J=6.8 Hz, 2H), 4.01 (t, J=6.7 Hz, 2H), 4.04 (t, J=6.8 Hz, 2H), 4.05-4.13 (m, 14H), 6.86-6.93 (m, 19H, ArH); GC RI: MS m/z (relative intensity, %): 1,2-diethoxy benzene 3a{2,2} 1244: 167 (M$^+$+H, 100), 166 (M$^+$, 81); 1-ethoxy-2-propoxy benzene 3a{2,3} 1335: 181 (M$^+$+H, 100), 180 (M$^+$, 60); 1-ethoxy-2-butoxy benzene 3a{2,4} 1429: 195 (M$^+$+H, 100), 194 (M$^+$, 83); 1-ethoxy-2-(3-methyl-butoxy) benzene 3a{2,5} 1486: 209 (M$^+$+H, 100), 208 (M$^+$, 72).

3a{3,1-5} Propyl library (Method A, 67% yield): $^1$H NMR δ: 0.96-0.99 (m, 7.4H), 1.04 (t, J=7.4 Hz, 16.5H, CH$_3$ (Pr)), 1.44 (t, J=7.0 Hz, 3H), 1.48-1.53 (m, 1.6H), 1.72 (q, J=6.8 Hz, 1.7H, CH$_2$ (i-Pent)), 1.77-1.91 (m, 14H), 3.87 (s, 3H, OCH$_3$ (Me)), 3.94-4.04 (m, 14.7H), 4.09 (q, J=7.0 Hz, 2H), 6.86-6.92 (m, 17H, ArH); GC RI: MS m/z (relative intensity, %): 1,2-dipropoxy benzene 3a{3,3} 1424: 195 (M$^+$+H, 100), 194 (M$^+$, 60); 1-butoxy-2-propoxy benzene 3a{3,4} 1518: 209 (M$^+$+H, 100), 208 (M$^+$, 84); 1-(3-methyl-butoxy)-2-propoxy benzene 3a{3,5} 1576: 223 (M$^+$+H, 100), 222 (M$^+$, 62).

3a{4,1-5} Butyl library (Method A, 62% yield): $^1$H NMR δ: 0.96-0.99 (m, 24H), 1.04 (t, J=7.5 Hz, 3.4H, CH$_3$ (Pr)), 1.44 (t, J=7.0 Hz, 3H), 1.46-1.54 (m, 12.6H), 1.71 (q, J=6.8 Hz, 2H, CH$_2$ (i-Pent)), 1.77-1.88 (m, 16H), 3.87 (s, 3H, OCH$_3$ (Me)), 3.96 (t, J=6.6 Hz, 2H), 3.98-4.05 (m, 15H), 4.07 (q, J=7.0 Hz, 2.4H), 6.82-6.94 (m, 20H, ArH); GC RI: MS m/z (relative intensity, %): 1,2-dibutoxy benzene 3a{4,4} 1608: 223 (M$^+$+H, 100), 222 (M$^+$, 64); 1-butoxy-2-(3-methyl-butoxy) benzene 3a{4,5} 1664: 237 (M$^+$+H, 100), 236 (M$^+$, 64).

3a{5,1-5} Isopentyl library. (Method A, 43% yield): $^1$H NMR δ: 0.96-0.99 (m, 41H), 1.04 (t, J=7.5 Hz, 3.4H, CH$_3$ (Pr)), 1.43 (t, J=7.0 Hz, 3.8H), 1.50 (q, J=7.5 Hz, 2.6H), 1.69-1.90 (m, 24H), 3.86 (s, 3H, OCH$_3$ (Me)), 3.96 (t, J=6.6 Hz, 2H), 3.98-4.10 (m, 18H), 6.84-6.93 (m, 20H, ArH); GC RI: MS m/z (relative intensity, %): 1,2-di(3-methyl-butoxy) benzene 3a{5,5} 1720: 251 (M$^+$+H, 20), 250 (M$^+$, 100).

3a{6,1-5} Allyl library. (Method B, 94% yield): $^1$H NMR δ: 0.96-1.00 (m, 7H), 1.05 (t, J=7.4 Hz, 3H, CH$_3$ (Pr)), 1.45 (t, J=7.0 Hz, 3.7H), 1.49-1.53 (m, 1.7H), 1.73 (q, J=6.9 Hz, 1.4H), 1.79-1.89 (m, 4.6H), 3.88 (s, 4H, OCH$_3$ (Me)), 3.98 (t, J=6.7 Hz, 1.8H), 4.01-4.06 (m, 3.3H), 4.10 (q, J=7.0 Hz, 2.4H), 4.58-4.63 (m, 10.6H), 5.25-5.30 (m, 5.1H), 5.38-5.44 (m, 5H), 6.04-6.14 (m, 5H), 6.84-6.95 (m, 21H, ArH); GC RI: MS m/z (relative intensity, %): 1-allyloxy-2-methoxy benzene 3a{6,1} 1281: 165 (M$^+$+H, 42), 164 (M$^+$, 100); 1-allyloxy-2-ethoxy benzene 3a{6,2} 1327: 179 (M$^+$+H, 100), 178 (M$^+$, 67); 1-allyloxy-2-propoxy benzene 3a{6,3} 1416: 193 (M$^+$+H, 100), 192 (M$^+$, 91); 1-allyloxy-2-butoxy benzene 3a{6,4} 1510: 207 (M$^+$+H, 100), 206 (M$^+$, 72); 1-allyloxy-2-(3-methyl-butoxy) benzene 3a{6,5} 1569: 221 (M$^+$+H, 100), 220 (M$^+$, 70).

3b{1,1-5} Methyl library (Method A, 85% yield): $^1$H NMR δ: 0.97 (d, J=6.6 Hz, 6H, CH$_3$ (i-Pent)), 1.04 (t, J=7.4 Hz, 3H, CH$_3$ (Pr)), 1.42 (t, J=7.0 Hz, 3H, CH$_3$ (Et)), 1.68 (apparent q, J=6.8 Hz, 2H, CH$_2$ (i-Pent)), 1.78-1.87 (m, 3H), 3.79-3.80 (m, 15H, OCH$_3$), 3.91 (t, J=6.6 Hz, 2H, OCH$_2$ (Pr)), 3.98 (t, J=6.7 Hz, 2H, OCH$_2$ (i-Pent)), 4.02 (q, J=7.0 Hz, 2H, OCH$_2$ (Et)), 6.47-6.53 (m, 9.6H, ArH), 7.18 (t, J=8.2 Hz, 3H, ArH); GC RI: MS m/z (relative intensity, %): 1,3-dimethoxy benzene 3b{1,1} 1180: 138 (M$^+$, 100); 1-ethoxy-3-methoxy benzene 3b{1,2} 1253: 153 (M$^+$+H, 25), 152 (M$^+$, 100); 1-methoxy-3-propoxy benzene 3b{1,3} 1345: 167 (M$^+$+H, 32), 166 (M$^+$, 100), 124 (22); 1-methoxy-3-(3-methyl-butyloxy) benzene 3b{1,5} 1508: 195 (M$^+$+H, 30), 194 (M$^+$, 100).

3b{2,1-5} Ethyl library (Method A, 66% yield), 3b{3,1-5} propyl library (Method A, 53% yield), 3b{4,1-5} butyl library (Method A, 69% yield) 3b{5,1-5} isopentyl library (Method A, 72% yield), 3b{6,1} (Method B, % yield), 3b{6,2-3} (Method B, % yield), 3b {6,4-5} (Method B, % yield) $^1$H NMR and GC-MS data:

3b{2,1-5} Ethyl library. (Method A, 66% yield): $^1$H NMR δ: 0.96 (d, J=6.6 Hz, 6H, CH$_3$ (i-Pent)), 1.03 (t, J=7.4 Hz, 3H, CH$_3$ (Pr)), 1.39-1.43 (m, 12.8H), 1.67 (apparent q, J=6.8 Hz, 2H, CH$_2$ (i-Pent)), 1.78-1.84 (m, 3H), 3.79 (s, 3H, CH$_3$ (Me)), 3.90 (t, J=6.6 Hz, 2H, OCH$_2$ (Pr)), 3.98 (t, J=6.7 Hz, 2H, OCH$_2$ (i-Pent)), 3.99-4.04 (m, 8H), 6.46-6.51 (m, 10H, ArH), 7.16 (t, J=8.2 Hz, 3H, ArH); GC RI: MS m/z (relative intensity, %): 1,3-diethoxy benzene 3b{2,2} 1318: 167 (M$^+$+H, 31), 166 (M$^+$, 100); 1-ethoxy-3-propoxy benzene 3b{2,3} 1409: 181 (M$^+$+H, 40), 180 (M$^+$, 100); 1-ethoxy-3-(3-methyl-butyloxy) benzene 3b{2,5} 1570: 209 (M$^+$+H, 35), 208 (M$^+$, 100).

3b{3,1-5} Propyl library (Method A, 53% yield): $^1$H NMR δ: 0.96 (d, J=6.6 Hz, 6H, CH$_3$ (i-Pent)), 1.02-1.05 (m, 10H), 1.40 (t, J=7.0 Hz, 2H, CH$_3$ (Et)), 1.67 (apparent q, J=6.8 Hz, 2H, CH$_2$ (i-Pent)), 1.77-1.85 (m, 8H), 3.79 (s, 1.5H, OCH$_3$ (Me)), 3.89-3.92 (m, 7H), 3.97 (t, J=6.7 Hz, 2H, OCH$_2$ (i-Pent)), 4.02 (q, J=7.0 Hz, 1.2H, OCH$_2$ (Et)), 6.46-6.51 (m, 7H, ArH), 7.16 (t, J=8.2 Hz, 2.5H, ArH); GC RI: MS m/z (relative intensity, %): 1,3-dipropoxy benzene 3b{3,3} 1501: 195 (M$^+$+H, 45), 194 (M$^+$, 100), 110 (85), 82(22); 1-(3-methyl-butyloxy)-3-propoxy benzene 3b{3,5} 1657: 223 (M$^+$+H, 44), 222 (M$^+$, 100).

3b{4,1-5} Butyl library (Method A, 69% yield): $^1$H NMR δ: 0.99-1.02 (m, 19H), 1.05 (t, J=7.0 Hz, 3H, CH$_3$ (Pr)), 1.41-1.45 (m, 3H), 1.48-1.56 (m, 8H), 1.70 (apparent q, J=6.7 Hz, 2.5H, CH$_2$ (i-Pent)), 1.76-1.91 (m, 8H), 3.81 (s, 3H, OCH$_3$ (Me)), 3.93 (t, J=6.6 Hz, 2H, OCH$_2$ (Pr)), 3.95-4.01 (m, 11H), 4.03 (q, J=7.0 Hz, 2H, OCH$_2$ (Et)), 6.45-6.54 (m, 11.7H, ArH), 7.16 (t, J=8.2 Hz, 4H, ArH); GC RI: MS m/z (relative intensity, %): 1-butoxy-3-methoxy benzene 3b{4,1} 1440: 181 (M$^+$+H, 25), 180 (M$^+$, 100); 1-butoxy-3-ethoxy benzene 3b{4,2} 1506: 193 (M$^+$+H, 33), 194 (M$^+$, 100); 1-butoxy-3-propoxy benzene 3b{4,3} 1596: 209 (M$^+$+H, 48), 208 (M$^+$, 100); 1-butoxy-3-(3-methyl-butyloxy) benzene 3b{4,5} 1754: 237 (M$^+$+H, 42), 236 (M$^+$, 100).

3b{5,1-5} Isopentyl library. (Method A, 72% yield): $^1$H NMR δ: 0.99 (d, J=6.7 Hz, 26H), 1.06 (t, J=7.4 Hz, 3H, CH$_3$ (Pr)), 1.41-1.45 (m, 3H), 1.70 (apparent q, J=6.7 Hz, 9H), 1.81-1.88 (m, 6.3H), 3.81 (s, 3H, OCH$_3$ (Me)), 3.92 (t, J=6.6 Hz, 2H, OCH$_2$ (Pr)), 3.98-4.04 (m, 11H), 6.50-6.54 (m, 11H, ArH), 7.18 (t, J=8.2 Hz, 4H, ArH); GC RI: MS m/z (relative intensity, %): 1-methoxy-3-(3-methyl-butyloxy) benzene 3b{5,1} 1500: 195 (M$^+$+H, 26), 194 (M$^+$, 100); 1-ethoxy-3-(3-methyl-butyloxy) benzene 3b{5,2} 1566: 209 (M$^+$+H, 35), 208 (M$^+$, 100); 1-(3-methyl-butyloxy)-3-propoxy benzene 3b{5,3} 1653: 223 (M$^+$+H, 48), 222 (M$^+$, 100); 1,3-di(3-methyl-butyloxy) benzene 3b{5,5} 1826: 251 (M$^+$+H, 40), 250 (M$^+$, 100).

The meta allyl library was synthesized in three portions (methyl by itself, ethyl+propyl and butyl+isopentyl), because upon Claisen rearrangement each compound gave rise to two rearrangement products.

3b{6,1} 1-allyloxy-3-methoxybenzene. (Method D, 98% yield): $^1$H NMR δ: 3.80 (s, 3H, CH$_3$), 4.53 (apparent d, J=5.5 Hz, 2H, allyl CH$_2$), 5.30 (apparent d, J=14 Hz, 1H), 5.43 (apparent d, J=22 Hz, 1H), 6.07 (m, 1H), 6.52 (m, 3H, ArH), 7.19 (apparent t, J=7.7 Hz, 1H ArH). GC RI: 1334 MS m/z (relative intensity, %): 164 (M$^+$, 100), 149 (M-CH$_3$, 10), 136 (M−28, 12).

3b{6,2-3} Allyl library (ethyl, propyl). (Method D, 60% yield, 35% 3b{6,2} by GC and 39% by $^1$H NMR and the rest is 3b{6,3}): $^1$H NMR δ: 1.04 (t, J=4 Hz, 3H, CH$_3$ propyl), 1.42 (t, J=3.7 Hz, 3H, CH$_3$ ethyl), 1.81 (m, 2H, CH$_2$, propyl), 3.95 (t, J=3.7 Hz, 2H propyl CH$_2$), 4.02 (q, J=7 Hz, 2H, ethyl), 4.53 (apparent d, J=7 Hz, 2H for each component), 5.29 (m, J=14 Hz, 1H for each component), 5.41 (m, J=22 Hz, 1H for each component), 6.07 (m, 1H for each component), 6.53 (m, 3H for each component), 7.17 (apparent t, J=8 Hz, 1H for each component). GC RI: MS m/z (relative intensity, %): 1-allyloxy-3-ethoxybenzene 3b{6,2} 1398: 179 (M+1, 72), 178 (1,100), 150 (M 28, 35); 1-allyloxy-3-propoxybenzene 3b{6,3} 1491: 193 (M+1, 93), 192 (M$^+$, 100), 164 (M 28, 12), 150 (31).

3b{6,4-5} Allyl library (butyl, isopentyl). (Method D, 71% yield, 3b{6,4} 34% by GC and 40% by $^1$H NMR and the rest is 3b{6,5}): $^1$H NMR δ: 0.98 (m, 6H, CH$_3$ isopentyl, 3H CH$_3$ butyl), 1.48 (m, 2H, CH$_2$ butyl), 1.68 (m, 2H, CH$_2$, isopentyl), 1.75 (m, 2H, CH$_2$, butyl), 1.83 (m, 1H, isopentyl), 3.96 (m, 2H for each component, CH$_2$), 4.52 (apparent d, J=8 Hz, 2H for each component), 5.29 (apparent d, J=14 Hz, 1H for each component), 5.42 (apparent d, J=22 Hz, 1H for each component), 6.06 (m, 1H for each component), 6.51 (m, 3H for each component, ArH), 7.17 (apparent t, J=7 Hz, 1H for each component, ArH). GC RI: MS m/z (relative intensity, %): 1-allyloxy-3-n-butoxybenzene 3b {6,4} 1592: 207 (M+1, 83), 206 (M$^+$, 100), 178 (M−28, 12), 150 (33). 1-allyloxy-3-isopentyloxybenzene 3b{6,5} 1654: 221 (M+1, 81), 220 (M$^+$, 100), 192 (M−28, 7), 150 (21).

3c{1,1-5} Methyl library (Method A, 65% yield): $^1$H NMR δ: 0.96 (d, J=6.7 Hz, 9H, CH$_3$ (i-Pent)), 1.03 (t, J=7.4 Hz, 3.3H, CH$_3$ (Pr)), 1.39 (t, J=6.7 Hz, 4H, CH$_3$ (Et)), 1.66 (apparent q, J=6.7 Hz, 3H, CH$_2$ (i-Pent)), 1.77-1.85 (m, 3H), 3.77, 3.78 (s, 15H, OCH$_3$), 3.87 (t, J=6.6 Hz, 2H, CH$_2$ (Pr)), 3.94 (t, J=6.6 Hz, 3H, CH$_2$ (i-Pent)), 3.98 (q, J=7.1 Hz, 3H, CH$_2$ (Et)), 6.83-6.85 (m, 16H, ArH); GC RI: MS m/z (relative intensity, %): 1,4-dimethoxy benzene 3c{1,1} 1122: 139 (M$^+$+H, 80), 138 (M$^+$, 100); 1-ethoxy-4-methoxy benzene 3c{1,2} 1188: 153 (M$^+$+H, 73), 152 (M$^+$, 100); 1-methoxy-4-propoxy-benzene 3c{1,3} 1281: 167 (M$^+$+H, 48), 166 (M$^+$, 100); 1-methoxy-4-(3-methyl-butyloxy) benzene 3c{1,5} 1442: 195 (M$^+$+H, 48), 194 (M$^+$, 100).

3c{2,1-5} Ethyl library (Method A, 31% yield), 3c{3,1-5} propyl library (Method A, 82% yield), 3c{4,1-5} butyl library (Method A, 76% yield), 3c{5,1-5} isopentyl (3-methyl-butyloxy) library (Method A, 82% yield), 3c{6, 1-5} allyl library (Method B, 95% yield); $^1$H NMR and GC-MS data:

3c{2,1-5} Ethyl library (Method A, 31% yield): $^1$H NMR δ: 0.96 (d, J=6.7 Hz, 6H, CH$_3$ (i-Pent)), 1.03 (t, J=7.4 Hz, 3H, CH$_3$ (Pr)), 1.39 (t, J=7.0 Hz, 15H, CH$_3$ (Et)), 1.66 (apparent q, J=6.8 Hz, 3H, CH$_2$ (i-Pent)), 1.77-1.83 (m, 4H), 3.77 (s, 3H, OCH$_3$ (Me)), 3.87 (t, J=6.6 Hz, 2H, OCH$_2$ (Pr)), 3.94 (t, J=6.7 Hz, 2H, OCH$_2$ (i-Pent)), 3.98 (q, J=7.0 Hz, 10H, OCH$_2$ (Et)), 6.83-6.84 (m, 16H, ArH)); GC RI: MS m/z (relative intensity, %): 1,4-diethoxy benzene 3c{2,2} 1248: 167 (M$^+$+H, 33), 166 (M$^+$, 100); 1-ethoxy-4-propoxy benzene 3c{2,3} 1337: 181 (M$^+$+H, 28), 180 (M$^+$, 100); 1-ethoxy-4-(3-methyl-butyloxy) benzene 3c{2,5} 1492: 209 (M$^+$+H, 31), 208 (M$^+$, 100).

3c{3,1-5} Propyl library (Method A, 82% yield): $^1$H NMR δ: 0.97 (d, J=6.6 Hz, 7H, CH$_3$ (i-Pent)), 1.03 (t, J=7.4 Hz, 15H, CH$_3$ (Pr)), 1.40 (t, J=6.9 Hz, 3H, CH$_3$ (Et)), 1.66 (apparent q, J=6.8 Hz, 3H, CH$_2$ (i-Pent)), 1.77-1.85 (m, 12H), 3.77 (s, 3H, OCH$_3$ (Me)), 3.87 (t, J=6.5 Hz, 10H, OCH$_2$ (Pr)), 3.94 (t, J=6.6 Hz, 2.8H, OCH$_2$ (i-Pent)), 3.98 (q, J=7.1 Hz, 2H, OCH$_2$ (Et)), 6.83-6.84 (m, 16H, ArH); GC RI: MS m/z (relative intensity, %): 1,4-dipropoxy benzene 3c{3,3} 1431: (M$^+$+H, 25), 194 (M$^+$, 100); 1-(3-methyl-butyloxy)-4-propoxy benzene 3c{3,5} 1589: 223 (M$^+$+H, 28), 222 (M$^+$, 100).

3c{4,1-5} Butyl library (Method A, 76% yield): $^1$H NMR δ: 0.96-0.99 (m, 18H), 1.02 (t, J=7.4 Hz, 3H, CH$_3$ (Pr)), 1.39 (t, J=6.9 Hz, 4H, CH$_3$ (Et)), 1.45-1.53 (m, 8H, CH$_2$ (Bu)), 1.66 (apparent q, J=6.7 Hz, 2H, CH$_2$ (i-Pent)), 1.72-1.81 (m, 11.6H), 3.77 (s, 3H, OCH$_3$ (Me)), 3.87 (t, J=6.6 Hz, 2H, OCH$_2$ (Pr)), 3.90-3.95 (m, 10.4H), 3.98 (q, J=7.0 Hz, 2H, OCH$_2$ (Et)), 6.83-6.84 (m, 16H, ArH); GC RI: MS m/z (relative intensity, %): 1-butoxy-4-methoxy benzene 3c{4,1} 1371: 181 (M$^+$+H, 29), 180 (M$^+$, 100); 1-butoxy-4-ethoxy benzene 3c{4,2} 1437: 195 (M$^+$+H, 23), 194 (M$^+$, 100); 1-butoxy-4-propoxy benzene 3c{4,3} 1529: 209 (M$^+$+H, 40), 208 (M$^+$, 100); 1-butoxy-4-(3-methyl-butyloxy) benzene 3c{4,5} 1681: 237 (M$^+$+H, 42), 236 (M$^+$, 100).

3c{5,1-5} Isopentyl (3-methyl-butyloxy) library. (Method A, 82% yield): $^1$H NMR δ: 0.96 (d, J=7.0 Hz 30H, CH$_3$ (i-Pent)), 1.02 (t, J=7.4 Hz, 3H, CH$_3$ (Pr)), 1.39 (t, J=6.9 Hz, 3H, CH$_3$ (Et)), 1.66 (apparent q, J=6.8 Hz, 10H, CH$_2$ (i-Pent)), 1.75-1.86 (m, 7.5H), 3.77 (s, 3H, OCH$_3$ (Me)), 3.87 (t, J=6.4 Hz, 2H, OCH$_2$ (Pr)), 3.94 (t, J=6.9 Hz, 10H, OCH$_2$ (i-Pent)), 3.98 (q, J=6.8 Hz, 2H, OCH$_2$ (Et)), 6.83-6.84 (m, 16H, ArH); GC RI: MS m/z (relative intensity, %): 1,4-di(3-methyl-butyloxy)-benzene 3c{5,5} 1850: 251 (M$^+$+H, 25), 250 (M$^+$, 100).

3c{6,1-5} Allyl library. (Method B, 95% yield): GC (RI): $^1$H NMR δ: 0.95-0.98 (m, 8H), 1.03 (t, J=7.4 Hz, 3H, CH$_3$ (Pr)), 1.39 (t, J=7.0 Hz, 3.9H, CH$_3$ (Et)), 1.46-1.50 (m, 1.5H), 1.56 (d, J=3.8 Hz, 1.3H), 1.65 (apparent q, J=6.8 Hz, 2H, CH$_2$ (i-Pent)), 1.71-1.85 (m, 5H), 3.78 (s, 4H, OCH$_3$ (Me)), 3.87 (t, J=6.6 Hz, 2H, OCH$_2$ (Pr)), 3.90-3.95 (m, 3.7H), 3.98 (q, J=7.0 Hz, 2.5H, OCH$_2$ (Et)), 4.47-4.49 (m, 10.9H), 5.25-5.29 (m, 5.H), 5.38-5.42 (m, 5H), 6.01-6.09 (m, 5H), 6.81-6.87 (m, 21H, ArH); GC RI: MS m/z (relative intensity, %): 1-allyloxy-4-methoxy benzene 3c{6,1} 1326: 165 (M$^+$+H, 20), 164 (M$^+$, 100); 1-allyloxy-4-ethoxy benzene 3c{6,2} 1394: 179 (M$^+$+H, 70), 178 (M$^+$, 100); 1-allyloxy-4-propoxy benzene 3c{6,3} 1491: 193 (M$^+$+H, 65), 192 (M$^+$, 100); 1-allyloxy-4-butoxy benzene 3c{6,4} 1594: 207 (M$^+$+H, 56), 206 (M$^+$, 100); 1-allyloxy-4-(3-methyl-butoxy) benzene 3c{6,5} 1659: 221 (M$^+$+H, 46), 220 (M$^+$, 100).

The following procedures were used to generate mini-libraries in Set B.

The allyloxy-alkoxy mini-library 3(a-c){6,1-5} was heated at 180° C. in a sealed tube, under a nitrogen atmosphere. Reaction progress was monitored by GC. In order to remove the color, the crude libraries were passed through a silica column (top charcoal layer, chloroform as eluent).

The following data were generated for mini-libraries in Set B

4a{1-5} 95% yield: $^1$H NMR δ: 0.97-1.00 (m, 7.3H), 1.05 (t, J=7.4 Hz, 3H, CH$_3$ (Pr)), 1.44 (t, J=7.0 Hz, 3.8H, CH$_3$ (Et)), 1.50 (q, J=7.6 Hz, 1.7H), 1.71 (apparent q, J=6.8 Hz, 1.5H, CH$_2$ (i-Pent)), 1.77-1.88 (m, 4.4H), 3.42 (d, J=6.6 Hz, 9.3H), 3.89 (s, 3.7H, OCH$_3$ (Me)), 3.99 (t, J=6.5 Hz, 2H, OCH$_2$ (Pr)), 4.02-4.07 (m, 3.8H), 4.10 (q, J=7.0 Hz, 2.7H, OCH$_2$ (Et)), 5.04-5.11 (m, 10.2H), 1.69 (s, 1.2H, OH), 5.73 (s, 0.5H, OH), 5.74 (s, 0.8H, OH), 5.75 (s, 1.8H, OH), 5.98-6.06 (m, 4H), 6.70-6.86 (m, 13.8H, ArH); GC RI: MS m/z (relative intensity, %): 2-allyl-6-methoxy phenol 4a{1} 1358: 165 (M$^+$+H, 23), 164 (M$^+$, 100); 2-allyl-6-ethoxy phenol 4a{2} 1413: 179 (M$^+$+H, 25), 178 (M$^+$, 100); 2-allyl-6-propoxy phenol 4a{3} 1504: 193 (M$^+$+H, 22), 192 (M$^+$, 100); 2-allyl-6-butoxy phenol 4a{4} 1603: 207 (M$^+$+H, 22), 206 (M$^+$, 100); 2-allyl-6-(3-methyl-butoxy) phenol 4a{5} 1664: 221 (M$^+$+H, 21), 220 (M$^+$, 100).

4b$^{x,y}${1} 82% yield: $^1$H NMR δ: 3.35 (m, 3.8H, CH$_2$ (Allyl$^x$)), 3.47 (m, 2H, CH$_2$ (Allyl$^y$)), 3.77 (s, 6.6H, OCH$_3$ (Me$^x$)), 3.81 (s, 3H, OCH$_3$(Me$^y$)), 5.01 (s, 1H, OH$^y$), 5.04 (s, 1.7H, OH$^x$), 5.08-5.13 (m, 2.1H), 5.14-5.18 (m, 3.8H), 5.95-6.04 (m, 2.6H), 6.42 (d, J=2.5 Hz, 1.7H, ArH$^x$), 6.46 (dd, J=2.5 and 8.3 Hz, 1.7H, ArH$^x$), 6.50 (dd, J=6.5 and 7.9 Hz, 2H, ArH$^y$), 7.00 (d, J=8.3 Hz, 1.7H, ArH$^x$), 7.08 (t, J=8.2 Hz, 1H, ArH$^y$); GC RI: MS m/z (relative intensity, %): 2-allyl-5-methoxy phenol 4b$^x${1} 1393: 165 (M$^+$+H, 30), 164 (M$^+$, 100); 2-allyl-3-methoxy phenol 4b$^y${1} 1446: 165 (M$^+$+H, 37), 164 (M$^+$, 100).

4b$^{x,y}${2-3} 64% yield: $^1$H NMR δ: 1.01-1.06 (m, 10.9H, CH$_3$ (Pr)), 1.38-1.42 (m, 7.7H, CH$_3$ (Et)), 1.75-1.84 (m, 7.6H, CH$_2$CH$_3$ (Pr)), 3.34-3.35 (m, 7.3H), 3.47-3.49 (m, 4.2H), 3.86-3.92 (m, 7.5H, OCH$_2$ (Pr)), 3.97-4.04 (m, 5.4H, OCH$_2$ (Et)), 5.06-5.09 (m, 7.4H), 5.11-5.12 (m, 1.3H), 5.13-5.15 (m, 6.5H), 5.17-5.18 (m, 2H), 5.94-6.04 (m, 5.6H), 6.41-6.49 (m, 11.5H, ArH), 6.98 (m, 3.5H, ArH$^y$), 7.05 (m, 2H, ArH$^y$); GC RI: MS m/z (relative intensity, %): 2-allyl-5-ethoxy phenol 4b$^x${2} 1455: 179 (M$^+$+H, 54), 178 (M$^+$, 100); 2-allyl-3-ethoxy phenol 4b$^y${2} 1517: 179 (M$^+$+H, 38), 178 (M$^+$, 100); 2-allyl-5-propoxy phenol 4b$^x${3} 1549: 193 (M$^+$+H, 62), 192 (M$^+$, 100); 2-allyl-3-propoxy phenol 4b$^y${3} 1615: 193 (M$^+$+H, 47), 192 (M$^+$, 100).

4b$^{x,y}${4-5} 31% yield: $^1$H NMR δ: 0.94-0.99 (m, 30.1H), 1.44-1.53 (m, 8.5H, CH$_2$CH$_3$ (Bu)), 1.61-1.87 (m, 17.6H), 3.34-3.35 (m, 9.5H), 3.46-3.48 (m, 4.4H), 3.90-3.98 (m, 14.6H), 5.01-5.03 (m, 6.0H), 5.06-5.09 (m, 2.2H), 5.10-5.12 (m, 1.1H), 5.13-5.18 (m, 10.1H), 5.93-6.04 (m, 6.1H), 6.41-6.50 (m, 13.6H), 6.97-6.98 (m, 4.4H, ArH$^x$), 7.03-7.07 (m, 2H, ArH$^y$); GC RI: MS m/z (relative intensity, %): 2-allyl-5-butoxy phenol 4b$^x${4} 1649: 207 (M$^+$+H, 11), 206 (M$^+$, 54), 135 (M 71, 100); 2-allyl-3-butoxy phenol 4b$^y${4} 1721: 207 (M$^+$+H, 17), 206 (M$^+$, 94), 149 (M 57, 100); 2-allyl-5-isopentoxy phenol 4b$^x${5} 1706: 221 (M$^+$+H, 11), 220 (M$^+$, 54), 135 (M 85, 100); 2-allyl-3-(3-methyl-butoxy) phenol 4b$^y${5} 1786: 221 (M$^+$+H, 17), 220 (M$^+$, 90), 150 (M 70, 100).

4c{1-5} 97% yield: $^1$H NMR δ: 0.97-0.99 (m, 8.8H), 1.03 (t, J=7.4 Hz, 3.7H, CH$_3$ (Pr)), 1.39 (t, J=7.0 Hz, 4.2H, CH$_3$ (Et)), 1.45-1.53 (m, 2H), 1.66 (apparent q, J=6.8 Hz, 2H, CH$_2$ (i-Pent)), 1.72-1.86 (m, 5.4H), 3.37-3.40 (m, 11.5H), 3.77 (s, 4.3H, OCH$_3$ (Me)), 3.86 (t, J=6.6 Hz, 2.5H, OCH$_2$ (Pr)), 3.89-3.95 (m, 3.5H), 3.98 (q, J=7.0 Hz, 2.6H, OCH$_2$ (Et)), 5.21 (broad s, 5.2H, OH), 5.13-5.17 (m, 10.6H), 5.98-6.06 (m, 5H), 6.66-6.77 (m, 16H, ArH); GC RI: MS m/z (relative intensity, %): 2-allyl-4-methoxy phenol 4c{1} 1432: 165 (M$^+$+H, 31), 164 (M$^+$, 100); 2-allyl-4-ethoxy phenol 4c{2} 1494: 179 (M$^+$+H, 31), 178 (M$^+$, 100); 2-allyl-4-propoxy phenol 4c{3} 1587: 193 (M$^+$+H, 31), 192 (M$^+$, 100); 2-allyl-4-butoxy phenol 4c{4} 1687: 207 (M$^+$+H, 29), 206 (M$^+$, 100); 2-allyl-4-(3-methyl-butoxy) phenol 4c{5} 1750: 221 (M$^+$+H, 31), 220 (M$^+$, 100).

The following data were generated for Set C

5a{1,1-5} Allyl-methyl library. (Method B, 90% yield): $^1$H NMR δ: 0.96-1.00 (m, 8.4H), 1.06 (t, J=7.4, 3.2H, CH$_3$ (Pr)), 1.44-1.47 (m, 4.4H), 1.50-1.55 (m, 2.3H), 1.73 (apparent q, J=6.8 Hz, 1.7H, CH$_2$ (i-Pent)), 1.79-1.91 (m, 5.9H), 3.40-3.43 (m, 10H), 3.81, 3.82, 3.83, 3.834, 3.84 (s, 15.2H, OCH$_3$), 3.86 (s, 4.8H, OCH$_3$), 3.95 (t, J=6.5 Hz, 2H, OCH$_2$ (Pr)), 3.98-4.03 (m, 4.4H), 4.07 (q, J=7.0 Hz, 2.7H, OCH$_2$ (Et)), 5.02-5.09 (m, 10H), 5.94-6.02 (m, 5H), 6.71-6.82 (m, 12H, ArH), 6.95-7.01 (m, 5H, ArH); GC RI: MS m/z (relative intensity, %): 1-allyl-2,3-dimethoxy benzene 5a{1,1} 1333: 179 (M$^+$+H, 50), 178 (M$^+$, 100); 1-allyl-3-ethoxy-2-methoxy benzene 5a{1,2} 1386: 193 (M$^+$+H, 79), 192 (M$^+$, 100); 1-allyl-2-methoxy-3-propoxy benzene 5a{1,3} 1481: 207 (M$^+$+H, 65), 206 (M$^+$, 100); 1-allyl-2-butoxy-3-methoxy benzene 5a{1,4} 1578: 221 (M$^+$+H, 66), 220 (M$^+$, 100); 1-allyl-2-methoxy-3-(3-methyl-butoxy) benzene 5a{1,5} 1632: 235 (M$^+$+H, 62), 234 (M$^+$, 100).

5a{2,1-5} Allyl-ethyl library (Method B, 91% yield), 5a{3,1-5} allyl-propyl library (Method B, 96% yield), 5a{4,1-5} allyl-butyl library (Method B, 92% yield), 5a{5,1-5} allyl-iPentyl library (Method B, 90% yield), 5a{6, 1-5} allyl-allyl library (Method B, 90% yield); $^1$H NMR and GC-MS data:

5a{2,1-5} Allyl-ethyl library (Method B, 91% yield): $^1$H NMR δ: 0.97-1.00 (m, 11.5H), 1.35-1.40 (m, 14.8H), 1.42-1.16 (m, 10.5H), 1.72 (apparent q, J=6.7 Hz, 1.8H, CH$_2$ (i-Pent)), 1.78-1.91 (m, 5.7H), 3.43 (d, J=6.6 Hz, 9.2H), 3.84 (s, 3.9H, OCH$_3$), 3.91-4.12 (m, 20.9H), 5.01-5.10 (m, 10.3H), 5.94-6.02 (m, 5H), 6.69-6.83 (m, 11.4H, ArH), 6.90-7.00 (m, 6.7H, ArH); GC RI: MS m/z (relative intensity, %): 1-allyl-2,3-diethoxy benzene 5a{2,2} 1435: 207 (M$^+$+H, 63), 206 (M$^+$, 100); 1-allyl-2-ethoxy-3-propoxy benzene 5a{2,3} 1523: 221 (M$^+$+H, 56), 220 (M$^+$, 100); 1-allyl-2-butoxy-3-ethoxy benzene 5a{2,4} 1616: 235 (M$^+$+H, 88), 234 (M$^+$, 100); 1-allyl-2-ethoxy-3-(3-methyl-butoxy) benzene 5a{2,5} 1669: 249 (M$^+$+H, 79), 248 (M$^+$, 100).

5a{3,1-5} Allyl-propyl library. (Method B, 96% yield): $^1$H NMR δ: 0.97-1.08 (m, 27.8H), 1.44 (t, J=7.0 Hz, 4H), 1.49-1.56 (m, 2.3H), 1.69-1.89 (m, 16.3H), 3.42 (d, J=6.6 Hz, 9.5H), 3.84 (s, 4H, OCH$_3$), 3.86-4.09 (m, 21H), 5.02-5.08 (m, 10H), 5.94-6.02 (m, 5H), 6.69-6.83 (m, 11.4H, ArH), 6.89-6.99 (m, 6H, ArH); GC RI: MS m/z (relative intensity, %): 1-allyl-2,3-dipropoxy benzene 5a{3,3} 1608: 235 (M$^+$+H, 57), 234 (M$^+$, 100); 1-allyl-3-butoxy-2-propoxy benzene 5a{3,4} 1699: 249 (M$^+$+H, 100), 248 (M$^+$, 72); 1-allyl-3-(3-methyl-butoxy)-2-propoxy benzene 5a{3,5} 1751: 263 (M$^+$+H, 50), 262 (M$^+$, 90), 249 (100).

5a{4,1-5} Allyl-butyl library. (Method B, 92% yield): $^1$H NMR δ: 0.96-0.99 (m, 22.3H), 1.05 (t, J=7.4 Hz, 2.7H), 1.43 (t, J=6.9 Hz, 4.2H), 1.47-1.54 (m, 12.2H), 1.69-1.89 (m, 16.7H), 3.42 (d, J=6.6 Hz, 9.2H), 3.84 (s, 4H, OCH$_3$), 3.88-4.11 (m, 19H), 5.02-5.10 (m, 10.3H), 5.93-6.01 (m, 5H), 6.69-6.83 (m, 11.4H, ArH), 6.89-6.99 (m, 6.5H, ArH); GC RI: MS m/z (relative intensity, %): 1-allyl-2,3-dibutoxy benzene 5a{4,4} 1784: 263 (M$^+$+H, 27), 262 (M$^+$, 100); 1-allyl-2-butoxy-3-(3-methyl-butoxy) benzene 5a{4,5} 1833: 277 (M$^+$+H, 25), 276 (M$^+$, 100).

5a{5,1-5} Allyl-iPentyl library. (Method B, 90% yield): $^1$H NMR δ: 0.95-1.00 (m, 37.6H), 1.06 (t, J=7.5 Hz, 2.7H), 1.44 (t, J=7.0 Hz, 4.3H), 1.49-1.55 (m, 2.1H), 1.65-1.72 (m, 12.4H), 1.78-1.90 (m, 10H), 3.41 (d, J=6.6 Hz, 9.4H), 3.84 (s, 4H, OCH$_3$), 3.91-4.08 (m, 19H), 5.01-5.09 (m, 10.2H), 5.93-6.01 (m, 5H), 6.69-6.83 (m, 11.1H, ArH), 6.89-6.99 (m, 7.2H, ArH); GC RI: MS m/z (relative intensity, %): 1-allyl-2,3-di(3-methyl-butoxy) benzene 5a{5,5} 1879: 291 (M$^+$+H, 23), 290 (M$^+$, 100).

5a{6,1-5} Allyl-allyl library. (Method B, 90% yield): $^1$H NMR δ: 0.88-0.93 (m, 11.3H), 0.96-1.01 (m, 2.7H), 1.36-1.39 (m, 2.7H), 1.45 (t, J=7.3 Hz, 2.7H), 1.65 (q, J=6.7 Hz, 2.3H), 1.70-1.83 (m, 6H), 3.25 (d, J=7.0 Hz, 1.5H), 3.35 (d, J=6.6 Hz, 8.7H), 3.78 (s, 2.5H, OCH$_3$), 3.86-4.04 (m, 9.5H), 4.40-4.54 (m, 10.3H), 4.95-5.02 (m, 10.2H), 5.13-5.20 (m, 5H), 5.27-5.36 (m, 5H), 5.84-5.92 (m, 5H), 5.97-6.08 (m, 5H), 6.61-6.76 (m, 11.1H, ArH), 6.82-6.94 (m, 5H, ArH); GC RI: MS m/z (relative intensity, %): 1-allyl-2-allyloxy-3-metoxy benzene 5a{6,1} 1463: 205 (M$^+$+H, 84), 204 (M$^+$, 100); 1-allyl-2-allyloxy-3-ethoxy benzene 5a{6,2} 1509: 219 (M$^+$+H, 100), 218 (M$^+$, 95); 1-allyl-2-allyloxy-3-propoxy benzene 5a{6,3} 1597: 233 (M$^+$+H, 100), 232 (M$^+$, 87); 1-allyl-2-allyloxy-3-butoxy benzene 5a{6,4} 1688: 247 (M$^+$+H, 100), 246 (M$^+$, 91); 1-allyl-2-allyloxy-3-(3-methyl-butoxy) benzene 5a{6,5} 1740: 261 (M$^+$+H, 100), 260 (M$^+$, 92).

5b$^{x,y}${1,1} Allyl-methyl library A. (Method B, 90% yield): $^1$H NMR δ: 3.30-3.31 (m, 3.9H, CH$_2$(Allyl$^x$)), 3.41 (dt, J=1.6 and 6.1 Hz, 2H, CH$_2$ (Allyl$^y$)), 3.79 (s, 6H (1\46), 3.80 (s, 5.4H (Me$^x$)), 3.81 (s, 5.4H (Me$^y$)), 4.91-4.95 (m, 1.6H), 4.97-5.04 (m, 4.2H), 5.91-6.01 (m, 2.8H), 6.42-6.45 (m, 3.7H, ArH$^x$), 6.55 (d, J=8.3 Hz, 2H, ArH$^y$), 7.03 (d, J=8.1 Hz, 1.7H, ArH$^x$), 7.15 (t, J=8.3 Hz, 1H, ArH$^y$); GC RI: MS m/z (relative intensity, %): 2-allyl-1,3-dimethoxy benzene 5b$^y${1,1} 1378: 179 (M$^+$+H, 30), 178 (M$^+$, 100), 1-allyl-2,4-dimethoxy benzene 5b$^x${1,1} 1411: 179 (M$^+$+H, 28), 178 (M$^+$, 100).

5b$^{x,y}${1,2-3} Allyl-methyl library B. (Method B, 61% yield): $^1$H NMR δ: 1.02-1.06 (m, 11.4H, CH$_3$ (Pr)), 1.38-1.42 (m, 7.6H, CH$_3$ (Et)), 1.77-1.84 (m, 7.9H, CH$_2$ (Pr)), 3.30-3.31 (m, 7.1H), 3.42-3.44 (m, 4.4H), 3.80 (m, 10.4H (Me$^x$)), 3.81 (m, 6.1H (Me$^y$)), 3.89-3.93 (m, 7.8H), 4.00-4.05 (m, 4.9H), 4.91-4.93 (m, 2.1H), 4.98-5.04 (m, 8.8H), 5.91-6.01 (m, 5.2H), 6.42-6.46 (m, 7.3H, ArH$^x$), 6.52-6.54 (m, 4.2H, ArH$^y$), 7.00-7.01 (m, 3.2H, ArH$^x$), 7.10-7.13 (m, 2.0H, ArH$^y$); GC RI: MS m/z (relative intensity, %): 2-allyl-1-ethoxy-3-methoxy benzene 5b$^y${1,2} 1435: 193 (M$^+$+H, 30), 192 (M$^+$, 70), 163 (M 29, 100); 1-allyl-4-ethoxy-2-methoxy benzene 5b$^x${1,2} 1480: 193 (M$^+$+H, 41), 192 (M$^+$, 100), 163 (M 29, 28); 2-allyl-1-methoxy-3-propoxy benzene 5b$^y${1,3} 1527: 207 (M$^+$+H, 62), 206 (M$^+$, 100), 177 (M 29, 68); 1-allyl-2-methoxy-4-propoxy benzene 5b$^x${1,3} 1573: 207 (M$^+$+H, 52), 206 (M$^+$, 100), 177 (M 29, 1).

5b$^{x,y}${1,4-5} Allyl-methyl library C. (Method B, 77% yield): $^1$H NMR δ: 0.95-0.99 (m, 30.7H), 1.45-1.54 (m, 8.7H, CH$_2$ (Bu)), 1.65-1.69 (m, 6.4H), 1.73-1.90 (m, 11.8H), 3.29-3.31 (m, 8.3H), 3.41-3.42 (m, 4.4H), 3.80 (m, 11.7H (Me$^x$)), 3.81 (m, 6.0H (Me$^y$)), 3.93-3.99 (m, 14.4H), 4.90-4.93 (m, 2.1H), 4.96-5.04 (m, 10.1H), 5.90-6.01 (m, 5.6H), 6.41-6.45 (m, 8.6H, ArH$^x$), 6.52-6.54 (m, 4.2H, ArH$^y$), 6.99-7.01 (m, 3.8H, ArH$^x$), 7.10-7.14 (m, 2H, ArH$^y$); GC RI: MS m/z (relative intensity, %): 2-allyl-3-methoxy-1-butoxy benzene 5b$^y${1,4} 1624: 221 (M$^+$+H, 36), 220 (M$^+$, 100), 191 (M−29, 79); 1-allyl-2-methoxy-4-butoxy benzene 5b$^x${1,4} 1672: 221 (M$^+$+H, 34), 220 (M$^+$, 100), 191 (M−29, 1); 2-allyl-1-methoxy-3-(3-methyl-butoxy) benzene 5b$^y${1,5} 1680: 235 (M$^+$+H, 32), 234 (M$^+$, 100), 205 (M−29, 47); 1-allyl-2-methoxy-4-(3-methyl-butoxy) benzene 5b$^x${1,5} 1731: 235 (M$^+$+H, 31), 234 (M$^+$, 100), 205 (M−29, 0).

5b$^{x,y}${2,1} Allyl-ethyl library A (Method B, 70% yield), 5b$^{x,y}${2,2-3} allyl-ethyl library B (Method B, 80% yield), 5b$^{x,y}${2,4-5} allyl-ethyl library C (Method B, 48% yield), 5b$^{x,y}${3,1} allyl-propyl library A (Method B, 88% yield), 5b$^{x,y}${3,2-3} allyl-propyl library B (Method B, 80% yield), 5b$^{x,y}${3,4-5} allyl-propyl library C (Method B, 62% yield), 5b$^{x,y}${4,1} allyl-butyl library A (Method B, 81% yield), 5b$^{x,y}${4,2-3} allyl-butyl library B (Method B, 52% yield), 5b$^{x,y}${4,4-5} allyl-butyl library C (Method B, 64% yield), 5b$^{x,y}${5,1} allyl-ipentyl library A (Method B, 64% yield), 5b$^{x,y}${5,2-3} allyl-ipentyl library B (Method B, 74% yield), 5b$^{x,y}${5,4-5} allyl-ipentyl library C (Method B, 82% yield), 5b$^{x,y}${6,1} allyl-allyl library A (Method B, 67% yield), 5b$^{x,y}${6,2-3} allyl-allyl library B (Method B, 53% yield), 5b$^{x,y}${6,4-5} allyl-allyl library C (Method B, 76% yield): $^1$H NMR and GC-MS:

5b$^{x,y}${2,1} Allyl-ethyl library A. (Method B, 70% yield): $^1$H NMR δ: 1.38-1.42 (m, 8.9H, CH$_3$ (Et)), 3.31-3.32 (m, 3.5H, CH$_2$(Allyl$^x$)), 3.42 (dt, J=1.5 and 6.3 Hz, 2H CH$_2$ (Allyl$^y$)), 3.78 (s, 5.2H Me$^x$), 3.82 (s, 3H (MO), 3.99-4.05 (m, 6.2H), 4.91-4.94 (m, 1H), 4.98-5.07 (m, 4.6H), 5.91-6.01 (m, 2.5H), 6.42-6.44 (m, 3.4H, ArH$^x$), 6.54 (d, J=8.3 Hz, 2H, ArH$^y$), 7.03 (d, J=7.9 Hz, 1.6H, ArH$^x$), 7.12 (t, J=8.3 Hz, 1H, ArH$^y$); GC RI: MS m/z (relative intensity, %): 2-allyl-1-ethoxy-3-methoxy benzene 5b$^y${2,1} 1435: 193 (M$^+$+H, 75), 192 (M$^+$, 100); 1-allyl-2-ethoxy-4-methoxy benzene 5b$^x${2,1} 1471: 193 (M$^+$+H, 47), 192 (M$^+$, 100).

5b$^{x,y}${2,2-3} Allyl-ethyl library B. (Method B, 80% yield): $^1$H NMR δ: 1.01-1.06 (m, 11.6H, CH$_3$ (Pr)), 1.39-1.42 (m, 26.6H, CH$_3$ (Et)), 1.76-1.84 (m, 8H, CH$_2$ (Pr)), 3.31-3.32 (m, 7.7H), 3.42-3.45 (m, 4.4H), 3.88-3.93 (m, 8H, OCH$_2$ (Pr)), 3.98-4.04 (m, 18.1H, OCH$_2$ (Et)), 4.91-4.93 (m, 2.1H), 4.99-5.07 (m, 9.5H), 5.91-6.01 (m, 5.4H), 6.40-6.45 (m, 7.6H, ArH$^x$), 6.50-6.52 (d, 4.1H, ArH$^y$), 7.00-7.02 (m, 3.5H, ArH$^x$), 7.07-7.11 (m, 2H, ArH$^y$); GC RI: MS m/z (relative intensity, %): 2-allyl-1,3-diethoxy benzene 5W{2,2} 1490: 207 (M$^+$+H, 80), 206 (M$^+$, 100); 1-allyl-2,4-diethoxy benzene 5b$^x${2,2} 1535: 207 (M$^+$+H, 62), 206 (M$^+$, 100); 2-allyl-1-ethoxy-3-propoxy benzene 5b$^y${2,3} 1587: 221 (M$^+$+H, 100), 220 (M$^+$, 94); 1-allyl-2-ethoxy-4-propoxy benzene 5b$^x${2,3} 1627: 221 (M$^+$+H, 67), 220 (M$^+$, 100).

5b$^{x,y}${2,4-5} Allyl-ethyl library C. (Method B, 48% yield): $^1$H NMR δ: 0.95-0.99 (m, 29.6H), 1.38-1.42 (m, 21.5H, CH$_3$ (Et)), 1.45-1.53 (m, 8.5H, CH$_2$CH$_3$ (Bu)), 1.64-1.70 (m, 6.4H, CH$_2$CH (iPent)), 1.72-1.91 (m, 11.2H), 3.30-3.32 (m, 9.1H), 3.42-3.43 (m, 4.3H), 3.92-4.04 (m, 29.2H), 4.90-4.93 (m, 2.1H), 4.98-5.06 (m, 10.7H), 5.90-6.01 (m, 6H), 6.40-6.44 (m, 9H, ArH$^x$), 6.50-6.53 (m, 4.2H, ArH$^y$), 7.00-7.01 (m, 4.2H, ArH$^x$), 7.07-7.11 (m, 2H ArH$^y$); GC RI: MS m/z (relative intensity, %): 2-allyl-1-butoxy-3-ethoxy benzene 5b$^y${2,4} 1682: 235 (M$^+$+H, 43), 234 (M$^+$, 85), 149 (M−86, 100); 1-allyl-4-butoxy-2-ethoxy benzene 5b$^x${2,4} 1724: 235 (M$^+$+H, 42), 234 (M$^+$, 100); 2-allyl-1-ethoxy-3-(3-methyl-butoxy) benzene 5b$^y${2,5} 1739: 249 (M$^+$+H, 31), 248 (M$^+$, 69), 149 (M−99, 100); 1-allyl-2-ethoxy-4-(3-methyl-butoxy) benzene 5b$^x${2,5} 1784: 249 (M$^+$+H, 34), 248 (M$^+$, 98), 149 (M−99, 100).

5b$^{x,y}${3,1} Allyl-propyl library A. (Method B, 88% yield): $^1$H NMR δ: 1.03-1.06 (m, 9.1H, CH$_3$ (Pr)), 1.77-1.85 (m, 6.4H, CH$_2$CH$_3$ (Pr)), 3.32-3.33 (m, 3.9H, CH$_2$ (Allyl$^x$)), 3.43-3.44 (m, 2.2H, CH$_2$ (Allyl$^y$)), 3.79 (s, 5.6H (Me$^x$)), 3.82 (s, 3H (MO), 3.89-3.93 (m, 6.2H, OCH$_2$ (Pr)), 4.91-4.94 (m, 1.1H), 4.98-5.07 (m, 4.7H), 5.91-6.01 (m, 2.8H), 6.41-6.44 (m, 3.8H, ArH$^x$), 6.52-6.54 (m, 2H, ArH$^y$), 7.03 (d, J=8.0 Hz, 1.6H, ArH$^x$), 7.12 (t, J=8.3 Hz, 1H, ArH$^y$); GC RI: MS m/z (relative intensity, %): 2-allyl-1-methoxy-3-propoxy benzene 5b$^y${3,1} 1527: 207 (M$^+$+H, 100), 206 (M$^+$, 97); 1-allyl-4-methoxy-2-propoxy benzene 5b$^x${3,1} 1573: 207 (M$^+$+H, 51), 206 (M$^+$, 100).

5b$^{x,y}${3,2-3} Allyl-propyl library B. (Method B, 80% yield): $^1$H NMR δ: 1.03-1.08 (m, 30H, CH$_3$ (Pr)), 1.40-1.43 (m, 7.4H, CH$_3$ (Et)), 1.78-1.86 (m, 20.8H, CH$_2$CH$_3$ (Pr)), 3.33-3.34 (m, 7.5H), 3.45-3.47 (m, 4.4H), 3.90-3.94 (m, 20.4H, OCH$_2$ (Pr)), 4.00-4.06 (m, 5.3H, OCH$_2$ (Et)), 4.92-4.95 (m, 2H), 5.00-5.08 (m, 9H), 5.93-6.03 (m, 4.8H), 6.41-6.46 (m, 7.3H, ArH$^x$), 6.51-6.53 (m, 4.2H, ArH$^y$), 7.01-7.03 (m, 3.4H, ArH$^x$), 7.09-7.12 (m, 2H, ArH$^y$); GC RI: MS m/z (relative intensity, %): 2-allyl-1-ethoxy-3-propoxy benzene 5b$^y${3,2} 1587: 221 (M$^+$+H, 39), 220 (M$^+$, 89), 149 (M−71, 100); 1-allyl-4-ethoxy-2-propoxy benzene 5b$^x${3,2} 1624: 221 (M$^+$+H, 29), 220 (M$^+$, 100), 149 (M−71, 53); 2-allyl-1,3-dipropoxy benzene 5b$^y${3,3} 1682: 235 (M$^+$+H, 50), 234 (M$^+$, 100); 1-allyl-2,4-dipropoxy benzene 5b$^x${3,3} 1713: 235 (M$^+$+H, 39), 234 (M$^+$, 100).

5b$^{x,y}${3,4-5} Allyl-propyl library C. (Method B, 62% yield): $^1$H NMR δ: 0.95-0.98 (m, 29.4H), 1.02-1.06 (m, 20.9H, CH$_3$ (Pr)), 1.44-1.53 (m, 8.2H, CH$_2$CH$_3$ (Bu)), 1.64-1.69 (m, 6.4H, CH$_2$CH (iPent)), 1.72-1.89 (m, 26.1H), 2.17 (m, 5.8H (Me)), 3.31-3.32 (m, 9H), 3.42-3.44 (m, 4.3H), 3.88-3.98 (m, 29.1H), 4.89-4.92 (m, 2H), 4.98-5.06 (m, 10.6H), 5.89-6.00 (m, 5.8H), 6.39-6.43 (m, 8.9H, ArH$^x$), 6.49-6.52 (m, 4.9H, ArH$^y$), 6.99-7.01 (m, 4.2H, ArH$^x$), 7.07-7.10 (m, 2H, ArH$^y$); GC RI: MS m/z (relative intensity, %): 2-allyl-1-butoxy-3-propoxy benzene 5b$^y${3,4} 1778: 249 (M$^+$+H, 85), 248 (M$^+$, 100); 1-allyl-4-butoxy-2-propoxy benzene 5b$^x${3,4} 1813: 249 (M$^+$+H, 46), 248 (M$^+$, 100); 2-allyl-1-(3-methyl-butoxy)-3-propoxy benzene 5b$^y${3,5} 1835: 263 (M$^+$+H, 69), 262 (M$^+$, 100), 1-allyl-2-propoxy-4-(3-methyl-butoxy) benzene 5b$^x${3,5} 1870: 263 (M$^+$+H, 45), 262 (M$^+$, 100).

5b$^{x,y}${4,1} Allyl-butyl library A. (Method B, 81% yield): $^1$H NMR δ: 0.95-0.98 (m, 9.9H, CH$_3$ (Bu)), 1.46-1.54 (m, 6.1H, CH$_2$CH$_3$ (Bu)), 1.73-1.79 (m, 6.3H, OCH$_2$CH$_2$ (Bu)), 3.30-3.32 (m, 3.7H, CH$_2$ (Allyl$^x$)), 3.42 (dt, J=1.3 and 6.3 Hz, 2H, CH$_2$ (Allyl$^y$)), 3.78 (s, 5.3H (Me$^x$)), 3.81 (s, 3H (MO), 3.92-3.96 (m, 6.3H, OCH$_2$ (Bu)), 4.99-4.93 (m, 1H), 4.96-5.05 (m, 4.7H), 5.90-6.00 (m, 2.7H), 6.40-6.43 (m, 3.6H, ArH$^x$), 6.53 (d, J=8.3 Hz, 2H, ArH$^y$), 7.02 (d, J=8.1 Hz, 1.7H, ArH$^x$), 7.11 (t, J=8.3 Hz, 1H, ArH$^y$); GC RI: MS m/z (relative intensity, %): 2-allyl-1-butoxy-3-methoxy benzene 5W{4,1} 1625: 221 (M$^+$+H, 66), 220 (M$^+$, 100); 1-allyl-2-butoxy-4-methoxy benzene 5b$^x${4,1} 1656: 221 (M$^+$+H, 37), 220 (M$^+$, 100).

5b$^{x,y}${4,2-3} Allyl-butyl library B. (Method B, 52% yield): $^1$H NMR δ: 0.95-0.98 (m, 17.7H, CH$_3$ (Bu)), 1.01-1.06 (m, 8.6H, CH$_3$ (Pr)), 1.38-1.41 (m, 9.5H, CH$_3$ (Et)), 1.46-1.54 (m, 12.3H), 1.74-1.83 (m, 18.4H), 3.31-3.32 (m, 7.8H), 3.43-3.45 (m, 3.9H), 3.88-4.04 (m, 25.8H), 4.91-4.93 (m, 1.9H), 4.99-5.06 (m, 9.6H), 5.90-6.01 (m, 5.7H), 6.40-6.45 (m, 8H, ArH$^x$), 6.50-6.52 (m, 4H, ArH$^y$), 7.00-7.01 (m, 3.8H, ArH$^x$), 7.07-7.11 (m, 2H, ArH$^y$); GC RI: MS m/z (relative intensity, %): 2-allyl-1-butoxy-3-ethoxy benzene 5b$^y${4,2} 1681: 235 (M$^+$+H, 55), 234 (M$^+$, 88), 149 (M−85, 100); 1-allyl-2-butoxy-4-ethoxy benzene 5b$^x${4,2} 1714: 235 (M$^+$+H, 38), 234 (M$^+$, 100); 2-allyl-1-butoxy-3-propoxy benzene 5b$^y${4,3} 1777: 249 (M$^+$+H, 59), 248 (M$^+$, 100); 1-allyl-2-butoxy-4-propoxy benzene 5b$^x${4,3} 1803: 249 (M$^+$+H, 41), 248 (M$^+$, 100).

5b$^{x,y}${4,4-5} Allyl-butyl library C. (Method B, 64% yield): $^1$H NMR δ: 0.95-0.99 (m, 48.9H), 1.43-1.55 (m, 20H, CH$_2$CH$_3$ (Bu)), 1.64-1.70 (m, 8.2H), 1.72-1.90 (m, 25.5H), 3.30-3.32 (m, 7H), 3.42-3.44 (m, 4.1H), 3.92-3.99 (m, 25.5H), 4.90-4.93 (m, 2H), 4.98-5.05 (m, 9.1H), 5.89-6.01 (m, 5.2H), 6.39-6.44 (m, 7.3H, ArH$^x$), 6.50-6.52 (m, 4.1H, ArH$^y$), 6.99-7.01 (m, 3.3H, ArH$^x$), 7.07-7.11 (m, 2H, ArH$^y$); 2-allyl-1,3-dibutoxy benzene 5b$^y${4,4} 1871: 263 (M$^+$+H, 72), 262 (M$^+$, 100); 1-allyl-2,4-dibutoxy benzene 5b$^x${4,4} 1899: 263 (M$^+$+H, 41), 262 (M$^+$, 100); 2-allyl-1-butoxy-3-(3-methyl-butoxy) benzene 5b$^y${4,5} 1926: 277 (M$^+$+H, 65), 276 (M$^+$, 100); 1-allyl-2-butoxy-4-(3-methyl-butoxy) benzene 5b$^x${4,5} 1955: 277 (M$^+$+H, 42), 276 (M$^+$, 100).

5b$^{x,y}${5,1} Allyl-ipentyl library A. (Method B, 64% yield): $^1$H NMR δ: 0.95-0.97 (m, 16.8H, CH$_3$ (iPent)), 1.66-1.71 (m, 5.8H, CH$_2$CH (iPent)), 1.82-1.91 (m, 3H, CH (iPent)), 3.31-3.32 (m, 3.6H, CH$_2$ (Allyl$^x$)), 3.41-3.43 (dt, J=1.3 and 6.3 Hz, 2.2H, CH$_2$ (Allyl$^y$)), 3.79 (s, 5.2H, CH$_3$ (Me$^x$)), 3.81 (s, 3H, CH$_3$ (MO), 3.95-3.99 (m, 6H, OCH$_2$ (iPent)), 4.90-4.93 (m, 1H), 4.97-5.06 (m, 4.7H), 5.90-6.00 (m, 2.7H), 6.41-6.45 (m, 3.5H), 6.53-6.55 (m, 2H), 7.03 (d, J=8.2 Hz, 1.7H), 7.12 (t, J=8.3 Hz, 1H); GC RI: MS m/z (relative intensity, %): 2-allyl-1-methoxy-3-(3-methyl-butoxy) benzene 5b$^y${5,1} 1684: 235 (M$^+$+H, 43), 234 (M$^+$, 100); 1-allyl-4-methoxy-2-(3-methyl-butoxy) benzene 5b$^x${5,1} 1711: 235 (M$^+$+H, 30), 234 (M$^+$, 100).

5b$^{x,y}${5,2-3} Allyl-ipentyl library B. (Method B, 74% yield): $^1$H NMR δ: 0.94-0.96 (m, 37.1H, CH$_3$ (iPent)), 1.01-1.05 (m, 9.6H, CH$_3$ (Pr)), 1.38-1.41 (m, 10.4H, CH$_3$ (Et)), 1.65-1.69 (m, 13H), 1.74-1.89 (m, 13.8H), 3.29-3.30 (m, 8.1H), 3.40-3.43 (m, 4.3H), 3.88-4.04 (m, 27H), 4.89-4.92 (m, 2.1H), 4.98-5.05 (m, 10.6H), 5.89-5.99 (m, 6.2H), 6.39-6.44 (m, 8.4H), 6.49-6.52 (m, 4.2H), 6.99-7.00 (m, 4H), 7.07-7.10 (m, 2H); GC RI: MS m/z (relative intensity, %): 2-allyl-1-ethoxy-3-(3-methyl-butoxy) benzene 5b$^y${5,2} 1736: 249 (M$^+$+H, 14), 248 (M$^+$, 52), 149 (M−99, 100); 1-allyl-4-ethoxy-2-(3-methyl-butoxy) benzene 5b$^x${5,2} 1820: 249 (M$^+$+H, 22), 248 (M$^+$, 100); 2-allyl-1-(3-methyl-butoxy)-3-propoxy benzene 5b$^y${5,3} 1834: 263 (M$^+$+H, 22), 262 (M$^+$, 80), 135 (M−127, 100); 1-allyl-2-(3-methyl-butoxy)-4-propoxy benzene 5b$^x${5,3} 1855: 263 (M$^+$+H, 26), 262 (M$^+$, 100).

5b$^{x,y}${5,4-5} Allyl-ipentyl library C. (Method B, 82% yield): $^1$H NMR δ: 0.96-1.00 (m, 68H), 1.45-1.54 (m, 8.6H, CH$_2$CH$_3$ (Bu)), 1.65-1.92 (m, 40.4H), 3.31-3.32 (m, 6.2H), 3.42-3.44 (m, 4H), 3.93-4.00 (m, 24.7H), 4.90-4.93 (m, 2H), 4.99-5.06 (m, 9.41H), 5.89-6.01 (m, 5.65H), 6.41-6.45 (m, 7.3H), 6.51-6.53 (m, 3.8H), 7.00-7.01 (m, 3.2H), 7.07-7.11 (m, 2H); GC RI: MS m/z (relative intensity, %): 2-allyl-1-butoxy-3-isopentoxy benzene 5b$^y${5,4} 1927: 277 (M$^+$+H, 42), 276 (M$^+$, 100); 1-allyl-4-butoxy-2-isopentoxy benzene 5b$^x${5,4} 1950: 277 (M$^+$+H, 32), 276 (M$^+$, 100); 2-allyl-1,3-di(3-methyl-butoxy)benzene 5b$^y${5,5} 1984: 291 (M$^+$+H, 36), 290 (M$^+$, 89), 150 (M−140, 100); 1-allyl-2,4-di(3-methyl-butoxy) benzene 5b$^x${5,5} 2006: 291 (M$^+$+H, 32), 290 (M$^+$, 100).

5b$^{x,y}${6,1} Allyl-allyl library A. (Method B, 67% yield): $^1$H NMR δ: 3.35-3.36 (m, 3.8H, CH$_2$ (Allyl$^x$)), 3.46-3.47 (m, 2H, CH$_2$ (Allyl$^y$)), 3.79 (s, 5.4H, CH$_3$ (Me$^x$)), 3.83 (s, 3H, CH$_3$ (MO), 4.52-4.55 (m, 6.3H), 4.92-4.95 (m, 1.1H), 4.99-5.08 (m, 5H), 5.25-5.30 (m, 3H), 5.41-5.46 (m, 3H), 5.93-6.10 (m, 5.7H), 6.44-6.47 (m, 3.6H), 6.55 (t, J=8.5 Hz, 2H), 7.05 (d, J=8.7 Hz, 1.7H), 7.13 (t, J=8.3 Hz, 1H); GC RI: MS m/z (relative intensity, %): 2-allyl-1-allyloxy-3-methoxy benzene 5b$^y${6,1} 1524: 205 (M$^+$+H, 29), 204 (M$^+$, 100); 1-allyl-2-allyloxy-4-methoxy benzene 5b$^x${6,1} 1554: 205 (M$^+$+H, 31), 204 (M$^+$, 100).

5b$^{x,y}${6,2-3} Allyl-allyl library B. (Method B, 53% yield): $^1$H NMR δ: 1.02-1.07 (m, 8.8H, CH$_3$ (Pr)), 1.39-1.42 (m, 9.4H, CH$_3$ (Et)), 1.76-1.85 (m, 6.2H, CH$_2$CH$_3$ (Pr)), 3.34-3.35 (m, 7.7H), 3.46-3.48 (m, 4.3H), 3.88-3.93 (m, 6H, OCH$_2$ (Pr)), 3.98-4.05 (m, 6.5H, OCH$_2$ (Et)), 4.51-4.54 (m, 12.2H), 4.91-4.94 (m, 2H), 5.00-5.07 (m, 10H), 5.24-5.28 (m, 6H), 5.40-5.45 (m, 6H), 5.92-6.09 (m, 12.1H), 6.42-6.45 (m, 7.6H), 6.51-6.54 (m, 4.2H), 7.01-7.03 (m, 3.7H), 7.08-7.11 (m, 2H); GC RI: MS m/z (relative intensity, %): 2-allyl-1-allyloxy-3-ethoxy benzene 5b$^y${6,2} 1581: 219 (M$^+$+H, 42), 218 (M$^+$, 100); 1-allyl-2-allyloxy-4-ethoxy benzene 5b$^x${6,2} 1613: 219 (M$^+$+H, 46), 218 (M$^+$, 100); 2-allyl-1-allyloxy-3-propoxy benzene 5b$^y${6,3} 1674: 233 (M$^+$+H, 31), 232 (M$^+$, 59), 149 (M−83, 100); 1-allyl-2-allyloxy-4-propoxy benzene 5b$^x${6,2} 1706: 233 (M$^+$+H, 50), 232 (M$^+$, 100).

5b$^{x,y}${6,4-5} Allyl-allyl library C. (Method B, 76% yield): $^1$H NMR δ: 0.96-0.99 (m, 28.1H), 1.45-1.54 (m, 7.5H, CH$_2$CH$_3$ (Bu)), 1.65-1.71 (m, 7H), 1.73-1.92 (m, 10.9H), 3.34-3.36 (m, 6.2H), 3.46-3.47 (m, 3.9H), 3.92-4.00 (m, 12.8H), 4.51-4.55 (m, 10.6H), 4.91-4.94 (m, 2.1H), 5.00-5.07 (m, 9.2H), 5.24-5.29 (m, 5.8H), 5.40-5.45 (m, 5.7H), 5.92-6.10 (m, 11.9H), 6.42-6.45 (m, 6.6H), 6.51-6.55 (m, 4.1H), 7.02-7.04 (m, 3.1H), 7.08-7.12 (m, 2H); GC RI: MS m/z (relative intensity, %): 2-allyl-1-allyloxy-3-butoxy benzene 5b$^y${6,4} 1771: 247 (M$^+$+H, 43), 246 (M$^+$, 63), 149 (M−97, 100); 1-allyl-2-allyloxy-4-butoxy benzene 5b$^x${6,4} 1801: 247 (M$^+$+H, 61), 246 (M$^+$, 100); 2-allyl-1-allyloxy-3-(3-methyl-butoxy) benzene 5b$^y${6,5} 1827: 261 (M$^+$+H, 74), 260 (M$^+$, 78), 149 (M−111, 100); 1-allyl-2-allyloxy-4-(3-methyl-butoxy) benzene 5b$^x${6,5} 1861: 261 (M$^+$+H, 62), 260 (M$^+$, 100).

5c{1,1-5} Allyl-methyl library. (Method B, 98% yield): $^1$H NMR δ: 0.95-0.99 (m, 8.6H), 1.03 (t, J=7.5, 3.2H, CH$_3$ (Pr)), 1.38 (t, J=7.0 Hz, 4H), 1.45-1.52 (m, 2H), 1.65 (apparent q, J=6.7 Hz, 2H, CH$_2$ (i-Pent)), 1.71-1.86 (m, 5.2H), 3.35-3.36 (m, 10.8H), 3.76 (s, 4H, OCH$_3$), 3.78-3.79 (m, 16.5H, OCH$_3$), 3.86 (t, J=6.6 Hz, 2.3H, OCH$_2$ (Pr)), 3.89-3.94 (m, 3.6H), 3.97 (q, J=7.0 Hz, 2.4H, OCH$_2$ (Et)), 5.04-5.08 (m, 10H), 5.94-6.02 (m, 4.7H), 6.70-6.80 (m, 15.6H, ArH); GC RI: MS m/z (relative intensity, %): 1-allyl-2,5-dimethoxy benzene 5c{1,1} 1397: 179 (M$^+$+H, 28), 178 (M$^+$, 100); 1-allyl-5-ethoxy-2-methoxy benzene 5c{1,2} 1462: 193 (M$^+$+H, 32), 192 (M$^+$, 100); 1-allyl-2-methoxy-5-propoxy benzene 5c{1,3} 1557: 207 (M$^+$+H, 33), 206 (M$^+$, 100); 1-allyl-5-butoxy-2-methoxy benzene 5c{1,4} 1650: 221 (M$^+$+H, 32), 220 (M$^+$, 100); 1-allyl-2-methoxy-5-(3-methyl-butoxy) benzene 5c{1,5} 1709: 235 (M$^+$+H, 29), 234 (M$^+$, 100).

5c{2,1-5} Allyl-ethyl library. (Method B, 89% yield), 5c{3,1-5} Allyl-propyl library. (Method B, 95% yield), 5c{4,1-5} Allyl-butyl library. (Method B, 95% yield), 5c{5,1-5} Allyl-iPentyl library. (Method B, 95% yield); $^1$H NMR and GC-MS data:

5c{2,1-5} Allyl-ethyl library. (Method B, 89% yield): $^1$H NMR δ: 0.94-0.98 (m, 8.7H), 1.02 (t, J=7.4 Hz, 3.7H), 1.36-1.41 (m, 21H), 1.44-1.52 (m, 2.2H), 1.62-1.66 (m, 4.5H), 1.70-1.86 (m, 5.6H), 3.36-3.38 (m, 10.9H), 3.76 (s, 4H, OCH$_3$), 3.86 (t, J=6.6 Hz, 2.6H), 3.88-3.93 (m, 4H), 3.95-3.99 (m, 14H), 5.03-5.10 (m, 10H), 5.93-6.02 (m, 4.7H), 6.66-6.78 (m, 16.2H, ArH); GC RI: MS m/z (relative intensity, %): 1-allyl-2,5-diethoxy benzene 5c{2,2} 1518: 207 (M$^+$+H, 31), 206 (M$^+$, 100); 1-allyl-2-ethoxy-5-propoxy benzene 5c{2,3} 1605: 221 (M$^+$+H, 29), 220 (M$^+$, 100); 1-allyl-5-butoxy-2-ethoxy benzene 5c{2,4} 1704: 235 (M$^+$+

H, 29), 234 (M$^+$, 100); 1-allyl-2-ethoxy-5-(3-methyl-butoxy) benzene 5c{2,5} 1763: 249 (M$^+$+H, 27), 248 (M$^+$, 100).

5c{3,1-5} Allyl-propyl library. (Method B, 95% yield): $^1$H NMR δ: 0.96-1.06 (m, 27.6H), 1.37-1.41 (m, 4H), 1.44-1.53 (m, 2H), 1.64-1.68 (m, 2.9H), 1.72-1.92 (m, 16H), 3.38 (d, J=6.4 Hz, 10.9H), 3.80 (s, 3.8H, OCH$_3$), 3.82-3.99 (m, 19.9H), 4.99-5.18 (m, 10.5H), 5.92-6.05 (m, 5H), 6.67-6.85 (m, 17.5H, ArH); GC RI: MS m/z (relative intensity, %): 1-allyl-2,5-dipropoxy benzene 5c{3,3} 1699: 235 (M$^+$+H, 26), 234 (M$^+$, 100); 1-allyl-5-butoxy-2-propoxy benzene 5c{3,4} 1798: 249 (M$^+$+H, 27), 248 (M$^+$, 100); 1-allyl-5-(3-methyl-butoxy)-2-propoxy benzene 5c{3,5} 1857: 263 (M$^+$+H, 27), 262 (M$^+$, 90), 249 (100).

5c{4,1-5} Allyl-butyl library. (Method B, 95% yield): $^1$H NMR δ: 0.94-0.98 (m, 19.5H), 1.00-1.04 (m, 3.4H), 1.36-1.39 (m, 3.6H), 1.44-1.54 (m, 9.3H), 1.57-1.58 (m, 2H), 1.64 (t, J=6.8 Hz, 1.8H), 1.70-1.85 (m, 12.5H), 3.35-3.39 (m, 10H), 3.76 (s, 3.7H, OCH$_3$), 3.86 (t, J=6.6 Hz, 2.2H), 3.88-3.93 (m, 11.2H), 3.97 (q, J=6.9 Hz, 2.4H), 5.03-5.17 (m, 9.5H), 5.93-6.06 (m, 4.5H), 6.65-6.87 (m, 16.1H, ArH); GC RI: MS m/z (relative intensity, %): 1-allyl-2,5-dibutoxy benzene 5c{4,4} 1892: 263 (M$^+$+H, 28), 262 (M$^+$, 100); 1-allyl-2-butoxy-5-(3-methyl-butoxy) benzene 5c{4,5} 1949: 277 (M$^+$+H, 28), 276 (M$^+$, 100).

5c{5,1-5} Allyl-iPentyl library. (Method B, 95% yield): $^1$H NMR δ: 0.93-0.99 (m, 27.7H), 1.03 (t, J=7.4 Hz, 3.7H), 1.39 (t, J=7.0 Hz, 4H), 1.44-1.52 (m, 2.2H), 1.63-1.88 (m, 18.5H), 3.36-3.39 (m, 10.7H), 3.76 (s, 4H, OCH$_3$), 3.84-3.99 (m, 15.7H), 5.01-5.18 (m, 10.5H), 5.93-6.05 (m, 5H), 6.66-6.85 (m, 17H, ArH); GC RI: MS m/z (relative intensity, %): 1-allyl-2,5-di(3-methyl-butoxy) benzene 5c{5,5} 2001: 291 (M$^+$+H, 27), 290 (M$^+$, 100).

The following procedures were used to generate mini-libraries in Set D

The 3c{6,1-5} mini-library (2.7224 g) was heated at 180° C. in a sealed tube, under a nitrogen atmosphere for 30 hours. The viscous dark black oil was purified by column chromatography with chloroform to afford 1.6334 g of pure 6c{1-5} library in 60% yield.

The following data were generated for Set D as set out in Table 2.

$^1$H NMR δ: 0.92-0.97 (m, 9.5H), 1.02 (t, J=7.4 Hz, 3.6H), 1.37 (t, J=7.0 Hz, 4.2H), 1.45 (d, J=6.2 Hz, 15.7H), 1.57-1.58 (m, 1.4H), 1.64 (q, J=6.8 Hz, 2H), 1.70-1.85 (m, 5.7H), 2.77-2.82 (m, 4.8H), 3.24-3.30 (m, 5H), 3.75 (s, 3.4H, OCH$_3$), 3.85 (t, J=6.6 Hz, 2.2H), 3.87-3.92 (m, 3.9H), 3.96 (q, J=7.0 Hz, 2.3H), 4.85-4.93 (m, 4.2H), 6.63-6.82 (m, 17.6H, ArH); GC RI: MS m/z (relative intensity, %): 5-methoxy-2-methyl-2,3-dihydro benzofuran 6c{1} 1365: 165 (M$^+$+H, 24), 164 (M$^+$, 100), 149 (65); 5-ethoxy-2-methyl-2,3-dihydro benzofuran 6c{2} 1434: 179 (M$^+$+H, 22), 178 (M$^+$, 100), 149 (25); 5-propoxy-2-methyl-2,3-dihydro benzofuran 6c{3} 1533: 193 (M$^+$+H, 22), 192 (M$^+$, 100); 5-butoxy-2-methyl-2,3-dihydro benzofuran 6c{4} 1634: 207 (M$^+$+H, 22), 206 (M$^+$, 100); 5-(3-methyl-butoxy)-2-methyl-2,3-dihydro benzofuran 6c{5} 1699: 221 (M$^+$+H, 22), 220 (M$^+$, 100).

Spectral Data and Analysis of Ethyl, Propyl, Butyl, Isopentyl and Allyl Sets

Data for Compounds in Set A(dialkoxybenzenes)

Ortho

3a{2, 1-5} Ethyl library (Method A, 57% yield): $^1$H NMR δ: 0.96-0.99 (m, 9.4H), 1.04 (t, J=7.5 Hz, 3H, CH$_3$ (Pr)), 1.41-1.53 (m, 5H), 1.73 (q, J=6.9 Hz, 2H, CH$_2$ (i-Pent)), 1.79-1.89 (m, 5.4H), 3.88 (s, 3H, OCH$_3$ (Me)), 3.97 (t, J=6.8 Hz, 2H), 4.01 (t, J=6.7 Hz, 2H), 4.04 (t, J=6.8 Hz, 2H), 4.05-4.13 (m, 14H), 6.86-6.93 (m, 19H, ArH); GC RI: MS m/z (relative intensity, %): 1,2-diethoxy benzene 3a{2,2} 1244: 167 (M$^+$+H, 100), 166 (M$^+$, 81); 1-ethoxy-2-propoxy benzene 3a{2,3} 1335: 181 (M$^+$+H, 100), 180 (M$^+$, 60); 1-ethoxy-2-butoxy benzene 3a{2,4} 1429: 195 (M$^+$+H, 100), 194 (M$^+$, 83); 1-ethoxy-2-(3-methyl-butoxy) benzene 3a{2,5} 1486: 209 (M$^+$+H, 100), 208 (M$^+$, 72).

3a{3,1-5} Propyl library (Method A, 67% yield): $^1$H NMR δ: 0.96-0.99 (m, 7.4H), 1.04 (t, J=7.4 Hz, 16.5H, CH$_3$ (Pr)), 1.44 (t, J=7.0 Hz, 3H), 1.48-1.53 (m, 1.6H), 1.72 (q, J=6.8 Hz, 1.7H, CH$_2$ (i-Pent)), 1.77-1.91 (m, 14H), 3.87 (s, 3H, OCH$_3$ (Me)), 3.94-4.04 (m, 14.7H), 4.09 (q, J=7.0 Hz, 2H), 6.86-6.92 (m, 17H, ArH); GC RI: MS m/z (relative intensity, %): 1,2-dipropoxy benzene 3a{3,3} 1424: 195 (M$^+$+H, 100), 194 (M$^+$, 60); 1-butoxy-2-propoxy benzene 3a{3,4} 1518: 209 (M$^+$+H, 100), 208 (M$^+$, 84); 1-(3-methyl-butoxy)-2-propoxy benzene 3a{3,5} 1576: 223 (M$^+$+H, 100), 222 (M$^+$, 62).

3a{4,1-5} Butyl library (Method A, 62% yield): $^1$H NMR δ: 0.96-0.99 (m, 24H), 1.04 (t, J=7.5 Hz, 3.4H, CH$_3$ (Pr)), 1.44 (t, J=7.0 Hz, 3H), 1.46-1.54 (m, 12.6H), 1.71 (q, J=6.8 Hz, 2H, CH$_2$ (i-Pent)), 1.77-1.88 (m, 16H), 3.87 (s, 3H, OCH$_3$ (Me)), 3.96 (t, J=6.6 Hz, 2H), 3.98-4.05 (m, 15H), 4.07 (q, J=7.0 Hz, 2.4H), 6.82-6.94 (m, 20H, ArH); GC RI: MS m/z (relative intensity, %): 1,2-dibutoxy benzene 3a{4,4} 1608: 223 (M$^+$+H, 100), 222 (M$^+$, 64); 1-butoxy-2-(3-methyl-butoxy) benzene 3a{4,5} 1664: 237 (M$^+$+H, 100), 236 (M$^+$, 64).

3a{5,1-5} Isopentyl library. (Method A, 43% yield): $^1$H NMR δ: 0.96-0.99 (m, 41H), 1.04 (t, J=7.5 Hz, 3.4H, CH$_3$ (Pr)), 1.43 (t, J=7.0 Hz, 3.8H), 1.50 (q, J=7.5 Hz, 2.6H), 1.69-1.90 (m, 24H), 3.86 (s, 3H, OCH$_3$ (Me)), 3.96 (t, J=6.6 Hz, 2H), 3.98-4.10 (m, 18H), 6.84-6.93 (m, 20H, ArH); GC RI: MS m/z (relative intensity, %): 1,2-di(3-methyl-butoxy) benzene 3a{5,5} 1720: 251 (M$^+$+H, 20), 250 (M$^+$, 100).

3a{6,1-5} Allyl library. (Method B, 94% yield): $^1$H NMR δ: 0.96-1.00 (m, 7H), 1.05 (t, J=7.4 Hz, 3H, CH$_3$ (Pr)), 1.45 (t, J=7.0 Hz, 3.7H), 1.49-1.53 (m, 1.7H), 1.73 (q, J=6.9 Hz, 1.4H), 1.79-1.89 (m, 4.6H), 3.88 (s, 4H, OCH$_3$ (Me)), 3.98 (t, J=6.7 Hz, 1.8H), 4.01-4.06 (m, 3.3H), 4.10 (q, J=7.0 Hz, 2.4H), 4.58-4.63 (m, 10.6H), 5.25-5.30 (m, 5.1H), 5.38-5.44 (m, 5H), 6.04-6.14 (m, 5H), 6.84-6.95 (m, 21H, ArH); GC RI: MS m/z (relative intensity, %): 1-allyloxy-2-methoxy benzene 3a{6,1} 1281: 165 (M$^+$+H, 42), 164 (M$^+$, 100); 1-allyloxy-2-ethoxy benzene 3a{6,2} 1327: 179 (M$^+$+H, 100), 178 (M$^+$, 67); 1-allyloxy-2-propoxy benzene 3a{6,3} 1416: 193 (M$^+$+H, 100), 192 (M$^+$, 91); 1-allyloxy-2-butoxy benzene 3a{6,4} 1510: 207 (M$^+$+H, 100), 206 (M$^+$, 72); 1-allyloxy-2-(3-methyl-butoxy) benzene 3a{6,5} 1569: 221 (M$^+$+H, 100), 220 (M$^+$, 70).

Meta

3b{2,1-5} Ethyl library. (Method A, 66% yield): $^1$H NMR δ: 0.96 (d, J=6.6 Hz, 6H, CH$_3$ (i-Pent)), 1.03 (t, J=7.4 Hz, 3H, CH$_3$ (Pr)), 1.39-1.43 (m, 12.8H), 1.67 (apparent q, J=6.8 Hz, 2H, CH$_2$ (i-Pent)), 1.78-1.84 (m, 3H), 3.79 (s, 3H, CH$_3$ (Me)), 3.90 (t, J=6.6 Hz, 2H, OCH$_2$ (Pr)), 3.98 (t, J=6.7 Hz, 2H, OCH$_2$ (i-Pent)), 3.99-4.04 (m, 8H), 6.46-6.51 (m, 10H, ArH), 7.16 (t, J=8.2 Hz, 3H, ArH); GC RI: MS m/z (relative intensity, %): 1,3-diethoxy benzene 3b{2,2} 1318: 167 (M$^+$+H, 31), 166 (M$^+$, 100); 1-ethoxy-3-propoxy benzene 3b{2,3} 1409: 181 (M$^+$+H, 40), 180 (M$^+$, 100); 1-ethoxy-3-(3-methyl-butyloxy) benzene 3b{2,5} 1570: 209 (M$^+$+H, 35), 208 (M$^+$, 100).

3b{3,1-5} Propyl library. (Method A, 53% yield): $^1$H NMR δ: 0.96 (d, J=6.6 Hz, 6H, CH$_3$ (i-Pent)), 1.02-1.05 (m, 10H), 1.40 (t, J=7.0 Hz, 2H, CH$_3$ (Et)), 1.67 (apparent q, J=6.8 Hz, 2H, CH$_2$ (i-Pent)), 1.77-1.85 (m, 8H), 3.79 (s, 1.5H, OCH$_3$ (Me)), 3.89-3.92 (m, 7H), 3.97 (t, J=6.7 Hz, 2H, OCH$_2$ (i-Pent)), 4.02 (q, J=7.0 Hz, 1.2H, OCH$_2$ (Et)), 6.46-6.51 (m, 7H, ArH), 7.16 (t, J=8.2 Hz, 2.5H, ArH); GC RI: MS m/z (relative intensity, %): 1,3-dipropoxy benzene 3b{3,3} 1501: 195 (M$^+$+H, 45), 194 (M$^+$, 100), 110 (85), 82(22); 1-(3-methyl-butyloxy)-3-propoxy benzene 3b{3,5} 1657: 223 (M$^+$+H, 44), 222 (M$^+$, 100).

3b{4,1-5} Butyl library (Method A, 69% yield): $^1$H NMR δ: 0.99-1.02 (m, 19H), 1.05 (t, J=7.0 Hz, 3H, CH$_3$ (Pr)), 1.41-1.45 (m, 3H), 1.48-1.56 (m, 8H), 1.70 (apparent q, J=6.7 Hz, 2.5H, CH$_2$ (i-Pent)), 1.76-1.91 (m, 8H), 3.81 (s, 3H, OCH$_3$ (Me)), 3.93 (t, J=6.6 Hz, 2H, OCH$_2$ (Pr)), 3.95-4.01 (m, 11H), 4.03 (q, J=7.0 Hz, 2H, OCH$_2$ (Et)), 6.45-6.54 (m, 11.7H, ArH), 7.16 (t, J=8.2 Hz, 4H, ArH); GC RI: MS m/z (relative intensity, %): 1-butoxy-3-methoxy benzene 3b{4,1} 1440: 181 (M$^+$+H, 25), 180 (M$^+$, 100); 1-butoxy-3-ethoxy benzene 3b{4,2} 1506: 193 (M$^+$+H, 33), 194 (M$^+$, 100); 1-butoxy-3-propoxy benzene 3b{4,3} 1596: 209 (M$^+$+H, 48), 208 (M$^+$, 100); 1-butoxy-3-(3-methyl-butyloxy) benzene 3b{4,5} 1754: 237 (M$^+$+H, 42), 236 (M$^+$, 100).

3b{5,1-5} Isopentyl library. (Method A, 72% yield): $^1$H NMR δ: 0.99 (d, J=6.7 Hz, 26H), 1.06 (t, J=7.4 Hz, 3H, CH$_3$ (Pr)), 1.41-1.45 (m, 3H), 1.70 (apparent q, J=6.7 Hz, 9H), 1.81-1.88 (m, 6.3H), 3.81 (s, 3H, OCH$_3$ (Me)), 3.92 (t, J=6.6 Hz, 2H, OCH$_2$ (Pr)), 3.98-4.04 (m, 11H), 6.50-6.54 (m, 11H, ArH), 7.18 (t, J=8.2 Hz, 4H, ArH); GC RI: MS m/z (relative intensity, %): 1-methoxy-3-(3-methyl-butyloxy) benzene 3b{5,1} 1500: 195 (M$^+$+H, 26), 194 (M$^+$, 100); 1-ethoxy-3-(3-methyl-butyloxy) benzene 3b{5,2} 1566: 209 (M$^+$+H, 35), 208 (M$^+$, 100); 1-(3-methyl-butyloxy)-3-propoxy benzene 3b{5,3} 1653: 223 (M$^+$+H, 48), 222 (M$^+$, 100); 1,3-di(3-methyl-butyloxy) benzene 3b{5,5} 1826: 251 (M$^+$+H, 40), 250 (M$^+$, 100).

The meta allyl library was synthesized in three portions (methyl by itself, ethyl+propyl and butyl+isopentyl), because upon Claisen rearrangement each compound gave rise to two rearrangement products.

3b{6,1} 1-allyloxy-3-methoxybenzene. (Method D, 98% yield): $^1$H NMR δ: 3.80 (s, 3H, CH$_3$), 4.53 (apparent d, J=5.5 Hz, 2H, allyl CH$_2$), 5.30 (apparent d, J=14 Hz, 1H), 5.43 (apparent d, J=22 Hz, 1H), 6.07 (m, 1H), 6.52 (m, 3H, ArH), 7.19 (apparent t, J=7.7 Hz, 1H ArH). GC RI: 1334 MS m/z (relative intensity, %): 164 (M$^+$, 100), 149 (M-CH$_3$, 10), 136 (M-28, 12).

3b{6,2-3} Allyl library (ethyl, propyl). (Method D, 60% yield, 35% 3b{6,2} by GC and 39% by $^1$H NMR and the rest is 3b{6,3}): $^1$H NMR δ: 1.04 (t, J=4 Hz, 3H, CH$_3$ propyl), 1.42 (t, J=3.7 Hz, 3H, CH$_3$ ethyl), 1.81 (m, 2H, CH$_2$, propyl), 3.95 (t, J=3.7 Hz, 2H propyl CH$_2$), 4.02 (q, J=7 Hz, 2H, ethyl), 4.53 (apparent d, J=7 Hz, 2H for each component), 5.29 (m, J=14 Hz, 1H for each component), 5.41 (m, J=22 Hz, 1H for each component), 6.07 (m, 1H for each component), 6.53 (m, 3H for each component), 7.17 (apparent t, J=8 Hz, 1H for each component). GC RI: MS m/z (relative intensity, %): 1-allyloxy-3-ethoxybenzene 3b{6,2} 1398: 179 (M+1, 72), 178 (M$^+$, 100), 150 (M 28, 35); 1-allyloxy-3-propoxybenzene 3b{6,3} 1491: 193 (M+1, 93), 192 (M$^+$, 100), 164 (M 28, 12), 150 (31).

3b{6,4-5} Allyl library (butyl, isopentyl). (Method D, 71% yield, 3b{6,4} 34% by GC and 40% by $^1$H NMR and the rest is 3b{6,5}): $^1$H NMR δ: 0.98 (m, 6H, CH$_3$ isopentyl, 3H CH$_3$ butyl), 1.48 (m, 2H, CH$_2$ butyl), 1.68 (m, 2H, CH$_2$, isopentyl), 1.75 (m, 2H, CH$_2$, butyl), 1.83 (m, 1H, isopentyl), 3.96 (m, 2H for each component, CH$_2$), 4.52 (apparent d, J=8 Hz, 2H for each component), 5.29 (apparent d, J=14 Hz, 1H for each component), 5.42 (apparent d, J=22 Hz, 1H for each component), 6.06 (m, 1H for each component), 6.51 (m, 3H for each component, ArH), 7.17 (apparent t, J=7 Hz, 1H for each component, ArH). GC RI: MS m/z (relative intensity, %): 1-allyloxy-3-n-butoxybenzene 3b{6,4} 1592: 207 (M+1, 83), 206 (M$^+$, 100), 178 (M−28, 12), 150 (33). 1-allyloxy-3-isopentyloxybenzene 3b{6,5} 1654: 221 (M+1, 81), 220 (M$^+$, 100), 192 (M−28, 7), 150 (21).

Para

3c{2,1-5} Ethyl library (Method A, 31% yield): $^1$H NMR δ: 0.96 (d, J=6.7 Hz, 6H, CH$_3$ (i-Pent)), 1.03 (t, J=7.4 Hz, 3H, CH$_3$ (Pr)), 1.39 (t, J=7.0 Hz, 15H, CH$_3$ (Et)), 1.66 (apparent q, J=6.8 Hz, 3H, CH$_2$ (i-Pent)), 1.77-1.83 (m, 4H), 3.77 (s, 3H, OCH$_3$ (Me)), 3.87 (t, J=6.6 Hz, 2H, OCH$_2$ (Pr)), 3.94 (t, J=6.7 Hz, 2H, OCH$_2$ (i-Pent)), 3.98 (q, J=7.0 Hz, 10H, OCH$_2$ (Et)), 6.83-6.84 (m, 16H, ArH); GC RI: MS m/z (relative intensity, %): 1,4-diethoxy benzene 3c{2,2} 1248: 167 (M$^+$+H, 33), 166 (M$^+$, 100); 1-ethoxy-4-propoxy benzene 3c{2,3} 1337: 181 (M$^+$+H, 28), 180 (M$^+$, 100); 1-ethoxy-4-(3-methyl-butyloxy) benzene 3c{2,5} 1492: 209 (M$^+$+H, 31), 208 (M$^+$, 100).

3c{3,1-5} Propyl library (Method A, 82% yield): $^1$H NMR δ: 0.97 (d, J=6.6 Hz, 7H, CH$_3$ (i-Pent)), 1.03 (t, J=7.4 Hz, 15H, CH$_3$ (Pr)), 1.40 (t, J=6.9 Hz, 3H, CH$_3$ (Et)), 1.66 (apparent q, J=6.8 Hz, 3H, CH$_2$ (i-Pent)), 1.77-1.85 (m, 12H), 3.77 (s, 3H, OCH$_3$ (Me)), 3.87 (t, J=6.5 Hz, 10H, OCH$_2$ (Pr)), 3.94 (t, J=6.6 Hz, 2.8H, OCH$_2$ (i-Pent)), 3.98 (q, J=7.1 Hz, 2H, OCH$_2$ (Et)), 6.83-6.84 (m, 16H, ArH); GC RI: MS m/z (relative intensity, %): 1,4-dipropoxy benzene 3c{3,3} 1431: (M$^+$+H, 25), 194 (M$^+$, 100); 1-(3-methyl-butyloxy)-4-propoxy benzene 3c{3,5} 1589: 223 (M$^+$+H, 28), 222 (M$^+$, 100).

3c{4,1-5} Butyl library (Method A, 76% yield): $^1$H NMR δ: 0.96-0.99 (m, 18H), 1.02 (t, J=7.4 Hz, 3H, CH$_3$ (Pr)), 1.39 (t, J=6.9 Hz, 4H, CH$_3$ (Et)), 1.45-1.53 (m, 8H, CH$_2$ (Bu)), 1.66 (apparent q, J=6.7 Hz, 2H, CH$_2$ (i-Pent)), 1.72-1.81 (m, 11.6H), 3.77 (s, 3H, OCH$_3$ (Me)), 3.87 (t, J=6.6 Hz, 2H, OCH$_2$ (Pr)), 3.90-3.95 (m, 10.4H), 3.98 (q, J=7.0 Hz, 2H, OCH$_2$ (Et)), 6.83-6.84 (m, 16H, ArH); GC RI: MS m/z (relative intensity, %): 1-butoxy-4-methoxy benzene 3c{4,1} 1371: 181 (M$^+$+H, 29), 180 (M$^+$, 100); 1-butoxy-4-ethoxy benzene 3c{4,2} 1437: 195 (M$^+$+H, 23), 194 (M$^+$, 100); 1-butoxy-4-propoxy benzene 3c{4,3} 1529: 209 (M$^+$+H, 40), 208 (M$^+$, 100); 1-butoxy-4-(3-methyl-butyloxy) benzene 3c{4,5} 1681: 237 (M$^+$+H, 42), 236 (M$^+$, 100).

3c{5,1-5} Isopentyl (3-methyl-butyloxy) library. (Method A, 82% yield): $^1$H NMR δ: 0.96 (d, J=7.0 Hz 30H, CH$_3$ (i-Pent)), 1.02 (t, J=7.4 Hz, 3H, CH$_3$ (Pr)), 1.39 (t, J=6.9 Hz, 3H, CH$_3$ (Et)), 1.66 (apparent q, J=6.8 Hz, 10H, CH$_2$ (i-Pent)), 1.75-1.86 (m, 7.5H), 3.77 (s, 3H, OCH$_3$ (Me)), 3.87 (t, J=6.4 Hz, 2H, OCH$_2$ (Pr)), 3.94 (t, J=6.9 Hz, 10H, OCH$_2$ (i-Pent)), 3.98 (q, J=6.8 Hz, 2H, OCH$_2$ (Et)), 6.83-6.84 (m, 16H, ArH); GC RI: MS m/z (relative intensity, %): 1,4-di(3-methyl-butyloxy)-benzene 3c{5,5} 1850: 251 (M$^+$+H, 25), 250 (M$^+$, 100).

3c{6,1-5} Allyl library. (Method B, 95% yield): GC (RI): $^1$H NMR δ: 0.95-0.98 (m, 8H), 1.03 (t, J=7.4 Hz, 3H, CH$_3$ (Pr)), 1.39 (t, J=7.0 Hz, 3.9H, CH$_3$ (Et)), 1.46-1.50 (m, 1.5H), 1.56 (d, J=3.8 Hz, 1.3H), 1.65 (apparent q, J=6.8 Hz, 2H, CH$_2$ (i-Pent)), 1.71-1.85 (m, 5H), 3.78 (s, 4H, OCH$_3$ (Me)), 3.87 (t, J=6.6 Hz, 2H, OCH$_2$ (Pr)), 3.90-3.95 (m, 3.7H), 3.98 (q, J=7.0 Hz, 2.5H, OCH$_2$ (Et)), 4.47-4.49 (m, 10.9H), 5.25-5.29 (m, 5.H), 5.38-5.42 (m, 5H), 6.01-6.09 (m, 5H), 6.81-6.87 (m, 21H, ArH); GC RI: MS m/z (relative intensity, %): 1-allyloxy-4-methoxy benzene 3c{6,1} 1326: 165 (M$^+$+H, 20), 164 (M$^+$, 100); 1-allyloxy-4-ethoxy benzene 3c{6,2} 1394: 179 (M$^+$+H, 70), 178 (M$^+$, 100); 1-allyloxy-4-propoxy benzene 3c{6,3} 1491: 193 (M$^+$+H, 65), 192 (M⁺, 100); 1-allyloxy-4-butoxy benzene 3c{6,4} 1594: 207 (M⁺+H, 56), 206 (M⁺, 100); 1-allyloxy-4-(3-methylbutoxy) benzene 3c{6,5} 1659: 221 (M⁺+H, 46), 220 (M⁺, 100).

Data for Compounds in Set C (allyl dialkoxybenzenes)

Ortho

5a{2,1-5} Allyl-ethyl library. (Method B, 91% yield): ¹H NMR δ: 0.97-1.00 (m, 11.5H), 1.35-1.40 (m, 14.8H), 1.42-1.16 (m, 10.5H), 1.72 (apparent q, J=6.7 Hz, 1.8H, CH₂ (i-Pent)), 1.78-1.91 (m, 5.7H), 3.43 (d, J=6.6 Hz, 9.2H), 3.84 (s, 3.9H, OCH₃), 3.91-4.12 (m, 20.9H), 5.01-5.10 (m, 10.3H), 5.94-6.02 (m, 5H), 6.69-6.83 (m, 11.4H, ArH), 6.90-7.00 (m, 6.7H, ArH); GC RI: MS m/z (relative intensity, %): 1-allyl-2,3-diethoxy benzene 5a{2,2} 1435: 207 (M⁺+H, 63), 206 (M⁺, 100); 1-allyl-2-ethoxy-3-propoxy benzene 5a{2,3} 1523: 221 (M⁺+H, 56), 220 (M⁺, 100); 1-allyl-2-butoxy-3-ethoxy benzene 5a{2,4} 1616: 235 (M⁺+H, 88), 234 (M⁺, 100); 1-allyl-2-ethoxy-3-(3-methyl-butoxy) benzene 5a{2,5} 1669: 249 (M⁺+H, 79), 248 (M⁺, 100).

5a{3,1-5} Allyl-propyl library. (Method B, 96% yield): ¹H NMR δ: 0.97-1.08 (m, 27.8H), 1.44 (t, J=7.0 Hz, 4H), 1.49-1.56 (m, 2.3H), 1.69-1.89 (m, 16.3H), 3.42 (d, J=6.6 Hz, 9.5H), 3.84 (s, 4H, OCH₃), 3.86-4.09 (m, 21H), 5.02-5.08 (m, 10H), 5.94-6.02 (m, 5H), 6.69-6.83 (m, 11.4H, ArH), 6.89-6.99 (m, 6H, ArH); GC RI: MS m/z (relative intensity, %): 1-allyl-2,3-dipropoxy benzene 5a{3,3} 1608: 235 (M⁺+H, 57), 234 (M⁺, 100); 1-allyl-3-butoxy-2-propoxy benzene 5a{3,4} 1699: 249 (M⁺+H, 100), 248 (M⁺, 72); 1-allyl-3-(3-methyl-butoxy)-2-propoxy benzene 5a{3,5} 1751: 263 (M⁺+H, 50), 262 (M⁺, 90), 249 (100).

5a{4,1-5} Allyl-butyl library. (Method B, 92% yield): ¹H NMR δ: 0.96-0.99 (m, 22.3H), 1.05 (t, J=7.4 Hz, 2.7H), 1.43 (t, J=6.9 Hz, 4.2H), 1.47-1.54 (m, 12.2H), 1.69-1.89 (m, 16.7H), 3.42 (d, J=6.6 Hz, 9.2H), 3.84 (s, 4H, OCH₃), 3.88-4.11 (m, 19H), 5.02-5.10 (m, 10.3H), 5.93-6.01 (m, 5H), 6.69-6.83 (m, 11.4H, ArH), 6.89-6.99 (m, 6.5H, ArH); GC RI: MS m/z (relative intensity, %): 1-allyl-2,3-dibutoxy benzene 5a{4,4} 1784: 263 (M⁺+H, 27), 262 (M⁺, 100); 1-allyl-2-butoxy-3-(3-methyl-butoxy) benzene 5a{4,5} 1833: 277 (M⁺+H, 25), 276 (M⁺, 100).

5a{5,1-5} Allyl-iPentyl library. (Method B, 90% yield): ¹H NMR δ: 0.95-1.00 (m, 37.6H), 1.06 (t, J=7.5 Hz, 2.7H), 1.44 (t, J=7.0 Hz, 4.3H), 1.49-1.55 (m, 2.1H), 1.65-1.72 (m, 12.4H), 1.78-1.90 (m, 10H), 3.41 (d, J=6.6 Hz, 9.4H), 3.84 (s, 4H, OCH₃), 3.91-4.08 (m, 19H), 5.01-5.09 (m, 10.2H), 5.93-6.01 (m, 5H), 6.69-6.83 (m, 11.1H, ArH), 6.89-6.99 (m, 7.2H, ArH); GC RI: MS m/z (relative intensity, %): 1-allyl-2,3-di(3-methyl-butoxy) benzene 5a{5,5} 1879: 291 (M⁺+H, 23), 290 (M⁺, 100).

5a{6,1-5} Allyl-allyl library. (Method B, 90% yield): ¹H NMR δ: 0.88-0.93 (m, 11.3H), 0.96-1.01 (m, 2.7H), 1.36-1.39 (m, 2.7H), 1.45 (t, J=7.3 Hz, 2.7H), 1.65 (q, J=6.7 Hz, 2.3H), 1.70-1.83 (m, 6H), 3.25 (d, J=7.0 Hz, 1.5H), 3.35 (d, J=6.6 Hz, 8.7H), 3.78 (s, 2.5H, OCH₃), 3.86-4.04 (m, 9.5H), 4.40-4.54 (m, 10.3H), 4.95-5.02 (m, 10.2H), 5.13-5.20 (m, 5H), 5.27-5.36 (m, 5H), 5.84-5.92 (m, 5H), 5.97-6.08 (m, 5H), 6.61-6.76 (m, 11.1H, ArH), 6.82-6.94 (m, 5H, ArH); GC RI: MS m/z (relative intensity, %): 1-allyl-2-allyloxy-3-metoxy benzene 5a{6,1} 1463: 205 (M⁺+H, 84), 204 (M⁺, 100); 1-allyl-2-allyloxy-3-ethoxy benzene 5a{6,2} 1509: 219 (M⁺+H, 100), 218 (M⁺, 95); 1-allyl-2-allyloxy-3-propoxy benzene 5a{6,3} 1597: 233 (M⁺+H, 100), 232 (M⁺, 87); 1-allyl-2-allyloxy-3-butoxy benzene 5a{6,4} 1688: 247 (M⁺+H, 100), 246 (M⁺, 91); 1-allyl-2-allyloxy-3-(3-methyl-butoxy) benzene 5a{6,5} 1740: 261 (M⁺+H, 100), 260 (M⁺, 92).

Meta

5b^{x,y}{2,1} Allyl-ethyl library A. (Method B, 70% yield): ¹H NMR δ: 1.38-1.42 (m, 8.9H, CH₃ (Et)), 3.31-3.32 (m, 3.5H, CH₂(Allyl^y)), 3.42 (dt, J=1.5 and 6.3 Hz, 2H CH₂ (Allyl^y')), 3.78 (s, 5.2H (Me^x)), 3.82 (s, 3H (MO), 3.99-4.05 (m, 6.2H), 4.91-4.94 (m, 1H), 4.98-5.07 (m, 4.6H), 5.91-6.01 (m, 2.5H), 6.42-6.44 (m, 3.4H, ArH^x), 6.54 (d, J=8.3 Hz, 2H, ArH^y'), 7.03 (d, J=7.9 Hz, 1.6H, ArH^x), 7.12 (t, J=8.3 Hz, 1H, ArH^y'); GC RI: MS m/z (relative intensity, %): 2-allyl-1-ethoxy-3-methoxy benzene 5b^y{2,1} 1435: 193 (M⁺+H, 75), 192 (M⁺, 100); 1-allyl-2-ethoxy-4-methoxy benzene 5b^x{2,1} 1471: 193 (M⁺+H, 47), 192 (M⁺, 100).

5b^{x,y}{2,2-3} Allyl-ethyl library B. (Method B, 80% yield): ¹H NMR δ: 1.01-1.06 (m, 11.6H, CH₃ (Pr)), 1.39-1.42 (m, 26.6H, CH₃ (Et)), 1.76-1.84 (m, 8H, CH₂ (Pr)), 3.31-3.32 (m, 7.7H), 3.42-3.45 (m, 4.4H), 3.88-3.93 (m, 8H, OCH₂ (Pr)), 3.98-4.04 (m, 18.1H, OCH₂ (Et)), 4.91-4.93 (m, 2.1H), 4.99-5.07 (m, 9.5H), 5.91-6.01 (m, 5.4H), 6.40-6.45 (m, 7.6H, ArH^x), 6.50-6.52 (d, 4.1H, ArH^y'), 7.00-7.02 (m, 3.5H, ArH^x), 7.07-7.11 (m, 2H, ArH^y'); GC RI: MS m/z (relative intensity, %): 2-allyl-1,3-diethoxy benzene 5b^y{2,2} 1490: 207 (M⁺+H, 80), 206 (M⁺, 100); 1-allyl-2,4-diethoxy benzene 5b^x{2,2} 1535: 207 (M⁺+H, 62), 206 (M⁺, 100); 2-allyl-1-ethoxy-3-propoxy benzene 5b^y{2,3} 1587: 221 (M⁺+H, 100), 220 (M⁺, 94); 1-allyl-2-ethoxy-4-propoxy benzene 5b^x{2,3} 1627: 221 (M⁺+H, 67), 220 (M⁺, 100).

5b^{x,y}{2,4-5} Allyl-ethyl library C. (Method B, 48% yield): ¹H NMR δ: 0.95-0.99 (m, 29.6H), 1.38-1.42 (m, 21.5H, CH₃ (Et)), 1.45-1.53 (m, 8.5H, CH₂CH₃ (Bu)), 1.64-1.70 (m, 6.4H, CH₂CH (iPent)), 1.72-1.91 (m, 11.2H), 3.30-3.32 (m, 9.1H), 3.42-3.43 (m, 4.3H), 3.92-4.04 (m, 29.2H), 4.90-4.93 (m, 2.1H), 4.98-5.06 (m, 10.7H), 5.90-6.01 (m, 6H), 6.40-6.44 (m, 9H, ArH^x), 6.50-6.53 (m, 4.2H, ArH^y'), 7.00-7.01 (m, 4.2H, ArH^x), 7.07-7.11 (m, 2H ArH^y'); GC RI: MS m/z (relative intensity, %): 2-allyl-1-butoxy-3-ethoxy benzene 5b^y{2,4} 1682: 235 (M⁺+H, 43), 234 (M⁺, 85), 149 (M−86, 100); 1-allyl-4-butoxy-2-ethoxy benzene 5b^x{2,4} 1724: 235 (M⁺+H, 42), 234 (M⁺, 100); 2-allyl-1-ethoxy-3-(3-methyl-butoxy) benzene 5b^y{2,5} 1739: 249 (M⁺+H, 31), 248 (M⁺, 69), 149 (M−99, 100); 1-allyl-2-ethoxy-4-(3-methyl-butoxy) benzene 5b^x{2,5} 1784: 249 (M⁺+H, 34), 248 (M⁺, 98), 149 (M−99, 100).

5b^{x,y}{3,1} Allyl-propyl library A. (Method B, 88% yield): ¹H NMR δ: 1.03-1.06 (m, 9.1H, CH₃ (Pr)), 1.77-1.85 (m, 6.4H, CH₂CH₃ (Pr)), 3.32-3.33 (m, 3.9H, CH₂ (Allyl^y)), 3.43-3.44 (m, 2.2H, CH₂ (Allyl^y')), 3.79 (s, 5.6H (Me^x)), 3.82 (s, 3H (MO), 3.89-3.93 (m, 6.2H, OCH₂ (Pr)), 4.91-4.94 (m, 1.1H), 4.98-5.07 (m, 4.7H), 5.91-6.01 (m, 2.8H), 6.41-6.44 (m, 3.8H, ArH^x), 6.52-6.54 (m, 2H, ArH^y'), 7.03 (d, J=8.0 Hz, 1.6H, ArH^x), 7.12 (t, J=8.3 Hz, 1H, ArH^y'); GC RI: MS m/z (relative intensity, %): 2-allyl-1-methoxy-3-propoxy benzene 5b^y{3,1} 1527: 207 (M⁺+H, 100), 206 (M⁺, 97); 1-allyl-4-methoxy-2-propoxy benzene 5b^x{3,1} 1573: 207 (M⁺+H, 51), 206 (M⁺, 100).

5b^{x,y}{3,2-3} Allyl-propyl library B. (Method B, 80% yield): ¹H NMR δ: 1.03-1.08 (m, 30H, CH₃ (Pr)), 1.40-1.43 (m, 7.4H, CH₃ (Et)), 1.78-1.86 (m, 20.8H, CH₂CH₃ (Pr)), 3.33-3.34 (m, 7.5H), 3.45-3.47 (m, 4.4H), 3.90-3.94 (m, 20.4H, OCH₂ (Pr)), 4.00-4.06 (m, 5.3H, OCH₂ (Et)), 4.92-4.95 (m, 2H), 5.00-5.08 (m, 9H), 5.93-6.03 (m, 4.8H), 6.41-6.46 (m, 7.3H, ArH^x), 6.51-6.53 (m, 4.2H, ArH^y'), 7.01-7.03 (m, 3.4H, ArH^x), 7.09-7.12 (m, 2H, ArH^y'); GC RI: MS m/z (relative intensity, %): 2-allyl-1-ethoxy-3-propoxy benzene 5b^y{3,2} 1587: 221 (M⁺+H, 39), 220 (M⁺, 89), 149 (M−71, 100); 1-allyl-4-ethoxy-2-propoxy benzene 5b^x{3,2} 1624: 221 (M⁺+H, 29), 220 (M⁺, 100), 149 (M−71, 53); 2-allyl-1,3-dipropoxy benzene 5b^y{3,3} 1682: 235 (M⁺+H, 50), 234 (M⁺, 100); 1-allyl-2,4-dipropoxy benzene 5b$^x${3,3} 1713: 235 (M⁺+H, 39), 234 (M⁺, 100).

5b$^{x,y}${3,4-5} Allyl-propyl library C. (Method B, 62% yield): ¹H NMR δ: 0.95-0.98 (m, 29.4H), 1.02-1.06 (m, 20.9H, CH₃ (Pr)), 1.44-1.53 (m, 8.2H, CH₂CH₃ (Bu)), 1.64-1.69 (m, 6.4H, CH₂CH (iPent)), 1.72-1.89 (m, 26.1H), 2.17 (m, 5.8H (Me)), 3.31-3.32 (m, 9H), 3.42-3.44 (m, 4.3H), 3.88-3.98 (m, 29.1H), 4.89-4.92 (m, 2H), 4.98-5.06 (m, 10.6H), 5.89-6.00 (m, 5.8H), 6.39-6.43 (m, 8.9H, ArH$^x$), 6.49-6.52 (m, 4.9H, ArH$^y$), 6.99-7.01 (m, 4.2H, ArH$^x$), 7.07-7.10 (m, 2H, ArH$^y$); GC RI: MS m/z (relative intensity, %): 2-allyl-1-butoxy-3-propoxy benzene 5b$^y${3,4} 1778: 249 (M⁺+H, 85), 248 (M⁺, 100); 1-allyl-4-butoxy-2-propoxy benzene 5b$^x${3,4} 1813: 249 (M⁺+H, 46), 248 (M⁺, 100); 2-allyl-1-(3-methyl-butoxy)-3-propoxy benzene 5b$^y${3,5} 1835: 263 (M⁺+H, 69), 262 (M⁺, 100), 1-allyl-2-propoxy-4-(3-methyl-butoxy) benzene 5b$^x${3,5} 1870: 263 (M⁺+H, 45), 262 (M⁺, 100).

5b$^{x,y}${4,1} Allyl-butyl library A. (Method B, 81% yield): ¹H NMR δ: 0.95-0.98 (m, 9.9H, CH₃ (Bu)), 1.46-1.54 (m, 6.1H, CH₂CH₃ (Bu)), 1.73-1.79 (m, 6.3H, OCH₂CH₂ (Bu)), 3.30-3.32 (m, 3.7H, CH₂ (Allyl$^x$)), 3.42 (dt, J=1.3 and 6.3 Hz, 2H, CH₂ (Allyl$^y$)), 3.78 (s, 5.3H (Me$^x$)), 3.81 (s, 3H (MO)), 3.92-3.96 (m, 6.3H, OCH₂ (Bu)), 4.99-4.93 (m, 1H), 4.96-5.05 (m, 4.7H), 5.90-6.00 (m, 2.7H), 6.40-6.43 (m, 3.6H, ArH$^x$), 6.53 (d, J=8.3 Hz, 2H, ArH$^y$), 7.02 (d, J=8.1 Hz, 1.7H, ArH$^x$), 7.11 (t, J=8.3 Hz, 1H, ArH$^y$); GC RI: MS m/z (relative intensity, %): 2-allyl-1-butoxy-3-methoxy benzene 5b$^y${4,1} 1625: 221 (M⁺+H, 66), 220 (M⁺, 100); 1-allyl-2-butoxy-4-methoxy benzene 5b$^x${4,1} 1656: 221 (M⁺+H, 37), 220 (M⁺, 100).

5b$^{x,y}${4,2-3} Allyl-butyl library B. (Method B, 52% yield): ¹H NMR δ: 0.95-0.98 (m, 17.7H, CH₃ (Bu)), 1.01-1.06 (m, 8.6H, CH₃ (Pr)), 1.38-1.41 (m, 9.5H, CH₃ (Et)), 1.46-1.54 (m, 12.3H), 1.74-1.83 (m, 18.4H), 3.31-3.32 (m, 7.8H), 3.43-3.45 (m, 3.9H), 3.88-4.04 (m, 25.8H), 4.91-4.93 (m, 1.9H), 4.99-5.06 (m, 9.6H), 5.90-6.01 (m, 5.7H), 6.40-6.45 (m, 8H, ArH$^x$), 6.50-6.52 (m, 4H, ArH$^y$), 7.00-7.01 (m, 3.8H, ArH$^x$), 7.07-7.11 (m, 2H, ArH$^y$); GC RI: MS m/z (relative intensity, %): 2-allyl-1-butoxy-3-ethoxy benzene 5b$^y${4,2} 1681: 235 (M⁺+H, 55), 234 (M⁺, 88), 149 (M−85, 100); 1-allyl-2-butoxy-4-ethoxy benzene 5b$^x${4,2} 1714: 235 (M⁺+H, 38), 234 (M⁺, 100); 2-allyl-1-butoxy-3-propoxy benzene 5b$^y${4,3} 1777: 249 (M⁺+H, 59), 248 (M⁺, 100); 1-allyl-2-butoxy-4-propoxy benzene 5b$^x${4,3} 1803: 249 (M⁺+H, 41), 248 (M⁺, 100).

5b$^{x,y}${4,4-5} Allyl-butyl library C. (Method B, 64% yield): ¹H NMR δ: 0.95-0.99 (m, 48.9H), 1.43-1.55 (m, 20H, CH₂CH₃ (Bu)), 1.64-1.70 (m, 8.2H), 1.72-1.90 (m, 25.5H), 3.30-3.32 (m, 7H), 3.42-3.44 (m, 4.1H), 3.92-3.99 (m, 25.5H), 4.90-4.93 (m, 2H), 4.98-5.05 (m, 9.1H), 5.89-6.01 (m, 5.2H), 6.39-6.44 (m, 7.3H, ArH$^x$), 6.50-6.52 (m, 4.1H, ArH$^y$), 6.99-7.01 (m, 3.3H, ArH$^x$), 7.07-7.11 (m, 2H, ArH$^y$); 2-allyl-1,3-dibutoxy benzene 5b$^y${4,4} 1871: 263 (M⁺+H, 72), 262 (M⁺, 100); 1-allyl-2,4-dibutoxy benzene 5b$^x${4,4} 1899: 263 (M⁺+H, 41), 262 (M⁺, 100); 2-allyl-1-butoxy-3-(3-methyl-butoxy) benzene 5b$^y${4,5} 1926: 277 (M⁺+H, 65), 276 (M⁺, 100); 1-allyl-2-butoxy-4-(3-methyl-butoxy) benzene 5b$^x${4,5} 1955: 277 (M⁺+H, 42), 276 (M⁺, 100).

5b$^{x,y}${5,1} Allyl-ipentyl library A. (Method B, 64% yield): ¹H NMR δ: 0.95-0.97 (m, 16.8H, CH₃ (iPent)), 1.66-1.71 (m, 5.8H, CH₂CH (iPent)), 1.82-1.91 (m, 3H, CH (iPent)), 3.31-3.32 (m, 3.6H, CH₂ (Allyl$^x$)), 3.41-3.43 (dt, J=1.3 and 6.3 Hz, 2.2H, CH₂ (Allyl$^y$)), 3.79 (s, 5.2H, CH₃ (Me$^x$)), 3.81 (s, 3H, CH₃ (MO)), 3.95-3.99 (m, 6H, OCH₂ (iPent)), 4.90-4.93 (m, 1H), 4.97-5.06 (m, 4.7H), 5.90-6.00 (m, 2.7H), 6.41-6.45 (m, 3.5H), 6.53-6.55 (m, 2H), 7.03 (d, J=8.2 Hz, 1.7H), 7.12 (t, J=8.3 Hz, 1H); GC RI: MS m/z (relative intensity, %): 2-allyl-1-methoxy-3-(3-methyl-butoxy) benzene 5b$^y${5,1} 1684: 235 (M⁺+H, 43), 234 (M⁺, 100); 1-allyl-4-methoxy-2-(3-methyl-butoxy) benzene 5b$^x${5,1} 1711: 235 (M⁺+H, 30), 234 (M⁺, 100).

5b$^{x,y}${5,2-3} Allyl-ipentyl library B. (Method B, 74% yield): ¹H NMR δ: 0.94-0.96 (m, 37.1H, CH₃ (iPent)), 1.01-1.05 (m, 9.6H, CH₃ (Pr)), 1.38-1.41 (m, 10.4H, CH₃ (Et)), 1.65-1.69 (m, 13H), 1.74-1.89 (m, 13.8H), 3.29-3.30 (m, 8.1H), 3.40-3.43 (m, 4.3H), 3.88-4.04 (m, 27H), 4.89-4.92 (m, 2.1H), 4.98-5.05 (m, 10.6H), 5.89-5.99 (m, 6.2H), 6.39-6.44 (m, 8.4H), 6.49-6.52 (m, 4.2H), 6.99-7.00 (m, 4H), 7.07-7.10 (m, 2H): GC RI: MS m/z (relative intensity, %): 2-allyl-1-ethoxy-3-(3-methyl-butoxy) benzene 5b$^y${5,2} 1736: 249 (M⁺+H, 14), 248 (M⁺, 52), 149 (M−99, 100); 1-allyl-4-ethoxy-2-(3-methyl-butoxy) benzene 5b$^x${5,2} 1820: 249 (M⁺+H, 22), 248 (M⁺, 100); 2-allyl-1-(3-methyl-butoxy)-3-propoxy benzene 5b$^y${5,3} 1834: 263 (M⁺+H, 22), 262 (M⁺, 80), 135 (M−127, 100); 1-allyl-2-(3-methyl-butoxy)-4-propoxy benzene 5b$^x${5,3} 1855: 263 (M⁺+H, 26), 262 (M⁺, 100).

5b$^{x,y}${5,4-5} Allyl-ipentyl library C. (Method B, 82% yield): ¹H NMR δ: 0.96-1.00 (m, 68H), 1.45-1.54 (m, 8.6H, CH₂CH₃ (Bu)), 1.65-1.92 (m, 40.4H), 3.31-3.32 (m, 6.2H), 3.42-3.44 (m, 4H), 3.93-4.00 (m, 24.7H), 4.90-4.93 (m, 2H), 4.99-5.06 (m, 9.41H), 5.89-6.01 (m, 5.65H), 6.41-6.45 (m, 7.3H), 6.51-6.53 (m, 3.8H), 7.00-7.01 (m, 3.2H), 7.07-7.11 (m, 2H); GC RI: MS m/z (relative intensity, %): 2-allyl-1-butoxy-3-isopentoxy benzene 5b$^y${5,4} 1927: 277 (M⁺+H, 42), 276 (M⁺, 100); 1-allyl-4-butoxy-2-isopentoxy benzene 5b$^x${5,4} 1950: 277 (M⁺+H, 32), 276 (M⁺, 100); 2-allyl-1,3-di(3-methyl-butoxy)benzene 5b$^y${5,5} 1984: 291 (M⁺+H, 36), 290 (M⁺, 89), 150 (M−140, 100); 1-allyl-2,4-di(3-methyl-butoxy) benzene 5b$^x${5,5} 2006: 291 (M⁺+H, 32), 290 (M⁺, 100).

5b$^{x,y}${6,1} Allyl-allyl library A. (Method B, 67% yield): ¹H NMR δ: 3.35-3.36 (m, 3.8H, CH₂ (Allyl$^x$)), 3.46-3.47 (m, 2H, CH₂ (Allyl$^y$)), 3.79 (s, 5.4H, CH₃ (Me$^x$)), 3.83 (s, 3H, CH₃ (Me$^y$)), 4.52-4.55 (m, 6.3H), 4.92-4.95 (m, 1.1H), 4.99-5.08 (m, 5H), 5.25-5.30 (m, 3H), 5.41-5.46 (m, 3H), 5.93-6.10 (m, 5.7H), 6.44-6.47 (m, 3.6H), 6.55 (t, J=8.5 Hz, 2H), 7.05 (d, J=8.7 Hz, 1.7H), 7.13 (t, J=8.3 Hz, 1H); GC RI: MS m/z (relative intensity, %): 2-allyl-1-allyloxy-3-methoxy benzene 5b$^y${6,1} 1524: 205 (M⁺+H, 29), 204 (M⁺, 100); 1-allyl-2-allyloxy-4-methoxy benzene 5b$^x${6,1} 1554: 205 (M⁺+H, 31), 204 (M⁺, 100).

5b$^{x,y}${6,2-3} Allyl-allyl library B. (Method B, 53% yield): ¹H NMR δ: 1.02-1.07 (m, 8.8H, CH₃ (Pr)), 1.39-1.42 (m, 9.4H, CH₃ (Et)), 1.76-1.85 (m, 6.2H, CH₂CH₃ (Pr)), 3.34-3.35 (m, 7.7H), 3.46-3.48 (m, 4.3H), 3.88-3.93 (m, 6H, OCH₂ (Pr)), 3.98-4.05 (m, 6.5H, OCH₂ (Et)), 4.51-4.54 (m, 12.2H), 4.91-4.94 (m, 2H), 5.00-5.07 (m, 10H), 5.24-5.28 (m, 6H), 5.40-5.45 (m, 6H), 5.92-6.09 (m, 12.1H), 6.42-6.45 (m, 7.6H), 6.51-6.54 (m, 4.2H), 7.01-7.03 (m, 3.7H), 7.08-7.11 (m, 2H); GC RI: MS m/z (relative intensity, %): 2-allyl-1-allyloxy-3-ethoxy benzene 5b$^y${6,2} 1581: 219 (M⁺+H, 42), 218 (M⁺, 100); 1-allyl-2-allyloxy-4-ethoxy benzene 5b$^x${6,2} 1613: 219 (M⁺+H, 46), 218 (M⁺, 100); 2-allyl-1-allyloxy-3-propoxy benzene 5b$^y${6,3} 1674: 233 (M⁺+H, 31), 232 (M⁺, 59), 149 (M−83, 100); 1-allyl-2-allyloxy-4-propoxy benzene 5b$^x${6,2} 1706: 233 (M⁺+H, 50), 232 (M⁺, 100).

5b$^{x,y}${6,4-5} Allyl-allyl library C. (Method B, 76% yield): ¹H NMR δ: 0.96-0.99 (m, 28.1H), 1.45-1.54 (m, 7.5H, CH₂CH₃ (Bu)), 1.65-1.71 (m, 7H), 1.73-1.92 (m, 10.9H), 3.34-3.36 (m, 6.2H), 3.46-3.47 (m, 3.9H), 3.92-4.00 (m, 12.8H), 4.51-4.55 (m, 10.6H), 4.91-4.94 (m, 2.1H), 5.00-

5.07 (m, 9.2H), 5.24-5.29 (m, 5.8H), 5.40-5.45 (m, 5.7H), 5.92-6.10 (m, 11.9H), 6.42-6.45 (m, 6.6H), 6.51-6.55 (m, 4.1H), 7.02-7.04 (m, 3.1H), 7.08-7.12 (m, 2H); GC RI: MS m/z (relative intensity, %): 2-allyl-1-allyloxy-3-butoxy benzene 5b$^y$\{6,4\} 1771: 247 (M$^+$+H, 43), 246 (M$^+$, 63), 149 (M−97, 100); 1-allyl-2-allyloxy-4-butoxy benzene 5b$^x$\{6,4\} 1801: 247 (M$^+$+H, 61), 246 (M$^+$, 100); 2-allyl-1-allyloxy-3-(3-methyl-butoxy) benzene 5b$^y$\{6,5\} 1827: 261 (M$^+$+H, 74), 260 (M$^+$, 78), 149 (M−111, 100); 1-allyl-2-allyloxy-4-(3-methyl-butoxy) benzene 5b$^x$\{6,5\} 1861: 261 (M$^+$+H, 62), 260 (M$^+$, 100).

Para

5c\{2,1-5\} Allyl-ethyl library. (Method B, 89% yield): $^1$H NMR δ: 0.94-0.98 (m, 8.7H), 1.02 (t, J=7.4 Hz, 3.7H), 1.36-1.41 (m, 21H), 1.44-1.52 (m, 2.2H), 1.62-1.66 (m, 4.5H), 1.70-1.86 (m, 5.6H), 3.36-3.38 (m, 10.9H), 3.76 (s, 4H, OCH$_3$), 3.86 (t, J=6.6 Hz, 2.6H), 3.88-3.93 (m, 4H), 3.95-3.99 (m, 14H), 5.03-5.10 (m, 10H), 5.93-6.02 (m, 4.7H), 6.66-6.78 (m, 16.2H, ArH); GC RI: MS m/z (relative intensity, %): 1-allyl-2,5-diethoxy benzene 5c\{2,2\} 1518: 207 (M$^+$+H, 31), 206 (M$^+$, 100); 1-allyl-2-ethoxy-5-propoxy benzene 5c\{2,3\} 1605: 221 (M$^+$+H, 29), 220 (M$^+$, 100); 1-allyl-5-butoxy-2-ethoxy benzene 5c\{2,4\} 1704: 235 (M$^+$+H, 29), 234 (M$^+$, 100); 1-allyl-2-ethoxy-5-(3-methyl-butoxy) benzene 5c\{2,5\} 1763: 249 (M$^+$+H, 27), 248 (M$^+$, 100).

5c\{3,1-5\} Allyl-propyl library. (Method B, 95% yield): $^1$H NMR δ: 0.96-1.06 (m, 27.6H), 1.37-1.41 (m, 4H), 1.44-1.53 (m, 2H), 1.64-1.68 (m, 2.9H), 1.72-1.92 (m, 16H), 3.38 (d, J=6.4 Hz, 10.9H), 3.80 (s, 3.8H, OCH$_3$), 3.82-3.99 (m, 19.9H), 4.99-5.18 (m, 10.5H), 5.92-6.05 (m, 5H), 6.67-6.85 (m, 17.5H, ArH); GC RI: MS m/z (relative intensity, %): 1-allyl-2,5-dipropoxy benzene 5c\{3,3\} 1699: 235 (M$^+$+H, 26), 234 (M$^+$, 100); 1-allyl-5-butoxy-2-propoxy benzene 5c\{3,4\} 1798: 249 (M$^+$+H, 27), 248 (M$^+$, 100); 1-allyl-5-(3-methyl-butoxy)-2-propoxy benzene 5c\{3,5\} 1857: 263 (M$^+$+H, 27), 262 (M$^+$, 90), 249 (100).

5c\{4,1-5\} Allyl-butyl library. (Method B, 95% yield): $^1$H NMR δ: 0.94-0.98 (m, 19.5H), 1.00-1.04 (m, 3.4H), 1.36-1.39 (m, 3.6H), 1.44-1.54 (m, 9.3H), 1.57-1.58 (m, 2H), 1.64 (t, J=6.8 Hz, 1.8H), 1.70-1.85 (m, 12.5H), 3.35-3.39 (m, 10H), 3.76 (s, 3.7H, OCH$_3$), 3.86 (t, J=6.6 Hz, 2.2H), 3.88-3.93 (m, 11.2H), 3.97 (q, J=6.9 Hz, 2.4H), 5.03-5.17 (m, 9.5H), 5.93-6.06 (m, 4.5H), 6.65-6.87 (m, 16.1H, ArH); GC RI: MS m/z (relative intensity, %): 1-allyl-2,5-dibutoxy benzene 5c\{4,4\} 1892: 263 (M$^+$+H, 28), 262 (M$^+$, 100); 1-allyl-2-butoxy-5-(3-methyl-butoxy) benzene 5c\{4,5\} 1949: 277 (M$^+$+H, 28), 276 (M$^+$, 100).

5c\{5,1-5\} Allyl-iPentyl library. (Method B, 95% yield): $^1$H NMR δ: 0.93-0.99 (m, 27.7H), 1.03 (t, J=7.4 Hz, 3.7H), 1.39 (t, J=7.0 Hz, 4H), 1.44-1.52 (m, 2.2H), 1.63-1.88 (m, 18.5H), 3.36-3.39 (m, 10.7H), 3.76 (s, 4H, OCH$_3$), 3.84-3.99 (m, 15.7H), 5.01-5.18 (m, 10.5H), 5.93-6.05 (m, 5H), 6.66-6.85 (m, 17H, ArH); GC RI: MS m/z (relative intensity, %): 1-allyl-2,5-di(3-methyl-butoxy) benzene 5c\{5,5\} 2001: 291 (M$^+$+H, 27), 290 (M$^+$, 100).

$^1$H NMR Data for Individual Compounds (Group II)

1-allyloxy-2-propoxybenzene, 3a\{3,6\} (5.1 g, 74%): liquid; GC (RI 12.51, 99%); $^1$H NMR (600 MHz, CDCl$_3$) δ: 6.68-7.15 (m, 4H), 6.14 (ddt, 1H, J=17.3, 10.5, 5.3 Hz), 5.42 (dq, 1H, J=17.3, 1.6 Hz), 5.26 (dq, 1H, J=10.5, 1.6 Hz), 4.60 (dt, 2H, J=5.3, 1.6 Hz), 3.98 (t, 2H, J=6.7 Hz), 1.80-1.91 (m, 2H), 1.05 (t, 3H, J=7.4 Hz). MS m/z (relative intensity): 193 (M$^+$+1, 100%), 109 (78%), 81 (42%).

1-allyloxy-2-butoxybenzene, 3a\{4,6\}, (1.3 g, 98%): $^1$H NMR (400 MHz, CDCl$_3$) δ: 6.91 (m, 4H), 6.08 (m, 1H), 5.41 (br dd, 1H, J=17.2, 1.2 Hz), 5.26 (br dd, 1H, J=10.4, 1.2 Hz), 4.60 (br d, 2H, J=5.2 Hz), 4.02 (t, 2H, J=6.4 Hz), 1.83 (m, 1H), 1.52 (m, 2H), 0.99 (t, 3H, J=6.8 Hz). MS m/z (relative intensity): 206 (25%), 109 (100%), 81 (26%).

1-propoxy-2-butoxybenzene, 3a\{3,4\}, (1.0 g, 85%): $^1$H NMR (400 MHz, CDCl$_3$) δ: 6.90 (br s, 4H), 4.01 (t, 2H, J=6.4 Hz), 3.97 (t, 2H, J=6.8 Hz), 1.84 (m, 4H), 1.51 (m, 2H), 1.05 (t, 3H, J=6.8 Hz), 0.98 (t, 3H, J=7.6 Hz). MS m/z (relative intensity): 208 (27%), 110 (100%).

1-allyloxy-2-isopentoxybenzene, 3a\{5,6\}, (440 mg, 64%): $^1$H NMR (400 MHz, CDCl$_3$) δ: 6.90 (m, 4H), 6.08 (m, 1H), 5.42 (m, 1H), 5.26 (m, 1H), 4.59 (dt, 2H, J=5.2, 1.2 Hz), 4.04 (t, 2H, J=6.8 Hz), 1.84 (m, 1H), 1.75 (q, 2H, J=6.8 Hz), 0.97 (d, 6H, J=6.8 Hz). MS m/z (relative intensity): 220 (65%), 150 (25%), 121 (30%), 109 (100%), 43 (32%).

3-propoxy-1-isopentoxybenzene, 3b\{3,5\} (7.4 g, 57%): liquid; GC (RI 1251, 100%); $^1$H NMR (400 MHz, CDCl$_3$) δ 0.97 (d, 6H, J=6.7 Hz), 1.05 (t, 3H, J=7.4 Hz), 1.69 (q, 2H, J=6.8 Hz), 1.74-1.90 (m, 3H), 3.92 (t, 2H, J=6.6 Hz), 3.97 (t, 2H, J=6.6 Hz), 6.52-6.46 (m, 3H), 7.15 (t, 1H, J=8.1 Hz); MS m/z (relative intensity): 223 (M$^+$+1, 100%), 110 (61%).

1-methoxy-2-isopentoxybenzene, 3b\{1,5\}, (1.3 g, 85%): $^1$H NMR (400 MHz, CDCl$_3$) δ: 7.17 (t, 1H, J=8.4 Hz), 6.50 (br dt, 2H, J=8.4, 2.4 Hz), 6.46 (br t, 1H, J=2.0 Hz), 3.97 (t, 2H, J=6.8 Hz), 3.79 (s, 3H), 1.82 (m, 1H), 1.67 (dt, 2H, J=6.8, 6.8 Hz), 0.96 (d, 6H, J=6.4 Hz). MS m/z (relative intensity): 194 (20%), 124 (100%), 95 (22%).

1-methoxy-2-allyloxybenzene, 3b\{1,6\}, (499 mg, 38%): $^1$H NMR (400 MHz, CDCl$_3$) δ: 7.16 (br t, 1H, J=8.4 Hz), 6.53 (br t, 1H, J=2.0 Hz), 6.50 (m, 2H), 6.05 (m, 1H), 5.41 (br dq, 1H, J=17.2, 1.6 Hz), 5.28 (br dq, 1H, J=10.4, 1.2 Hz), 4.52 (dt, 2H, J=5.2, 1.6 Hz), 3.79 (s, 3H). MS m/z (relative intensity): 164 (5%), 57 (45%), 56 (99%), 41 (100%).

1-allyloxy-2-allyloxybenzene, 3b\{6,6\}, (1.1 g, 90%): $^1$H NMR (400 MHz, CDCl$_3$) δ: 7.20 (br dt, 1H, J=5.2, 0.4 Hz), 6.56 (m, 3H), 6.09 (m, 2H), 5.45 (ddd, 2H, J=11.6, 2.4, 1.2 Hz), 5.32 (ddd, 2H, J=6.8, 2.0, 0.8 Hz), 4.55 (dt, 4H, J=3.6, 0.8 Hz). MS m/z (relative intensity): 190 (70%), 120 (30%).

1-allyloxy-3-isopentoxybenzene, 3b\{5,6\}, (616 mg, 99%): $^1$H NMR (400 MHz, CDCl$_3$) δ: 7.16 (br t, 1H, J=8.8 Hz), 6.52 (br d, 1H, J=2.4 Hz), 6.49 (m, 2H), 6.06 (m, 1H, J=Hz), 5.42 (dq, 1H, J=17.2, 1.6 Hz), 5.28 (dq, 1H, J=10.4, 1.2 Hz), 4.52 (dt, 2H, J=5.2, 1.6 Hz), 3.97 (t, 2H, J=6.8 Hz), 1.82 (m, 1H), 1.67 (q, 2H, J=6.4 Hz), 0.96 (d, 3H, J=6.4 Hz). MS m/z (relative intensity): 220 (25%), 150 (100%), 149 (30%), 135 (20%), 107 (22%).

1-allyloxy-4-methoxybenzene, 3c\{1,6\} (10.4 g, 99%): liquid; GC (RI 1251, 97%);

$^1$H NMR (600 MHz, CDCl$_3$) δ: 3.78 (s, 3H), 4.50 (dt, 2H, J=5.3, 1.5 Hz), 5.27 (dq, 1H, J=10.5, 1.4 Hz), 5.40 (dq, 1H, J=17.3, 1.6 Hz), 6.01-6.09 (ddt, 1H, J=17.2, 10.6, 5.3 Hz), 6.81-6.89 (m, 4H); MS m/z (relative intensity): 164 (M$^+$, 38%), 123 (100%), 95 (43%).

1-allyloxy-4-ethoxybenzene, 3c\{2,6\} (6.2 g, 82%): solid; GC (RI 1251, 98%); $^1$H NMR (600 MHz, CDCl$_3$) δ: 1.39 (t, 3H, J=7.0 Hz), 3.98 (q, 2H, J=7.0 Hz), 4.48 (dt, 2H, J=5.3, 1.5 Hz), 5.27 (dq, 1H, J=10.5, 1.4 Hz), 5.40 (dq, 1H, J=17.3, 1.6 Hz), 6.05 (ddt, 1H, J=17.2, 10.6, 5.3 Hz), 6.78-6.89 (m, 4H); MS m/z (relative intensity): 179 (M$^+$+1, 84%), 178 (M$^+$, 100%), 137 (74%).

1-allyloxy-4-propoxybenzene, 3c\{3,6\} (4.2 g, 81%): solid; GC (RI 1251, 100%);

$^1$H NMR (600 MHz, CDCl$_3$) δ: 1.01 (t, 3H, J=7.4 Hz), 1.73-1.80 (m, 2H), 3.85 (t, 2H, J=6.6 Hz), 4.47 (dt, 2H, J=5.3, 1.5 Hz), 5.25 (dq, 1H, J=10.5, 1.4 Hz), 5.38 (dq, 1H, J=17.3, 1.6 Hz), 6.03 (ddt, 1H, J=17.3, 10.5, 5.3 Hz), 6.86-6.79 (m, 4H); $^{13}$C NMR (400 MHz, CDCl$_3$) δ: 153.4, 152.6, 133.6, 117.4, 115.7 (2C), 115.3 (2C), 70.1, 69.5, 22.6, 10.5. MS m/z (relative intensity): 193 (M$^+$+1, 53%), 192 (M, 88%), 151 (40%), 109 (100%). HRMS-ESI calcd for C$_{12}$H$_{17}$O$_2$ (M+H)$^+$, m/z 193.1223. found m/z 193.1215.

1-allyloxy-4-isopentoxybenzene, 3c{5,6}, (510 mg, 84%): $^1$H NMR (400 MHz, CDCl$_3$) δ: 6.84 (m, 4H), 6.05 (m, 1H), 5.40 (dq, 1H, J=17.2, 1.6 Hz), 5.27 (dq, 1H, J=10.4, 1.2 Hz), 4.49 (dt, 2H, J=5.2, 1.2 Hz), 3.94 (t, 2H, J=6.4 Hz), 1.82 (m, 1H), 1.65 (q, 2H, J=6.8 Hz), 0.96 (d, 3H, J=6.8 Hz). MS m/z (relative intensity): 220 (60%), 150 (24%), 109 (100%), 71 (84%), 43 (82%).

4-ethoxy-1-propoxybenzene, 3c{2,3}, (700 mg, 49%): solid; $^1$H NMR (400 MHz, CDCl$_3$) δ: 1.02 (t, 3H, J=7.6 Hz), 1.39 (t, 3H, J=7.2 Hz), 1.78 (m, 2H), 3.87 (t, 1H, J=6.4 Hz), 3.98 (q, 1H, J=6.8 Hz), 6.82 (s, 4H). MS m/z (relative intensity): 180 (25%), 138 (20%), 110 (100%), 41 (28%).

1,4-dimethoxy-2-allyl-benzene, 5c{1,1}: (9.4 g, 58% yield of the Claisen rearrangement): liquid, $^1$H NMR (600 MHz, CDCl$_3$) δ: 3.40 (d, 2H, J=6.7 Hz), 3.80 (s, 3H), 3.82 (s, 3H), 5.14-5.06 (m, 2H), 6.02 (ddt, 1H, J=6.6, 10.1, 16.8 Hz), 6.88-6.70 (m, 3H).

1-methoxy-2-allyl-4-propoxy-benzene, 5c{3,1}: (7.7 g, 81% yield of the Claisen rearrangement): liquid, $^1$H NMR (600 MHz, CDCl$_3$) δ: 1.03 (t, 3H, J=7.4 Hz), 1.84-1.73 (m, 2H, J=7.5 Hz), 3.37 (d, 2H, J=6.7 Hz), 3.75 (s, 3H), 3.86 (t, 2H, J=6.4 Hz), 5.16-4.98 (m, 2H), 6.06-5.89 (m, 1H), 6.86-6.58 (m, 3H), MS m/z (relative intensity): 208 (100%), 206 (M$^+$, 61%), 164 (41%), 150 (94%), 149 (56%).

1-allyl-2,4-dimethoxybenzene and 1,3-dimethoxy-2-allylbenzene, 5b{1,1} (isomers x and y, ratio 1.8:1), 2.6 g, 79% yield of the Claisen rearrangement, liquid, $^1$H NMR (600 MHz, CDCl$_3$) δ: 3.37 (d, 2H, J=6.5 Hz, isomer x), 3.48 (d, 2H, J=4.6 Hz, isomer y), 3.92-3.80 (s, 3H, isomers x and y), 5.00 (m, 1H, isomer y), 5.09 (m, 1H, isomer y), 5.16-5.25 (m, 2H, isomer x), 6.10-5.96 (m, isomers x and y), 6.49 (d, 1H, J=8.3 Hz, isomer x), 6.51 (br s, 1H, isomer x) 6.60 (d, 2H, J=8.3 Hz, isomer y), 7.08 (d, 1H, J=8.3 Hz, isomer x), 7.20 (t, 1H, J=8.3 Hz, isomer y), MS m/z (relative intensity): isomer x (retention time 5.81 min) 178 (M$^+$, 100%), 177 (41%), 151 (26%), 149 (28%), 147 (40%), 121 (40%), 91 (27%). isomer y (retention time 5.48 min) 178 (M$^+$, 100%), 149 (57%), 121 (26%), 91 (41%). HRMS-ESI calcd for C$_{11}$H$_{15}$O$_2$ (M+H)$^+$, m/z 179.1067. found m/z 179.1061.

1-allyl-4-methoxy-2-propoxy-benzene and 1-methoxy-2-allyl-3-propoxy-benzene, 5b{3,1} (isomers x and y, ratio 1.2:1), 11.1 g, 88% yield of Claisen rearrangement, liquid, $^1$H NMR (600 MHz, CDCl$_3$) δ: 1.07 (dt, 6H, J=7.4, 1.3 Hz), 1.79-1.87 (m, 4H), 3.35 (d, 2H, J=6.7 Hz), 3.46 (d, 2H, J=6.3 Hz), 3.79-3.81 (m, 3H), 3.82-3.84 (m, 3H), 3.92 (td, 4H, J=9.7, 6.4 Hz), 4.92-5.10 (m, 4H), 5.93-6.04 (m, 2H), 6.42-6.47 (m, 2H), 6.55 (d, 2H, J=8.3 Hz), 7.05 (d, 1H, J=8.1 Hz), 7.14 (t, 1H, J=8.3 Hz). HRMS-ESI calcd for C$_{13}$H$_{19}$O$_2$ (M+H)$^+$, m/z 207.1380. found m/z 207.1371.

1-allyl-4-methoxy-2-propoxy-benzene, 5b{3,1} (isomer x), 15 mg, 96% enriched, liquid, $^1$H NMR of isomer x (600 MHz, CDCl$_3$) δ: 1.05 (t, 3H, J=7.4 Hz), 1.77-1.85 (m, 2H), 3.43 (td, 2H, J=6.3, 1.4 Hz), 3.78 (s, 3H), 3.92 (t, 2H, J=6.4 Hz), 5.00 (ddd, 1H, J=10.0, 3.6, 1.4 Hz), 5.03 (ddd, 1H, J=17.1, 3.6, 1.4 Hz), 5.95 (tdd, 1H, J=17.1, 10.0, 6.3 Hz), 6.46 (m, 2H), 7.12 (d, 1H, J=8.3 Hz), MS m/z (relative intensity): 206 (M$^+$, 100%), 177 (25%), 164 (38%), 163 (74%), 149 (27%).

1-methoxy-2-allyl-3-propoxy-benzene, 5b{3,1} (isomer y), 48 mg, 100% enriched, 2.6 g 86% enriched, liquid, $^1$H NMR of pure y (600 MHz, CDCl$_3$) δ: 1.04 (t, 3H, J=7.4 Hz), 1.76-1.84 (m, 2H), 3.30-3.34 (m, 2H), 3.78 (s, 3H), 3.87-3.93 (t, 2H, J=Hz), 4.89-5.06 (m, 2H), 5.90-6.00 (m, 1H), 6.39-6.45 (d, 2H, J=8.3 Hz), 7.02 (t, 1H, J=8.3 Hz). $^{13}$C NMR (400 MHz, CDCl$_3$) δ: 158.2, 157.7, 137.0, 127.0, 116.8, 114.0, 104.8, 103.6, 69.9, 55.8, 27.4, 22.8, 10.7. MS m/z (relative intensity): 206 (M$^+$, 100%), 177 (90%), 164 (25%), 163 (30%), 149 (71%), 135 (81%), 133 (34%), 121 (76%), 107 (52%). HRMS-ESI calcd for C$_{13}$H$_{19}$O$_2$ (M+H)$^+$, m/z 207.1380. found m/z 207.1370.

1-allyl-4-ethoxy-2-propoxy-benzene and 1-ethoxy-2-allyl-3-propoxy-benzene, 5b{3,2} (isomers x and y, ratio: 2.3:1), 2.6 g, 89% yield of the Claisen rearrangement, liquid, $^1$H NMR (600 MHz, CDCl$_3$) δ: 1.09 (m, 6H), 1.44 (m, 6H), 1.79-1.92 (m, 4H), 3.36 (m, 2H), 3.50 (m, 2H), 3.94 (m, 4H), 3.99-4.10 (m, 4H), 4.91-5.12 (m, 4H), 6.00 (m, 2H), 6.42-6.56 (m, 4H), 7.00-7.16 (m, 2H). HRMS-ESI calcd for C$_{14}$H$_{21}$O$_2$ (M+H)$^+$, m/z 221.1536. found m/z 221.1528.

1-allyl-4-ethoxy-2-propoxy-benzene, 5b{3,2} (isomer x), 13.2 mg, 96% enriched, liquid, $^1$H NMR (600 MHz, CDCl$_3$) δ: 1.02 (t, 3H, J=7.4 Hz), 1.38 (t, 3H, J=7.0 Hz), 1.72-1.85 (m, 2H), 3.30 (d, 2H, J=6.7 Hz), 3.88 (m, 2H), 4.05 (q, 2H, J=7.0 Hz), 4.94 (ddd, 1H, J=10.2, 2.1, 1.2 Hz), 5.05 (ddd, 1H, J=16.8, 2.4, 1.2 Hz), 5.88-5.99 (m, 1H), 6.38 (dd, 1H, J=8.4, 2.4 Hz), 6.42 (d, 1H, J=2.4 Hz), 6.98 (d, 1H, J=8.4 Hz), MS m/z (relative intensity): 220 (M$^+$, 100%), 191 (25%), 177 (16%), 149 (58%).

1-ethoxy-2-allyl-3-propoxy-benzene, 5b{3,2} (isomer y), 49.7 mg, 100% enriched, liquid, $^1$H NMR (600 MHz, CDCl$_3$) δ: 1.07 (t, 3H, J=7.4 Hz), 1.42 (t, 3H, J=7.0 Hz), 1.77-1.89 (m, 2H), 3.46 (dt, 2H, J=6.5, 1.3 Hz), 3.94 (t, 2H, J=6.4 Hz), 4.05 (q, 2H, J=7.0 Hz), 4.94 (ddt, 1H, J=10.0, 2.4, 1.3 Hz), 5.05 (ddd, 1H, J=17.0, 3.8, 1.6 Hz), 5.97 (ddt, 1H, J=17.0, 10.0, 6.5 Hz), 6.53 (d, 2H, J=8.3 Hz), 7.11 (t, 1H, J=8.3 Hz). $^{13}$C NMR (400 MHz, CDCl$_3$) δ: 157.7, 157.6, 137.1, 126.9, 117.1, 114.0, 104.7, 104.6, 69.8, 63.9, 27.6, 22.8, 15.0, 10.7. MS m/z (relative intensity): 220 (M$^+$, 60%), 191 (62%), 177 (12%), 149 (100%), 135 (46%), 121 (59%), 107 (29%). HRMS-ESI calcd for C$_{14}$H$_{21}$O$_2$ (M+H)$^+$, m/z 221.1536. found m/z 221.1532.

1-allyl-4-methoxy-3-isopentoxybenzene and 1-methoxy-2-allyl-3-isopentoxybenzene, 5b{5,1} (isomers x and y, ratio 1.8:1), 11.0 g, 91% yield of the Claisen rearrangement, liquid, $^1$H NMR (600 MHz, CDCl$_3$) δ: 0.99 (d and s, 12H, J=6.9 Hz), 1.75-1.68 (m, 4H), 1.95-1.85 (m, 2H), 3.34 (d, 2H, J=6.7 Hz), 3.45 (d, 2H, J=6.3 Hz), 3.80-3.82 (m, 3H), 3.83-3.84 (m, 3H), 3.97-4.03 (m, 6H), 4.93-5.09 (m, 4H), 5.93-6.04 (m, 2H), 6.43-6.48 (m, 2H), 6.56 (dd, 2H, J=8.3, 5.3 Hz), 7.05 (d, 1H, J=8.3 Hz), 7.15 (t, 1H, J=8.3 Hz), MS m/z (relative intensity): isomer x (retention time 8.03 min) 234 (M$^+$, 80%), 177 (2%), 164 (95%), 163 (100%), 149 (33%), 147 (37%), 133 (28%). isomer y (retention time 7.83 min) 234 (M$^+$, 100%), 205 (35%), 177 (7%), 164 (72%), 163 (39%), 135 (99%), 133 (41%), 121 (71%), 107 (40%), 77 (28%). HRMS-ESI calcd for C$_{15}$H$_{23}$O$_2$ (M+H)$^+$, m/z 235.1693. found m/z 235.1691.

1-allyl-3-allyloxy-4-methoxybenzene and 1-methoxy-2-allyl-3allyloxybenzene, 5b{6,1} (isomers x and y, ratio 2.3:1), 8.6 g, 69% yield of the Claisen rearrangement, liquid, $^1$H NMR (600 MHz, CDCl$_3$) δ: 3.37 (br d, 2H, J=6.6 Hz, isomer x), 3.48 (br d, 2H, J=6.0 Hz, isomer y), 3.80 (s, 3H, isomer x), 3.85 (s, 3H, isomer y), 4.54 (ddd, 2H, J=5.4, 1.8, 1.8 Hz, isomer x), 4.55 (ddd, 2H, J=4.8, 1.2, 1.2 Hz, isomer y), 4.90 (m, 1H, isomer y), 5.02 (m, 1H, isomer y), 5.03 (m, 1H, isomer x), 5.07 (m, 1H, isomer x), 5.00-5.10 (m, 2H isomer x+1H isomer y), 5.27 (m, 1H, isomer y), 5.28 (m, 1H, isomer x), 5.44 (ddd, 1H, J=17.4, 3.6, 1.8 Hz, isomer y), 5.45 (ddd, 1H, J=16.8, 3.0, 1.2 Hz, isomer x), 5.95-6.12 (m, 2H, isomer y), 6.44-6.49 (m, 2H, isomer x), 6.55 (d, J=8.4 Hz, 1H isomer x), 6.57 (d, J=9.0 Hz, 1H isomer y), 7.04-7.08 (br d, J=9.0 Hz, 2H, isomer x), 7.14 (t, 1H, J=8.4

Hz, isomer y), MS m/z (relative intensity): isomer x (retention time 6.92 min) 204 (M+, 100%), 203 (32%), 177 (9%), 163 (44%), 161 (28%), 135 (43%), isomer y (retention time 6.70 min) 204 (M+, 100%), 189 (26%), 177 (20%), 175 (25%), 163 (85%), 161 (42%), 147 (30%), 135 (89%), 107 (88%), 105 (42%), 103 (50%), 91 (47%), 77 (52%). HRMS-ESI calcd for $C_{13}H_{17}O_2$ (M+H)+, m/z 205.1223. found m/z 205.1232.

For the synthesis of the first set of mini-libraries (Set A, Scheme 1 or 1-1, and Table 2), equimolar mixtures of monoalkoxy 2(a-c){n} compounds were alkylated to afford chemsets of 4 or 5 members 3(a-c){1,1-5}. In order to effect complete deprotonation of the monoalkoxy compounds 2(a-c){n}, the alkylation was conducted with NaH as the base, in DMF, at room temperature. The reaction was monitored by GC and it proceeded at similar rates for all the components, affording crude products of high purity (>90% by GC). However, the removal of DMF resulted in losses of material. Further, the more volatile dialkoxy members 3(a-c){n,1-5} evaporated in sufficient quantities to introduce biases (e.g Table 2, entry 2). Following optimization, the $K_2CO_3$/acetone base/solvent system afforded better yields and much less bias (e.g. Table 2, entry 6).

TABLE 2

Purity of the Libraries and % Distribution of the Members in Libraries

| no. | Library[a] | n | Purity[b] | {n,1}[c] | {n,2} | {n,3} | {n,4} | {n,5} |
|---|---|---|---|---|---|---|---|---|
| | | | Set A | | | | | |
| 1 | 3a{1,1-5} | 1 | 100 | 13.7 | 13.0 | 16.9 | 26.0 | 30.4 |
| 2 | 3a{2 1-5} | 2 | 99 | 7.0 | 8.8 | 15.3 | 32.5 | 35.0 |
| 3 | 3a{3,1-5} | 3 | 99 | 9.7 | 12.3 | 20.2 | 25.8 | 30.7 |
| 4 | 3a{4,1-5} | 4 | 99 | 9.0 | 14.7 | 18.8 | 27.9 | 27.2 |
| 5 | 3a{5,1-5} | 5 | 99 | 7.7 | 12.9 | 17.9 | 31.2 | 29.6 |
| 6 | 3a{6,1-5} | 6 | 100 | 13.2 | 15.9 | 19.2 | 27.3 | 24.3 |
| 7 | 3b{1,1-5}* | 1 | 99 | 21.1 | 21.7 | 26.1 | — | 30.0 |
| 8 | 3b{2,1-5}* | 2 | 95 | 16.2 | 20.4 | 26.4 | — | 32.3 |
| 9 | 3b{3,1-5}* | 3 | 97 | 12.0 | 16.2 | 28.6 | — | 39.7 |
| 10 | 3b{4,1-5}* | 4 | 100 | 19.1 | 20.7 | 27.7 | — | 32.2 |
| 11 | 3b{5,1-5}* | 5 | 97 | 22.5 | 22.9 | 27.3 | — | 24.3 |
| 12 | 3b{6,1} | 6 | 100 | 100 | — | — | — | — |
| 13 | 3b{6,2-3} | 6 | 97 | — | 62 | 38 | — | — |
| 14 | 3b{6,4-5} | 6 | 97 | — | — | — | 59 | 41 |
| 15 | 3c{1,1-5}* | 1 | 97 | 15.1 | 20.2 | 23.2 | — | 38.2 |
| 16 | 3c{2,1-5}* | 2 | 98 | 20.1 | 23.6 | 23.9 | — | 30.7 |
| 17 | 3c{3,1-5}* | 3 | 96 | 19.7 | 18.6 | 24.9 | — | 32.9 |
| 18 | 3c{4,1-5}* | 4 | 97 | 24.6 | 23.0 | 24.7 | — | 24.8 |
| 19 | 3c{5,1-5}* | 5 | 95 | 22.7 | 21.2 | 24.5 | — | 26.7 |
| 20 | 3c{6,1-5} | 6 | 100 | 10.1 | 13.6 | 18.6 | 23.8 | 33.9 |
| | | | Set B | | | | | |
| 21 | 4a{1-5} | — | 95 | 13.7 | 17.3 | 18.9 | 23.1 | 22.0 |
| 22 | 4b{1}[e] | — | 100 | 61/39 | — | — | — | — |
| 23 | 4b{2-3}[e] | — | 100 | — | 22/20 | 32/27 | — | — |
| 24 | 4b{4-5}[e] | — | 100 | — | — | — | 26/24 | 28/22 |
| 25 | 4c{1-5} | — | 100 | 9.1 | 14.3 | 20.6 | 22.9 | 33.1 |
| | | | Set C | | | | | |
| 26 | 5a{1,1-5} | 1 | 92 | 12.9 | 14.5 | 17.2 | 24.1 | 23.7 |
| 27 | 5a{2,1-5} | 2 | 93 | 14.3 | 15.5 | 17.0 | 23.2 | 23.1 |
| 28 | 5a{3,1-5} | 3 | 94 | 14.0 | 15.2 | 17.6 | 23.7 | 23.1 |
| 29 | 5a{4,1-5} | 4 | 90 | 16.7 | 16.7 | 15.7 | 22.3 | 18.5 |
| 30 | 5a{5,1-5} | 5 | 90 | 19.9 | 20.7 | 15.6 | 19.7 | 14.5 |
| 31 | 5a{6,1-5} | 6 | 96 | 17.6 | 21.5 | 18.0 | 22.5 | 16.4 |
| 32 | 5b{1,1} | 1 | 99 | 60/40 | — | — | — | — |
| 33 | 5b{1,2-3}[e] | 1 | 96 | — | 23/16 | 38/24 | — | — |
| 34 | 5b{1,4-5}[e] | 1 | 100 | — | — | — | 34/20 | 29/17 |
| 35 | 5b{2,1}[e] | 2 | 100 | 62/38 | — | — | — | — |
| 36 | 5b{2,2-3}[e] | 2 | 98 | — | 24/16 | 38/22 | — | — |
| 37 | 5b{2,4-5}[e] | 2 | 100 | — | — | — | 36/20 | 27/17 |
| 38 | 5b{3,1}[e] | 3 | 100 | 61/39 | — | — | — | — |
| 39 | 5b{3,2-3}[e] | 3 | 100 | — | 25/16 | 35/23 | — | — |
| 40 | 5b{3,4-5}[e] | 3 | 100 | — | — | — | 35/19 | 31/15 |
| 41 | 5b{4,1}[e,f] | 4 | 98 | 62/38 | — | — | — | — |
| 42 | 5b{4,2-3}[e,f] | 4 | 98 | — | 34/20 | 31/15 | — | — |
| 43 | 5b{4,4-5}[e,f] | 4 | 95 | — | — | — | 30/18 | 32/20 |
| 44 | 5b{5,1}[e,f] | 5 | 99 | 62/38 | — | — | — | — |
| 45 | 5b{5,2-3}[e,f] | 5 | 100 | — | 34/20 | 31/15 | — | — |
| 46 | 5b{5,4-5}[e,f] | 5 | 99 | — | — | — | 30/19 | 31/20 |
| 47 | 5b{6,1}[e,f] | 6 | 94 | 61/39 | — | — | — | — |
| 48 | 5b{6,2-3}[e,f] | 6 | 94 | — | 36/21 | 26/17 | — | — |
| 49 | 5b{6,4-5}[e,f] | 6 | 88 | — | — | — | 29/20 | 30/21 |
| 50 | 5c{1,1-5} | 1 | 99 | 11.0 | 14.0 | 19.9 | 23.7 | 30.0 |
| 51 | 5c{2,1-5} | 2 | 100 | 12.6 | 16.5 | 22.8 | 21.3 | 26.8 |
| 52 | 5c{3,1-5} | 3 | 100 | 12.5 | 15.9 | 21.9 | 22.7 | 26.9 |
| 53 | 5c{4,1-5} | 4 | 100 | 9.8 | 14.5 | 23.1 | 24.1 | 28.5 |
| 54 | 5c{5,1-5} | 5 | 99 | 16.5 | 18.9 | 22.0 | 20.3 | 21.3 |
| 55 | 5c{6,1-5} | 6 | 100 | 14.1 | 21.5 | 27.5 | 18.6 | 18.3 |
| | | | Set D | | | | | |
| 56 | 6c{1-5} | — | 100 | 10.5 | 15.1 | 19.9 | 24.6 | 29.9 |

*These libraries do not contain the {n,4} member;
[a]Sequence of alkyl substituents in the brackets is interchangeable: e.g. member 3a{1,2} is identical with member 3a{2,1};
[b]Purity was determined by GC;
[c]"n" has the same significance as in Scheme 1 and it corresponds to the first number in the bracket of the respective chemset;
[d]Percent distribution of the library members was determined by GC and validated by NMR and GC-MS data;
[e]Meta compounds undergoing a Claisen Rearrangement yielded two products, and the "5-alkoxy-2-allyl phenol" (x) is listed first; the same format holds for the alkylated derivatives of the meta Claisen Rearrangement products;
[f]Initial lot of starting material, 4b{n}, was used completely and re-synthesized as a second lot.

Further expansion of the libraries was accomplished via the ortho-Claisen rearrangement of chemsets 3(a-c){6,1-5} at 180° C. and afforded pure libraries (Set B, Table 2). For the ortho library, 4a{1-5}, traces (2-5%) of the para-Claisen rearrangement products were detected (Scheme 2). For the meta 4b libraries no para-Claisen rearrangement was detected and for para 4c libraries the para-Claisen rearrangement was not possible and not observed (Scheme 2). Under thermal conditions, the para-Claisen rearrangement of allyl phenyl ethers is not an important pathway (Ito, F et al. 2007). Under selected Lewis acid or metal catalysis conditions, and when the ortho positions are blocked the para-Claisen rearrangement can be significant (Kuntz et al. 2006; Ollevier et al. 2006; Yadav et al. 2007). The meta compounds 3b{6,1-5} yielded two products: 5-alkoxy-2-allylphenol, x, and 3-alkoxy-2-allylphenol, y (Table 2, Scheme 2) upon ortho-Claisen rearrangement. The rearrangement to the less sterically hindered side was slightly more prevalent (1.4-1.8×) than the alternative rearrangement to the hindered position, consistent with previous literature on the thermal Claisen rearrangement of meta-substituted allyl phenol ethers (Ito, F et al. 2007; Gozzo et al 2003; White and Slater 1961).

Scheme 2.

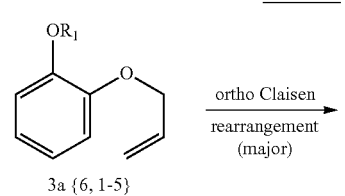

3a {6, 1-5} ortho Claisen rearrangement (major)

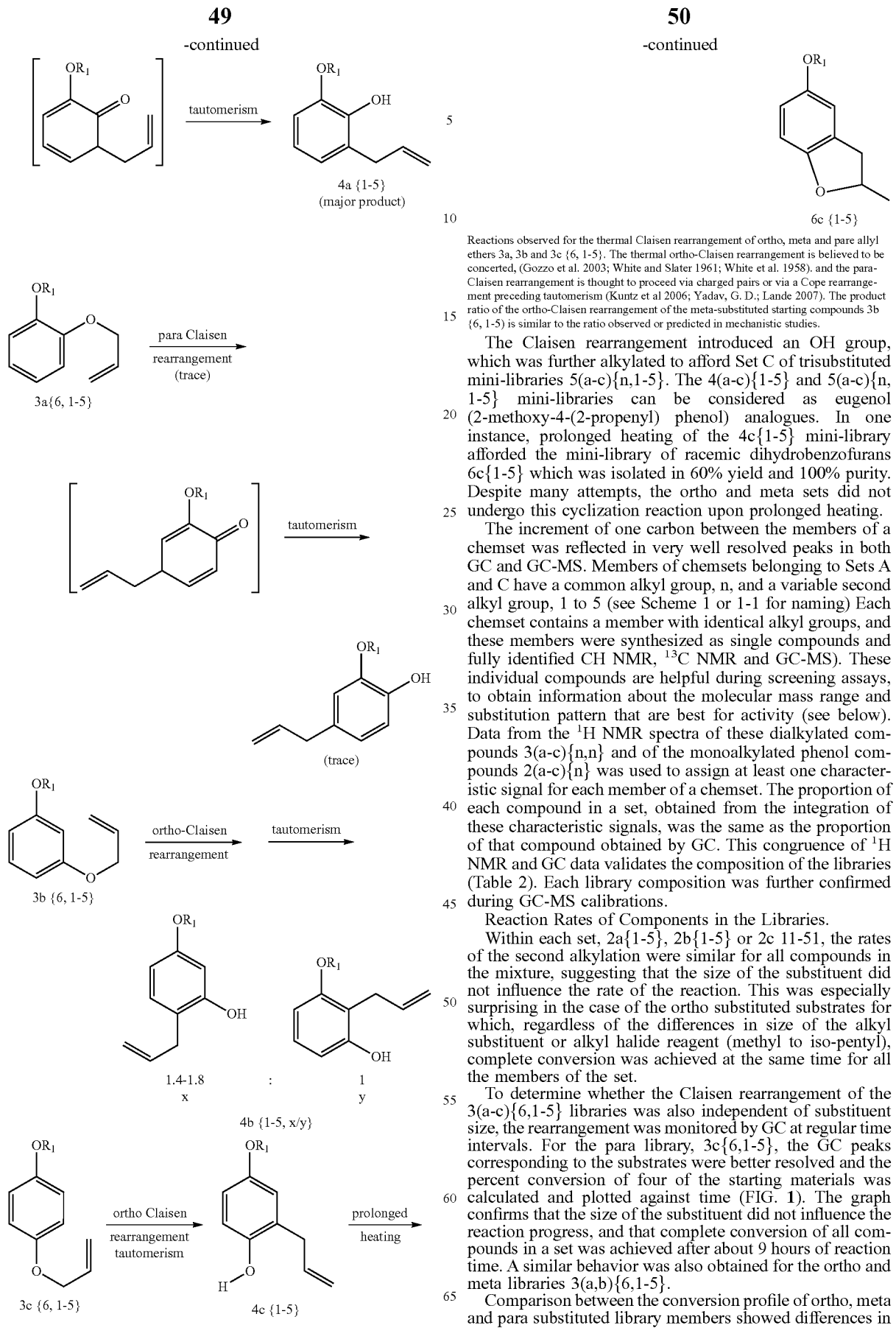

Reactions observed for the thermal Claisen rearrangement of ortho, meta and para allyl ethers 3a, 3b and 3c {6, 1-5}. The thermal ortho-Claisen rearrangement is believed to be concerted, (Gozzo et al. 2003; White and Slater 1961; White et al. 1958). and the para-Claisen rearrangement is thought to proceed via charged pairs or via a Cope rearrangement preceding tautomerism (Kuntz et al 2006; Yadav, G. D.; Lande 2007). The product ratio of the ortho-Claisen rearrangement of the meta-substituted starting compounds 3b {6, 1-5} is similar to the ratio observed or predicted in mechanistic studies.

The Claisen rearrangement introduced an OH group, which was further alkylated to afford Set C of trisubstituted mini-libraries 5(a-c){n,1-5}. The 4(a-c){1-5} and 5(a-c){n, 1-5} mini-libraries can be considered as eugenol (2-methoxy-4-(2-propenyl) phenol) analogues. In one instance, prolonged heating of the 4c{1-5} mini-library afforded the mini-library of racemic dihydrobenzofurans 6c{1-5} which was isolated in 60% yield and 100% purity. Despite many attempts, the ortho and meta sets did not undergo this cyclization reaction upon prolonged heating.

The increment of one carbon between the members of a chemset was reflected in very well resolved peaks in both GC and GC-MS. Members of chemsets belonging to Sets A and C have a common alkyl group, n, and a variable second alkyl group, 1 to 5 (see Scheme 1 or 1-1 for naming) Each chemset contains a member with identical alkyl groups, and these members were synthesized as single compounds and fully identified CH NMR, $^{13}$C NMR and GC-MS). These individual compounds are helpful during screening assays, to obtain information about the molecular mass range and substitution pattern that are best for activity (see below). Data from the $^1$H NMR spectra of these dialkylated compounds 3(a-c){n,n} and of the monoalkylated phenol compounds 2(a-c){n} was used to assign at least one characteristic signal for each member of a chemset. The proportion of each compound in a set, obtained from the integration of these characteristic signals, was the same as the proportion of that compound obtained by GC. This congruence of $^1$H NMR and GC data validates the composition of the libraries (Table 2). Each library composition was further confirmed during GC-MS calibrations.

Reaction Rates of Components in the Libraries.

Within each set, 2a{1-5}, 2b{1-5} or 2c 11-51, the rates of the second alkylation were similar for all compounds in the mixture, suggesting that the size of the substituent did not influence the rate of the reaction. This was especially surprising in the case of the ortho substituted substrates for which, regardless of the differences in size of the alkyl substituent or alkyl halide reagent (methyl to iso-pentyl), complete conversion was achieved at the same time for all the members of the set.

To determine whether the Claisen rearrangement of the 3(a-c){6,1-5} libraries was also independent of substituent size, the rearrangement was monitored by GC at regular time intervals. For the para library, 3c{6,1-5}, the GC peaks corresponding to the substrates were better resolved and the percent conversion of four of the starting materials was calculated and plotted against time (FIG. 1). The graph confirms that the size of the substituent did not influence the reaction progress, and that complete conversion of all compounds in a set was achieved after about 9 hours of reaction time. A similar behavior was also obtained for the ortho and meta libraries 3(a,b){6,1-5}.

Figure 2:
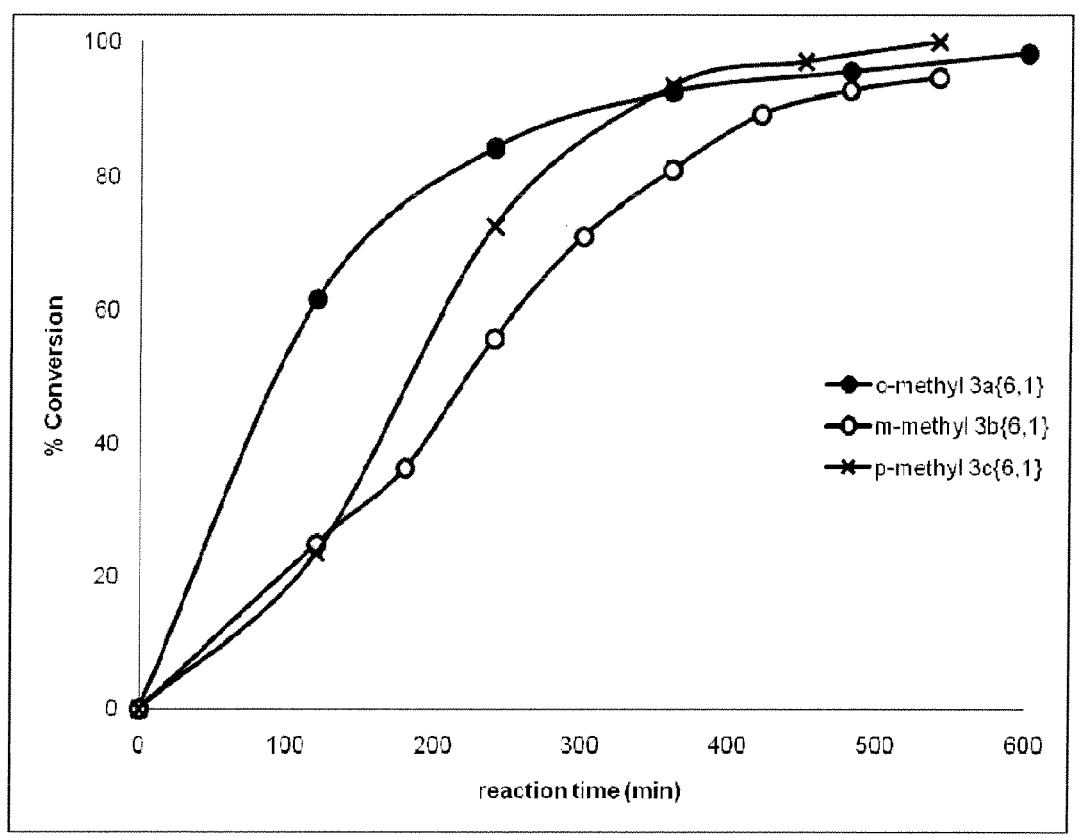
FIG. 2 shows graphs with the progress of the Claisen rearrangement reaction: comparison between the ortho methoxy 3a{6,1}, meta methoxy 3b{6,1} and para methoxy 3c{6,1} library members.

Comparison between the conversion profile of ortho, meta and para substituted library members showed differences in the half-time to total conversion, but not in the total reaction time. Members of the ortho library 3a{6,1-5} achieved 50% conversion in 1 hour while it took 3 and 4 hours for the members of the para library 3c{6,1-5} and meta library 3b{6,1-5}, respectively, to reach the same point. The time necessary to achieve total conversion was not dependent upon the substitution pattern. For clarity, only data for one member in each library are shown (FIG. 2).

Dihydrobenzofuran Formation.

When the para library 3c{6,1-5} was heated three times longer (30 hours) than required for the completion of the Claisen rearrangement, dihydrobenzofurans 6c{1-5} were obtained. Reported spectral data for the known compound, 6c{1}, was used to confirm the identity of the products (Grant and Liu 2005). As a further proof we synthesized 6c{3} as a single compound, and its spectra as well as GC retention time matched the data for the respective library member. Interestingly, cyclization occurred only on the para substituted compounds 3c{6,1-5} and not on the ortho 3a{6,1-5} or meta 3b{6,1-5} substituted ones. Ortho and meta allyl ethers began decomposing when heated longer than was necessary to complete the Claisen rearrangement. Further, we learned that the cyclization reaction followed the Claisen rearrangement and, therefore library 6c{1-5} could also be obtained directly from the 4c{1-5} library. The cyclization reaction proceeded in a Markovnikov sense, and this selectivity has been observed also with (3'-methyl)-2'-butenyl (dimethylallyl) substituents (Ollevier et al. 2006). In previous literature, allyl aryl ethers were rearranged and cyclized to dihydrobenzofurans in the presence of a copper (II) triflate catalyst (Ito et al. 2007), an iridium (III)/silver triflate catalyst (Grant and Liu 2005), aluminum-containing mesoporous molecular sieves (Mathew et al. 2004), a gold (I)-catalyst (Reich et al. 2006) or a bismuth triflate catalyst (Ollevier et al. 2006). These studies also suggest that the Claisen rearrangement occurs first, followed by the Markovnikov addition of the new phenol OH to the allyl double bond (Reich et al. 2006). In fact, few catalysts promoted the tandem reaction; some only catalyzed the Claisen reaction and others caused decomposition. Further, the allyl phenyl ethers that cyclized best, generally had electron-releasing groups or no additional substituents on the benzene ring.

Preparation of Compounds Group II

For the meta compounds, the Claisen rearrangement gave two isomers. For the alkoxy substituents that were used, the isomer in which the allyl group migrates to position 4 (isomer x) is slightly favoured thermodynamically over the isomer in which the allyl group migrates to position 2 (isomer y) (White and Slater1961; Gozzo et al. 2003). Typical ratios of compounds x:y range from 2.3:1 to 1.2:1. Isomers x and y from the Claisen rearrangement of meta substituted allyloxybenzenes were separated by flash chromatography on $AgNO_3$-silica.

The two isomers x and y were separated for selected cases of series 5b. Briefly, 1% (w/v) $AgNO_3$ was dissolved in water, to which was added silica gel to form a thick slurry. The slurry dried overnight (120° C.), before being packed into the column. Care was taken not to expose the silver nitrate silica to light, by wrapping the beaker with the slurry and later the column with aluminum foil. The silver-silica column was equilibrated with hexane-toluene: 99:1, and the loaded compounds were eluted with 90:10 hexane-toluene. To monitor the separation, 1% $AgNO_3$ TLC plates were prepared by running the silver nitrate solution up the plates and drying them. The plates could be stained with anisaldehyde solution. Isomer y ran faster than x, and it was possible to obtain several fractions that contained pure y. However, y also tailed into the x peak, so that it was not possible to obtain fractions with 100% x by FCC. Alternatively, 5b{3,1}y and 5b{3,1}x as well as 5b{3,2}y and 5b{3,2}x could be separated by preparative TLC (100% hexanes) with multiple developments.

The more compact isomer y was more volatile than x, eluting usually 0.5-1 min earlier from the GC (DB-5 column). Also, in general, isomer y formed an M+1 ion in the mass spectrum more readily and fragmented more extensively (for example, to the tropylium ion m/z 91) than isomer x.

Example 2

Gas Chromatographic-Electroantennographic Detection (GC-EAD) of Selected Compounds and Mixtures In GC-EAD assays, the analyte is processed by gas chromatography (GC). The column effluent is split, such that molecules of each chromatographic peak arrive simultaneously at the flame ionization detector of the GC and at an anectomized but otherwise intact insect antenna as the biological detector. This procedure detects specific compounds in the analyte that elicit an electrical potential from the antenna.

Coupled gas chromatographic-electroantennographic detection (GC-EAD) analyses were conducted employing a Hewlett-Packard (HP) 5890 gas chromatograph fitted with a GC-column (30 m×0.32 mm ID) coated with DB-5 (J&W Scientific, Folsom, Calif., USA). For GC-EAD recordings, an antenna was carefully dislodged from a male moth's head, and the antennal base placed into the opening of a glass capillary electrode (0.58 mm ID×65 mm length) (A-M Systems, Inc., Carlsborg, Wash., USA) filled with saline solution. The tip of the antenna was removed by spring microscissors (Fine Science Tools Inc., North Vancouver, British Columbia, Canada) and then placed into the opening of the recording electrode mounted on a portable micromanipulator and positioned in front of a constant stream of warm air (Praxair Canada Inc., Mississauga, Ontario, Canada) which delivered the GC column eluent. Antennal receptor potentials (measured in mV) elicited by specific compounds were recorded by a HP 3392A chart recorder. Identical retention times of compounds detected by the flame ionization detector of the GC and by the insect antenna allowed assignment of antennal responses to specific compounds in the eluent.

Results:

The results of GC-EAD indicated that compounds and mini-libraries tested 2c{n}, 2c{n,n} and 3c{1-5} elicited little antennal response by themselves. This is desirable, as it implies that the moths cannot detect these compounds with their antennae.

Example 3

Pheromone-Binding Protein (PBP) Assays for Selected Compounds and Mixtures

Figure 3:
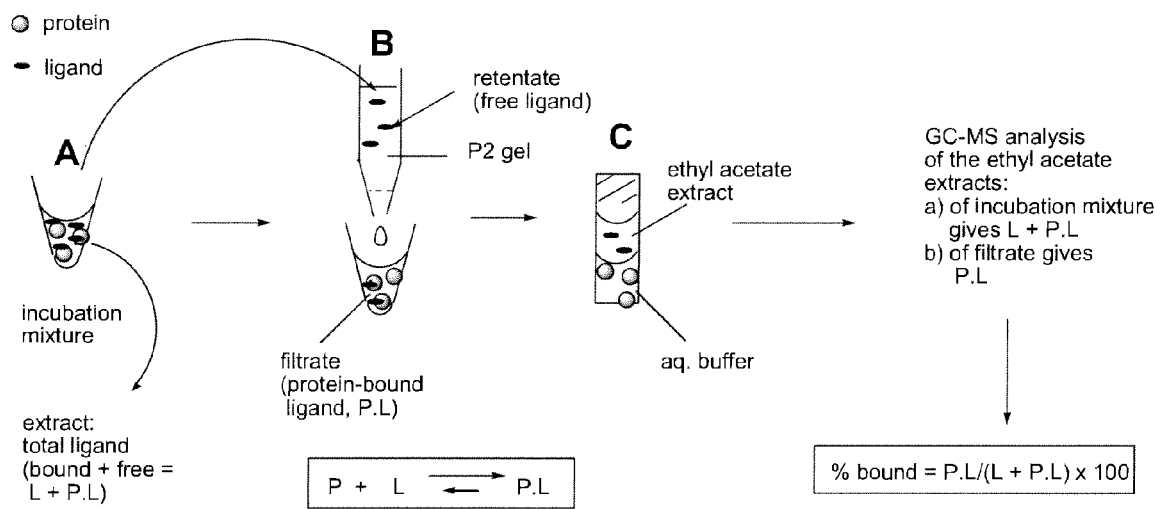
FIG. 3 shows a scheme for the insect pheromone-binding protein (PBP) ligand binding assay. A. The protein and ligand are incubated in buffer overnight. B. For half of the incubation mixture, the free ligand (L) is separated from the protein-bound ligand (P.L) by size-exclusion chromatography on P2 Gel (BioRad, exclusion limit 2000 Da). The protein elutes from the small column bed, with its ligand bound (see Examples and Plettner et al. 2000; Staddon and Everton 1980), while the free ligand is retained on the column (Plettner et al. 2000). C. The remaining half of the incubation mixture and the filtrate are transferred to glass vials and extracted with ethyl acetate, containing an internal standard (see methods). The extract from the filtrate (B) contains the protein-bound ligand and the extract from the incubation mixture (A) contains all the ligand (bound and free) present in the aqueous phase. The extracts are analyzed by GC-MS, to obtain values for total ligand in solution (L+P.L) and for protein-bound ligand (P.L). These can then be used to calculate % bound (Table 3).

These assays were performed as described in FIG. 3 and as follows: L. dispar PBP 1 or PBP 2 was incubated with the test compound or mini-library. The PBP and the ligand(s) (L) were left to equilibrate (eq 2) overnight. The non-bound ligand was then separated from the protein-bound material (PBP.L) by size-exclusion chromatography. By determining the total ligand in solution at equilibrium (eq. 3) and the protein-bound ligand, it is possible to estimate the percentage of ligand bound to the protein at equilibrium (eq. 4).

This assay is possible because dissociation of the ligand from the internal binding site of the PBP is very slow ($t_{1/2} \geq 2$ h), so no significant dissociation occurs during the size-exclusion chromatography. This binding assay has been validated extensively in previous studies (Plettner et al. 2000). The components of each mini-library separated cleanly by GC, so it was possible to monitor binding of individual components.

$$PBP + L \rightleftharpoons PBP \cdot L \qquad \text{(eq. 2)}$$

$$[L]_{tot} = [L] + [PBP \cdot L] \qquad \text{(eq. 3)}$$

$$\% \text{ bound} = 100 \times [PBP \cdot L]/[L]_{tot} \qquad \text{(eq. 4)}$$

Results: The members of each mini-library separated cleanly by GC, therefore it was possible to monitor binding of individual members to PBP1 or PBP2, the two known PBPs in the gypsy moth, by extraction from the aqueous incubation mixture, followed by GC analysis of the extract (FIG. 3).

PBPs exhibit non-linear behavior in the presence of blends. In this study, blend effects manifested themselves as different binding affinities for one compound, depending on the composition of the mini-library tested (Table 3).

TABLE 3

Binding affinity of two pheromone-binding proteins (PBPs) from gypsy moth towards members in the para 3c{n, 1-5}* libraries and para dialkoxy 3c{n, n} compounds.

| Library/compound | Member | PBP1 (% bound)[a] | PBP2 (% bound)[a] |
|---|---|---|---|
| (+)-disparlure | | 54 ± 16 | 71 ± 23 |
| 3c{1, 1-5}* | 3c{1, 1} | 24 ± 0.3 | 19 ± 0.9 |
| | 3c{1, 2} | 15 ± 0.4 | 12 ± 1.5 |
| | 3c{1, 3} | 7 ± 0.5 | 5 ± 2.1 |
| | 3c{1, 5} | 1 ± 0.7 | 2 ± 2.5 |
| 3c{1, 1} | | 40 ± 2.5 | 13 ± 2.1 |
| 3c{2, 1-5}* | 3c{2, 1} | 30 ± 0.2 | 40 ± 0.1 |
| | 3c{2, 2} | 14 ± 0.5 | 33 ± 0.6 |
| | 3c{2, 3} | 10 ± 0.3 | 22 ± 0.3 |
| | 3c{2, 5} | 4 ± 0.2 | 14 ± 0.2 |
| 3c{2, 2} | | 28 ± 0.1 | 19 ± 0.2 |
| 3c{3, 1-5}* | 3c{3, 1} | 13 ± 0.3 | 7 ± 0.2 |
| | 3c{3, 2} | 13 ± 0.3 | 6 ± 0.2 |
| | 3c{3, 3} | 4 ± 0.3 | 3 ± 0.1 |
| | 3c{3, 5} | 1 ± 0.2 | Nd |
| 3c{3, 3} | | 15 ± 0.7 | 5 ± 0.2 |
| 3c{4, 1-5}* | 3c{4, 1} | 20 ± 0.4 | Nd |
| | 3c{4, 2} | 10 ± 0.4 | Nd |
| | 3c{4, 3} | 4 ± 0.3 | Nd |
| | 3c{4, 5} | 4 ± 0.4 | Nd |
| 3c{4, 4} | | 4 ± 0.1 | 8 ± 0.3 |
| 3c{5, 1-5}* | 3c{5, 1} | 7 ± 0.1 | 5 ± 0.1 |
| | 3c{5, 2} | 2 ± 0.1 | 3 ± 0.03 |
| | 3c{5, 3} | 3 ± 0.1 | 2 ± 0.02 |
| | 3c{5, 5} | 5 ± 0.1 | 1 ± 0.1 |
| 3c{5, 5} | | 9 ± 0.7 | 8 ± 0.2 |

*These libraries do not contain the {n, 4} member;
[a]Percentage of compound bound to the protein, according to eq. 4. Data shown are means ± S.E. for 4 replicates. Nd = not detected in the GC-MS quantitations.

For example, 3c{1,2} bound to PBP1 and PBP2 as a member of the 3c{2,1-5} ethyl library more strongly than as a member of the 3c{1,1-5} methyl library. Similarly, 3c{2, 3} bound more strongly to PBP2 as a member of the 3c{2,1-5} ethyl library than as a member of the 3c{3,1-5} propyl library. Further, the pure compounds 3c{1,1}, 3c{2, 2}, and 3c{3,3} bound more strongly to PBP1 by themselves than as part of the mini-libraries that contain these compounds. For PBP2 binding of the pure compounds with identical alkyl group, 3c{n,n} was either weaker or the same as in the libraries.

Overall, binding was strongest to both PBPs in the 3c{2, 1-5} ethyl library and binding became weaker as the average molecular size in the series increased. These results suggest that there a minimal and a maximal size requirement for binding for these compounds. There was little correlation between the percentage bound of the single compounds or the strongest binder from the mini libraries and the EAG inhibition activity ($R^2 < 0.2$). There were moderate negative correlations between PBP binding of 3c{2,2}, 3c{3,3}, 3c{5,5}, as well as binding of individual isopentyl members of the libraries (3c{1,5}, 3c{2,5}, 3c{3,5}, 3c{4,5}, 3c{5, 5}) and the EAG inhibitory responses of the 3c{n,n} compounds or the mini-libraries (correlations: $R^2 = 0.57$, PBP1; $R^2 = 0.81$, PBP2). This suggests that, for some of the compounds, the stronger the PBP binding the weaker the EAG inhibition activity.

Example 4

Competitive Electroantennogram (EAG) Screens

Figure 4:
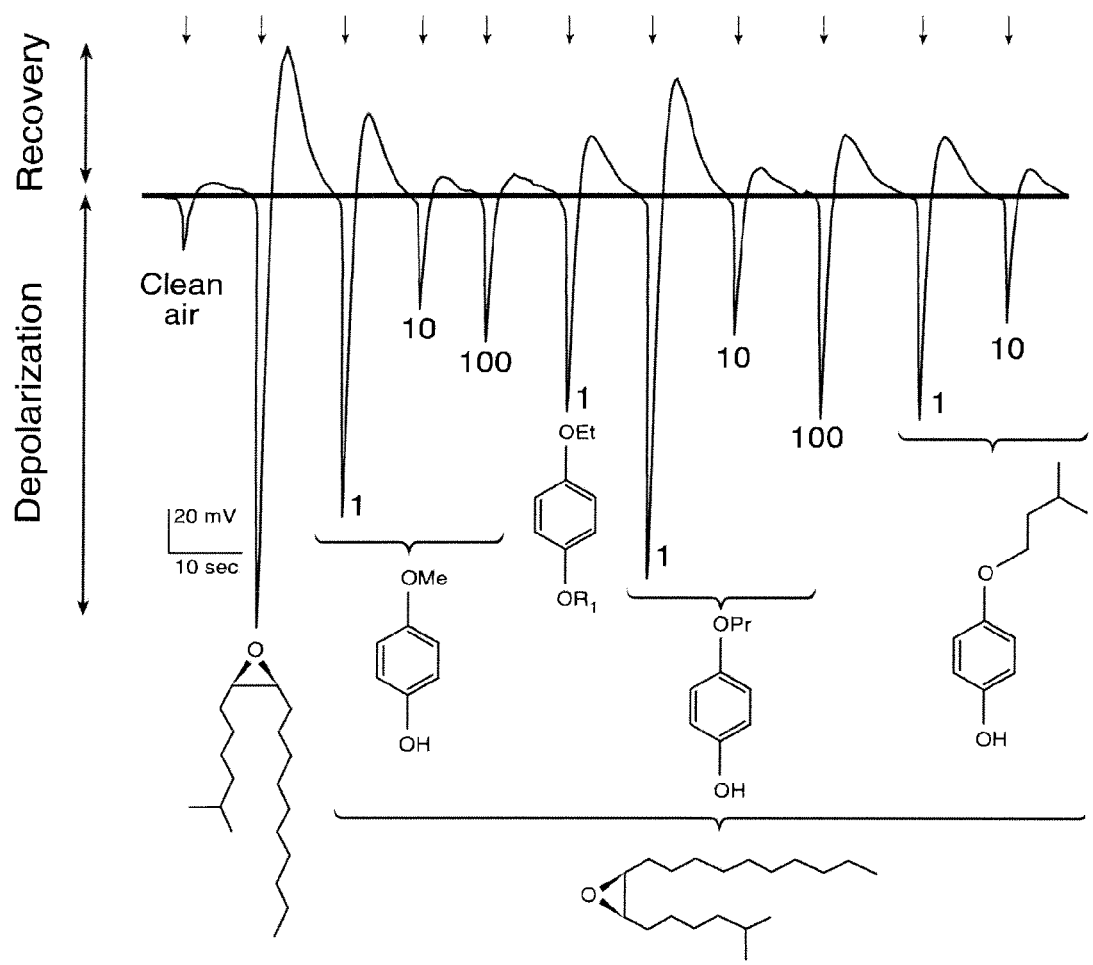
FIG. 4 shows graphs with competitive electroantennogram (EAG) assay, with an antenna of a male gypsy moth, *Lyamantria dispar*, responding to puffs of clean air or to chemicals delivered in puffs of air. In this assay, libraries and individual compounds are tested for their ability to inhibit the antennal response to the sex attractant pheromone of the gypsy moth, (7R,8S) 2-methyl-7,8-epoxyoctadecane, also known as (+)-disparlure. The controls consisted of a puff of clean air (negative) or of air passed over a cartridge impregnated with (+)-disparlure (100 ng) (positive). The treatments consisted of 100 ng of (+)-disparlure in combination with a compound or library at 1, 10 or 100 μg, on a cartridge over which the air puff was passed. The small arrows above the trace denote the times where the air was puffed over the antenna.

For some compounds, such as the para Compounds 2c{n}, 2c{n,n} and libraries 3c{n,1-5}, EAG competitive assays were performed to investigate whether the diethers inhibit the response of *L. dispar* antennae to the main component of the sex attractant pheromone cis-(7R,8S)-epoxy-2-methyloctadecane [(+)-disparlure] (FIG. 4). For EAGs a male moth antenna was mounted and placed in front of a stimulus-delivery glass tubing (160×5 mm ID) with a side orifice (2 mm diam) near (2 cm) the distal opening. The tubing was connected to one port of an apparatus (Stimulus Controller CS-05, Syntech Research and Equipment, NL-1200BM Hilversum, The Netherlands) that generated a constant stream of clean air (300 ml/min). The second port of the apparatus was connected to a Pasteur pipette inserted through the side orifice of the stimulus-delivery tubing. The test stimulus was applied to a disc of Whatman #1 filter paper inside the Pasteur pipette and was discharged through a 0.3-sec pulse of air (600 ml/min) Receptor potentials of the antennae in response to test stimuli were recorded with a Syntech IDAC probe, amplifier and interfaced board, and were analyzed with EAG Syntech Software Version 2.4 (1996) Inhibition (%) was calculated as:

$$\% \text{ inhibition} = (D_d - D_s)/D_d \times 100 \qquad \text{(eq. 1)}$$

Where $D_d$ is the depolarization observed with pure disparlure (corrected for clean air background) and $D_s$ is the depolarization with disparlure+sample. See FIG. 4 for a representative EAG inhibition assay trace.

For other compounds, EAG traces were recorded as follows: a fully dislodged antenna from a male gypsy moth was mounted on the end of a reference electrode (a glass capillary with a silver wire, filled with buffered saline: 5 mM $NaH_2PO_4$, 10 mM $Na_2SO_4$, 4.5 mM $KHCO_3$, 18 mM $MgCl_2$, 4 mM $CaCl_2$, 6 mM KCl, the pH is adjusted to 6.8 using 5 mM $Na_2HPO_4$). The tip of the antenna was severed with microscissors and placed in the recording electrode, which was mounted on a micromanipulator. A constant stream of air, that had been purified (charcoal filter), was blown over the antenna at a rate of 300 mL/min. Test samples were delivered through a stimulus delivery tube with a side opening 2 cm from the distal opening. The proximal end of the delivery tube was connected to a controlled stimulus delivery apparatus (Stimulus controller CS-05 Syntech Research and Equipment, NL 1200BM, Hilversum, The Netherlands). The distal end of the delivery tube pointed at the antenna (1 cm from the antenna). The side opening was connected to a cartridge fashioned from a Pasteur pipette which contained a small filter paper (Whatman No. 1) with the stimulus. These pipette cartridges could be prepared a few days in advance and stored at −80° C. wrapped in Al foil and in sealable plastic bags. Sample cartridges were mounted once they had reached room temperature. The stimulus delivery apparatus delivered a second stream of air (a puff) through the Pasteur pipette at a velocity of 600 mL/min, at a specified point in time, for 0.3 s. Receptor potentials of the antennae in response to test stimuli were recorded with a Syntech IDAC probe, amplifier and interfaced board, and were analyzed with EAG Syntech Software Version 2.4 (1996). See FIG. 4 for a representative EAG trace. The EAG traces were evaluated as follows (see FIG. 5).

The net depolarizations, $d_{(net)}$ (in mV), of puffs ii-vi, $d_{(sample)}$, (corrected for the depolarization with clean air, $d_{(air)}$)

$$d_{(net)} = d_{(sample)} - d_{(air)} \quad \text{(Eq. 1)}$$

The percentage short-term inhibition for each compound ($STI_{(compound)}$) of puffs iii-v, relative to the first pure pheromone puff (ii)

$$STI_{(compound)} = 100 \times (d_{(net)(ii)} - d_{(net)(compound)}) / d_{(net)(ii)} \quad \text{(Eq. 2)}$$

c) the percentage long-term inhibition for each compound ($LTI_{(compound)}$) of the pure pheromone puff that followed the last mixed puff (vi) relative to the first pure pheromone puff (ii)

$$LTI_{(compound)} = 100 \times (d_{(net)(ii)} - d_{(net)(vi)}) / d_{(net)(ii)} \quad \text{(Eq. 3)}$$

Results:

The results from testing the monoalkoxy phenols 2c{n} and the para-substituted dialkoxybenzenes (Table 4) showed some selectivity in the inhibitory activity of the tested compounds. The monoalkyl phenols showed moderate or weak inhibition of antennal pheromone responses at any dose. Among the bis phenol ethers 2c{n,n}, some moderate inhibitory activity was seen with 2c{3,3} and with 2c{5,5}. This suggested that a certain minimal compound size was required for activity for these compounds. Three mini-libraries showed robust inhibitory activity (>80% inhibition). The activity was moderate when the common alkyl group was either methyl 3c{1,1-5} or isopentyl 3c{5,1-5} and strong when the common group was either ethyl 3c{2,1-5}, propyl 3c{3,1-5} or butyl 3c{4,1-5}. This suggests that there is a certain minimal and maximal compound size required for these compounds. Further, the activity of compound 3c{5,5} was lower than of the 3c{5,1-5} mini-library and the activity of compound 3c{3,3} was significantly lower than that of 3c{3,1-5} or 3c{4,1-5} mini-libraries, suggesting that at least one of the ether moieties in the diethers may be medium-sized (propyl, butyl) and straight-chain.

TABLE 4

Inhibitory activity of para compounds 2c{n}, 2c{n, n} and libraries 3c{n, 1-5}*.

| Compound/Library | Dose (µg) | Activity | Compound/Library | Activity |
|---|---|---|---|---|
| 2c{1} | 1 | 10 ± 5 (15) | 3c{1, 1} | 4 ± 6 (4) |
|  | 10 | 55 ± 11 (15) |  | −8 ± 9 (5) |
|  | 100 | 43 ± 12 (15) |  | 38 ± 7 (4) |
| 2c{2} | 1 | 49 ± 10 (22) | 3c{2, 2} | 4 ± 13 (5) |
|  | 10 | 64 ± 9 (6) |  | 45 ± 6 (6) |
|  | 100 | 45 ± 8 (6) |  | −3 ± 13 (5) |
| 2c{3} | 1 | 17 ± 14 (16) | 3c{3, 3} | 5 ± 16 (5) |
|  | 10 | 43 ± 14 (16) |  | 55 ± 7 (6) |
|  | 100 | 35 ± 12 (16) |  | −3 ± 15 (6) |
| 2c{5} | 1 | 38 ± 17 (16) | 3c{5, 5} | 63 ± 12 (12) |
|  | 10 | 38 ± 27 (16) |  | 38 ± 22 (13) |
|  | 100 | 19 ± 20 (14) |  | 64 ± 11 (11) |
| 3c{1, 1-5}* | 100[a] | 73 ± 9 (14) | 3c{4, 1-5}* | 90 ± 6 (12) |
| 3c{2, 1-5}* | 100 | 86 ± 11 (14) | 3c{5, 1-5}* | 74 ± 6 (12) |
| 3c{3, 1-5}* | 100 | 89 ± 6 (13) |  |  |

*These libraries do not contain the {n, 4} member. Data are for % inhibition of the EAG response to the sex attractant pheromone of the gypsy moth (+)-disparlure (eq. 1); means ± S.E. The number of replicates is shown in parenthesis. Signals were corrected for clean air background. Entries in bold showed >70% inhibition of the (+)-disparlure signal. The dose is the amount of material placed on a paper cartridge, over which a puff of air is passed to stimulate the insect antenna. Responses are corrected relative to the antennal response to a puff of clean air.
[a]Response of the libraries to 1 and 10 µg doses was not determined.

Example 5

Further EAG Studies

Experiment 1

Short-Term and Long-Term Inhibitors of Pheromone Signaling

The following classes of compounds were assayed by electroantennogram (EAG) experiments: monoalkoxyphenols (2 series), dialkoxybenzenes (3 series), monoalkoxy allyl phenols (4 series), dialkoxyallylbenzenes (5 series) and eugenol and alkyl eugenols.

Figure 5A:
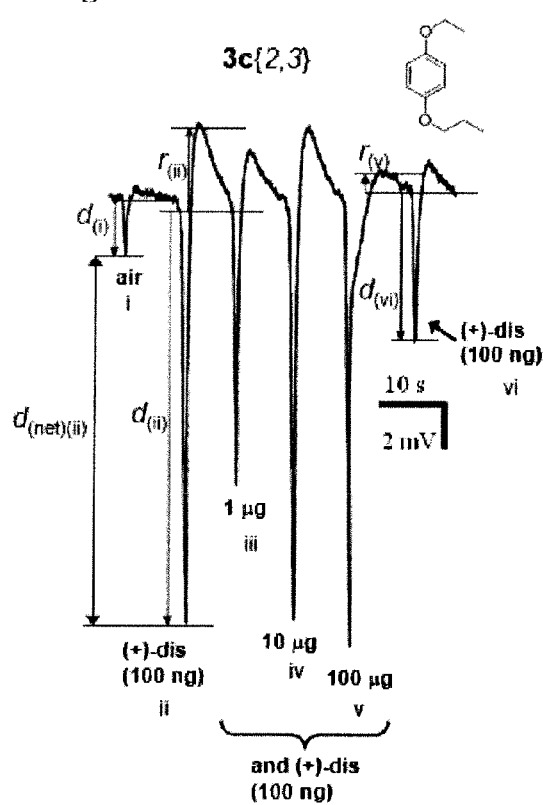
FIG. 5A. Typical trace for compound 3c{2,3}.
Figure 5B:
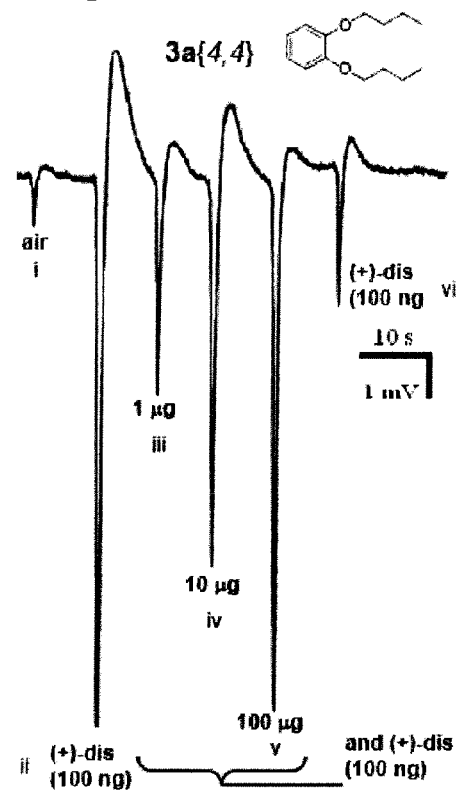
FIG. 5B. Typical trace for compound 3a{4,4}.

The compounds we tested gave weak or no olfactory responses by themselves in electroantennogram (EAG) experiments. The EAG trace reflects the change in the potential across the antenna when an air puff with an odorant is passed over the antenna. To understand the agonistic or antagonistic effect of the compounds on pheromone responses by male moth antennae, four types of EAG experiment were conducted. First, the response of the antenna elicited by a stimulus of pure (+)-1 was compared to the responses elicited by blends of (+)-1 with the test compound (FIG. 5). The mixed plumes often gave a significantly different response, compared to the pure (+)-1 stimuli. This effect was termed short-term inhibition (STI). A pure (+)-1 stimulus, given after the mixed stimuli was sometimes significantly inhibited, compared to the initial pure (+)-1 stimulus, and this was termed long-term inhibition (LTI). Second, the time decay and dose responses for LTI activities were studied. Third, the strongest inhibitors were tested for their ability to cause LTI by themselves. Fourth, the strongest long-term inhibitors were tested 1) against other host plant and pheromone odorants and 2) against mixtures of (+)-1 and host plant odorants.

This experiment explored the agonistic or antagonistic activity of the synthetic aromatic compounds (Scheme 1 and eugenol and alkyl eugenols) with the gypsy moth pheromone (+)-1. The pheromone was kept constant at 100 ng/cartridge, and 6 puffs were recorded for each replicate: i) clean air, ii) pure (+)-1 (100 ng on the cartridge), iii) (+)-1 (100 ng) and the compound (1 µg on the cartridge, mixed with the pheromone), iv) (+)-1 (100 ng) and the compound (10 µg), v) (+)-1 (100 ng) and the compound (100 µg), vi) pure (+)-1 (100 ng).

The following four parameters were measured with this experiment, using the various phases of the EAG signal (FIG. 5):

a) the net depolarizations, $d_{(net)}$ (in mV), of puffs ii-vi,d $_{(sample)}$, (corrected for the depolarization with clean air, $d_{(air)}$)

$$d_{(net)} = d_{(sample)} - d_{(air)} \quad \text{(Eq. 1)}$$

b) the percentage short-term inhibition for each compound ($STI_{(compound)}$) of puffs iii-v, relative to the first pure pheromone puff (ii)

$$STI_{(compound)} = 100 \times (d_{(net)(ii)} - d_{(net)(compound)})/d_{(net)(ii)} \quad \text{(Eq. 2)}$$

c) the percentage long-term inhibition for each compound ($LTI_{(compound)}$) of the pure pheromone puff that followed the last mixed puff (vi) relative to the first pure pheromone puff (ii)

$$LTI_{(compound)} = 100 \times (d_{(net)(ii)} - d_{(net)(vi)}/d_{(net)(ii)} \quad \text{(Eq. 3)}$$

d) the percentage inhibition of the recovery period ($RI_{(compound)}$) of the mixed puff with the highest dose of the compound (v) (Eq. 6).

The height of the recovery (hyperpolarization), $r_{(puff)}$, above the baseline is usually 20% of the total deviation of the signal from the baseline ($r_{(puff)} + d_{(puff)}$, e.g., FIG. 1). For many of the mixed puffs, the proportional height of the recovery was either greater or less, depending on the compound. The proportional height of the recovery for the first pure (+)-1 puff (ii) is $$R_{(puff\ ii)} = 100 \times r_{(ii)}/[r_{(ii)} + d_{(ii)}] \quad \text{(Eq. 4)}$$

and the proportional height of the highest dose mixed puff (v) is $$R_{(puff\ v)} = 100 \times r_{(v)}/[r_{(v)} - d_{(v)}] \quad \text{(Eq. 5)}$$

The relative change in the recovery is $$RI_{(compound)} = 100 \times [R_{(puff\ ii)} - R_{(puff\ v)}]/R_{(puff\ ii)} \quad \text{(Eq. 6)}$$

Results:

The complete set of STI and LTI obtained is shown in Tables 5-7. STI showed structure-activity patterns for some compounds or sets (Tables 5-7 and FIG. 8), but for many compounds it varied between different batches of moths. The strongest, most robust short-term inhibitor was set 5b{1,1} (a mixture of 1-allyl-2,4-dimethoxybenzene and 2-allyl-1,3-dimethoxybenzene). The eugenols showed consistent negative STI values, signifying that they enhanced the antennal responses to the pheromone.

Long-term inhibition (LTI) showed robust structure-activity patterns that could be reproduced from year to year and between different sources and lots of moths. The alkoxyphenols showed less activity than the dialkoxybenzenes (FIG. 6 A-D). For ortho alkoxyphenols the LTI increased from methyl to propyl and then decreased for butyl and isopentyl. The dialkoxybenzenes with $R_1 = R_2$ gave higher LTI and showed structure-activity patterns (FIG. 6B): ortho compounds showed increasing LTI with increasing group size from methyl to butyl, and a loss of activity for isopentyl, meta compounds had highest activity for mid-sized groups, and para compounds had moderate and variable activity. The dialkoxybenzene sets (FIG. 6C) showed moderate activity for all the ortho and meta sets, with the methyl sets being highest. The para sets showed a structure-activity pattern: the propyl set had the highest LTI activity. Individual compounds from the propyl set tested (FIG. 2 D), and compound 3c{2,3} (1-ethoxy-4-propoxybenzene) was the strongest long-term inhibitor. The meta allyl series of compounds (3b{n,6}) was also tested (FIG. 6E), and 3b{3,6} (1-allyloxy-3-propoxybenzene) was the most active long-term inhibitor.

Figure 6A:
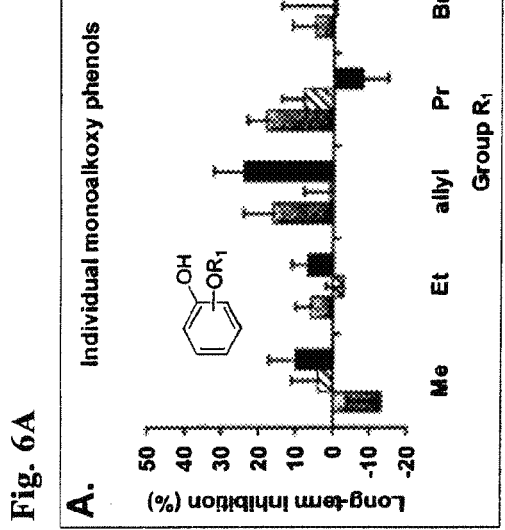
FIG. 6A. Alkoxyphenols.
Figure 6B:
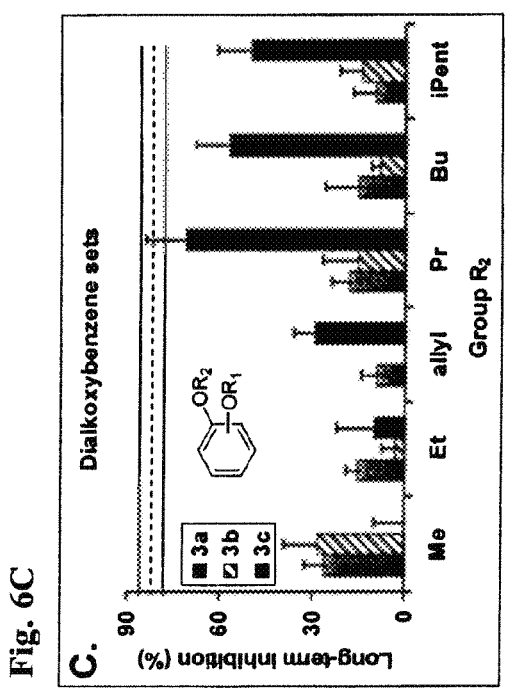
FIG. 6B. Dialkoxybenzenes with equal substituents.
Figure 6C:
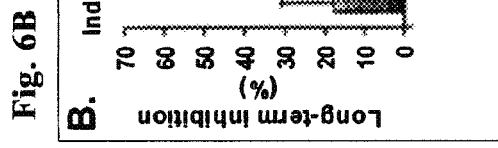
FIG. 6C. Dialkoxybenzene sets.
Figure 6D:
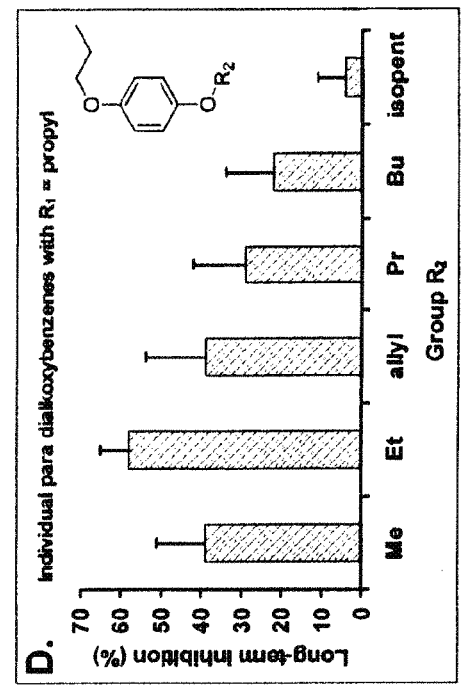
Figure 6F:
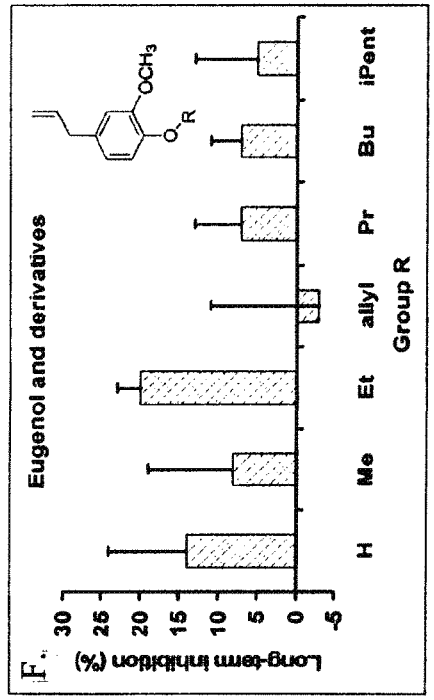
FIG. 6F. Eugenol and derivatives.
Figure 6H:
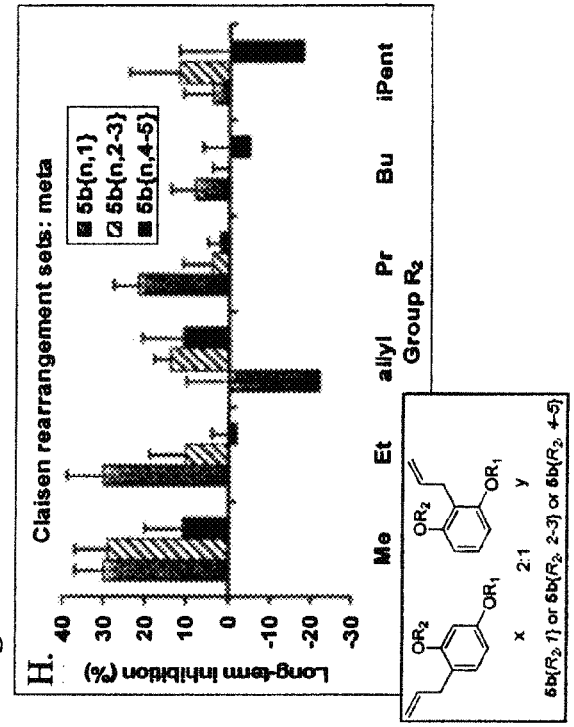
FIG. 6H. Allyl dialkoxybenzene sets obtained from Claisen rearrangement of 1-allyloxy-3-alkoxybenzenes (Scheme 1)
Figure 6E:
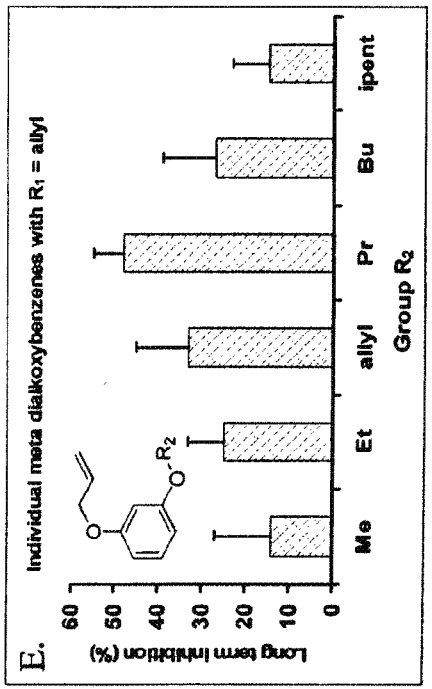
FIG. 6E. Individual meta dialkoxybenzenes (3b{n,6},1-allyloxy-3-alkoxybenzenes).
Figure 6G:
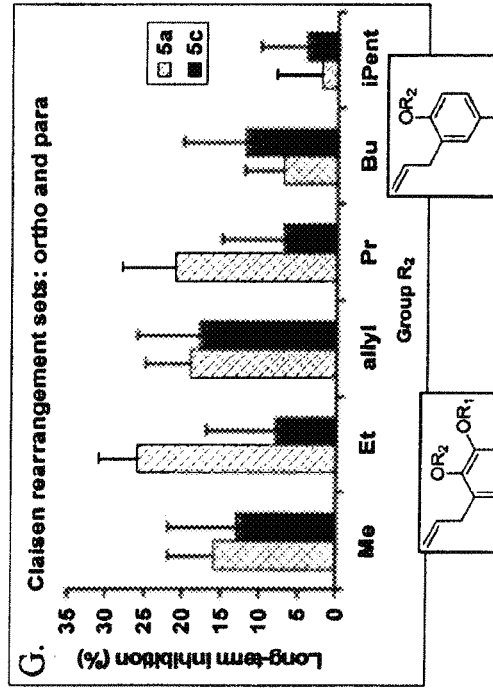
FIG. 6G. Allyl dialkoxybenzene sets obtained from Claisen rearrangement of 1-allyloxy-2-alkoxybenzenes and 1-allyloxy-4-alkoxybenzenes, followed by alkylation of the new phenol group (Scheme 1).

The ortho and para 1-allyloxy, 2- or 4-alkoxybenzene sets (3a{6,1-5} and 3c{6,1-5}) were subjected to thermal Claisen rearrangement to provide sets 4a{1-5} and 4c{1-5}, respectively. These sets of phenols were divided and alkylated, to give six new sets of compounds: 5a{1, 1-5} to 5a{6,1-5} and 5c{1,1-5} to 5c{6,1-5}. In the meta case, the 1-allyloxy-3-alkoxybenzene precursors were kept in smaller groups (methyl by itself, ethyl and propyl, butyl and isopentyl) (FIG. 6H), because each precursor could form two products. These Claisen rearranged products or the eugenols showed little LTI compared to the most active dialkoxybenzenes. Among the 5a compounds, the ones with a mid-sized second alkyl group ($R_2$) were most active (FIG. 6G) and among the 5b compounds the ones with the methyl group were most active (FIG. 6H).

The strongest long-term inhibitors were DEET and set 3c{3,1-5} (1-alkoxy-4-propoxybenzene), of which compound 3c{2, 3} (1-ethoxy-4-propoxybenzene) was the most active.

TABLE 5

EAG inhibition activity of the bis-phenol-mono-ethers and allyl bisphenol-mono-ethers.

| Dose (μg) | Compound[c] | Activity (%)[d] | Compound | Activity (%) | Compound | Activity (%) |
|---|---|---|---|---|---|---|
| 1[a] | 2a{1} | 26 ± 14 (13)[e] | 2b{1} | 6 ± 11 (9) | 2c{1} | 8 ± 12 (7) |
| 10[a] | | −27 ± 24 (13) | | 14 ± 22 (9) | | 21 ± 20 (7) |
| 100[a] | | 9 ± 11 (13) | | 49 ± 8 (9) | | −16 ± 25 (7) |
| LT[b] | | −13 ± 9 (13) | | 4 ± 7 (9) | | 10 ± 7 (7) |
| 1 | 2a{2} | 42 ± 12 (11) | 2b{2} | 4 ± 20 (7) | 2c{2} | −3 ± 4 (13) |
| 10 | | 26 ± 12 (11) | | 0 ± 27 (7) | | 55 ± 5 (13) |
| 100 | | 58 ± 11 (11) | | 44 ± 18 (7) | | 47 ± 5 (13) |
| LT | | 6 ± 4 (11) | | −3 ± 5 (7) | | 7 ± 4 (13) |
| 1 | 2a{3} | −26 ± 14 (11) | 2b{3} | −6 ± 14 (7) | 2c{3} | 7 ± 31 (7) |
| 10 | | 32 ± 9 (11) | | 36 ± 19 (7) | | 29 ± 34 (7) |
| 100 | | 46 ± 13 (11) | | 65 ± 14 (7) | | 38 ± 12 (7) |
| LT | | 18 ± 5 (11)' | | 8 ± 6 (7) | | −8 ± 7 (7) |
| 1 | 2a{4} | 26 ± 12 (10) | 2b{4} | −6 ± 18 (7) | 2c{4} | 12 ± 37 (6) |
| 10 | | 21 ± 11 (10) | | −20 ± 31 (7) | | 38 ± 11 (6) |
| 100 | | 56 ± 9 (10) | | −74 ± 71 (7) | | −122 ± 84 (6) |
| LT | | 5 ± 6 (10) | | −1 ± 15 (7) | | 26 ± 13 (6) |
| 1 | 2a{5} | 22 ± 8 (12) | 2b{5} | −87 ± 63 (8) | 2c{5} | 47 ± 14 (5) |
| 10 | | −44 ± 26 (12) | | −111 ± 78 (8) | | 77 ± 7 (5) |
| 100 | | −37 ± 33 (12) | | −9 ± 58 (8) | | 49 ± 7 (5) |

TABLE 5-continued

EAG inhibition activity of the bis-phenol-mono-ethers and allyl bisphenol-mono-ethers.

| Dose (μg) | Compound[c] | Activity (%)[d] | Compound | Activity (%) | Compound | Activity (%) |
|---|---|---|---|---|---|---|
| LT |  | 6 ± 6 (12) |  | 4 ± 7 (8) |  | 2 ± 4 (5) |
| 1 | 2a{6} | −63 ± 62 (7) | 2b{6} | 24 ± 23 (7) | 2c{6} | 19 ± 10 (8) |
| 10 |  | −33 ± 40 (7) |  | 28 ± 20 (7) |  | 42 ± 8 (8) |
| 100 |  | −31 ± 71 (7) |  | 5 ± 32 (7) |  | 46 ± 10 (8) |
| LT |  | 16 ± 8 (7) |  | 1 ± 7 (7) |  | 24 ± 8 (8) |
| 1 | 4a{1-5} | 40 ± 19 (10) | 4b{1} | 11 ± 31 (7) | 4c{1-5} | 46 ± 15 (7) |
| 10 |  | 52 ± 16 (10) |  | 41 ± 19 (7) |  | 5 ± 39 (7) |
| 100 |  | 66 ± 11 (10) |  | 12 ± 32 (7) |  | −18 ± 47 (7) |
| LT |  | 26 ± 8 (10) |  | −11 ± 10 (4) |  | 18 ± 5 (7) |
| 1 |  |  | 4b{2-3} | −4 ± 17 (7) |  |  |
| 10 |  |  |  | 31 ± 11 (7) |  |  |
| 100 |  |  |  | −33 ± 59 (7) |  |  |
| LT |  |  |  | 8 ± 8 (7) |  |  |
| 1 |  |  | 4b{4-5} | −23 ± 39 (5) |  |  |
| 10 |  |  |  | 7 ± 56 (5) |  |  |
| 100 |  |  |  | −8 ± 65 (5) |  |  |
| LT |  |  |  | 1 ± 3 (5) |  |  |

[a]Short-term inhibition (STI) for a mixed plume of (+)-1 (100 ng in the cartridge) and the compound (indicated amount in the cartridge).
[b]Long-term inhibition (LTI) for a plume of pure (+)-1 (100 ng in the cartridge) following the mixed plume with (+)-1 and 100 μg of the compound.
[c]For compound naming, please see Scheme 1
[d]Calculated from the EAG traces from Example 5, according to the methods. Negative values represent and enhancement and positive values represent an inhibition of the EAG response.
[e]Values are mean ± S.E., with the number of replicates shown in parenthesis after each entry.

TABLE 6

EAG inhibition activity of the bis-phenol diethers.

| Dose (μg) | Compound[c] | Activity (%)[d] | Compound | Activity (%) | Compound | Activity (%) |
|---|---|---|---|---|---|---|
| 1[a] | 3a{1,1-5} | 35 ± 7 (7)[e] | 3b{1,1-5} | 63 ± 6 (5) | 3c{1,1-5} | −63 ± 15 (5) |
| 10[a] |  | 9 ± 20 (7) |  | 41 ± 7 (5) |  | 4 ± 18 (5) |
| 100[a] |  | −33 ± 50 (7) |  | 73 ± 2 (5) |  | 72 ± 17 (5) |
| LT[b] |  | 26 ± 6 (7) |  | 28 ± 11 (5) |  | 0 ± 10 (5) |
| 1 | 3a{2,1-5} | 72 ± 6 (9) | 3b{2,1-5} | 48 ± 8 (6) | 3c{2,1-5} | 42 ± 20 (5) |
| 10 |  | 47 ± 13 (9) |  | 39 ± 10 (6) |  | 42 ± 17 (5) |
| 100 |  | 71 ± 7 (9) |  | 62 ± 7 (6) |  | 50 ± 19 (5) |
| LT |  | 15 ± 4 (9) |  | 3 ± 4 (6) |  | 10 ± 12 (5) |
| 1 | 3a{3,1-5} | 23 ± 25 (7) | 3b{3,1-5} | 1 ± 9 (3) | 3c{3,1-5} | −12 ± 22 (6) |
| 10 |  | 20 ± 23 (7) |  | 8 ± 8 (3) |  | 51 ± 11 (6) |
| 100 |  | −35 ± 57 (7) |  | −11 ± 9 (3) |  | 105 ± 11 (6) |
| LT |  | 18 ± 6 (7) |  | 15 ± 12 (3) |  | 71 ± 13 (6) |
| 1 | 3a{4,1-5} | 38 ± 12 (12) | 3b{4,1-5} | 5 ± 14 (13) | 3c{4,1-5} | −11 ± 15 (6) |
| 10 |  | 0 ± 34 (12) |  | 5 ± 12 (13) |  | 33 ± 8 (6) |
| 100 |  | 38 ± 10 (12) |  | −23 ± 24 (13) |  | 87 ± 6 (6) |
| LT |  | 15 ± 11 (12) |  | 8 ± 3 (13) |  | 57 ± 11 (6) |
| 1 | 3a{5,1-5} | 42 ± 15 (4) | 3b{5,1-5} | 47 ± 11 (12) | 3c{5,1-5} | −20 ± 23 (5) |
| 10 |  | 9 ± 15 (4) |  | 4 ± 17 (12) |  | −51 ± 29 (5) |
| 100 |  | 39 ± 9 (4) |  | −32 ± 26 (12) |  | 71 ± 9 (5) |
| LT |  | 10 ± 7 (4) |  | 14 ± 7 (12) |  | 50 ± 11 (5) |
| 1 | 3a{6,1-5} | 40 ± 9 (8) | 3b{6,n} | | 3c{6,1-5} | 29 ± 27 (9) |
| 10 |  | 36 ± 16 (8) | tested as |  |  | 29 ± 17 (9) |
| 100 |  | 53 ± 10 (8) | individual |  |  | 59 ± 9 (9) |
| LT |  | 9 ± 5 (8) | compounds |  |  | 29 ± 7 (9) |
| 1 | 3a{1,1} | 4 ± 24 (7) | 3b{1,1} | 25 ± 18 (7) | 3c{1,1} | 24 ± 8 (7) |
| 10 |  | 12 ± 25 (7) |  | 9 ± 40 (7) |  | 23 ± 9 (7) |
| 100 |  | −8 ± 77 (7) |  | 44 ± 36 (7) |  | 15 ± 25 (7) |
| LT |  | 18 ± 13 (7) |  | 1 ± 8 (7) |  | −7 ± 10 (7) |
| 1 | 3a{2,2} | −10 ± 29 (7) | 3b{2,2} | −100 ± 51 (8) | 3c{2,2} | 7 ± 12 (6) |
| 10 |  | −23 ± 42 (7) |  | −12 ± 70 (8) |  | −19 ± 8 (6) |
| 100 |  | −22 ± 69 (7) |  | 63 ± 65 (8) |  | −27 ± 15 (6) |
| LT |  | 15 ± 11 (7) |  | 39 ± 6 (8) |  | 17 ± 11 (6) |
| 1 | 3a{3,3} | 37 ± 14 (7) | 3b{3,3} | 36 ± 11 (7) | 3c{3,3} | −3 ± 13 (8) |
| 10 |  | 4 ± 21 (7) |  | 1 ± 26 (7) |  | −60 ± 38 (8) |
| 100 |  | −11 ± 36 (7) |  | −2 ± 34 (7) |  | −100 ± 40 (8) |
| LT |  | 36 ± 9 (7) |  | 45 ± 12 (7) |  | 29 ± 13 (8) |
| 1 | 3a{4,4} | −48 ± 28 (8) | 3b{4,4} | 4 ± 45 (6) | 3c{4,4} | −107 ± 41 (6) |
| 10 |  | 14 ± 31 (8) |  | −72 ± 91 (6) |  | −90 ± 57 (6) |
| 100 |  | 27 ± 29 (8) |  | −42 ± 93 (6) |  | −205 ± 115 (6) |

TABLE 6-continued

EAG inhibition activity of the bis-phenol diethers.

| Dose (μg) | Compound[c] | Activity (%)[d] | Compound | Activity (%) | Compound | Activity (%) |
|---|---|---|---|---|---|---|
| LT |  | 49 ± 12 (8) |  | 8 ± 9 (6) |  | 7 ± 14 (6) |
| 1 | 3a{5,5} | −77 ± 58 (7) | 3b{5,5} | 41 ± 13 (7) | 3c{5,5} | 41 ± 14 (7) |
| 10 |  | −55 ± 67 (7) |  | −38 ± 41 (7) |  | 4 ± 26 (7) |
| 100 |  | −105 ± 81 (7) |  | −51 ± 51 (7) |  | 50 ± 9 (7) |
| LT |  | 0 ± 10 (7) |  | 9 ± 9 (7) |  | 7 ± 4 (7) |
| 1 | 3a{6,6} | 32 ± 16 (7) | 3b{6,6} | 11 ± 18 (7) | 3c{6,6} | −6 ± 10 (10) |
| 10 |  | 16 ± 24 (7) |  | 10 ± 22 (7) |  | 45 ± 6 (10) |
| 100 |  | −27 ± 48 (7) |  | −34 ± 41 (7) |  | 41 ± 8 (10) |
| LT |  | 17 ± 28 (7) |  | 33 ± 12 (7) |  | 4 ± 6 (10) |
| Individual compounds from the 3b{6,n} = 3b{n,6} series ||||||| 
| 1 | 3b{1,6} | −67 ± 61 (7) | 3b{2,6} | −115 ± 43 (7) | 3b{3,6} | −85 ± 30 (8) |
| 10 |  | −107 ± 88 (7) |  | −17 ± 54 (7) |  | −85 ± 80 (8) |
| 100 |  | −95 ± 106 (7) |  | −50 ± 74 (7) |  | −96 ± 98 (8) |
| LT |  | 14 ± 13 (7) |  | 25 ± 8 (7) |  | 48 ± 7 (8) |
| 1 | 3b{4,6} | −66 ± 43 (7) | 3b{5,6} | −69 ± 34 (7) |  |  |
| 10 |  | −101 ± 76 (7) |  | −85 ± 65 (7) |  |  |
| 100 |  | 8 ± 46 (7) |  | −99 ± 88 (7) |  |  |
| LT |  | 27 ± 12 (7) |  | 15 ± 8 (7) |  |  |
| Individual compounds from the 3c{3,n} = 3c{n,3} series |||||||
| 1 | 3c{1,3} | 28 ± 16 (6) | 3c{2,3} | 8 ± 20 (6) | 3c{3,4} | −11 ± 18 (6) |
| 10 |  | −2 ± 5 (6) |  | −30 ± 10 (6) |  | −90 ± 23 (6) |
| 100 |  | 48 ± 14 (6) |  | −62 ± 50 (6) |  | −180 ± 26 (6) |
| LT |  | 39 ± 12 (6) |  | 58 ± 7 (6) |  | 22 ± 12 (6) |
| 1 | 3c{3,5} | 10 ± 11 (6) | 3c{3,6} | −57 ± 46 (6) |  |  |
| 10 |  | −120 ± 20 (6) |  | −114 ± 51 (6) |  |  |
| 100 |  | −145 ± 35 (6) |  | −168 ± 76 (6) |  |  |
| LT |  | 4 ± 7 (6) |  | 39 ± 15 (6) |  |  |

[a]Short-term inhibition (STI) for a mixed plume of (+)-1 (100 ng in the cartridge) and the compound (indicated amount in the cartridge).
[b]Long-term inhibition (LTI) for a plume of pure (+)-1 (100 ng in the cartridge) following the mixed plume with (+)-1 and 100 μg of the compound.
[c]For compound naming, please see Scheme 1
[d]Calculated from the EAG traces from Example 5, according to the methods. Negative values represent and enhancement and positive values represent an inhibition of the EAG response.
[e]Values are mean ± S.E., with the number of replicates shown in parenthesis after each entry.

TABLE 7

EAG inhibition activity of alkylated Claisen mini-libraries.

| Dose (μg) | Compound | Activity (%) | Compound | Activity (%) | Compound | Activity (%) |
|---|---|---|---|---|---|---|
| 1 | 5a{1,1-5} | 37 ± 9 (10) | 5b{1,1} | 13 ± 17 (5) | 5c{1,1-5} | 67 ± 9 (9) |
| 10 |  | 37 ± 10 (10) |  | 48 ± 3 (5) |  | 51 ± 14 (9) |
| 100 |  | 52 ± 15 (10) |  | 107 ± 16 (5) |  | 50 ± 9 (9) |
| LT |  | 16 ± 6 (10) |  | 30 ± 7 (5) |  | 13 ± 9 (9) |
| 1 | 5a{2,1-5} | 54 ± 11 (6) | 5b{2,1} | 23 ± 23 (7) | 5c{2,1-5} | 70 ± 14 (4) |
| 10 |  | 46 ± 13 (6) |  | 34 ± 21 (7) |  | 20 ± 26 (4) |
| 100 |  | 74 ± 7 (6) |  | 85 ± 29 (7) |  | 57 ± 18 (4) |
| LT |  | 26 ± 5 (6) |  | 30 ± 9 (7) |  | 8 ± 9 (4) |
| 1 | 5a{3,1-5} | 29 ± 11 (11) | 5b{3,1} | 11 ± 48 (6) | 5c{3,1-5} | 62 ± 8 (9) |
| 10 |  | 45 ± 14 (11) |  | 52 ± 17 (6) |  | 54 ± 11 (9) |
| 100 |  | 33 ± 18 (11) |  | 68 ± 11 (6) |  | 58 ± 8 (9) |
| LT |  | 21 ± 7 (11) |  | 22 ± 6 (6) |  | 7 ± 8 (9) |
| 1 | 5a{4,1-5} | 75 ± 4 (7) | 5b{4,1} | −32 ± 46 (6) | 5c{4,1-5} | 49 ± 23 (4) |
| 10 |  | 77 ± 5 (7) |  | 12 ± 40 (6) |  | 52 ± 29 (4) |
| 100 |  | 60 ± 10 (7) |  | 52 ± 20 (6) |  | 69 ± 10 (4) |
| LT |  | 7 ± 5 (7) |  | 8 ± 6 (6) |  | 12 ± 8 (4) |
| 1 | 5a{5,1-5} | 25 ± 28 (12) | 5b{5,1} | −28 ± 34 (5) | 5c{5,1-5} | 22 ± 18 (9) |
| 10 |  | 35 ± 16 (12) |  | 8 ± 27 (5) |  | 23 ± 21 (9) |
| 100 |  | 28 ± 23 (12) |  | 41 ± 28 (5) |  | 46 ± 8 (9) |
| LT |  | 2 ± 6 (12) |  | 4 ± 7 (5) |  | 4 ± 6 (9) |
| Meta mini libraries |||||||
| 1 | 5b{1,2-3} | 31 ± 13 (6) | 5b{2,2-3} | 15 ± 17 (6) | 5b{3,2-3} | −32 ± 30 (6) |
| 10 |  | 59 ± 12 (6) |  | 38 ± 22 (6) |  | 70 ± 12 (6) |
| 100 |  | 96 ± 10 (6) |  | 57 ± 16 (6) |  | 55 ± 20 (6) |
| LT |  | 29 ± 8 (6) |  | 10 ± 9 (6) |  | 4 ± 7 (6) |
| 1 | 5b{4,2-3} | −2 ± 22 (6) | 5b{5,2-3} | −157 ± 141 (5) | 5b{1,4-5} | 18 ± 24 (6) |
| 10 |  | −27 ± 22 (6) |  | 21 ± 17 (5) |  | 54 ± 16 (6) |
| 100 |  | 53 ± 14 (6) |  | 45 ± 15 (5) |  | 80 ± 14 (6) |

TABLE 7-continued

EAG inhibition activity of alkylated Claisen mini-libraries.

| Dose (µg) | Compound | Activity (%) | Compound | Activity (%) | Compound | Activity (%) |
|---|---|---|---|---|---|---|
| LT |  | 0 ± 4 (6) |  | 12 ± 12 (5) |  | 11 ± 9 (6) |
| 1 | 5b{2,4-5} | 13 ± 21 (6) | 5b{3,4-5} | −4 ± 32 (6) | 5b{4,4-5} | 5 ± 29 (6) |
| 10 |  | 42 ± 12 (6) |  | 52 ± 17 (6) |  | −2 ± 38 (6) |
| 100 |  | 52 ± 11 (6) |  | 70 ± 10 (6) |  | 43 ± 14 (6) |
| LT |  | −2 ± 6 (6) |  | 2 ± 3 (6) |  | −5 ± 11 (6) |
| 1 | 5b{5,4-5} | −78 ± 32 (5) |  |  |  |  |
| 10 |  | 20 ± 19 (5) |  |  |  |  |
| 100 |  | 32 ± 10 (5) |  |  |  |  |
| LT |  | −18 ± 30 (5) |  |  |  |  |
| Dihydrobenzofuran set 6c{1-5}, $R_2$ = allyl sets and eugenols | | | | | | |
| 1 | 6c{1-5} | 7 ± 27 (11) | 5b{6,1} | −24 ± 24 (5) | 5b{6,2-3} | 6 ± 29 (5) |
| 10 |  | −16 ± 14 (11) |  | −32 ± 29 (5) |  | 46 ± 17 (5) |
| 100 |  | 42 ± 20 (11) |  | 13 ± 12 (5) |  | 56 ± 16 (5) |
| LT |  | 23 ± 9 (11) |  | −22 ± 32 (5) |  | 14 ± 4 (5) |
| 1 | 5b{6,4-5} | −47 ± 48 (4) | 5a{6,1-5} | 65 ± 11 (7) | 5c{6,1-5} | 29 ± 25 (4) |
| 10 |  | 58 ± 16 (4) |  | 68 ± 9 (7) |  | 68 ± 12 (4) |
| 100 |  | 42 ± 15 (4) |  | 73 ± 10 (7) |  | 41 ± 17 (4) |
| LT |  | 11 ± 10 (4) |  | 19 ± 6 (7) |  | 18 ± 8 (4) |
| 1 | eugenol | 48 ± 9 (6) | Me eugenol | −1 ± 13 (6) | Et eugenol | 3 ± 27 (6) |
| 10 |  | 4 ± 24 (6) |  | 76 ± 7 (6) |  | 19 ± 18 (6) |
| 100 |  | −132 ± 17 (6) |  | −152 ± 30 (6) |  | −121 ± 15 (6) |
| LT |  | 14 ± 10 (6) |  | 8 ± 11 (6) |  | 20 ± 3 (6) |
| 1 | Pr eugenol | 18 ± 37 (6) | Bu eugenol | 39 ± 17 (6) | iPent eugenol | 11 ± 33 (6) |
| 10 |  | 39 ± 23 (6) |  | −68 ± 29 (6) |  | −98 ± 26 (6) |
| 100 |  | −79 ± 25 (6) |  | −116 ± 24 (6) |  | −106 ± 24 (6) |
| LT |  | 7 ± 6 (6) |  | 7 ± 4 (6) |  | 5 ± 8 (6) |
| 1 | Allyl eugenol | −64 ± 49 (6) | DEET | −165 ± 51 (5) |  |  |
| 10 |  | −55 ± 23 (6) |  | −214 ± 48 (5) |  |  |
| 100 |  | −137 ± 30 (6) |  | −203 ± 42 (5) |  |  |
| LT |  | −3 ± 14 (6) |  | 78 ± 6 (5) |  |  |

The structure-activity relationships of short-term inhibition (STI) at the highest of the three inhibitor doses in Example 5 are shown FIG. 8. The alkoxyphenols (2a, ortho, 2b, meta and 2c, para) generally gave moderate STI (50%) (FIG. 8A). The butoxy-substituted phenols are interesting: 2a{4} (2-butoxyphenol) gave 50% STI, while 2b{4} (3-butoxyphenol) and 2c{4} (4-butoxyphenol) gave short-term enhancements of the pheromone signal, which manifest themselves in negative STI values. The isopentyl congeners, 2a{5}, 2b{5} and 2c{5} followed the opposite trend, with 2a{5} being slightly agonistic, 2c{5} being antagonistic and 2b{4} intermediate. A similar pattern can be seen for the STI of dialkoxybenzenes with $R_1$=$R_2$=butyl or isopentyl (FIG. 8B).

Figure 8A:
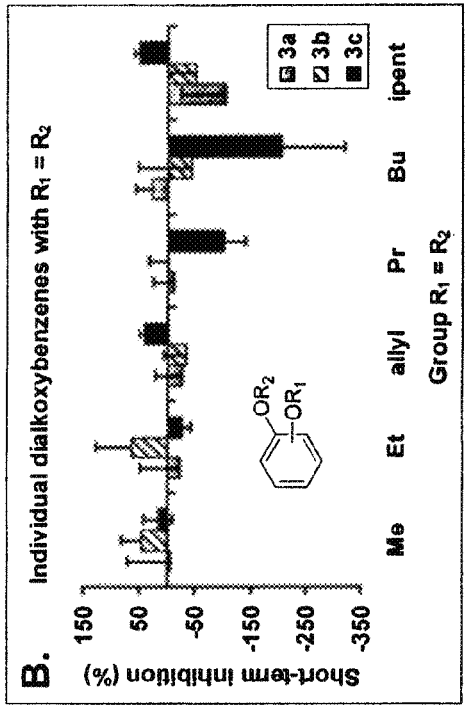
FIG. 8A. Alkoxy phenols 2 (a=ortho, b=meta, c=para). Me=methyl, Et=ethyl, Pr=n-propyl, Bu=n-butyl, iPent=isopentyl (3-methylbutyl).
Figure 8C:
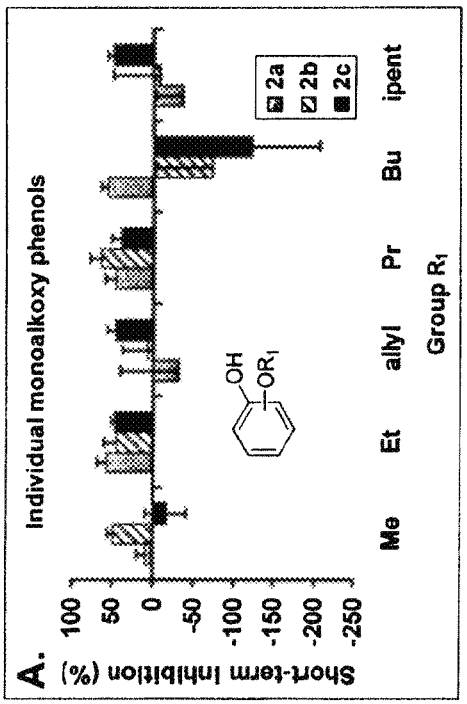
FIG. 8C. Dialkoxybenzene sets, with approximately equimolar mixtures of R1=Me, Et, Pr, Bu and iPent.
Figure 8B:
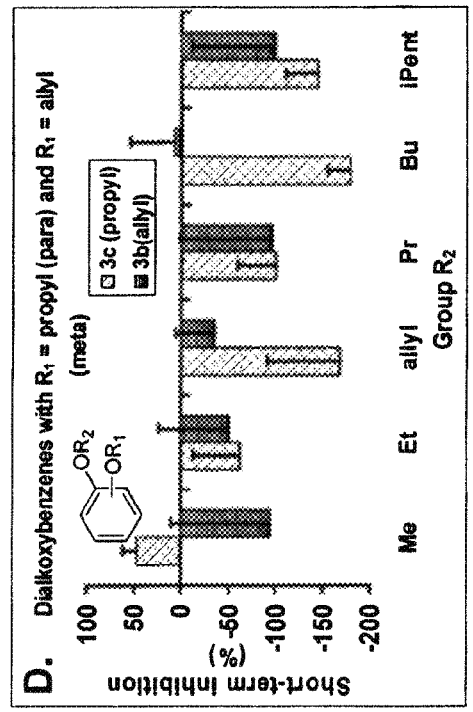
FIG. 8B. Dialkoxybenzenes with both substituents the same.
Figure 8D:
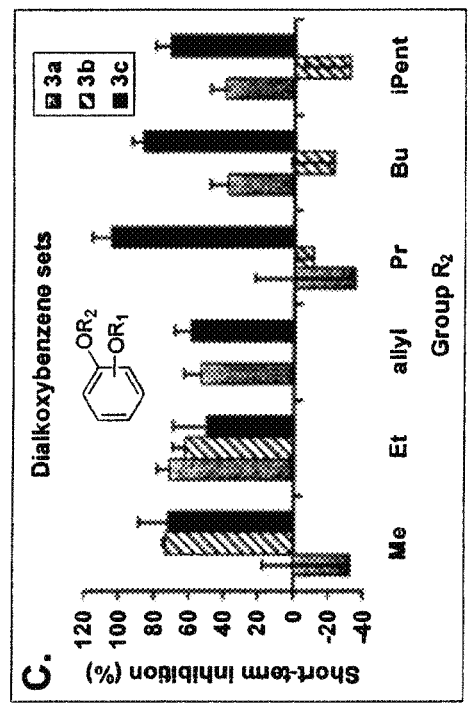
FIG. 8D. Individual dialkoxybenzenes: 3e{3,n} compounds (1-propoxy-4-alkoxybenzenes) and 3b{n,6} compounds (1-allyloxy-3-alkoxybenzenes).
Figure 8E:
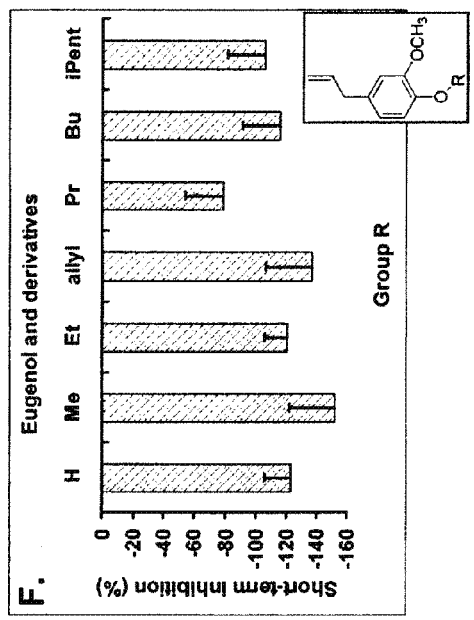
FIG. 8E. Typical Example 5 trace seen with eugenol: note the short-term enhancement (reflected in negative STI values) seen with the higher eugenol doses.
Figure 8F:
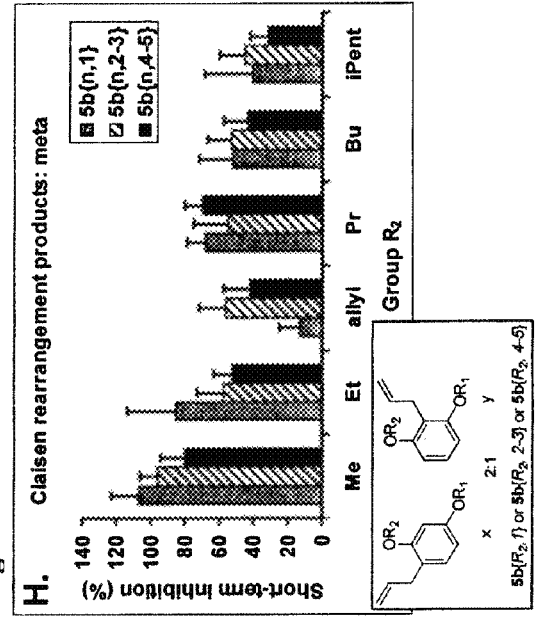
FIG. 8F. Eugenol and alkylated derivatives. For comparison, the commercial repellent DEET gave an STI value for puff v of −203±42%.

The ortho dialkoxybenzene sets showed short-term inhibition for $R_2$=ethyl, allyl butyl and isopentyl, but not for methyl and propyl. The meta sets showed a clear pattern of STI with increasing group size. The para sets showed a significant increase in STI, from $R_2$=allyl to the larger groups, particularly propyl and butyl (FIG. 8C). STI was variable between different batches of moths for some of the compounds tested. For example, most of the 3c{3, n} ($R_1$=propyl) compounds (FIG. 8D) were short-term agonists of the pheromone (which is reflected in negative STI values), but in a previous batch of moths the 3c sets were short-term inhibitory.

Eugenol and alkylated eugenols were tested for three reasons: first, eugenol is known to have insect repellent properties, 2) eugenol occurs in oak wood (Gunchu, 2009) and oak is a preferred host of *L. dispar*, (Montgomery, 1988; Plimmer, 1982) and 3) the eugenol substitution pattern was not accessible through the Claisen chemistry that was used to generate the 4 and 5 series of compounds. The eugenols were strong and robust short-term agonists (FIGS. 8E and 8F) at the highest doses tested.

Figure 8G:
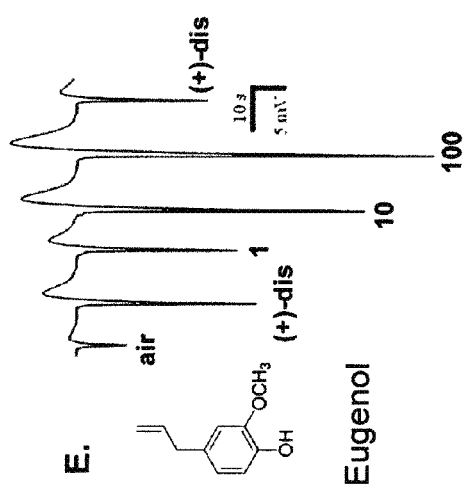
FIG. 8G. Allyl dialkoxybenzene sets obtained from Claisen rearrangement of 1-allyloxy-2-alkoxybenzenes and 1-allyloxy-4-alkoxybenzenes, followed by alkylation of the new phenol group (Scheme 1).
Figure 8H:
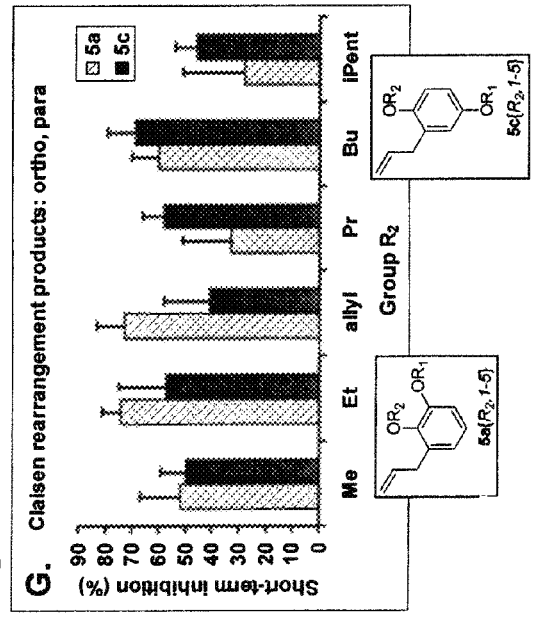
FIG. 8H. Allyl dialkoxybenzene sets obtained from Claisen rearrangement of 1-allyloxy-3-alkoxybenzenes (Scheme 1).

The Claisen rearrangement of ortho and para allyl ethers 3a{n,6} or 3c{n,6} gave one product for every allyl ether in a set, sets 4a{n} and 4c{n}. These sets were then divided and individually alkylated to furnish sets 5a{$R_2$,$R_1$} and 5c{$R_2$, $R_1$}, respectively. These sets all showed STI activity, with no clear structure-activity pattern (FIG. 8G). The meta allyl ethers gave two products upon Claisen rearrangement (Scheme 1) and were, therefore, prepared in separate sets (with $R_1$=methyl or ethyl+propyl or butyl+isopentyl). These sets of rearranged products also showed STI, with no significant structure-activity pattern. The strongest, most reproducible STI was seen with set 5b{1,1} (a 1:2 mixture of 2-allyl-1,3-dimethoxybenzene and 1-allyl-2,4-dimethoxybenzene).

Example 6

Decay of the Long-Term Inhibitory Effect and Dose Responses

The decay of the long-term inhibitory effect was investigated with the strongest long-term inhibitor, set 3c{3,1-5} and the strongest, most consistent short-term inhibitor, set 5b{1,1}. One hundred µg of the inhibitor were pre-mixed with different doses of (+)-1 and the following seven puffs were aimed at the antenna: i) clean air, ii) pure (+)-1 at the overall dose being tested (10 ng, 50 ng, 100 ng, 500 ng or 1000 ng), iii) the mixed puff with (+)-1 (test dose) and (10014) of 5b{1,1}, iv) the mixed puff with (+)-1 (test dose) and (10014) of 3c{3,1-5}, v-vii) pure (+)-1 at the dose being tested, administered sequentially, always allowing the antenna to recover back to baseline before a new puff. This recovery usually took 5-7 s. The short-term inhibition $STI_{(compound, dose)}$ was calculated for each mixed plume. The long-term inhibition $LTI_{(dose, time)}$ was calculated for each dose and for each of the three puffs following the mixed pheromone-inhibitor plume.

Figure 7B:
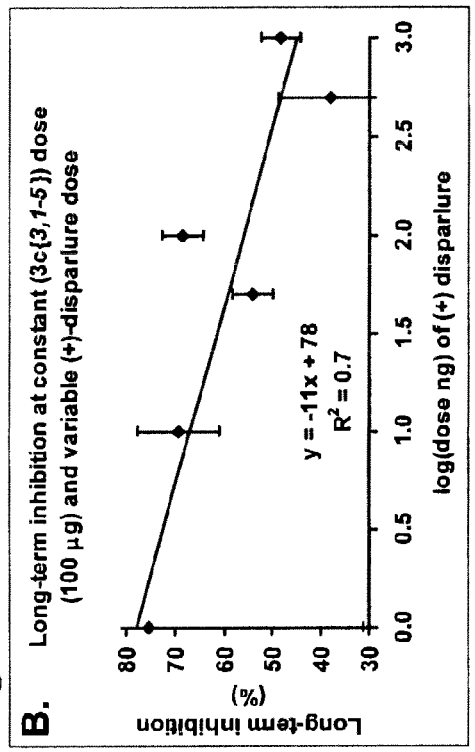
FIG. 7B. Dose response of LTI with respect to variable (+)-1 responses and time responses for the strongest long-term inhibition of EAG responses towards (+)-1.

Results:

The LTI was strongest 10 s after the mixed antagonist/pheromone stimulus, and the inhibition decayed to 20% within 30 s (FIG. 7A) The same decay pattern was seen for pheromone doses of 10 ng 1000 ng. This indicates that the antenna can fully recover from the LTI caused by a mixed antagonist/pheromone plume. The highest LTI was seen for the lowest competing doses of pheromone (+)-1, but even at very high doses of pheromone (1000 ng) there still was significant LTI (FIG. 7B). This dose-response pattern suggests that both the inhibitor and the pheromone are necessary, in a particular ratio, to cause LTI.

Figure 7D:
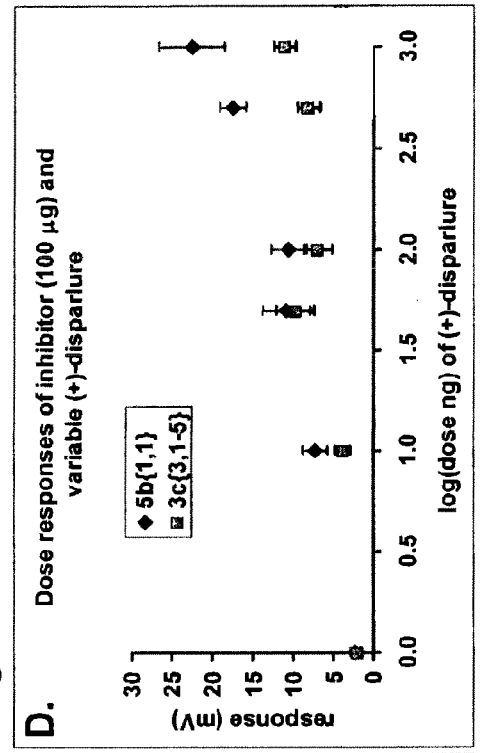
FIG. 7D. Dose response of (+)-1 mixed with 100 mg of either compound 5b{1,1} (the strongest short-term inhibitor) or set 3c{3,1-5} (the strongest long-term inhibitor).
Figure 7A:
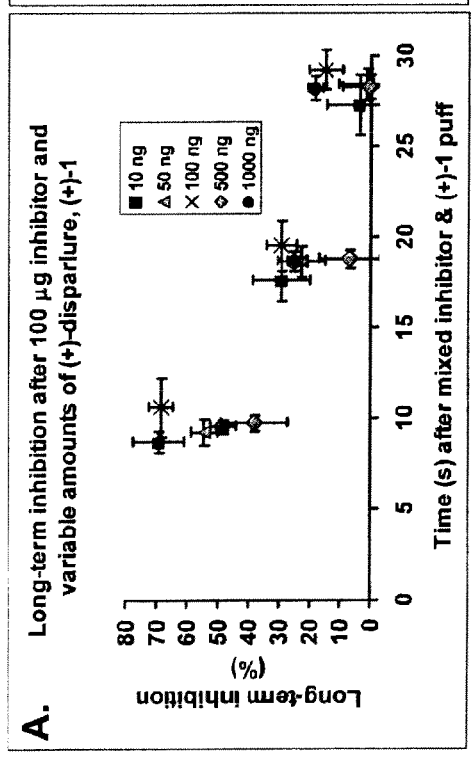
FIG. 7A shows a graph with dose and time decay properties of the long-term inhibition, LTI, activity by set 3c{3,1-5}. LTI dependence on the delay time of the pure (+)-1 puffs (v-vii, Example 6) after the mixed (+)-1/inhibitor puff. The amount of (+)-1 was varied from 10 ng to 1 μg and the amount of inhibitor was constant at 100 μg.
Figure 7C:
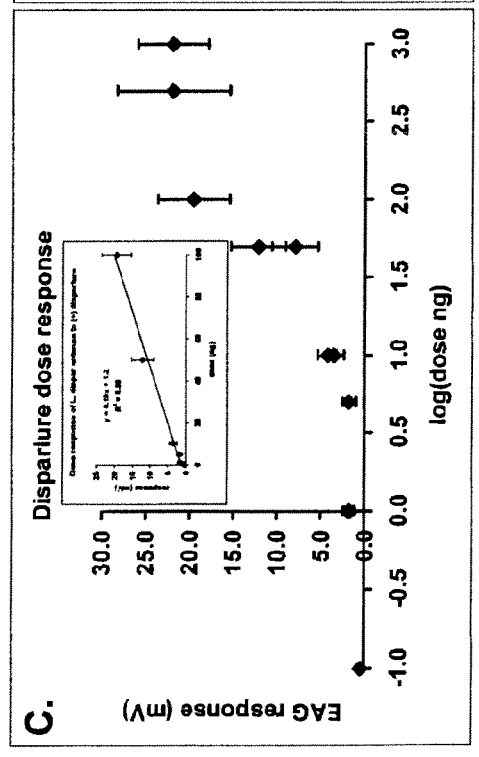
FIG. 7C. Dose response of pure pheromone (+)-1.

The dose response of male gypsy moth antennae to pure pheromone (+)-1 is shown in FIG. 7C. The LTI dose responses with respect to (+)-1 and antagonists 5b{1,1} or 3c{3,1-5} are shown in FIG. 7D. As noted previously, set 5b{1,1} (30±7% LTI) was a less effective long-term inhibitor than set 3c{3,1-5} (71±13% LTI). This was apparent in the dose response of the first pure pheromone puff after the mixed antagonist/pheromone plume. For example, at 100 ng of pure pheromone the depolarization was at its maximal value (20 mV on average), but after the mixed plume the depolarization for 100 ng of pheromone was only 10 mV for 5b{1,1} and 7 mV for 3c{3,1-5}. The difference between the two antagonists became magnified at higher doses (FIG. 7D). This suggests that LTI results from allosteric effects, caused by the antagonist and the pheromone in a particular ratio.

Example 7

Long-Term Inhibition after Pure Antagonist Plumes

The objective of this experiment was to determine whether the long-term or short-term inhibitors have any effect on the pheromone signal if puffed in pure form and well separated from the pheromone and whether these compounds elicit net EAG signals by themselves. This experiment was also done with sets 3c{3,1-5} and 5b{1,1}, tested at 1, 10 and 100 µg, and with (+)-1 cartridges containing 100 ng of the pheromone. The following stimuli were given: i) clean air, ii) (+)-1 (100 ng), iii) 5b{1,1} (variable dose) or 3c{3,1-5} (variable dose), iv-vi) (+)-1 (100 ng). Again, the latter puffs were given to test for any time decay of repeated disparlure signals following the pure inhibitor stimulus.

Figure 9A:
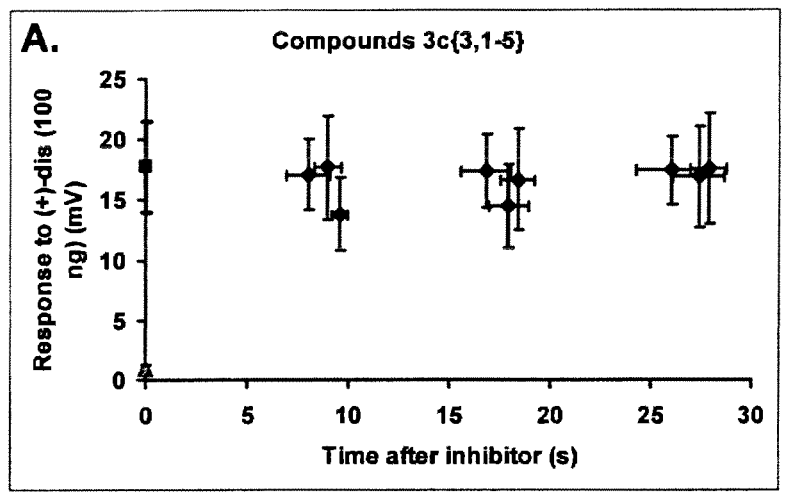
FIG. 9A. Set 3c{3,1-5} gave no significant depolarization by itself (triangle at time 0) and caused no LTI of the (+)-1 stimuli following the inhibitor puff. The square at time 0 represents the response of the antenna to (+)-1 prior to exposure to the inhibitor.
Figure 9B:
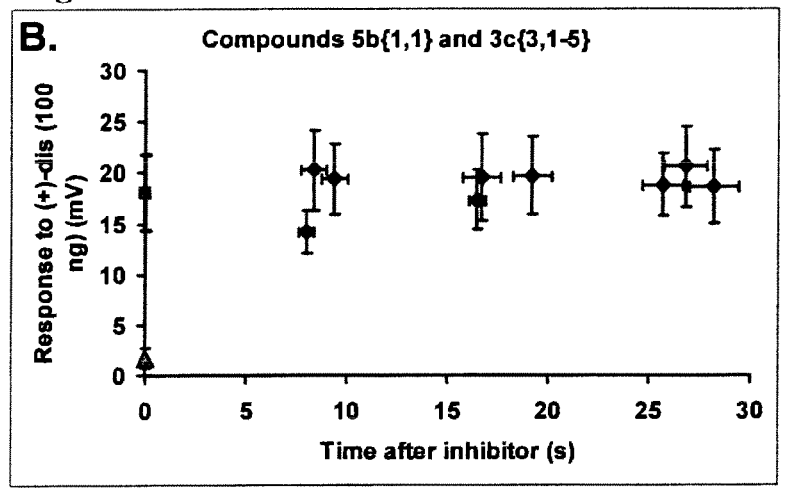
FIG. 9B. A mixture of sets 3c{3,1-5} and 5b {1, 1} gave no significant depolarization by itself and caused no LTI of (+)-1 stimuli following the inhibitor puff. The same picture was obtained for set 5b{1,1} in this experiment.

Results: Sets 5b{1,1} and 3c{3,1-5} showed no significant depolarization by themselves, indicating that these compounds do not function as odorants. Pure pheromone (+)-1 puffs (given at 10 s intervals, starting 10 s after the antagonist puff) showed no significant LTI for either set or for the mixture of 5b{1,1} and 3c{3,1-5} (FIG. 9). There was no significant change in the depolarization of the puffs that followed the antagonist, compared to the puff preceding the antagonist. This shows that the antenna does not exhaust itself with repeated puffs at 10 s intervals, and that the LTI seen in Examples 5 and 6 is due to the mixed pheromone/antagonist plumes and not due to antennal exhaustion. The data obtained in this experiment also indicate that LTI activity requires the exposure of the antenna to a mixed plume, consisting of the odorant being inhibited (pheromone (+)-1 in this case) and the antagonist. The long-term inhibitors are not odorants themselves, but interfere with the pheromone response in a mixed plume, leading to a reversible long-term effect.

Example 8

Long-Term Inhibition of Host Plant Odor Responses

To determine whether the long-term inhibitory effects of 3c{2,3} and DEET are specific to (+)-1 or also apply to other odorants, compound 3c{2,3} and DEET were tested further with other odorants: (−)-1, racemic 1, dispar alkene, methyl eugenol and 1-hexanol.

A first objective for this experiment was to determine whether the strongest long-term inhibitors (antagonists, see results, 3c{2,3} and DEET) could also alter the EAG responses to odorants other than (+)-1. These included (−)-1, racemic 1, dispar alkene (the alkene corresponding to the carbon framework of 1), methyl eugenol (a characteristic oak wood odorant) and 1-hexanol (a green leaf volatile, shown previously to be detected by gypsy moth antennae). For the pure odorant puffs, (−)-1 and racemic 1 were administered at 100 ng/cartridge, the alkene, methyl eugenol was administered at 1 µg/cartridge and 1-hexanol was administered at 100 µg/cartridge. The antagonists were both administered at 100 µg/cartridge, mixed with the appropriate dose of the odorant. The puff order was: i) air, ii) pure odorant, iii) odorant+antagonist, iv) pure odorant. All puffs were corrected for the air response as in Eq. 1. STI values were obtained from the depolarization in response to puff ii relative to the depolarization seen with puff i. LTI values were obtained by comparing the depolarization of puff iv relative to that of puff ii.

A second objective for this experiment was to determine whether the oak volatiles, methyl eugenol and 1-hexanol, can enhance the antennal response to (+)-1 and whether the mixed pheromone/plant odorant stimulus can be inhibited by compound 3c{2,3} or DEET. The puff order was: i) air, ii) pure (+)-1 (100 ng), iii) (+)-1 (100 ng) and plant odorant (1 µg for methyl eugenol and 100 µg for 1-hexanol), iv) (+)-1 and plant odorant as in iii+antagonist (100 µg), v) same as in iii. Depolarizations were corrected for the air response as in Eq. 1 and the short-term effects were calculated for puff iii relative to puff ii, and for puff iv relative to puff ii. Long-term effects were calculated for puff v relative to puff iii (for LTI of the mixed pheromone/plant odorant plume) and for puff v relative to puff ii (to determine whether long-term effects of the plant odorant and of the antagonist cancel).

Results:

Compound 3c{2,3} and DEET differed in their short-term and long-term effects on the other odorants tested Table 8. With (−)-1 or racemic 1, 3c{2,3} had a highly variable short-term enhancing effect, while DEET had a more consistent effect. Compound 3c{2,3} had a moderate LTI activity, and DEET was not active. With dispar alkene, both 3c{2,3} and DEET showed similar short-term enhancements and LTI activity. Methyl eugenol gave the same responses than clean air, yet the weak signal was enhanced short-term by both 3c{2,3} and DEET, an activity not seen with the test compounds by themselves. In terms of LTI, only 3c{2,3} was active, giving peaks that were smaller on average than the response to air. Leaf volatile 1-hexanol is a weak odorant whose response was not significantly affected short-term by either antagonist. There was weak LTI against 1-hexanol by 3c{2,3} but not by DEET. Compared to DEET, compound 3c{2,3} was the more broadly tuned long-term inhibitor. This broader inhibition of olfaction suggests that compound 3c{2,3} targets a component of several different populations of sensory hairs (sensilla) on the antenna.

TABLE 8

Interaction of several pheromone and plant odorants relevant to the gypsy moth with DEET or compound 3c{2, 3} in the EAG.

| odorant | antagonist | N | short-term activity (%) [b, d] | long-term activity (%) [c, d] |
|---|---|---|---|---|
| (−)-disparlure | 3c{2, 3} | 5 | −1226 ± 1056 | 43 ± 12 |
|  | DEET | 5 | −322 ± 66 | −10 ± 29 |
| racemic disparlure | 3c{2, 3} | 6 | −154 ± 45 | 69 ± 5 |
|  | DEET | 6 | −468 ± 231 | −126 ± 133 |
| dispar alkene [a] | 3c{2, 3} | 4 | −244 ± 15 | 39 ± 12 |
|  | DEET | 4 | −955 ± 647 | 52 ± 22 |
| methyl eugenol | 3c{2, 3} | 4 | −1158 ± 834 | 46 ± 24 |
|  | DEET | 4 | −598 ± 506 | 8 ± 8 |
| 1-hexanol | 3c{2, 3} | 4 | −34 ± 28 | 29 ± 18 |
|  | DEET | 4 | 6 ± 30 | 7 ± 18 |

[a] This compound is (Z) 2-methyloctadec-7-ene
[b] This refers to the short-term inhibition (positive) or enhancement (negative) of the mixed odorant/antagonist puff, relative to the first pure odorant puff.
[c] This refers to the long-term inhibition (positive) or enhancement (negative) of the pure odorant puff that followed the mixed odorant/antagonist puff, relative to the first pure odorant puff
[d] Mean ± S.E. of N replicates.

Because insect pheromone responses are altered by host plant odors and both methyl eugenol and 1-hexanol are odorants of oak, the ability of compound 3c{2,3} and DEET to alter the response of the male moth antennae to mixtures of pheromone and the plant odorant was compared (Table 8). Methyl eugenol, at 10× excess relative to (+)-1 enhanced the response to pheromone weakly in a few cases, consistent with the previous data with three different methyl eugenol doses (see Table 8). The ternary mixture of (+)-1, methyl eugenol and the antagonist gave a significantly enhanced short term response, relative to the (+)-1/plant odorant mixture. Also, there was no significant LTI for either antagonist on the (+)-1/plant odorant mixture or on a pure (+)-1 puff following the mixed puff. A similar picture was obtained with 1-hexanol, except that DEET was weakly long-term enhancing, while 3c{2,3} had no LTI activity. The similarities in activity between DEET and 3c{2,3} suggest that they may act on a similar target site, but the differences in activity also suggest that there are additional modes of action that differ between DEET and 3c{2,3}.

Example 9

Correlation Between Recovery from the Mixed Antagonist/Pheromone Plume and LTI, from Example 5

Figure 10A:
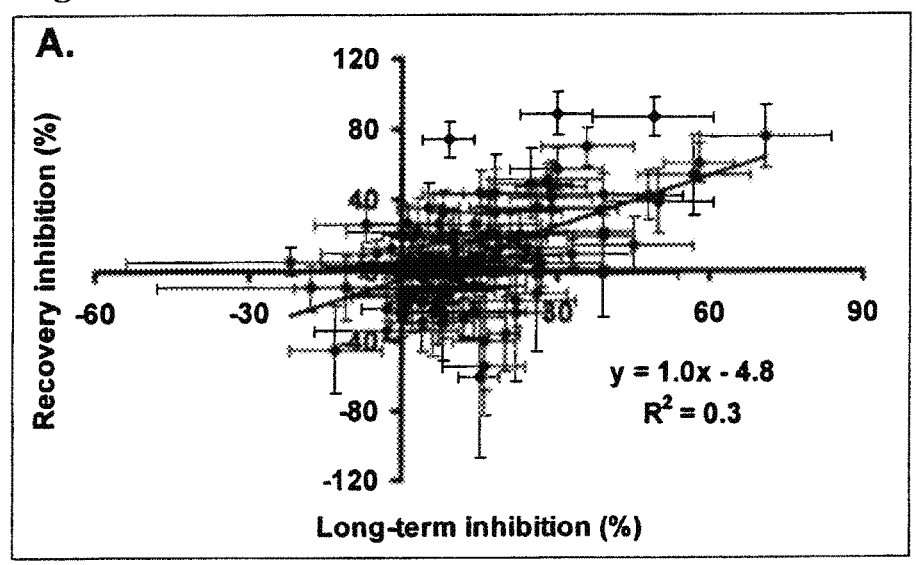
FIG. 10 shows graphs with the correlation between the inhibition of the hyperpolarization during the recovery phase of the EAG and LTI, FIG. 10A. For all compounds and sets (except DEET).
FIG. 10B. For ortho compounds and sets. The effect some long-term inhibitors had on the recovery phase can be seen in FIG. 5, for puffs v.
Figure 10B:
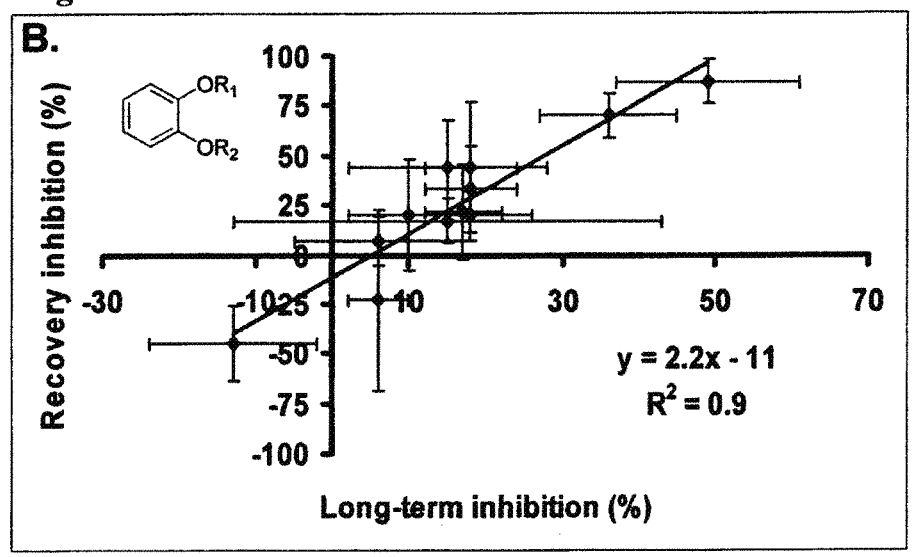
Figure 11A:
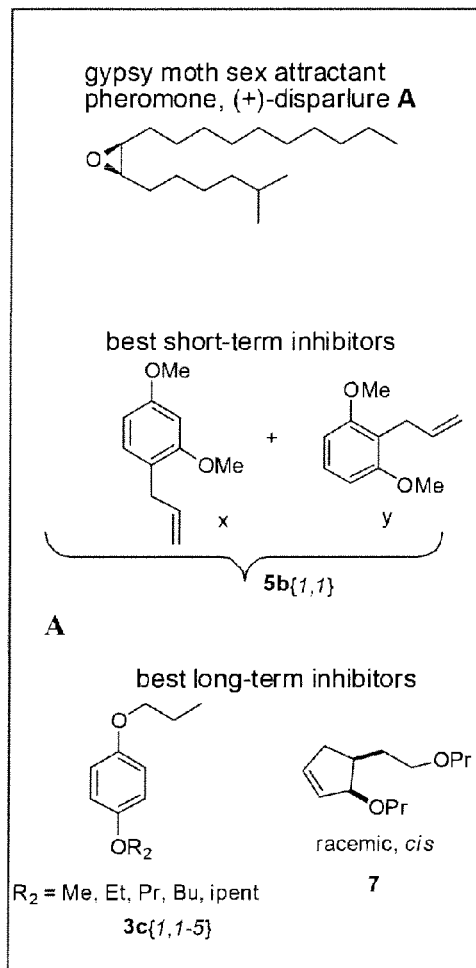
FIG. 11A shows compounds that are active against gypsy moth, *L. dispar*.
Figure 11B:
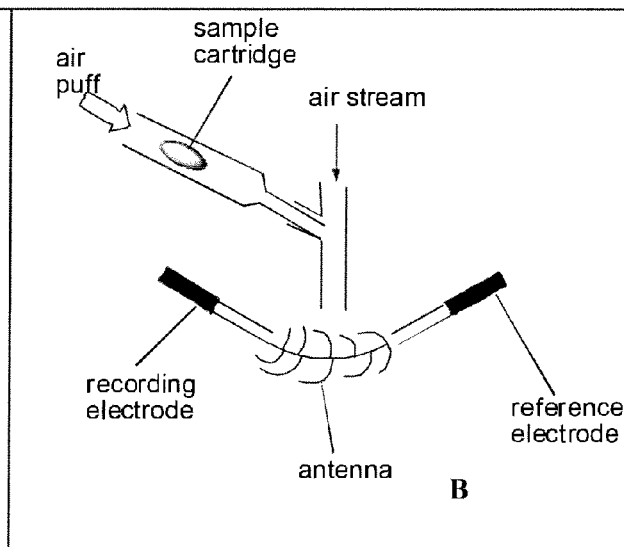
FIG. 11B shows the electroantennogram (EAG) setup. This experiment measures the potential (in mV) across the mounted antenna. As odorants are puffed over the antenna, the potential decreases temporarily, if the sensory hairs on the antenna respond to the odor.
Figure 11C:
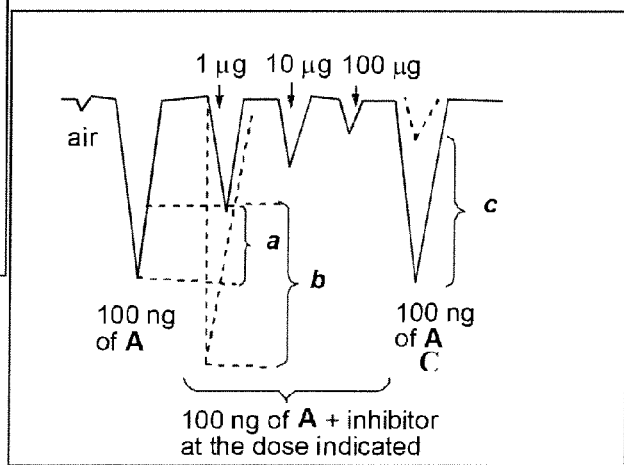
FIG. 11C shows the typical trace for an EAG experiment: the puff sequence starts with air, followed by pure pheromone A, then by A mixed with the inhibitor at three different doses, then pure A. The effects seen in the presence of inhibitors were: a=short-term inhibition, b=short-term enhancement (agonism), c=long-term inhibition. Compound mixture 5b{1,1} gave a 100% short-term inhibition, but only 30% long-term inhibition. Compound set 3c{1,1-5} gave 100% short-term inhibition and 70% long-term. Compound 7 gave a 300% short-term enhancement and a 66% long-term inhibition.
Figure 12:
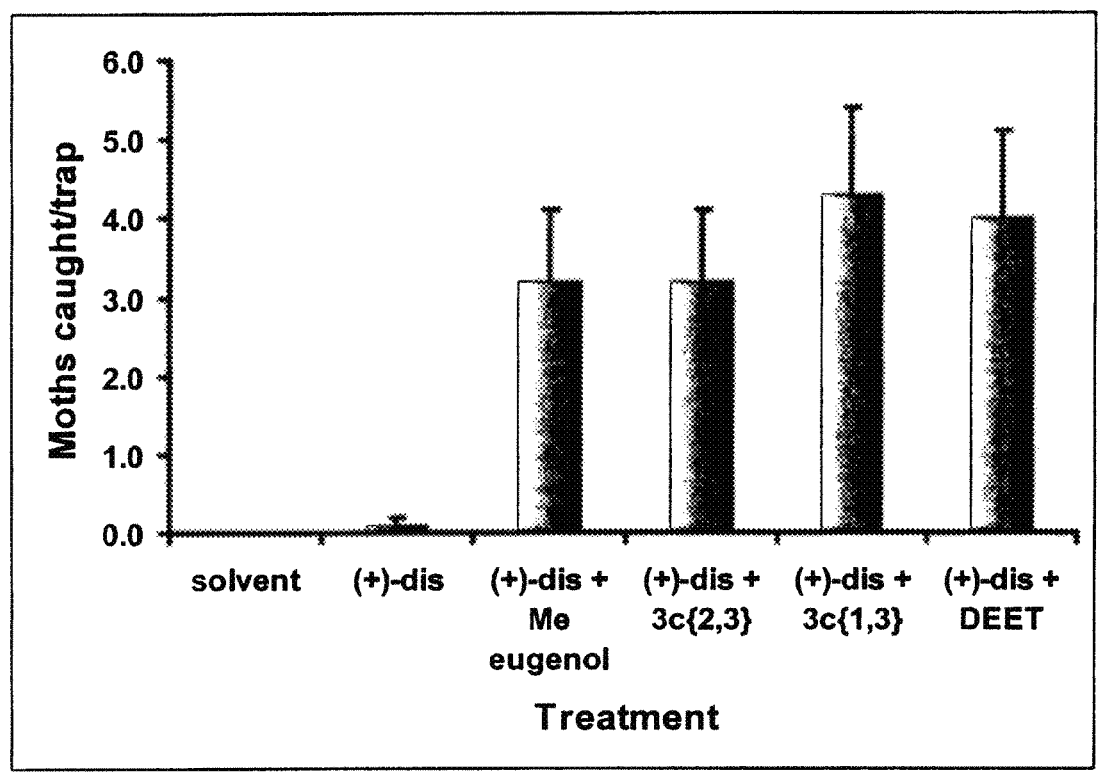
FIG. 12 shows a graph with moths caught per trap during a late-season field trial in Northern Japan, with gypsy moth pheromone, (+)-disparlure. Ten traps were used per treatment. The solvent used to deliver the compounds onto the lures was doubly distilled hexane. The hexane was evaporated prior to packing and shipping the lures.

The recovery phase (hyperpolarization) of a pheromone stimulus is proportional to the magnitude of the preceding depolarization (FIG. 5). Analysis of the correlation between the inhibition of the recovery phase, $R^1$ and the LTI revealed a strong positive correlation between these two parameters for all the compounds. (FIG. 10) Groups of compounds with similar structure also showed correlation between LTI and $R^1$, e.g., the ortho compounds (FIG. 10B, $R^2$ 0.9). This suggests that the recovery phase from the antagonist/pheromone plume can determine the ability of the antenna to respond to a pure pheromone plume: the more shallow the hyperpolarization of the mixed plume, the stronger the inhibition of a following pure pheromone plume. This indicates that the dialkoxybenzene long-term inhibitors can interfere with recovery processes in the antenna (see below). In contrast, DEET did not show significant $R^1$ activity (9±9%, N=6), but had strong LTI activity. This suggests that the dialkoxybenzenes cause LTI via at least two modes: one similar to DEET and a second mode that affects $R^1$ and is not affected by DEET.

Example 10

Data Obtained by Coupled Gas Chromatography-Electroantennogram Detection (GC-EAD) for the Compounds Tested

TABLE 10

GC-EAD activity of starting phenols 2 and diethers 3

| Compound | Activity [a] | Compound | Activity [a] | Compound | Activity [a] |
|---|---|---|---|---|---|
| 2a{1} | None | 2b{1} | None | 2c{1} | None |
| 2a{2} | None | 2b{2} | None | 2c{2} | None |
| 2a{3} | None | 2b{3} | None | 2c{3} | None |
| 2a{4} | None | 2b{4} | None | 2c{4} | None |
| 2a{5} | None | 2b{5} | None | 2c{5} | None |
| 2a{6} | None | 2b{6} | None | 2c{6} | None |
| 3a{1, 1} | ++ sharp | 3b{1, 1} | Trace | 3c{1, 1} | + sharp |

TABLE 9

Effect of plant odors and DEET or compound 3c{2, 3} on the EAG responses of male gypsy moth antennae to pheromone (+)-1. [a]

| plant synergist | antagonist | short-term effect with the plant synergist [d] | short-term effect with plant synergist + antagonist | long-term effect on the mixed (+)-1/ plant odor plumes | long-term effect on (+)-1 response |
|---|---|---|---|---|---|
| methyl eugenol [b] | 3c{2, 3} | −39 ± 37 (9) | −125 ± 95 (4) | 11 ± 47 (4) | 12 ± 33 (4) |
|  | DEET |  | −210 ± 120 (5) | 30 ± 27 (5) | 27 ± 29 (5) |
| 1-hexanol [c] | 3c{2, 3} | −19 ± 24 (10) | −99 ± 60 (5) | 5 ± 24 (5) | 20 ± 18 (5) |
|  | DEET |  | −339 ± 206 (5) | −24 ± 19 (5) | −53 ± 48 (5) |

[a] Pheromone (+)-1 was applied at 100 ng/cartridge
[b] Applied at 1 μg/cartridge.
[c] Applied at 100 μg/cartridge.
[d] Number of replicates given in parenthesis; means ± S. E.

TABLE 10-continued

GC-EAD activity of starting phenols 2 and diethers 3

| Compound | Activity[a] | Compound | Activity[a] | Compound | Activity[a] |
|---|---|---|---|---|---|
| 3a{1, 2} | ++ sharp | 3b{1, 2} | Trace | 3c{1, 2} | ++ sharp |
| 3a{1, 3} | + sharp | 3b{1, 3} | Trace | 3c{1, 3} | + sharp |
| 3a{1, 4} | Trace | 3b{1, 4} | None | 3c{1, 4} | None |
| 3a{1, 5} | + broad | 3b{1, 5} | None | 3c{1, 5} | None |
| 3a{1, 6} | + sharp | 3b{1, 6} | None | 3c{1, 6} | Trace |
| 3a{2, 2} | + sharp | 3b{2, 2} | Trace | 3c{2, 2} | Trace |
| 3a{2, 3} | + sharp | 3b{2, 3} | None | 3c{2, 3} | None |
| 3a{2, 4} | ++ sharp | 3b{2, 4} | None | 3c{2, 4} | None |
| 3a{2, 5} | ++ sharp | 3b{2, 5} | None | 3c{2, 5} | None |
| 3a{2, 6} | + broad | 3b{2, 6} | None | 3c{2, 6} | Trace |
| 3a{3, 3} | ++ sharp | 3b{3, 3} | None | 3c{3, 3} | None |
| 3a{3, 4} | ++ sharp | 3b{3, 4} | None | 3c{3, 4} | None |
| 3a{3, 5} | + broad | 3b{3, 5} | None | 3c{3, 5} | None |
| 3a{3, 6} | ++ broad | 3b{3, 6} | None | 3c{3, 6} | + broad |
| 3a{4, 4} | + broad | 3b{4, 4} | None | 3c{4, 4} | |
| 3a{4, 5} | + broad | 3b{4, 5} | None | 3c{4, 5} | None |
| 3a{4, 6} | ++ broad | 3b{4, 6} | None | 3c{4, 6} | None |
| 3a{5, 5} | None | 3b{5, 5} | None | 3c{5, 5} | None |
| 3a{5, 6} | + broad | 3b{5, 6} | None | 3c{5, 6} | None |
| 3a{6, 6} | None | 3b{6, 6} | None | 3c{6, 6} | Trace |

[a] The EAD activity was noted ++ if a peak of 1-2 cm matched exactly the retention time of the compound in the FID. A + peak is for a clear peak <1 cm but larger than noise and a "Trace" designation is for very small deflections within the noise that match the retention time precisely. By comparison, the (+)-disparlure signal was 100-200 times larger than the signals shown here.

TABLE 11

GC-EAD activity of starting phenols 4, diethers 5 and dihydropyrans 6c from Claisen rearrangement chemistry

| Compound | Activity | Compound | Activity | Compound | Activity |
|---|---|---|---|---|---|
| 4a{1} | ++ sharp | 4b{1} | None | 4c{1} | ++ sharp |
| 4a{2} | + sharp | 4b{2} | None | 4c{2} | + sharp |
| 4a{3} | + broad | 4b{3} | None | 4c{3} | Trace |
| 4a{4} | Trace | 4b{4} | None | 4c{4} | None |
| 4a{5} | Trace | 4b{5} | None | 4c{5} | None |
| 5a{$R_2$, $R_1$} | | 5b{$R_2$, $R_1$} | | 5c{$R_2$, $R_1$} | |
| 5a{1, 1} | Trace | 5b{1, 1} | None | 5c{1, 1} | None |
| 5a{1, 2} | Trace | 5b{1, 2} | None | 5c{1, 2} | None |
| 5a{1, 3} | None | 5b{1, 3} | None | 5c{1, 3} | None |
| 5a{1, 4} | None | 5b{1, 4} | None | 5c{1, 4} | None |
| 5a{1, 5} | None | 5b{1, 5} | None | 5c{1, 5} | None |
| 5a{1, 6} | None | 5b{1, 6} | None | 5c{1, 6} | None |
| 5a{2, 1} | Trace | 5b{2, 1} | None | 5c{2, 1} | None |
| 5a{2, 2} | None | 5b{2, 2} | None | 5c{2, 2} | None |
| 5a{2, 3} | None | 5b{2, 3} | None | 5c{2, 3} | None |
| 5a{2, 4} | None | 5b{2, 4} | None | 5c{2, 4} | None |
| 5a{2, 5} | None | 5b{2, 5} | None | 5c{2, 5} | None |
| 5a{2, 6} | None | 5b{2, 6} | None | 5c{2, 6} | None |
| 5a{3, 1} | + broad | 5b{3, 1} | None | 5c{3, 1} | Trace |
| 5a{3, 2} | + broad | 5b{3, 2} | None | 5c{3, 2} | None |
| 5a{3, 3} | Trace | 5b{3, 3} | None | 5c{3, 3} | None |
| 5a{3, 4} | None | 5b{3, 4} | None | 5c{3, 4} | None |
| 5a{3, 5} | None | 5b{3, 5} | None | 5c{3, 5} | None |
| 5a{3, 6} | None | 5b{3, 6} | None | 5c{3, 6} | Trace |
| 5a{4, 1} | None | 5b{4, 1} | None | 5c{4, 1} | None |
| 5a{4, 2} | None | 5b{4, 2} | None | 5c{4, 2} | None |
| 5a{4, 3} | None | 5b{4, 3} | None | 5c{4, 3} | None |
| 5a{4, 4} | None | 5b{4, 4} | None | 5c{4, 4} | None |
| 5a{4, 5} | None | 5b{4, 5} | None | 5c{4, 5} | None |
| 5a{4, 6} | None | 5b{4, 6} | None | 5c{4, 6} | None |
| 5a{5, 1} | Trace | 5b{5, 1} | None | 5c{5, 1} | None |
| 5a{5, 2} | None | 5b{5, 2} | None | 5c{5, 2} | None |
| 5a{5, 3} | None | 5b{5, 3} | None | 5c{5, 3} | None |
| 5a{5, 4} | None | 5b{5, 4} | None | 5c{5, 4} | None |
| 5a{5, 5} | None | 5b{5, 5} | None | 5c{5, 5} | None |
| 5a{5, 6} | None | 5b{5, 6} | None | 5c{5, 6} | None |
| | | | | 6c{1} | + sharp |
| | | | | 6c{2} | Trace |
| | | | | 6c{3} | Trace |
| | | | | 6c{4} | None |
| | | | | 6c{5} | None |

TABLE 12

GC-EAD activity of eugenols

| Compound | Activity | Compound | Activity | Compound | Activity |
|---|---|---|---|---|---|
| eugenol | None | Pr-eugenol | None | Allyl-eugenol | None |
| Me-eugenol | None | Bu-eugenol | None | | |
| Et-eugenol | None | iPent-eugenol | None | | |

Example 11

Peak Broadening

A mixed pheromone/modulator plume could elicit a prolonged response (FIG. 1A, puff v; FIG. 2), and this was termed peak broadening (PB). PB was calculated from the EAG traces as follows:

$$PB=100\times(\Delta t_v - \Delta t_{ii})/\Delta t_{ii}$$

Where Δt was the width of the EAG peak (in s) from the start of the depolarization to the return to background potential.

TABLE 13

Activity of the most active PB compounds (with ≥70% PB)

| compound | activity (% peak broadening) |
|---|---|
| 3c{1, 1} | 77 ± 12 |
| 3c{2, 2} | 71 ± 30 |
| 3c{1, 3} | 175 ± 23 |
| 3c{2, 3} | 94 ± 24 |
| 3c{3, 1-5} | 116 ± 47 |
| 3c{4, 1-5} | 74 ± 44 |
| 3c{5, 1-5} | 86 ± 61 |
| 3b{2, 6} | 77 ± 33 |
| 3a{1, 1} | 99 ± 25 |
| 3a{2, 2} | 106 ± 32 |
| 3a{3, 3} | 80 ± 31 |
| 3a{4, 4} | 86 ± 32 |
| 3a{2, 1-5} | 316 ± 94 |
| 5b{1, 1} | 192 ± 52 |

Example 12

Field Tests

The field test was conducted in 10 replicates in Northern Japan. The test was conducted Aug. 16-18, 2009, in an area where gypsy moths are known to live. The timing of the test was somewhat late: the main flight of the moths had already occurred at the end of July, so the population density was low. Traps were arranged randomized, placed on platforms. The experiment was conducted blind. The lures contained 40 μg disparlure/lure, a low dose for a field trial (typically 100 μg-1 mg are used).

Figure 15:
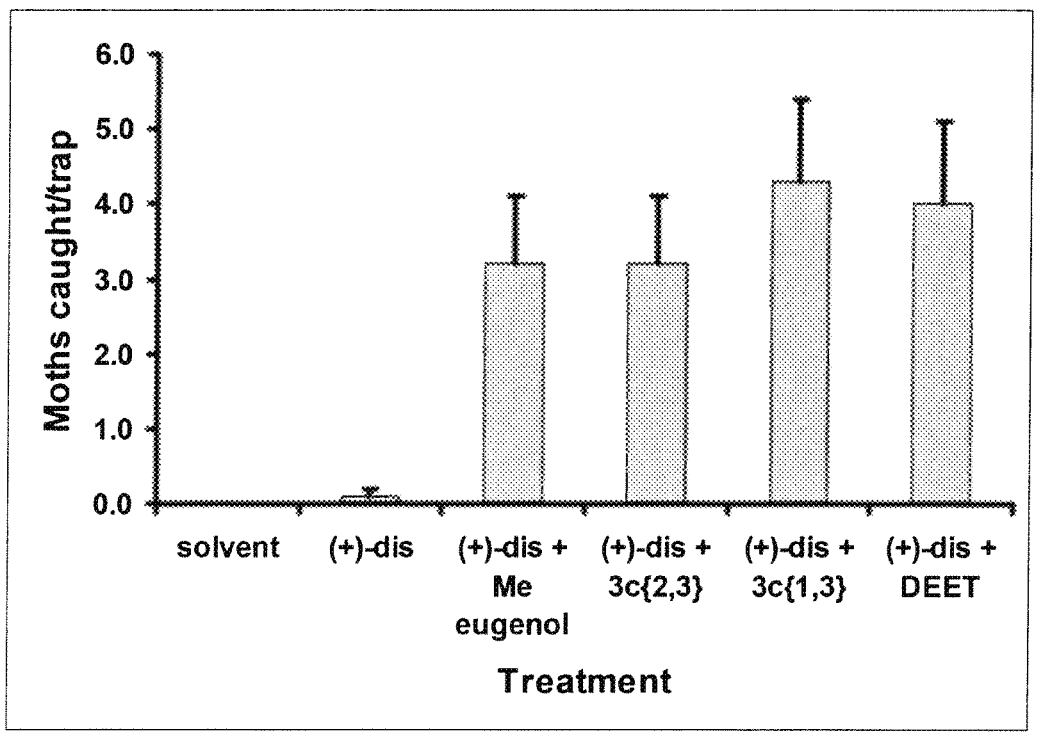
FIG. 15 shows the results of a field trial conducted in Japan in 2009.

For each treatment, 10 traps were deployed. The compounds and mixtures tested are shown as follows and in FIG. 15. (EP v. VIII, 90)

| Treatment function | Replicates | Compound |
|---|---|---|
| Control (Negative) | 10 | solvent |
| Control (Positive) | 10 | (+)-dis (40 µg/lure) |
| Test ST enhancer | 10 | (+)-dis (40 µg/lure) & Me-eugenol (40 mg/lure) |
| Test ST enhancer | 10 | (+)-dis (40 µg/lure) & 3c{2, 3} (40 mg/lure) |
| Test ST enhancer | 10 | (+)-dis (40 µg/lure) & 3c{1, 3} (40 mg/lure) |
| Test ST enhancer | 10 | (+)-dis (40 µg/lure) & DEET (40 mg/lure) |

The results (FIG. 13) show that compounds 3c{2,3} (good LTI and short-term enhancement, i.e. negative STI), 3c{1,3} (strong PB compound and short-term enhancer), methyl eugenol (a short-term enhancer) and DEET (a short-term enhancer and good LTI) all enhanced the trap catches significantly in the field. All these compounds had in common that they enhance the antennal responses to mixed pheromone/compound plumes, relative to the response seen with pure pheromone (=negative STI). This result suggests that an enhanced EAG response translates into an enhanced trap catch in the field. Accordingly, this results suggests that compounds or mixtures thereof that are strong short-term inhibitors (close to 100% STI), such as 5b{1,1}, may be used to deter moths from traps or from calling females, such that male moths could be deterred from certain sites (e.g., strong STI inhibitors could functions as repellants) and re-directed to different sites that contain attractants in a "deter and attract (and kill)" scheme.

Figures 13A, 13B, 13C:
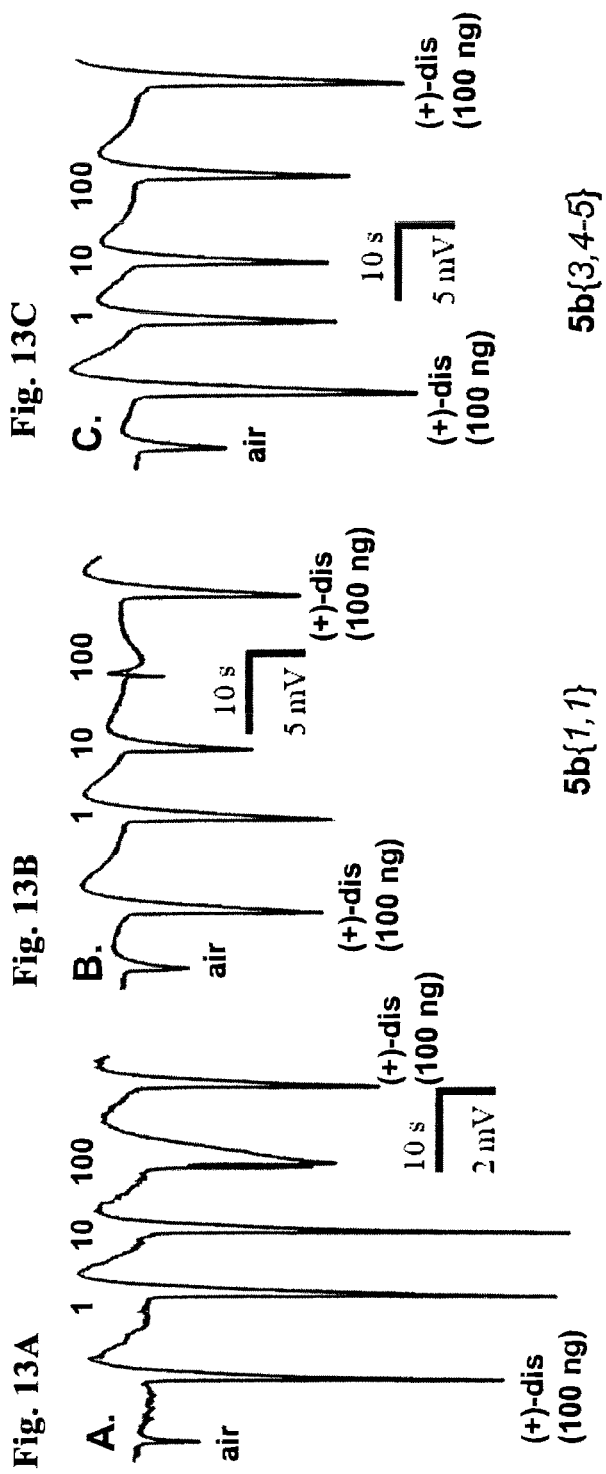
FIG. 13C. Example of a set that does not cause broadening (delayed activation) of the mixed plume.

FIG. 13 also shows that 3c{1,3} showed significant prolongation of the EAG signal (an effect called "peak broadening"). This peak broadening effect was seen at 1:1000 ratios and compound 3c{1,3} was the strongest peak broadening compound.

Figure 14:
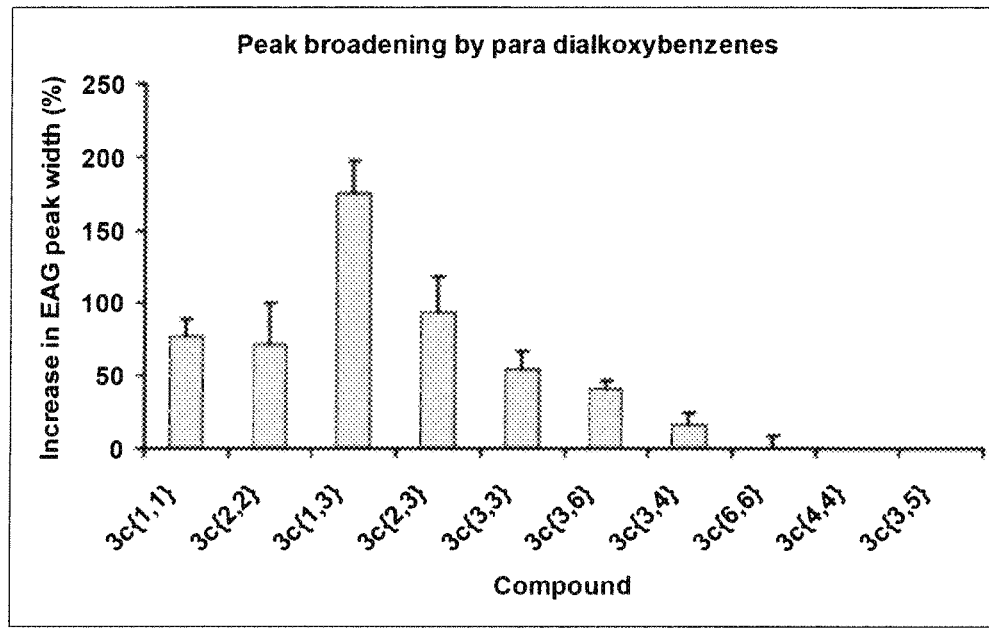
FIG. 14 shows peak broadening by para dialkoxybenzenes.

FIG. 14 shows peak broadening by para dialkoxybenzenes.

Single sensillum recordings show that the enhancement of neuronal activity when (+)-disparlure and 3c{1,3} are mixed 1:1000 is significant. Simple behavioural tests (films of moths exposed to puffs of (+)-disparlure alone and to (+)-disparlure:3c{1,3} at 1:1000 ratio), showed that the moths are excited and violently flap their wings much longer when exposed to the mixture than when exposed to the pheromone alone.

Compounds that consistently showed activity of peak broadening and that showed trap catch enhancement in two trials at 1:1000 relative to (+)-disparlure were as follows:

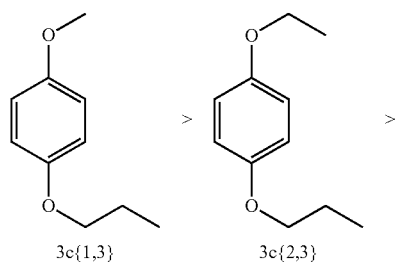

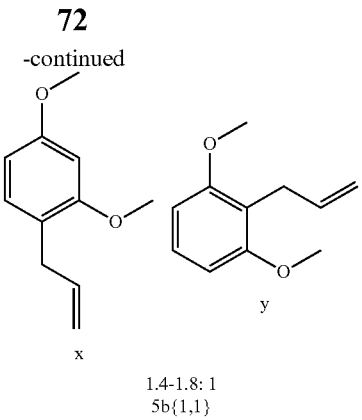

1.4–1.8: 1
5b{1,1}

The inequality signs suggest the strength, in terms of activity vs. ease of production.

Trap catch enhancement correlates with peak broadening of depolarization signals in the EAG. Similarly, hyperpolarisation of the EAG correlates with a lack of behavioural response, even when (+)-disparlure is present. Accordingly, the EAG patterns are a guide to field situations.

Example 13

Feeding Deterrence of Gypsy Moth Larvae

Gypsy moth larvae were tested at the Canadian Forest Service, for feeding deterrence. A selected set of compounds, based on the results with the electroantennogram testing and also based on feeding deterrence assay results with the cabbage looper, *T. ni*. The experiment was done with third instar larvae and oak leaf discs. Larvae were left to choose between a treated and a control disc for 17.5 hours. Measurements of leaf areas were used to calculate the amount of leaf consumed from control (C) and treated (T) leaves. Feeding deterrence was calculated using the following formula: $((C-T)/(C+T))*100$, and expressed in percent, where C=area of control leaf consumed and T=area of treated leaf consumed.

Table 14 outlines the results, in order of decreasing feeding deterrence. The most active feeding deterrents in this test were more active than DEET, a commercially used insect repellent.

TABLE 14

Feeding deterrence of selected compounds against third instar gypsy moth larvae.

| Compound Code | Feeding Deterrence (%) | SE | Actual Name |
|---|---|---|---|
| Me-Eugenol | 81.15 | 11.1 | Me-Eugenol |
| 3a{6, 6} | 79.87 | 10.4 | 1,2-diallyloxybenzene |
| repeat of 3c{3, 6} | 71.1 | 12.7 | 1-allyloxy-4-propoxybenzene |
| 3c{6, 6} | 62.01 | 14.6 | 1,4-diallyloxybenzene |
| 3b{6, 6} | 61.1 | 12.4 | 1,3-diallyloxybenzene |
| 3a{3, 3} | 53.57 | 12.5 | 1,2-dipropoxybenzene |
| 3c{3, 6} | 53.44 | 14.3 | 1-allyloxy-4-propoxybenzene |
| Pr-Eugenol | 52.67 | 14.8 | Pr-Eugenol |
| DEET | 47.76 | 11.1 | m-N,N-diethyltoluamide |
| 3c{2, 3} | 47.11 | 11.1 | 1-ethoxy-4-propoxybenzene |
| 3b{3, 3} | 46.55 | 10.5 | 1,3-dipropoxybenzene |
| 3c{3, 3} | 42.79 | 17.7 | 1,4-dipropoxybenzene |
| 3b{3, 6} | 37.33 | 10.7 | 1-allyloxy-3-propoxybenzene |
| 3c{2, 2} | 36.54 | 15.2 | 1,4-diethoxybenzene |
| 3a{4, 4} | 33.4 | 11.2 | 1,2-dibutoxybenzene |
| 3b{2, 2} | 26.42 | 11.9 | 1,3-diethoxybenzene |

TABLE 14-continued

Feeding deterrence of selected compounds against third instar gypsy moth larvae.

| Compound Code | Feeding Deterrence (%) | SE | Actual Name |
|---|---|---|---|
| 3c{1, 3} | 13.86 | 11.5 | 1-methoxy-3-propoxybenzene |
| 3a{2, 2} | 3.59 | 12.5 | 1,2-diethoxybenzene |
| Eugenol | −0.76 | 12.6 | Eugenol |
| 3c{1, 1} | −8.64 | 12.6 | 1,4-dimethoxybenzene |
| 5b{1, 1} | −14.94 | 11.2 | mixture of 2 isomers; see FIG. 2. |

Example 14

3c{1,3} and (+)-Disparlure Cause an Enhancement of Male Gypsy Moth Attraction

The compound has the following effects in the EAG at the following ratios:

TABLE 15

| (+)-disparlure | 3c{1, 3} | ratio (by mass) (+)dis:3c{1, 3} | STI | LTI |
|---|---|---|---|---|
| 100 ng | 1 µg | 1:10 | 28 ± 16 (6) | N/A |
| 100 ng | 10 µg | 1:100 | −2 ± 5 (6) | N/A |
| 100 ng | 100 µg | 1:1000 | 48 ± 14 (6) | 39 ± 12 (6) |

STI = short-term inhibition, the change seen in the mixture relative to the first puff of pure (+)-disparlure.
LTI = long-term inhibition, the change seen in the (+)-disparlure puff immediately after the last mixed puff (which always had a 1:1000 ratio), relative to the first (+)-disparlure reference puff.

FIG. 7 shows that the mini library 3c{3,1-5} contained compound 3c{1,3} and that LTI for 1:100,000, 1:10,000, 1:2000, 1:1000 was similar, but decreased for 1:200 and 1:100 (FIG. 7B), and STI was strongest for 1:100,000, followed by ratios of 1:10,000; 1:2000, 1:1000, 1:200 and 1:100 (FIG. 7D). Thus, all these ratios were short-term inhibitory, with the highest inhibitor concentration being the most inhibitory.

Example 15

Further Field Trials

Figure 16:
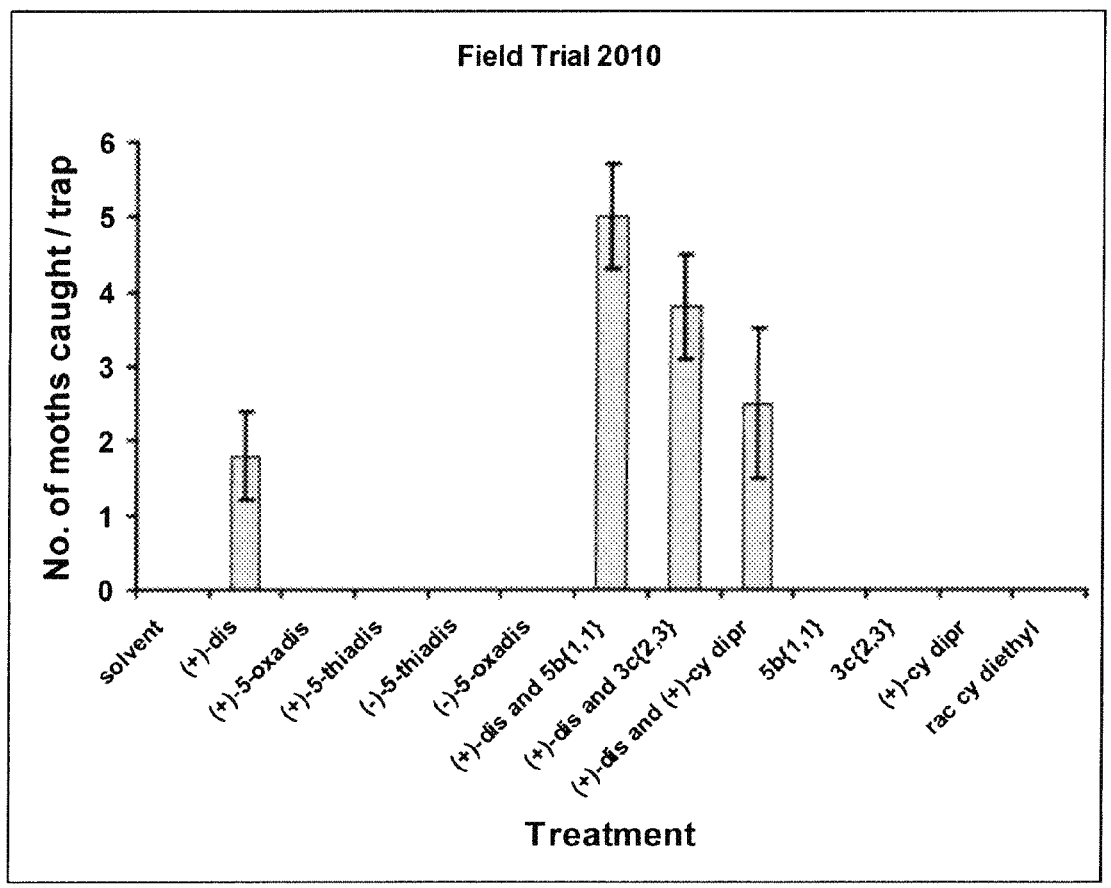
FIG. 16 shows the results of a field trial conducted in New Brunswick, Canada in 2010.

A field trial was conducted in New Brunswick (near Tracy, NB (45.64° N 66.74° W) on Provincial crown land) from Jul. 22 to Sep. 15, 2010. That year, the population density of gypsy moth was low in that area, but there was evidence of larval feeding in the hardwood forest (with mostly oak), and monitoring traps in that area had caught adult males. Traps were placed along trap lines, 30 m apart, on a randomized grid. For each treatment 5 traps were deployed. The trial was conducted blind, and the compounds and mixtures that were tested are shown as follows and in FIG. 16.

Treatments of the gypsy moth trapping trial in New Brunswick in 2010.

| Treatment function | Replicates | Compound |
|---|---|---|
| 1. Control (Negative) | 5 | solvent |
| 2. Control (Positive) | 5 * | (+)-disparlure (40 µg/lure) |
| 3. Test ST enhancer | 5 | (+)-disparlure + 3c{2, 3} (40 µg + 40 mg) |
| 4. Test ST inhibitor & PK broadening compound | 5 | (+)-disparlure + 5b{1, 1} (40 µg + 40 mg) |
| 5. Test ST enhancer & PKB | 5 | (+)-disparlure + Cy{dipropyl} (+)(40 µg + 0.4 mg) |
| 6. Mimic of rac dis | 5 | cy diethyl (racemic) (4 mg/lure) |
| 7. analog of (+)-dis | 5 | (−)-5-oxadisparlure (40 µg/lure) |
| 8. analog of (+)-dis | 5 | (−)-5-thiadisparlure (40 µg/lure) |
| 9. analog of (−)-dis | 5 | (+)- 5 oxadisparlure (40 µg/lure) |
| 10. analog of (−)-dis | 5 | (+)-5-thiadisparlure (40 µg/lure) |
| 11. Control (enhancer) | 5 | 3c{2, 3} (40 mg) |
| 12. Control (inhibitor) | 5 | 5b{1, 1} (40 mg) |
| 13. Mimic of (+) dis | 5 * | Cy{dipropyl} (+) (0.4 mg) |

* One replicate was lost due to a bear attack. (EP IX p 23, 27-29)

Figure 17:
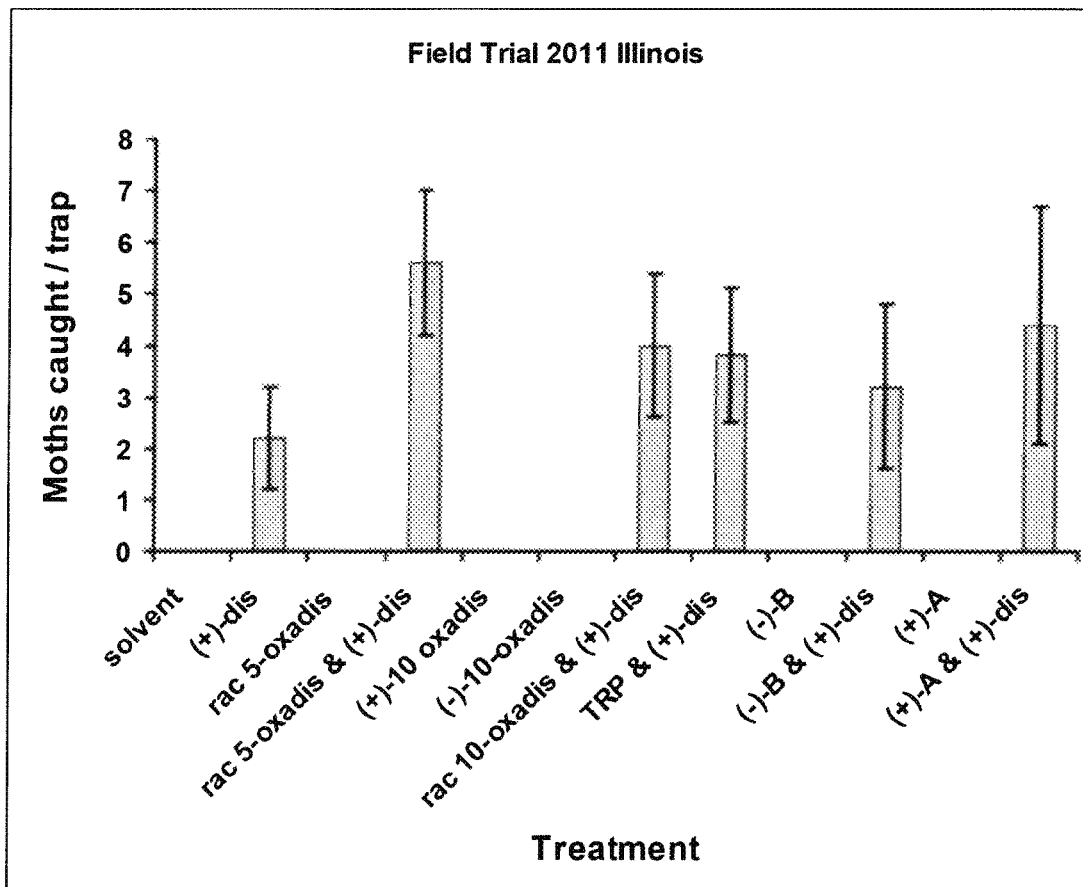
FIG. 17 shows the results of a field trial conducted in Illinois, U.S.A. in 2011.

A field trial was conducted in the Forest Preserve District of Cook County, Ill., from Jul. 18 to Jul. 23, 2011. Each compound or mixture was tested in 5 replicates as follows and in FIG. 17. (EP IX, pp 60-61)

Compounds and doses tested in Illinois in 2011.

| Treatment function | Replicates | Compound |
|---|---|---|
| Control (negative) | 5 | solvent |
| Control (positive) | 5 | (+)-disparlure (50 µg/lure) |
| (+)-disparlure analog | 5 | (+)-10-oxadisparlure (50 µg/lure) |
| (−)-disparlure analog | 5 | (−)-10-oxadisparlure (50 µg/lure) |
| Test enhancement effect by (rac)-10-oxadisparlure | 5 | (racemic)-10-oxadisparlure (50 µg/lure) + (+)-disparlure (50 µg/lure) |
| Test enhancement effect by (rac)-5-oxadisparlure | 5 | (racemic)-5-oxadisparlure (50 µg/lure) + (+)-disparlure (50 µg/lure) |
| (rac)-disparlure analog | 5 | (racemic)-5-oxadisparlure (50 µg/lure) |
| Test enhancement effect by TRP | 5 | Thermal rearrangement prod. (500 µg/lure) + (+)-disparlure (50 µg/lure) |
| EAG active (+)-dis analog | 5 | (−)-B ((−)-1-pentyloxy-5-(2'-ethylyloxyethyl)-cyclopent-2-ene) (100 µg/lure) |
| EAG active (+)-dis analog | 5 | (+)-A ((+)-1-ethoxy-5-(2'-pentyloxy-ethyl)-cyclopent-2-ene) (100 µg/lure) |
| Test enhancement by (−)-B | 5 | (−)-B (100 µg/lure) and (+)-disparlure (50 µg/lure) |
| Test enhancement by (+)-A | 5 | (+)-A (100 µg/lure) and (+)-disparlure (50 µg/lure) |

Figure 18:
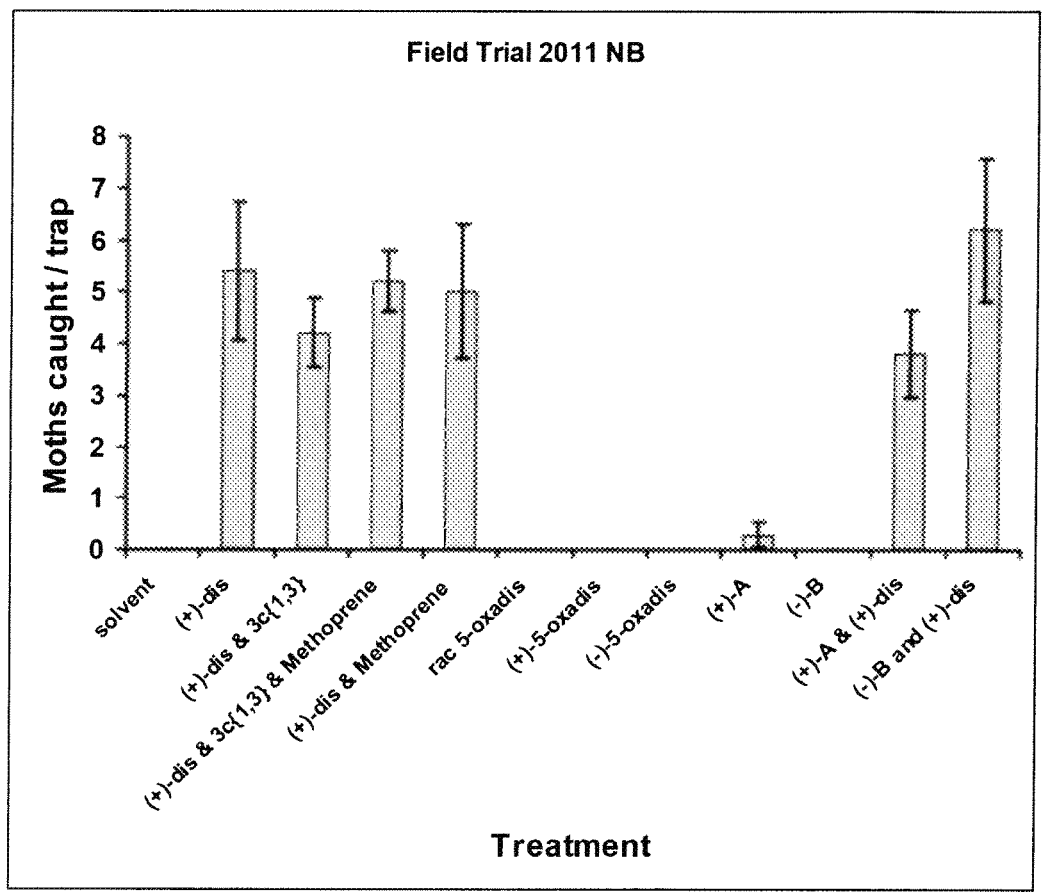
FIG. 18 shows the results of a field trial conducted in New Brunswick, Canada in 2011.

A second field trial was conducted near St. John's, New Brunswick (LAT 45 38 23.45 N, LONG 66 45 37.19 W), from Jul. 8 to Sep. 21, 2011, and each compound or mixture was tested in 5 replicates as follows and in FIG. 18). (EP IX, pp 60-61)

Compounds and mixtures tested in New Brunswick in 2011.

| Treatment function | Replicates | Compound |
|---|---|---|
| Control (negative) | 5 | solvent |
| Control (positive) | 5 | (+)-disparlure (50 µg/lure) |
| Test ST enhancer at 100:1 ratio | 5 | (+)-disparlure (50 µg/lure) and 3c{1, 3} (5000 µg/lure) |
| Test effect of methoprene | 5 | (+)-disparlure (50 µg/lure) & methoprene (100 µg/lure) |

-continued

Compounds and mixtures tested in New Brunswick in 2011.

| Treatment function | Replicates | Compound |
| --- | --- | --- |
| Test ST enhancer + methoprene | 5 | (+)-disparlure (50 µg/lure) and 3c{1, 3} (5000 µg/lure) and methoprene (100 µg/lure) |
| analog of (+)-dis | 5 | (−)-5-oxadisparlure (50 µg/lure) |
| analog of (−)-dis | 5 | (+)-5-oxadisparlure (50 µg/lure) |
| analog of rac dis | 5 | (racemic)-5-oxadisparlure (50 µg/lure) |
| mimic of (+)-dis | 5 | (−)-B ((−)-1-pentyloxy-5-(2'-ethylyloxyethyl)-cyclopent-2-ene) (100 µg/lure) |
| mimic of (+)-dis | 5 | (+)-A ((+)-1-ethoxy-5-(2'-pentyloxyethyl)-cyclopent-2-ene) (100 µg/lure) |
| Test enhancer and PKB | 5 | (−)-B (100 µg/lure) and (+)-disparlure (50 µg/lure) |
| Test enhancer and PKB | 5 | (+)-A (100 µg/lure) and (+)-disparlure (50 µg/lure) |

The field trials show that 1:1000 ratio gives a significant enhancement of trap catches, as summarized below.

| Field trial year and place | ratio of (+)-dis: agonist | relevant agonists tried | result |
| --- | --- | --- | --- |
| 2009, Japan | 1:1000 | Me eugenol, 3c{1, 3}, 3c{2, 3} and DEET | significant trap catch enhancement |
| 2010, New Brunswick | 1:1000 | 5b{1, 1}, 3c{2, 3} | significant trap catch enhancement |
| 2011 New Brunswick | 1:100 | 3c{1, 3} | no observed enhancement |
| 2011, Maryland | 1:100 | 3c{1, 3} and 5b{1, 1} | slight enhancement, but not significant |
| 2012 New Brunswick | 1:1000 | (awaiting results) | |

Example 16

Dose Response and Ratio Tests

Figure 19:
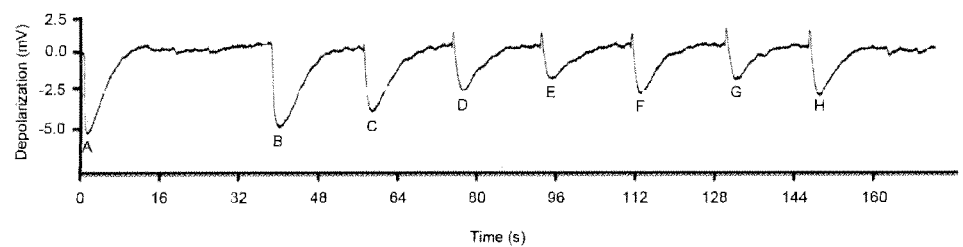
FIG. 19 shows the results of (+)-disparlure and 3c{1,3} in different ratios.

Dose response and ratio tests were done at each of the following (+)-disparlure concentrations: 1 ng, 10 ng, 50 ng, 100 ng, 500 ng and 1000 ng, the following ratios of (+)-disparlure:3c{1,3} were tested: 1:100, 1:300, 1:500, 1:700, 1:1000, 1:1500 and 1:2000 (FIG. 19). The results showed that the slope of the recovery phase of the EAG wave gets more and more shallow, indicating signal prolongation i.e., the antenna stays depolarized longer. Therefore, ratios from about 1:300 (0.3%) to about 1:2000 (0.5‰=500 ppm) or greater cause increasingly broad depolarizations and enhance trap catches, which may prove useful in monitoring and mating disruption applications.

Example 17

Monitoring of gypsy moths is an important tool for forest managers. In situations where no control measures are implemented at the time of monitoring, data from traps helps managers to decide whether to start control measures or not. In situations where control measures are being used, data from traps is useful to see whether the control measures are working. For example, a forest is treated with racemic disparlure (slowly released from chips), to cause mating disruption, and the managers wish to know if that level of racemic disparlure is causing changes in the male moth flight patterns. Normal traps tend not to work in this case, because the air is so saturated with racemic disparlure. Hyper attractive traps containing for example compound 3c{1,3} or another attractant compound as described herein would be useful in monitoring within a disparlure-saturated environment.

Disparlure is a hydrocarbon that can bioaccumulate, because it is so hydrophobic but racemic disparlure has been dropped onto forests to cause mating disruption. Accordingly, in another example, mixtures of (+)-disparlure and 3c{1,3} at ratios of about 1:300-1:2000 are useful in mating disruption, instead of large quantities of racemic disparlure.

Other Embodiments

Although various embodiments of the invention are disclosed herein, many adaptations and modifications may be made within the spirit and scope of the invention in accordance with the common general knowledge of those skilled in this art. Such modifications include the substitution of known equivalents for any aspect of the invention in order to achieve the same result in substantially the same way. Numeric ranges are inclusive of the numbers defining the range, and of sub-ranges encompassed therein. As used herein, the terms "comprising", "comprises", "having" or "has" are used as an open-ended terms, substantially equivalent to the phrase "including, but not limited to". Terms such as "the," "a," and "an" are to be construed as indicating either the singular or plural. Citation of references herein shall not be construed as an admission that such references are prior art to the present invention. All publications are incorporated herein by reference as if each individual publication were specifically and individually indicated to be incorporated by reference herein and as though fully set forth herein. The invention includes all embodiments and variations substantially as hereinbefore described and with reference to the examples and drawings.

REFERENCES

Cerboneschi 1998 Influence of microclimatic variations on EAG responses of *Lymantria dispar* (Lepidoptera, Lymantridae) males to sex pheromone. *Ital. J. Zool.* 1998, 65,267-272.

Goering, H. L.; Jacobson, R. R., A Kinetic Study of the ortho-Claisen Rearrangement. *J. Am. Chem. Soc.* 1958, 80, 3277-3285.

Grant, V. H.; Liu, B., Iridium(III)-catalyzed tandem Claisen rearrangement-intramolecular hydroaryloxylation of aryl allyl ethers to form dihydrobenzofurans. *Tetrahedron Lett.* 2005, 46, 1237-1240.

Ito, F.; Fusegi, K.; Kumamoto, T.; Ishikawa, T., Boron Trichloride Meidated Regioselective Claisen Rearrangement of Resorcinol Derivatives: Application to Resorcinol Carvonyl Ethers. *Synthesis* 2007, 12, 1785-1796.

Ito, Y.; Kato, R.; Hamashima, K.; Kataoka, Y.; Oe, Y.; Ohta, T.; Furukawa, I., Intramolecular cyclization of phenol derivatives with C=C double bond in a side chain. *J. Organometallic Chem.* 2007, 692, 691-697.

Montgomery, M. E., Wallner, W. E. 1988. The Gypsy Moth, A Westward Migrant. In: *Dynamics of Forest Insect Populations. Patterns, Causes, Implications.* Ed. Berryman, A. A., Plenum, N.Y. pp 353-375.

Ollevier, T.; Mwene-Mbeja, T. M., Bismuth Triflate Catalyzed [1,3] Rearrangement of Aryl 3-Methylbut-2-enyl Ethers. *Synthesis* 2006, 23, 3963-3966.

Plettner, E.; Lazar, J.; Prestwich, E. G.; Prestwich, G. D., Discrimination of Pheromone Enantiomers by Two Pheromone Binding Proteins from the Gypsy Moth *Lymnatria dispar*. *Biochemistry* 2000, 39, 8953-8962.

Staddon, B. W.; Everton, I. J., Haemolymph of the milkweed bug *Oncopeltus fasciatus* (Heteroptera; lygaeidae): Inorganic constituents and amino acids. *Comp. Biochem. Physiol. A* 1980, 65, 371-374.

Gunchu, E., Daz-Maroto, M. C., Daz-Maroto, I. J., Vila-Lameiro, P., and Prez-Coello, M. S. (2009) Influence of the Species and Geographical Location on Volatile Composition of Spanish Oak Wood (*Quercus petraea* Liebl. and *Quercus robur* L.). *J. Agric. Food Chem.* 54, 3062-3066.

Grant, V. H.; Liu, B., Iridium(III)-catalyzed tandem Claisen rearrangement-intramolecular hydroaryloxylation of aryl allyl ethers to form dihydrobenzofurans. *Tetrahedron Lett.* 2005, 46, 1237-1240.

Mathew, N. T.; Khaire, S.; Mayadevi, S.; Jha, R.; Sivasanker, S., Rearrangement of allyl phenyl ether over Al-MCM-41. *J. of Catalysis* 2004, 229, 105-113.

McCabe, E. T., Barthel, W. F., Gertler, S. I., and Hall, S. A. (1954) Insect Repellents. III. N,N-Diethylamides. *J. Org. Chem.* 19, 493-498.

Plimmer, J. R., Leonhardt, B. A., Webb, R. E., and Schwalbe, C. P. (1982) Management of the Gypsy Moth with Its Sex Attractant Pheromone, in *Insect Pheromone Technology: Chemistry and Applications* (Leonhardt, B. A., and Beroza, M., Eds.) pp 231-242, American Chemical Society, N.Y.

Reich, N. W.; Yang, C.-G.; Shi, Z.; He, C., Gold(I)-Catalyzed Synthesis of Dihydrobenzofurans from Aryl Allyl Ethers. *Synlett* 2006, 8, 1278-1280.

Schneider, D. (1969) Insect Olfaction: Deciphering System for Chemical Messages. *Science* 163, 1031-1037.

Staddon, B. W.; Everton, I. J., Haemolymph of the milkweed bug *Oncopeltus fasciatus* (Heteroptera; lygaeidae): Inorganic constituents and amino acids. *Comp. Biochem. Physiol. A* 1980, 65, 371-374.

Bierl, B., Beroza, M., and Collier, C. W. (1970) Potent Sex Attractant of the Gypsy Moth: Its Isolation, Identification and Synthesis. *Science* 170, 87-89.

Bierl, B. A., Beroza, M., and Collier, C. W. (1972) Isolation, Identification, and Synthesis of the Gypsy Moth Sex Attractant. *J. Econ. Entomol.* 65, 659-664.

Grant, G. G, Langevin, D., Liska, J., Kapitola, P., and Chong, J. M. (1996) Olefin Inhibitor of Gypsy Moth, *Lymantria dispar*, is a Synergistic Pheromone Component of Nun Moth, *L. monacha. Naturwissenschaften* 83, 328-330.

Gries, G., Gries, R., Khaskin, G., Slessor, K. N., Grant, G. G., Liska, J., and Kapitola, P. (1996) Specificity of Nun and Gypsy Moth Sexual Communication Through Multiple-Component Pheromone Blends. *Naturwissenschaften* 83, 382-385.

Hansen, K. (1984) Discrimination and production of disparlure enantiomers by the gypsy moth and the nun moth. *Physiol. Entomol.* 9, 9-18.

Miller, J. R., Mori, K., and Roelofs, W. L. (1977) Gypsy Moth Field Trapping and Electroantennogram Studies with Pheromone Enantiomers. *J. Insect Physiol.* 23, 1447-1453.

Carde, R. T., Doane, C. C., Baker, T. C., Iwaki, S., and Marumo, S. (1977) Attractancy of Optically Active Pheromone for Male Gypsy Moths. *Environ. Entomol.* 6, 768-772.

Plimmer, J. R., Schwalbe, C. P., Paszek, E. C., Bierl, B. A., Webb, R. E., Marumo, S., and Iwaki, S. (1977) Contrasting Effectiveness of (+) and (−) Enantiomers of Disparlure for Trapping Native Populations of Gypsy Moth in Massachusetts. *Environ. Entomol.* 6, 518-522.

Gries, G., Schaefer, P. W., Gries, R., Liska, J., and Gotoh, T. (2001) Reproductive character displacement in *Lymantria monacha* from Northern Japan. *J. Chem. Ecol.* 27, 1163-1175.

Gries, R., Khaskin, G., Schaefer, P. W., Hahn, R., Gotoh, T., and Gries, G. (2005) (7R,8S)-cis-7,8-Epoxy-2-methyloctadec-17-ene: a novel trace component from the sex pheromone gland of gypsy moth, *Lymantria dispar. J. Chem. Ecol.* 31, 49-62.

Schneider, D. (1969) Insect Olfaction: Deciphering System for Chemical Messages. *Science* 163, 1031-1037.

Hansen, K. (1984) Discrimination and production of disparlure enantiomers by the gypsy moth and the nun moth. *Physiol. Entomol.* 9, 9-18.

Miller, J. R., Mori, K., and Roelofs, W. L. (1977) Gypsy Moth Field Trapping and Electroantennogram Studies with Pheromone Enantiomers. *J. Insect Physiol.* 23, 1447-1453.

Campion, D. G. (1984) Survey of Pheromone Uses in Pest Control, in *Techniques in Pheromone Research* (Hummel, H. E., and Miller, T. A., Eds.) pp 405-449, Springer, N.Y.

Bengtsson, M., Jaastad, G., Knudsen, G., Kobro, S., Backman, A.-C., Pettersson, E., and Witzgall, P. (2006) Plant volatiles mediate attraction to host and non-host plant in apple fruit moth, *Argyresthia conjugella*. *Entomol. exp. appl.* 118, 77-85.

Dickens, J. C. (1989) Green leaf volatiles enhance aggregation pheromone of boll weevil, *Anthonomus grandis*. *Entomol. exp. appl.* 52, 191-203.

Dickens, J. C., Jang, E. B., Light, D. M., and Alford, A. R. (1990) Enhancement of Insect Pheromone Responses by Green Leaf Volatiles. *Naturwissenschaften* 77, 29-31.

Dickens, J. C., Smith, J. W., and Light, D. M. (1993) Green leaf volatiles enhance sex attractant pheromone of the tobacco budworm, *Heliothis virescens* (Lep.:Noctuidae). *Chemoecology* 4, 175-177.

Erbilgin, N., and Raffa, K. F. (2001) Modulation of predator attraction to pheromones of two prey species by stereochemistry of plant volatiles. *Oecologia* 127, 444-453.

Bengtsson et al. (2006); Dickens 1989; Dickens et al. 1990; Dickens et al. 1993; Erbilgin and Raffa 2001)

Landolt, P. J., and Phillips, T. W. (1997) Host Plant Influences on Sex Pheromone Behavior of Phytophagous Insects. *Annu. Rev. Entomol.* 42, 371-391.

Bau, J., Martinez, D., Renou, M., and Guerrero, A. (1999) Pheromone-triggered Orientation Flight of Male Moths can be Disrupted by Trifluoromethyl Ketones. *Chem. Senses* 24, 473-480.

Renou, M., Berthier, A., and Guerrero, A. (2002) Disruption of responses to pheromone by (Z)-11-hexadecenyl trifluoromethyl ketone, an analogue of the pheromone, in the cabbage armyworm *Mamestra brassicae. Pest Manag. Sci.* 58, 839-844.

What is claimed is:

1. A method for controlling infestation by a *Lymantria dispar* comprising applying an effective amount of a compound of Formula I:

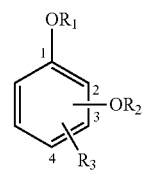

Formula I wherein R1 is methyl, ethyl, propyl, n-butyl, isopentyl (3-methylbutyl) or allyl;

R2 is at position 4 as labeled in Formula I and is H, methyl, ethyl, propyl, n-butyl, isopentyl (3-methylbutyl) or allyl; and R3 is absent;

wherein the compound of Formula I, or a mixture thereof, is selected from the group consisting of one or more of methyl eugenol, 1-ethoxy-4-propoxybenzene, and 1-methoxy-4-propoxybenzene, and wherein the compound of Formula I, or a mixture thereof, is provided together with (+)-disparlure at a ratio from about 1:300 to about 1:10,000, to an area or region that is infested with, or at risk of infestation by, *Lymantria dispar* whereby the *Lymantria dispar* infestation is controlled.

2. The method of claim 1 wherein the *L. dispar* is a larva or an adult.

3. The method of claim 1 wherein the site of interest comprises a plant or part thereof and wherein the plant is a plant within the host range of *L. dispar*.

4. The method of claim 1 wherein the compound of Formula I is provided in a formulation selected from one or more of the group consisting of spray, solid, liquid.

5. A method of protecting a plant from infestation by a *L. dispar* comprising applying an effective amount of a compound of Formula I:

Formula I wherein R1 is methyl, ethyl, propyl, n-butyl, isopentyl (3-methylbutyl) or allyl;

R2 is at position 4 as labeled in Formula I and is H, methyl, ethyl, propyl, n-butyl, isopentyl (3-methylbutyl) or allyl; and R3 is absent;

wherein the compound of Formula I, or a mixture thereof, is selected from the group consisting of one or more of methyl eugenol, 1-ethoxy-4-propoxybenzene, and 1-methoxy-4-propoxybenzene, and wherein the compound of Formula I, or a mixture thereof, is provided together with (+)-disparlure at a ratio from about 1:300 to about 1:10,000, to the plant or part thereof, wherein the plant is a plant within the host range of *L. dispar*, whereby the plant is protected from infestation.

6. The method of claim 1 wherein the area or region that is infested with, or at risk of infestation by, *Lymantria dispar* does not contain grass.

7. The method of claim 1 wherein the compound of Formula I or a mixture thereof and the (+)-disparlure is provided in a trap, bait, lure, or film.

8. The method of claim 1 wherein the area or region that is infested with, or at risk of infestation by, *Lymantria dispar*, is a forest, logging site, arboretum, or garden.

9. The method of claim 5 wherein the plant within the host range of *L. dispar* is a deciduous tree.

10. The method of claim 5 wherein the plant within the host range of *L. dispar* is an oak, aspen, ash, willow, hawthorn, apple, alder, birch, poplar, cottonwood, hemlock, cypress, pine, spruce, ash, sycamore, butternut, black walnut, balsam fir, cedar, or rhododendron.

* * * * *